US007812024B2

(12) United States Patent
Zhao et al.

(10) Patent No.: US 7,812,024 B2
(45) Date of Patent: Oct. 12, 2010

(54) MODULATORS OF SEROTONIN RECEPTORS

(75) Inventors: Guohua Zhao, Princeton, NJ (US); Chet Kwon, Newtown, PA (US); Philip D. Stein, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 438 days.

(21) Appl. No.: 11/748,078

(22) Filed: May 14, 2007

(65) Prior Publication Data
US 2007/0213337 A1 Sep. 13, 2007

Related U.S. Application Data

(62) Division of application No. 10/958,325, filed on Oct. 5, 2004, now Pat. No. 7,244,843.

(60) Provisional application No. 60/509,437, filed on Oct. 7, 2003, provisional application No. 60/541,746, filed on Feb. 4, 2004.

(51) Int. Cl.
*A01N 43/58* (2006.01)
*A01N 43/60* (2006.01)
*A61K 31/50* (2006.01)
*A61K 31/495* (2006.01)
*C07D 241/36* (2006.01)
*C07D 271/00* (2006.01)
*C07D 487/00* (2006.01)
*C07D 491/00* (2006.01)
*C07D 495/00* (2006.01)
*C07D 497/00* (2006.01)
*C07D 498/00* (2006.01)
*C07D 513/00* (2006.01)

(52) U.S. Cl. ........................................ 514/249; 544/338
(58) Field of Classification Search ........................ None
See application file for complete search history.

(56) References Cited

U.S. PATENT DOCUMENTS

| | | | |
|---|---|---|---|
| 3,517,012 | A | 6/1970 | Regnier et al. |
| 4,273,773 | A | 6/1981 | Demerson et al. |
| 5,028,607 | A | 7/1991 | Lavielle et al. |
| 5,929,085 | A | 7/1999 | MacDonald et al. |

FOREIGN PATENT DOCUMENTS

| | | |
|---|---|---|
| WO | WO 99/42456 | 8/1999 |
| WO | WO 02/059127 | 8/2002 |
| WO | WO 03/076440 | 9/2003 |

OTHER PUBLICATIONS

Singh et al., Indian Journal of Chemistry: Section B: Organic Chemistry including Medicinal Chemistry, 1977, 15(1), 70-72.*
Database Caplus 'Online! Chemical Abstracts Service, Columbus, Ohio, US; May 12, 1984, XP002316369, retrieved from STN, Database Accession No. 1973:537088 abstract.
Database Caplus 'Online! Chemical Abstracts Service, Columbus, Ohio, US; Jul. 27, 1985, XP002316399, retrieved from STN, Database Accession No. 1985:422553 abstrac.
Database Caplus 'Online! Chemical Abstracts Service, Columbus, Ohio, US; May 12, 1984, XP002316400, retrieved from STN, Database Accession No. 1975:531546 abstract.
Database Caplus 'Online! Chemical Abstracts Service, Columbus, Ohio, US; May 12, 1984, XP002316401, retrieved from STN, Database Accession No. 1977:468283 abstract.
Ferland, J. -M. et al., "Synthesis of derivatives of isoindole and of pyrazino[2,1-*a*]isoindole", Can. J. Chem., vol. 63, pp. 361-365 (1985).
Kato, H. et al., "Studies on 1-Azabicyclo Compounds. XV. Oxidation of 1,3,4,6,11,11a-Hexahydro-2*H*-pyrazino[1,2-*b*]isoquinolin-1-one Derivatives with Mercuric Acetate, and Their Conversion into 1,2,3,4,5,6,7,8-Octahydro-2-methyl-2,5-benzodiazecine and Related Compounds", Chem. Pharm. Bull., vol. 21, No. 9, pp. 2039-2047 (1973).
Rao, J. et al., "Synthesis of N-[3-Aryl(thio/sulphono)propyl]heterocyclics as Potential CNS/CVS Agents", Indian Journal of Chemistry, vol. 26B, pp. 761-765 (1987).
Saxena, A.K. et al., "Compounds Acting on the CNS: Part XXI—Synthesis of 2-Substituted 1,3,4,6,11,11a-Hexahydro-2(*H*)pyrazino[1,2-*b*]isoquinoline & Corresponding 8,9-Dimethoxy- & 6-Phenyl-8,9-dimethoxy Analogs", Indian Journal of Chemistry, vol. 13, pp. 230-237 (1975).
Saxena, M. et al., "Synthesis, Biological Evaluation, and Quantitative Structure-Activity Relationship Analysis of [β-(Aroylamino)ethyl]piperazines and -piperidines and [2-[(Arylamino)carbonyl]ethyl]piperazines, -piperidines, -pyrazinopyridoindoles, and -pyrazinoisoquinolines. A New Class of Potent $H_1$ Antagonists", J. Med. Chem., vol. 33, No. 11, pp. 2970-2976 (1990).
Singh, H. et al., "Studies in Potential Filaricides: Part X—Synthesis of 2-Substituted 1,3,4,6,11,11a-Hexahydro-2*H*-pyrazino[1,2-*b*] isoquinolin-6-ones", Indian Journal of Chemistry, vol. 15B, pp. 70-72 (1977).
Sullivan, H.B. et al., "Synthesis of 1,3,4,6,11,11a-Hexahydro-2*H*-pyrazino[1,2-*b*]isoquinoline and Perhydro-1*H*-pyrazino[1,2-*a*]quinoline", Journal of Organic Chemistry, vol. 29, pp. 326-328 (1964).
Welch, W.M., "Synthesis of the 1,2,3,4-Tetrahydropyrazino[2,1-*a*] isoindol-6(2*H*)-one Ring System", J. Org. Chem., vol. 47, No. 5, pp. 886-888 (1982).

* cited by examiner

*Primary Examiner*—James O Wilson
*Assistant Examiner*—Noble Jarrell
(74) *Attorney, Agent, or Firm*—Terence J. Bogie; Maureen S. Gibbons

(57) ABSTRACT

The present invention provides modulators of serotonin receptors, pharmaceutical compositions containing such modulators and methods for treating various diseases, conditions and disorders associated with modulation of serotonin receptors such as, for example: metabolic diseases, which includes but is not limited to obesity, diabetes, diabetic complications, atherosclerosis, impaired glucose tolerance and dyslipidemia; central nervous system diseases which includes but is not limited to, anxiety, depression, obsessive compulsive disorder, panic disorder, psychosis, schizophrenia, sleep disorder, sexual disorder and social phobias; cephalic pain; migraine; and gastrointestinal disorders using such compounds and compositions.

11 Claims, No Drawings

MODULATORS OF SEROTONIN RECEPTORS

RELATED APPLICATIONS

This application is a divisional application claiming priority benefit under Title 35 §121 of U.S. application Ser. No. 10/958,325, filed Oct. 5, 2004, now U.S. Pat. No. 7,244,843, issued Jul. 17, 2007, which claims priority to U.S. Application Nos. 60/509,437 and 60/541,746, filed Oct. 7, 2003 and Feb. 4, 2004, respectively, the contents of which are herein incorporated by reference.

BACKGROUND OF THE INVENTION

The neurotransmitter/hormone serotonin (5-hydroxytryptamine, 5-HT) regulates many physiological processes via a group of at least 14 distinct receptors that are organized into 7 subfamilies (Hoyer, D., et al., Pharmacol. Rev., 46, 1994). The $5\text{-}HT_2$ subfamily is composed of the $5\text{-}HT_{2A}$, $5\text{-}HT_{2B}$, and $5\text{-}HT_{2C}$ receptors as determined by gene homology and pharmacological properties. There exists a substantial correlation for the relationship between $5\text{-}HT_2$ receptor modulation and a variety of diseases and therapies. Prior to the early 1990's the $5\text{-}HT_{2C}$ and $5\text{-}HT_{2A}$ receptors were referred to as $5\text{-}HT_{1C}$ and $5\text{-}HT_2$, respectively.

The direct or indirect agonism or antagonism of $5\text{-}HT_2$ receptors, either selectively or non-selectively, has been associated with the treatment of various central nervous system (CNS) disorders including obesity, depression, schizophrenia and bi-polar disorders. In the recent past the contribution of serotonergic activity to the mode of action of anti-obesity drugs has been well documented. Compounds that increase the overall basal tone of serotonin in the CNS have been developed as anorectic drugs. The serotonin releasing agents, such as fenfluramine, function by increasing the amount of serotonin present in the nerve synapse. These breakthrough treatments, however, are not without side effects. Due to the mechanism of action of serotonin releasing agents, they affect the activity of a number of serotonin receptor subtypes in a wide variety of organs including those not associated with the desired mechanism of action. This non-specific modulation of the serotonin family of receptors most likely plays a significant role in the side effect profile. In addition, these compounds or their metabolites often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

The $5\text{-}HT_{2C}$ receptor is a G-protein coupled receptor. It is almost exclusively expressed in the central nervous system including the hypothalamus, hippocampus, amygdala, nucleus of the solitary tract, spinal cord, cortex, olfactory bulb, ventral tegmental area (VTA), nucleus accumbens and choroid plexus (Hoffman, B. and Mezey, E., FEBS Lett., 247, 1989). There is ample evidence to support the role of selective $5\text{-}HT_{2C}$ receptor ligands in a number of disease therapies. $5\text{-}HT_{2C}$ knockout mice develop a late stage obesity syndrome that is not reversed by fenfluramine or other direct acting $5\text{-}HT_{2C}$ agonists such as mCPP (Nonogaki, K., et al., Nature Med., 4, 1998; Vickers, S., et. al., Psychopharmacology, 143, 1999). Administration of selective $5\text{-}HT_{2C}$ agonists to rats causes a reduction in food intake and corresponding reduction in body weight (Vickers, S., et al., Br. J. Pharmacol., 130, 2000) and these responses can be blocked by administration of selective $5\text{-}HT_{2C}$ antagonists (Vicker, S., et al., Neuropharmacol., 41, 2001). $5\text{-}HT_{2C}$ receptor modulation in the hypothalamus can also influence thermoregulation (Mazzola-Pomietto, P, et al., Psychopharmacology, 123, 1996), sleep (Sharpley, A., et al., Neuropharmacology, 33, 1994), sexual behavior and neuroendocrine function (Rittenhouse, P. et al., J. Pharmacol. Exp. Ther., 271, 1994). Activation of $5\text{-}HT_{2C}$ receptors in the VTA modulates the activity of dopaminergic neurons that are involved in aspects of depression (Di Matteo, V. et al., Trends Pharmacol. Sci., 22, 2001) and $5\text{-}HT_{2C}$ receptor agonists such as WAY 161503, RO 60-0175 and RO 60-0332 are active in rodent models of depression (Cryan, J. and Lucki, I., J. Pharmacol. Exp. Ther., 295, 2000). $5\text{-}HT_{2C}$ agonists have been reported to reduce the rewarding effects of nicotine administration in rats (Grottick, A., et al., Psychopharmacology, 157, 2001) and influences rodent responses to cocaine administration (Grottick, A., et al., J. Pharmacol. Exp. Ther., 295, 2000). Modulation of $5\text{-}HT_{2C}$ receptors in the spinal cord can influence pain perception (Chojnacka-Wojcik, E., et al., Pol. J. Pharmacol., 46, 1994). There is also data indicating that the $5\text{-}HT_{2C}$ receptor agonists mCPP and RO 60-0175 mediate penile erections in rats (Millan, M., et al., Eur J. Pharmacol. 325, 1997).

DETAILED DESCRIPTION OF THE INVENTION

The present application describes compounds according to Formula I including pharmaceutically acceptable salts forms thereof, wherein A, B, D, m, n, $R^3$, $R^8$, $R^9$, $R^{10}$, $R^{11}$, W and X are described herein. Additionally, pharmaceutical compositions comprising at least one compound according to Formula I and optionally one or more additional therapeutic agents are described in the present application. Finally, methods of treatment using the compounds according to Formula I both alone and in combination with one or more additional therapeutic agents are described in the present application.

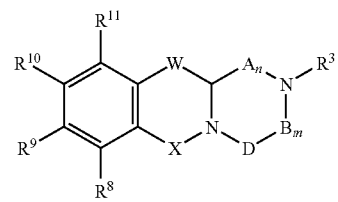

I

Definitions

The following definitions apply to the terms as used throughout this specification, unless otherwise limited in specific instances.

Unless otherwise indicated, the term "alkyl" as employed herein alone or as part of another group includes both straight and branched chain hydrocarbons, containing 1 to 40 carbons, preferably 1 to 20 carbons, more preferably 1 to 6 carbons, in the normal chain, such as, for example, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

The term "alkylene" as employed herein alone or as part of another group refers to alkyl linking groups above having single bonds for attachment to other groups at two different carbon atoms.

Unless otherwise indicated, the term "alkenyl" as used herein by itself or as part of another group refers to straight or branched chain radicals of 2 to 20 carbons, preferably 2 to 12 carbons, and more preferably 2 to 6 carbons in the normal chain, which include one or more double bonds in the normal chain, such as, for example, vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkenylene" and as employed herein alone or as part of another group refers to alkenyl linking groups, having single bonds for attachment at two different carbon atoms.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as, for example, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with one or more functional groups as defined above for alkyl.

The term "alkynylene" as employed herein alone or as part of another group refers to alkynyl linking groups, having single bonds for attachment at two different carbon atoms.

The term "halogen" or "halo" as used herein alone or as part of another group refers to chlorine, bromine, fluorine and iodine.

Unless otherwise indicated, the term "cycloalkyl" as employed herein alone or as part of another group refers to saturated or partially unsaturated (containing 1 or 2 double bonds) cyclic hydrocarbon groups containing 1 to 3 rings, including monocyclic alkyl, bicyclic alkyl and tricyclic alkyl, containing a total of 3 to 20 carbons forming the rings, preferably 4 to 10 carbons, forming the ring such as, for example, cyclopropyl, cyclobutyl, cyclopentyl, cyclohexyl, cycloheptyl, cyclooctyl, cyclodecyl, cyclododecyl, cyclohexenyl,

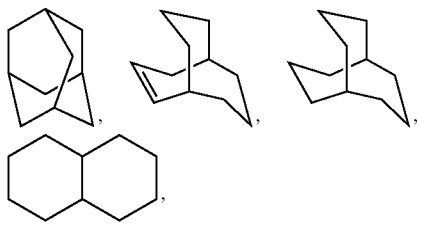

wherein the cycloalkyl may be fused to 1 aromatic ring as described for aryl.

The term "heterocyclyl", as used herein, refers to an unsubstituted or substituted stable 4-, 5-, 6- or 7-membered monocyclic ring system which may be saturated or unsaturated, and which consists of carbon atoms and from one to four heteroatoms selected from N, O, S, SO and/or SO$_2$ group, wherein the nitrogen heteroatoms may optionally be oxidized, and the nitrogen heteroatom may optionally be quaternized. The heterocyclic ring may be attached at any heteroatom or carbon atom which results in the creation of a stable structure such as, for example, piperidinyl, piperazinyl, oxopiperazinyl, oxopiperidinyl and oxadiazolyl.

The term "aryl" as employed herein alone or as part of another group refers to monocyclic and bicyclic aromatic groups containing 6 to 10 carbons in the ring portion such as, for example, phenyl or naphthyl and may optionally include one to three additional rings fused to "aryl" such as, for example, aryl, cycloalkyl, heteroaryl or cycloheteroalkyl rings.

The term "heteroaryl" as used herein refers to a 5-, 6- or 7-membered aromatic heterocyclic ring which contains one or more heteroatoms selected from nitrogen, sulfur, oxygen and/or a SO or SO$_2$ group. Such rings may be fused to another ring such as, for example, cycloalkyl, cycloheteroalkyl, aryl or heteroaryl and include possible N-oxides.

The term "oxy" as used herein as part of another group refers to an oxygen atom serving as a linker between two groups such as, for example, hydroxy, oxyalkyl, oxyalkenyl, oxyalkynyl, oxyperfluoroalkyl (e.g. —OCF$_3$), oxyaryl, oxyheteroaryl, oxycarboalkyl, oxycarboalkenyl, oxycarboalkynyl, oxycarboaryl, oxycarboheteroaryl, oxycarbocycloalkyl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl and aminocarboxyheteroaryl.

The term "carbo" as used herein as part of another group refers to a carbonyl (C=O) group serving as a linker between two groups such as, for example, carboalkyl, carboalkenyl, carboalkynyl, carboaryl, carboheteroaryl, carbocycloalkyl, carboxyalkyl, carboxyalkenyl, carboxyalkynyl, carboxyaryl, carboxyheteroaryl, carboxycycloalkyl, oxycarboalkyl, oxycarboalkenyl, oxycarboalkynyl, oxycarboaryl, oxycarboheteroaryl, oxycarbocycloalkyl, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl and aminocarboaminoheteroaryl.

The term "thio" as used herein as part of another group refers to a sulfur atom serving as a linker between two groups such as, for example, thioalkyl, thioalkenyl, thioalkynyl, thioaryl, thioheteroaryl, thioheterocyclyl and thiocycloalkyl.

The term "perfluoro" as used herein as part of another group refers to a group wherein more than one hydrogen atom attached to one or more carbon atoms in the group has been replaced with a fluorine atom such as, for example, perfluoroalkyl (e.g. —CF$_3$), perfluoroalkenyl, perfluoroalkynyl and oxyperfluoroalkyl.

The term "amino" as used herein alone or as part of another group refers to a nitrogen atom that may be either terminal or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine such as, for example, amino, aminoalkyl, aminoalkenyl, aminoalkynyl, aminoaryl, aminoheteroaryl, aminocycloalkyl, alkylamino, alkenylamino, alkynylamino, arylamino, heteroarylamino, cycloalkylamino, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl, aminocarboaminoheteroaryl, sulfoalkyl, sulfoalkenyl, sulfoalkynyl, sulfoaryl, sulfocycloalkyl, sulfoheterocyclyl and sulfoheteroaryl.

The term "nitrile" as used herein refers to a cyano (a carbon atom triple-bonded to a nitrogen atom) group.

The term "sulfo" as used herein as part of another group refers to an —SO$_2$— group such as, for example, sulfoalkyl, sulfoalkenyl, sulfoalkynyl, sulfoaryl, sulfocycloalkyl, sulfoheterocyclyl and sulfoheteroaryl.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

Any compound that can be converted in vivo to provide the bioactive agent (i.e., the compound of formula I) is a prodrug within the scope and spirit of the invention.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art and are described in:

a) *The Practice of Medicinal Chemistry*, Camille G. Wermuth et al., Ch. 31 (Academic Press, 1996);

b) *Design of Prodrugs*, edited by H. Bundgaard, (Elsevier, 1985); and c) *A Textbook of Drug Design and Development*, P. Krogsgaard-Larson and H. Bundgaard, eds. Ch. 5, pp. 113-191 (Harwood Academic Publishers, 1991). Said references are incorporated herein by reference.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques or fractional crystallization.

The pharmaceutically acceptable salts of the compounds of formula I of the invention include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, stearate and salts of naturally occurring amino acids such as arginine, lysine, alanine and the like, and prodrug esters thereof.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

SCHEME 1

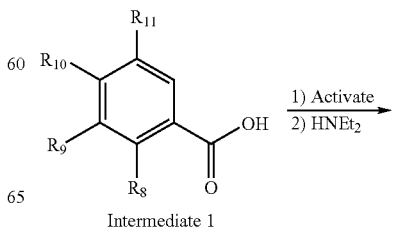

Intermediate 1

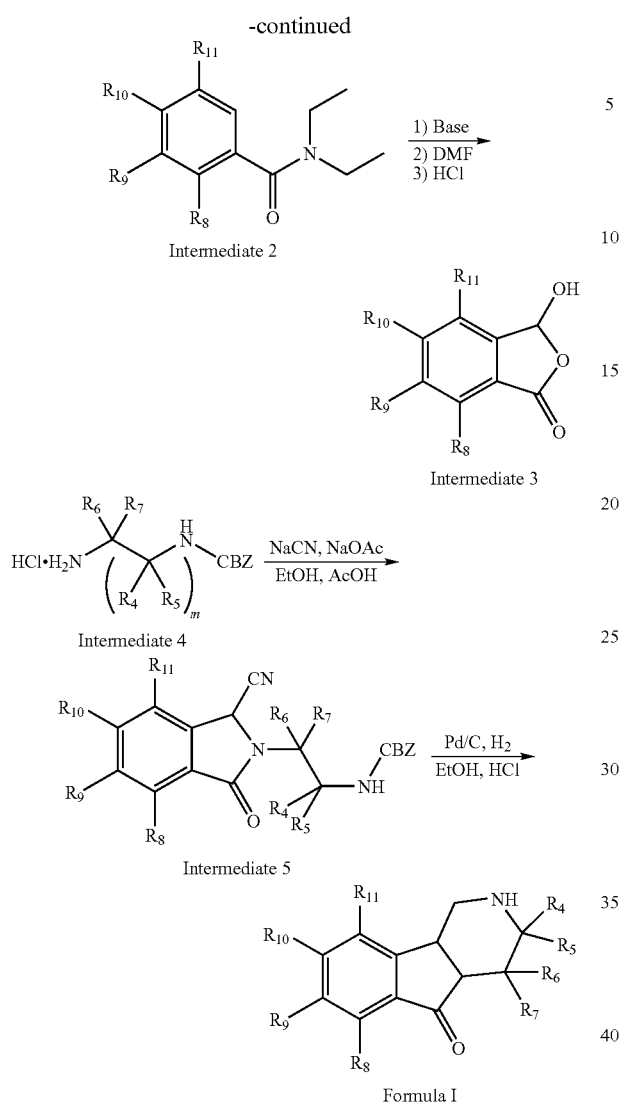

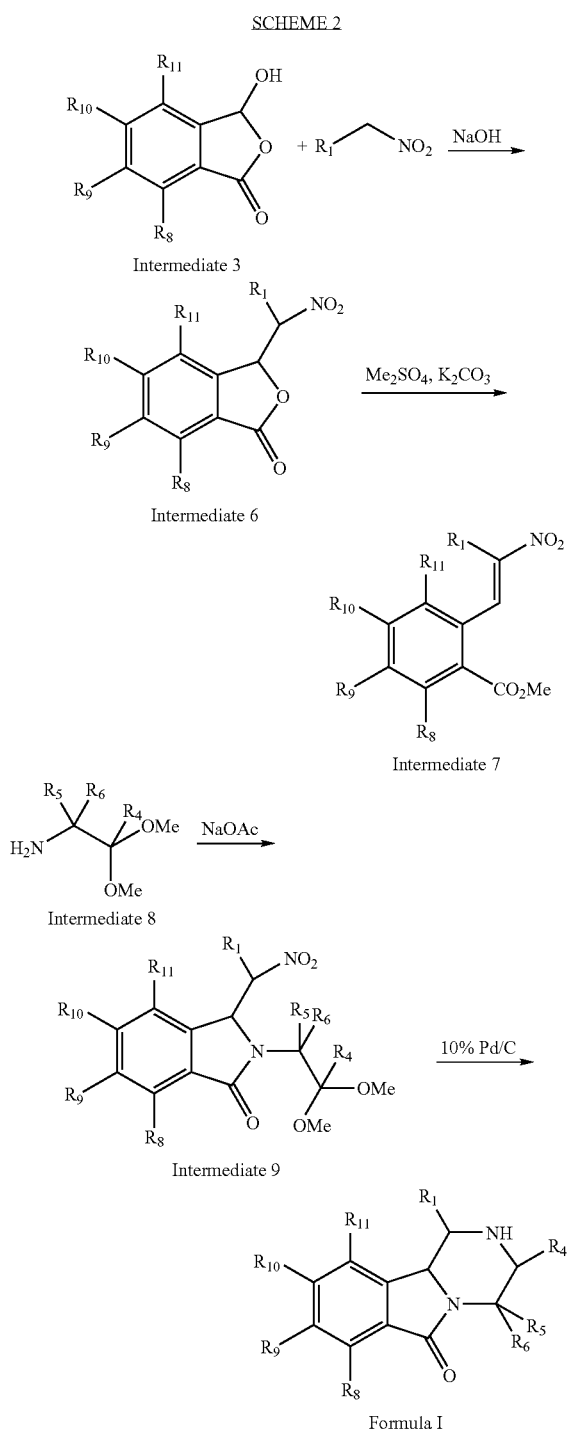

many synthetic methodologies readily recognized by one skilled in the art, in the presence of sodium cyamide, sodium acetate in ethanol and acetic acid to yield intermediate 5. Cyclization can be carried out under reductive condition with agents such as palladium, platinum, etc. with hydrogen in solvents such as ethanol, methanol, acetic acid, hydrochloric acid, etc. to yield compounds of Formula I.

SCHEME 2

Compounds of Formula I, wherein W is defined as a bond, may be prepared by procedures depicted in Scheme 1. Benzoic acids, which are commercially available or can be synthesized by many synthetic methodologies readily recognizable by one skilled in the art, can be activated with reagents such as oxalyl chloride, thionyl chloride, dicyclohexylcarbodiimide, etc. in a suitable solvent such as methylene chloride, chloroform, tetrahydrofuran, etc. at room temperature to reflux temperature of the solvent. The activated acid can then be treated with diethylamine in a suitable solvent such as methylene chloride, chloroform, tetrahydrofuran, etc. at room temperature to reflux temperature of the solvent to yield intermediate 2. Intermediate 2 can be formylated employing a base such as LDA, KHMDS, s-BuLi, etc. in THF, ether, dioxane, etc. at −78° C. to room temperature with or without a coordinating agent such as but not limited to TEMDA followed by the addition of DMF. The product is then treated with a strong acid such as hydrochloric, sulfuric, etc. in a suitable solvent such as water at room temperature to reflux temperature of the solvent to yield intermediate 3. Intermediate 3 can then be treated, according to the procedures of Welch, J. Org. Chem. 1982, 47, 886, with intermediate 4, which are commercially available or can be synthesized by Alternatively, compounds of Formula I may be synthesized by the procedures of Ferland et al., Can. J. Chem. 1985, 63, 361 and reference therein, with minor modifications depending on R1 which should be readily recognized by one skilled in the art. Intermediate 3 may be treated with a nitroalkane in the presence of a base such as sodium hydroxide, potassium hydroxide, etc. in a suitable solvent such as methanol, ethanol, water, etc. at −20° C. to room temperature to yield compounds of intermediate 6. The lactone can be opened with an alkylating agent such as but not limited to dimethyl sulfate in the presence of a base such as potassium carbonate, sodium carbonate, etc. in a suitable solvent such as acetone, acetonitrile, etc. to produce compounds of intermediate 7. The lactam may be formed by the addition of amines, intermediate 8, in the presence of weak bases such as but not limited to sodium acetate in a suitable solvent such as acetone, acetonitrile, etc. to produce compounds of intermediate 9. Finally the compounds can be cyclized under reductive conditions with agents such as palladium, platinum, etc. with hydrogen in solvents such as ethanol, methanol, acetic acid, hydrochloric acid, etc., to yield compounds of Formula I.

SCHEME 3

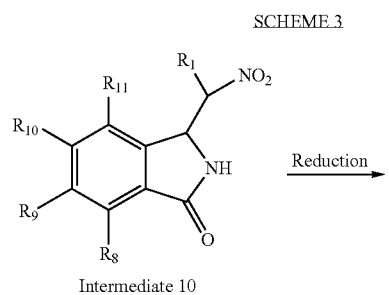

Intermediate 10

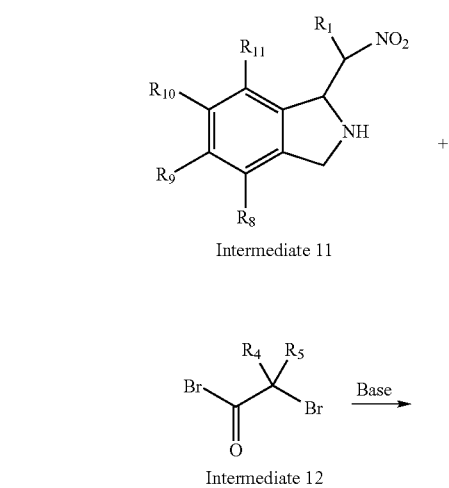

Intermediate 11

+

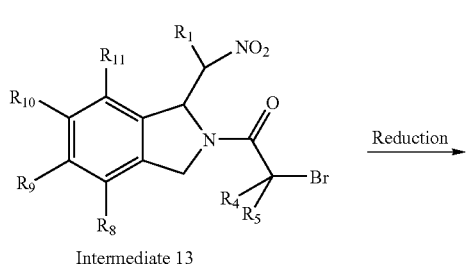

Intermediate 12

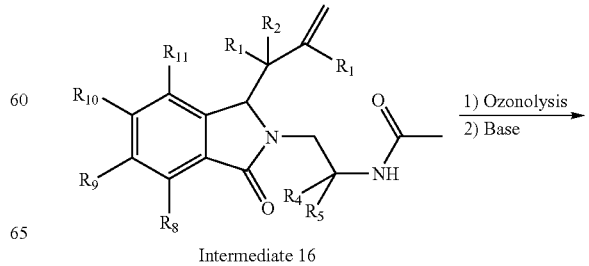

Intermediate 13

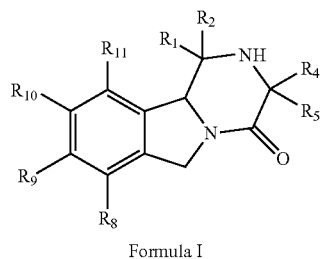

Formula I

Alternatively, compounds of Formula I can be synthesized according to procedures outlined in Scheme 3. Intermediate 10 can be made according to the synthesis described in Scheme 2 substituting ammonia for intermediate 8. Reduction of the lactam can be carried out with reagents such as sodium borohydride, borane, etc in a suitable solvent such as methylene chloride, tetrahydrofuran, etc. at room temperature to reflux temperature of the solvent to yield intermediate 11. Acylation of the amine with compounds of intermediate 12 in the presence of a base such as triethylamine, potassium carbonate, etc. in a suitable solvent such as methylene chloride, tetrahydrofuran, etc. to yield intermediate 13. Finally, cyclization can be accomplished by reducing the nitro group with reagents such palladium, platinum, etc. with hydrogen in solvents such as ethanol, methanol, acetic acid, hydrochloric acid, etc. to yield compounds of Formula I.

SCHEME 4

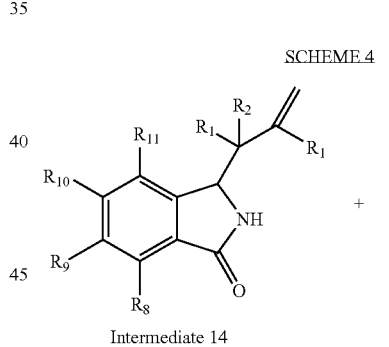

Intermediate 14

+

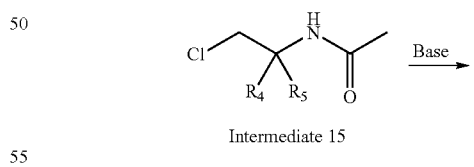

Intermediate 15

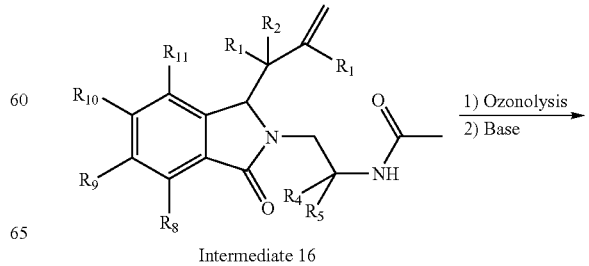

Intermediate 16

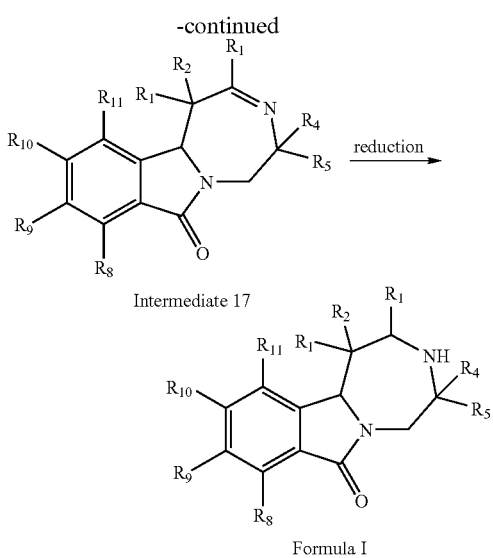

Compounds of Formula I may also be synthesized by the procedures outlined in Scheme 4. Compounds of intermediate 14, which can be synthesized by the procedures of Allin et al., Tetrahedron Lett. 1999, 40, 141, or Royer et al., Tetrahedron 2002, 58, 5103 and reference therein, with minor modifications depending on R1 which should be readily recognized by one skilled in the art, can be alkylated with intermediate 15 in the presence of a base such as triethylamine, potassium carbonate, etc. in a suitable solvent such as methylene chloride, tetrahydrofuran, etc. to yield intermediate 16. Cleavage of the double bond under conditions readily recognizable to one skilled in the art, such as but not limited to ozonolysis followed but cleavage of the amide under basic conditions such as sodium hydroxide, lithium hydroxide, etc in a suitable solvent such as methanol, ethanol, water, etc. produces compounds of intermediate 17. Reduction of the imine can be accomplished with reagents such as sodium borohydride, sodium cyanoborohydride, etc. in a suitable solvent such as methanol, methylene chloride, etc. to yield Formula I.

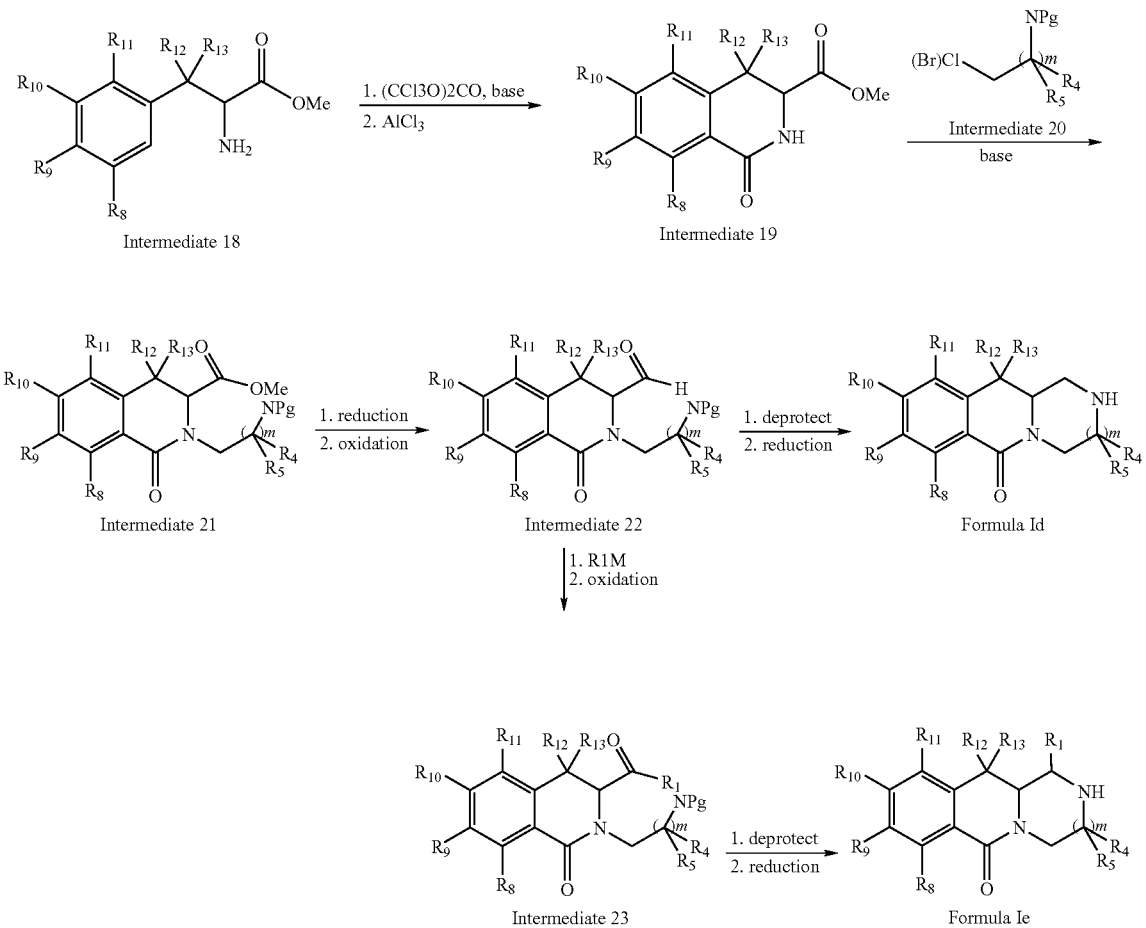

Compounds of Formula I, wherein W is defined as a carbon and X as a carbonyl, may be prepared by procedures depicted in Scheme 5. Amino esters, which are commercially available or can be synthesized by multiple synthetic methodologies readily recognizable by one skilled in the art, using the procedures of Tang et al. Chin. J. Chem. 2002, 20, 1070, can be acylated with triphosgene in a suitable solvent such as methylene chloride, chloroform, etc. The cyclization can be then accomplished by treating with reagents such as but not limited to aluminum trichloride. The lactam can then be alkylated with intermediate 20 in the presence of a base such as sodium hydride, NaHMDS, etc. in a suitable solvent such as ether, tetrahydrofuran, etc. to yield intermediate 21. The ester can be reduced with reagents such as lithium borohydride, DIBAL, etc. in a suitable solvent such as methylene chloride, methanol, etc. at room temperature to reflux temperature of the solvent and then oxidized to the aldehyde under conditions readily recognizable to one skilled in the art, such as but not limited to Swern oxidation, to yield intermediate 22. The intermediate can be cyclized to compounds of Formula Id by removing the protecting group, Pg, with the appropriate reagents well familiar to those skilled in the art (typical examples may be found in Greene, T and Wuts, P. G. M., *Protecting Groups in Organic Synthesis*, John Wiley & Sons, Inc., New York, N.Y., 1991 and references therein), and then treated with a reducing agent such as sodium triacetoxyborohydride, sodium cyanoborohydride, etc. Alternatively, compounds with R1 other than H, can be synthesized by treating intermediate 22 with R1-M, where M is a metal such as lithium, magnesium, etc., in an inert solvent such as THF, ether, etc. at −78° C. to room temperature and then oxidized to the ketone under conditions readily recognizable to one skilled in the art, such as but not limited to Swern oxidation, to yield intermediate 23. Intermediate 23 can be carried forward to compounds of Formula Ie according to the procedures described above for intermediate 22.

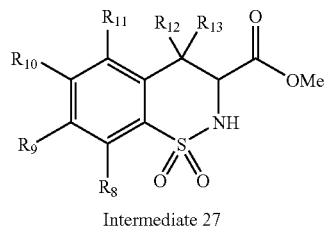

Intermediate 27

Compounds of Formula I, wherein W is defined as a carbon and X as a substituted carbon, may be prepared by procedures depicted in Scheme 6. Intermediate 24 can be converted to intermediate 25 under conditions described by Saxena, et al. Ind. J. Chem. 1978, 231, by treatment of intermediate 24 with a ketone or aldehyde in the presence of an acid such as hydrochloric, sulfuric, etc., and then esterified under conditions readily recognizable to one skilled in the art, such as but not limited to thionyl chloride and methanol, to yield compounds of intermediate 25. Alternatively, compounds of Formula I, wherein W is defined as a carbon and X as a sulfonyl, may be synthesized by the procedures of Wells et al. J. Med. Chem., 2001, 44, 3488. Treatment of intermediate 26 with chlorosulfonic acid in the presence of a base such as but not limited to triethylamine and dimethylaminopyridine affords intermediate 27. These two intermediates can then be carried forward to compounds of Formula I using the procedures described above in Scheme 5 substituting intermediate 25 or 27 for intermediate 19.

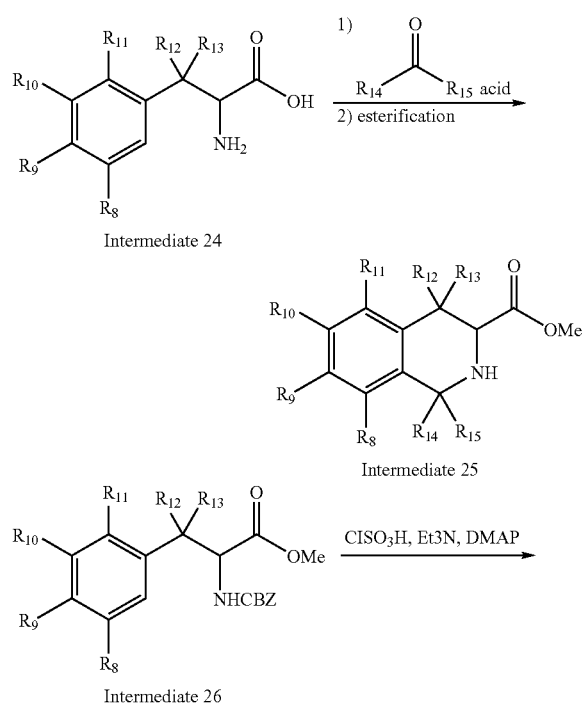

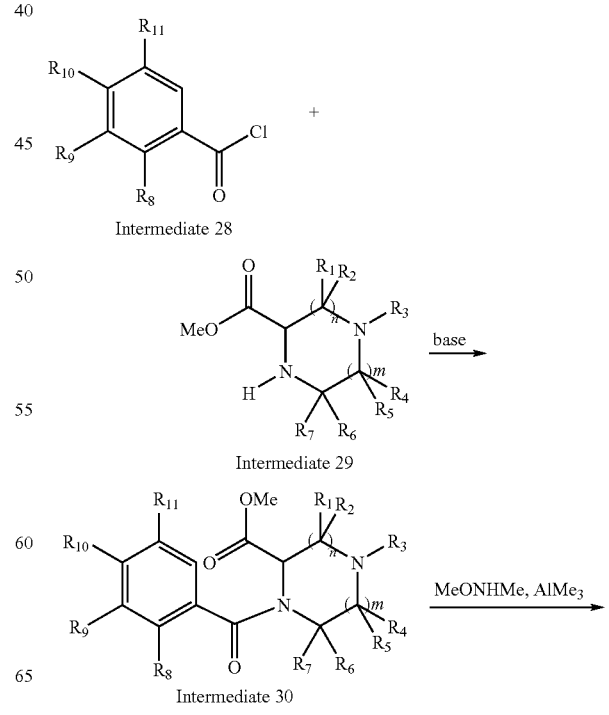

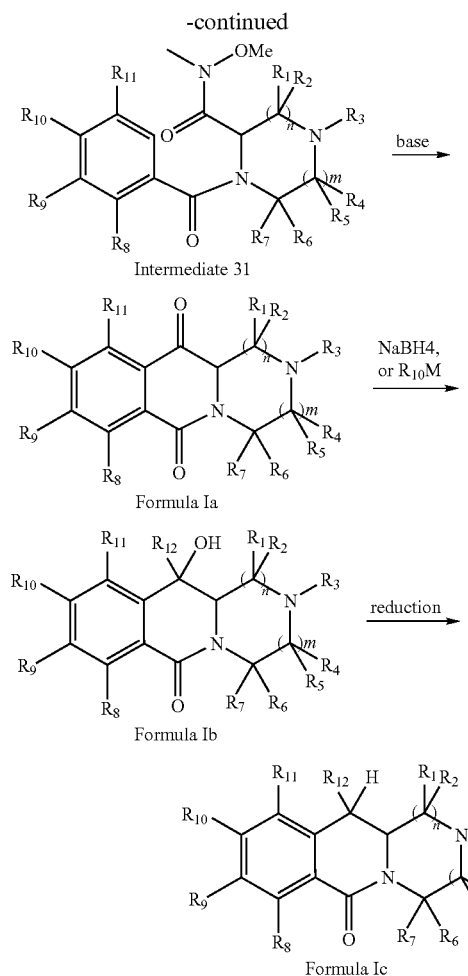

Intermediate 31

Formula Ia

Formula Ib

Formula Ic

Alternatively, compounds of Formula I, wherein W is defined as a carbon, may be prepared by procedures depicted in Scheme 7. Intermediate 28, which is commercially available or can be synthesized by many synthetic methodologies readily recognizable by one skilled in the art, can be reacted with intermediate 29, which are commercially available or can be synthesized by many synthetic methodologies readily recognizable by one skilled in the art, in the presence of a base such as triethylamine, potassium carbonate, etc. in a suitable solvent such as methylene chloride, tetrahydrofuran, etc. to afford intermediate 30. Conversion of the ester to the amide can be accomplished with N,O-dimethyl hydroxyamine hydrochloride in the presence of trimethyl aluminum in a suitable solvent to yield intermediate 31. This product can be cyclized with a base such as n-butyllithium, LDA, NaHMDS, etc. in an inert solvent such as tetrahydrofuran, ether, etc. at −78° C. to room temperature to afford compounds of Formula Ia. The compound can be further elaborated to compounds of Formula I by reducing the ketone with reagents such as but not limited to sodium borohydride or treating the ketone with R10M where M is a metal such as lithium, magnesium, etc. in an inert solvent such as THF, ether, etc. at −78° C. to room temperature to yield compounds of Formula Ib. These compounds can be reduced with reagents such as but not limited to palladium in the presence of hydrogen to yield Formula Ic.

SCHEME 8

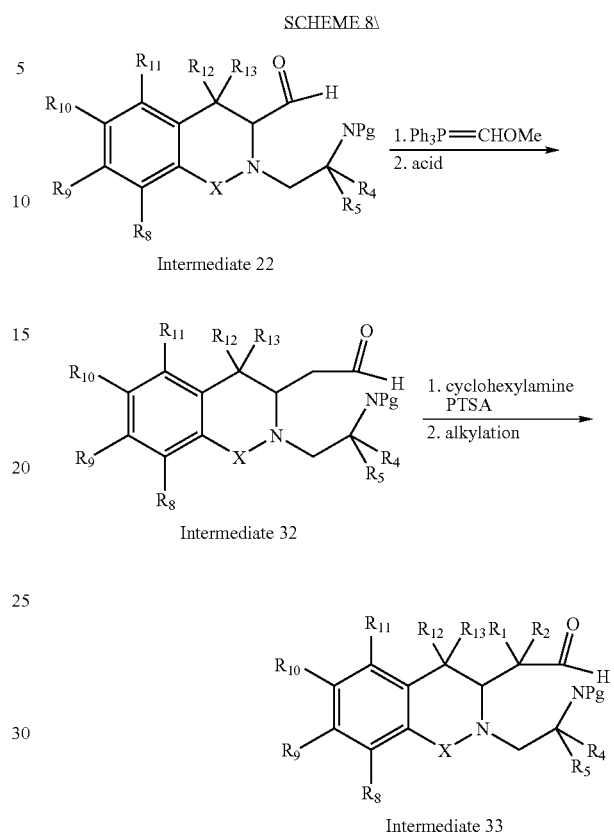

Intermediate 22

Intermediate 32

Intermediate 33

Alternative seven member ring compounds of Formula I can be synthesized according to Scheme 7. Intermediate 22 can be homologated with the commercially available Wittig reagent and then treated with an acid such as hydrochloric, sulfuric, etc. to yield intermediate 32. If substitution is desired for R1 and R2, then intermediate 32 can be treated with cyclohexylamine and PTSA followed by treatment with a base such as LDA, KHMDS, LHMDS, etc. in THF, ether, dioxane, etc., at −78° C. to room temperature and an alkylating R1X where X is a halide, mesylate, triflate, etc. This process can be repeated to incorporate R2 if necessary to yield intermediate 33. The intermediates can then be carried forward to compounds of Formula I using the procedures described above in Scheme 5 by substituting intermediate 33 for intermediate 22.

SCHEME 9

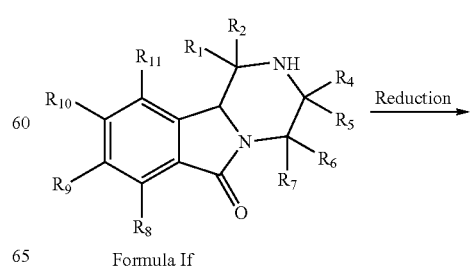

Formula If

-continued

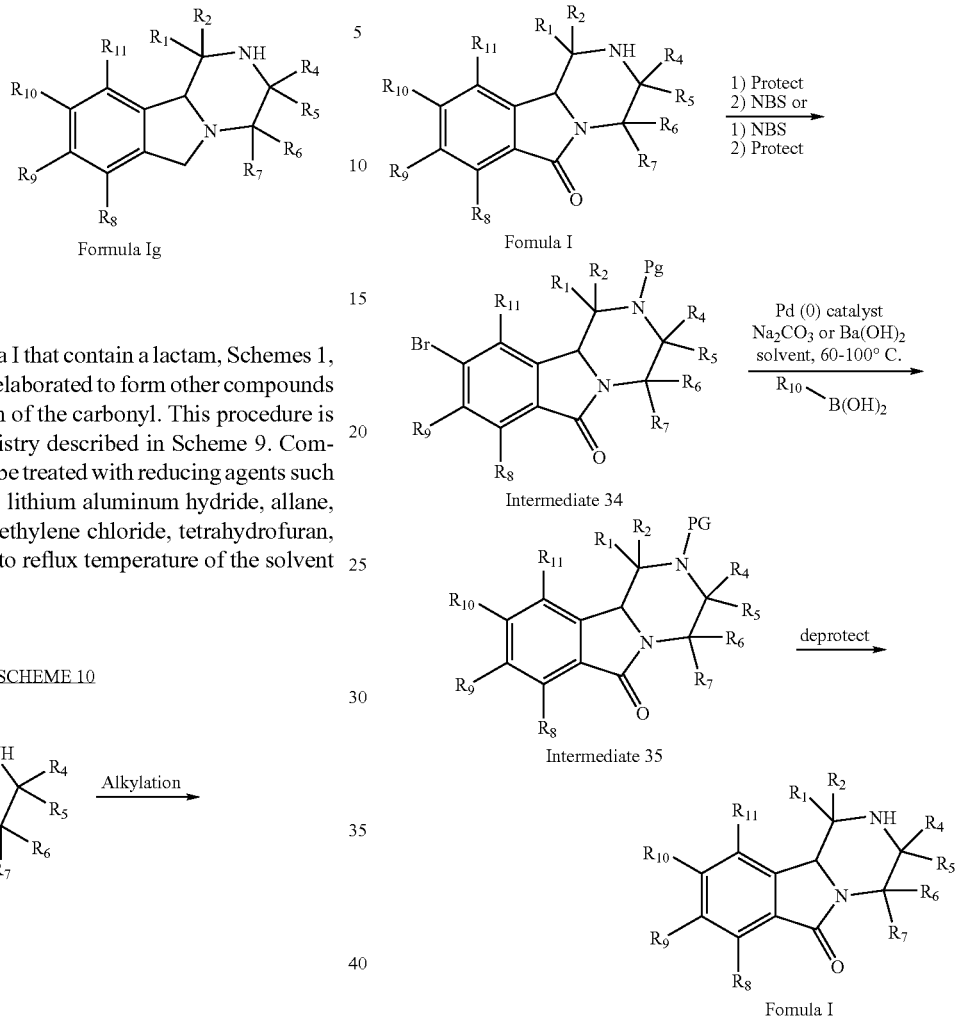

Compounds of Formula I that contain a lactam, Schemes 1, 2, 3, 4, 5, 7, and 8, can be elaborated to form other compounds of Formula I by reduction of the carbonyl. This procedure is exemplified by the chemistry described in Scheme 9. Compounds of Formula If can be treated with reducing agents such but not limited to borane, lithium aluminum hydride, allane, etc. in solvent such as methylene chloride, tetrahydrofuran, etc. at room temperature to reflux temperature of the solvent to yield Formula Ig.

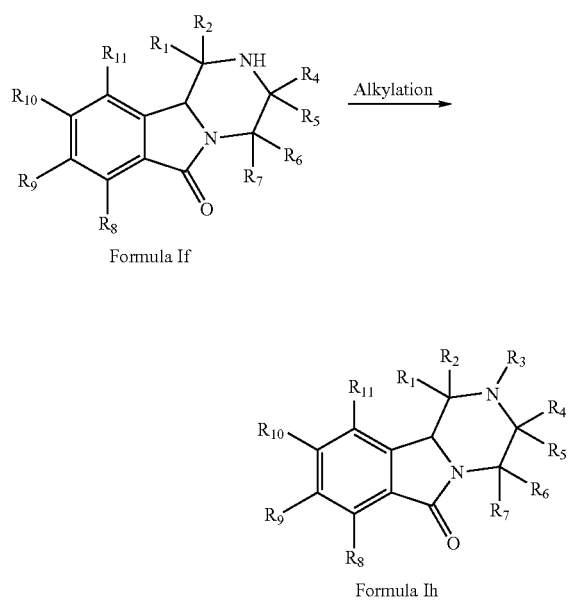

Compounds of Formula I in which R3 is other than H, Scheme 10, may be prepared by reductive alkylation with an aldehyde or ketone under conditions known in the art, for example, catalytic hydrogenation with hydrogen in the presence of palladium or platinum or with reducing agents such as sodium triacetoxyborohydride. Alternatively, a similar transformation can be accomplished with an alkylating agent R3X where X is a halide (halide=Cl, Br, I), mesylate, tosylate, triflate, etc. in the presence of a base such as triethylamine, pyridine, etc. in acetonitrile, DMF, DMSO, etc. at room temperature to reflux temperature of the solvent to yield Formula Ih.

Alternatively, compounds of Formula I can be synthesized by the procedures outlined in Scheme 11, as exemplified by the isoindoline core. It is understood that the aromatic substitution is shown for only one position on the aromatic ring and that similar transformations may be performed at R8, R9, and R11. Compounds of Formula I can be brominated in one of two procedures, the choice of procedures will be readily apparent to one skilled in the art, in which the nitrogen is protected with an amine protecting group (Pg) well familiar to those skilled in the art, and typical examples may be found in Greene, T and Wuts, P. G. M., *Protecting Groups in Organic Synthesis*, John Wiley & Sons, Inc., New York, N.Y., 1991 and references therein, and then treated with N-bromosuccinimide in a suitable solvent such as but not limited to DMF to yield intermediate 34. Alternatively, the compound can be treated with N-bromosuccinimide in a suitable solvent such as sulfuric acid, trifluoroacetic acid, etc. and then the amine protected to yield intermediate 34. Intermediate 34 can then be modified to yield compounds of Formula I by boronic acid couplings, which can be accomplished under Suzuki coupling protocols. For a review and leading references of palladium catalyzed cross coupling reactions, see Miyaura, N., Suzuki, A., Chem. Rev., 1995, 2457. One such procedure entails treatment of intermediate 34 with a functionalized aryl boronic acid in the presence of a catalytic Pd(0) species, such as Pd(PPh$_3$)$_4$, Pd(PPh$_3$)$_2$Cl$_2$, Pd(OAc)$_2$, Pd$_2$(dba)$_3$ and a suitable ligand such as PPh$_3$, AsPh$_3$, etc., or other such Pd(0) catalyst, and a base such as Na$_2$CO$_3$, Ba(OH)$_2$ or Et$_3$N in a suitable solvent such as DMF, toluene, THF, DME or the like, to afford intermediate 35. Removal of the protecting group, Pg, with the appropriate reagents, well familiar to those skilled in the art, and typical examples may be found in Greene, T and Wuts, P. G. M., *Protecting Groups in Organic Synthesis*, John Wiley & Sons, Inc., New York, N.Y., 1991 and references therein, yields compounds of Formula I.

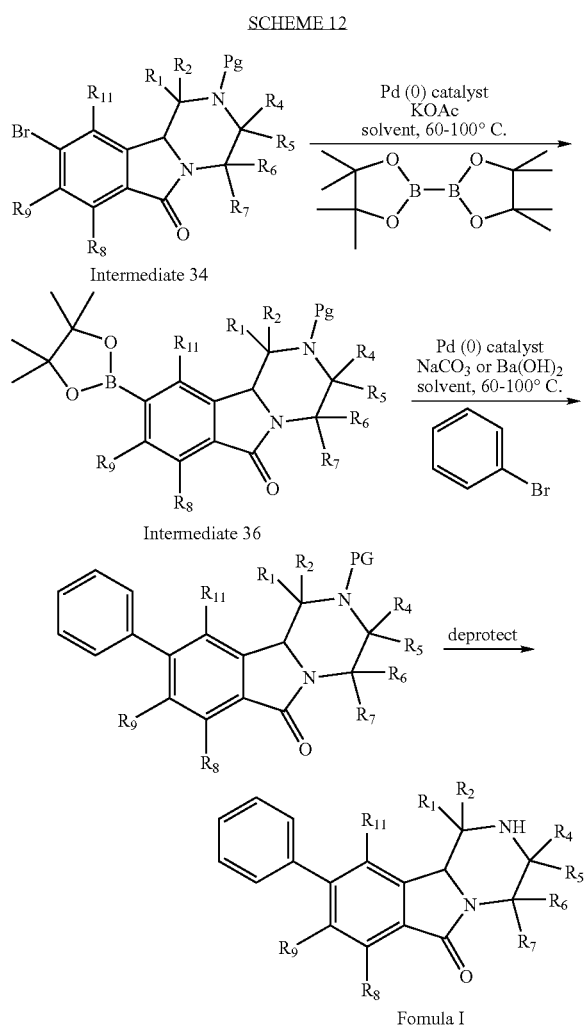

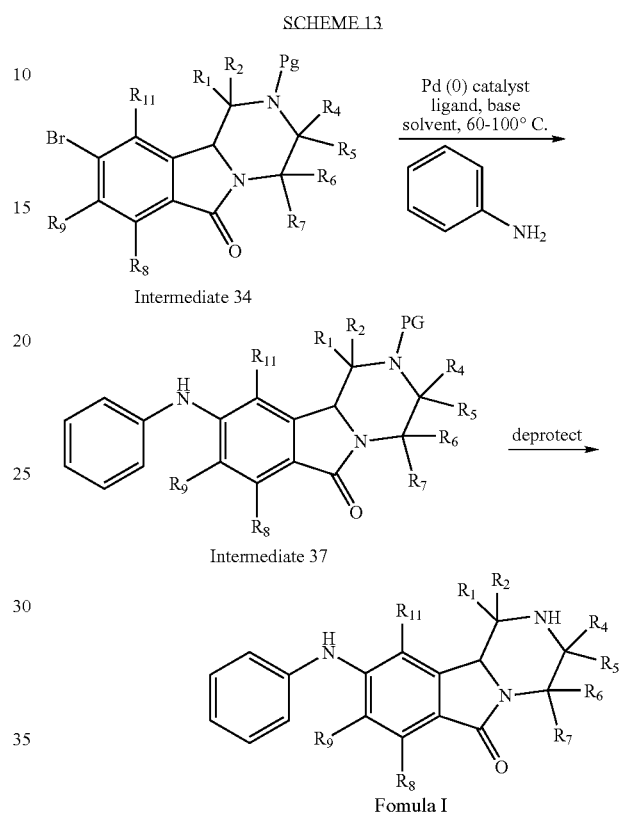

ester can undergo Suzuki coupling directly with a wide variety of commercially available aryl bromides under typical Suzuki conditions as described in Scheme 10 to yield intermediate 35, which can be deprotected as described above to afford compounds of Formula I.

Compounds of Formula I with an arylamino group attached to the aromatic ring can be synthesized by the procedures outlined in Scheme 13, as exemplified by the isoindoline core and it is understood that the aromatic substitution is shown for only one position on the aromatic ring and that similar transformations may be performed at R8, R9, R11. Treatment of intermediate 34 with a wide variety of commercially available anilines in the presence of a palladium (0) catalyst, such as Pd$_2$(dba)$_3$, Pd(PPh$_3$)$_4$ or Pd(PPh$_3$)$_2$Cl$_2$, and a suitable ligand such as BINAP or PPh$_3$, and a base such as NaOtBu in a suitable solvent such as DMF, toluene, THF, etc. to yield intermediate 37, which can be deprotected as described above to afford compounds of Formula I.

Alternatively formation of the boronic ester from intermediate 34 would allow for greater diversity in the subsequent coupling of this boronic acid with commercially available haloaromatic derivatives in a similar Suzuki coupling strategy as described above to afford compounds of Formula I. One such procedure is shown in Scheme 12, as exemplified by the isoindoline core and it is understood that the aromatic substitution is shown for only one position on the aromatic ring and that similar transformations may be performed at R8, R9, and R11. Treatment of intermediate 34 with a palladium catalyst such as Pd(PPh$_3$)$_4$ or Pd(PPh$_3$)$_2$Cl$_2$ and a suitable base, a preferred one being potassium acetate, in the presence of diboron pinacol ester affords intermediate 36. This boronic

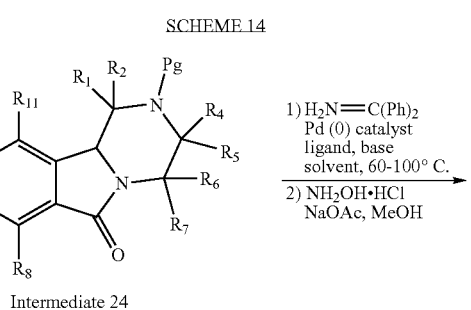

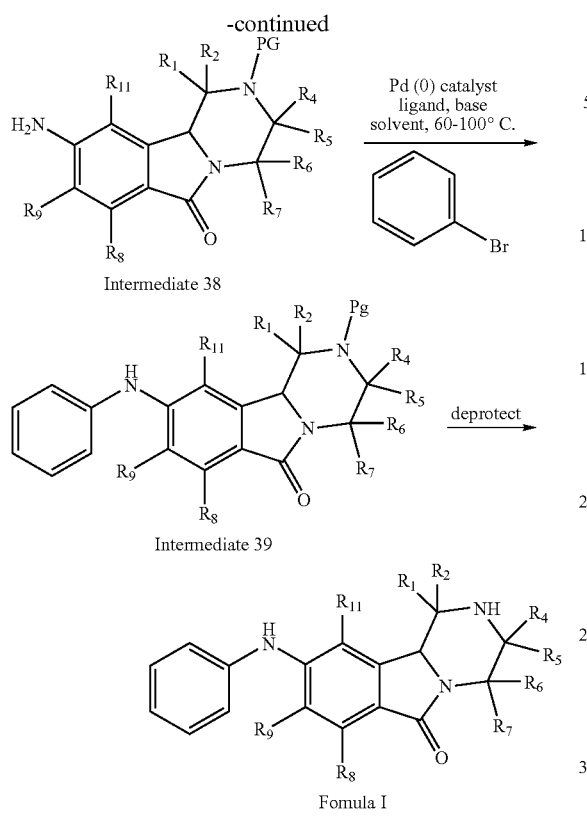

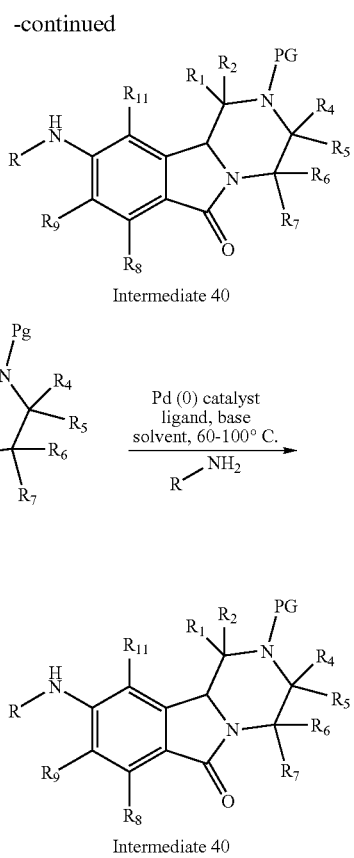

Alternatively, compounds of Formula I with an arylamino group attached to the aromatic ring can be synthesized by the procedures outlined in Scheme 14, as exemplified by the isoindoline core. Treatment of intermediate 34 with benzophenone imine in the presence of a palladium (0) catalyst, such as $Pd_2(dba)_3$, $Pd(PPh_3)_4$ or $Pd(PPh_3)_2Cl_2$, and a suitable ligand such as BINAP or $PPh_3$, and a base such as NaOtBu in a suitable solvent such as DMF, toluene, THF, DME, etc., affords an imine in which nitrogen is attached to the aromatic ring. Hydrolysis of this imine, for example with hydroxylamine and sodium acetate in methanol, affords intermediate 38. This aniline can be treated with a wide variety of commercially available aryl bromides in the presence of a palladium (0) catalyst, such as $Pd_2(dba)_3$, $Pd(PPh_3)_4$ or $Pd(PPh_3)_2Cl_2$, and a suitable ligand such as BINAP or $PPh_3$, and a base such as but not limited to NaOtBu in a suitable solvent such as DMF, toluene, THF, DME, etc. to yield intermediate 39, which can be deprotected as described above to afford compounds of Formula I.

Treatment of intermediate 38 with an appropriate aldehyde in the presence of a suitable reducing agent such as sodium triacetoxyborohydride or sodium cyanoborohydride and generally under mildly acidic conditions, such as in the presence of acetic acid, in a suitable solvent such as 1,2-dichloroethane, THF, methanol or acetonitrile, yields intermediate 40. An alternate method for preparing intermediate 40 is from intermediate 34. Treatment of intermediate 34 with amines in the presence of a palladium (0) catalyst, such as $Pd_2(dba)_3$, $Pd(PPh_3)_4$ or $Pd(PPh_3)_2Cl_2$, and a suitable ligand such as BINAP or $PPh_3$, and a base such as NaOtBu or $Na_2CO_3$ in a suitable solvent such as DMF, toluene, THF, DME, etc., affords intermediate 40. The above intermediates can be deprotected as described above to afford compounds of Formula I

SCHEME 15

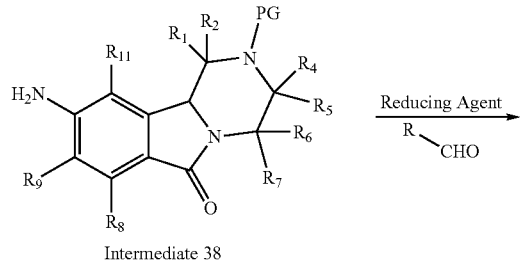

Intermediate 38

SCHEME 16

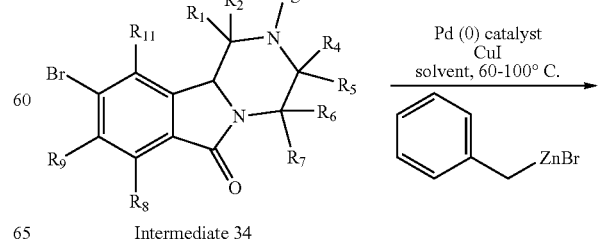

Intermediate 34

-continued

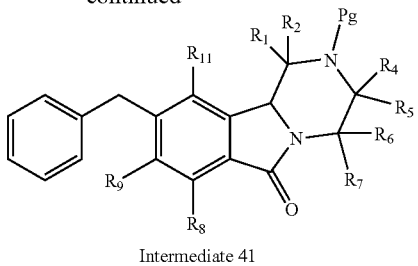

Intermediate 41

Treatment of intermediate 34 with an appropriate benzylzinc reagent, which can be generated from the corresponding benzyl halide, in the presence of a palladium (O) catalyst such as Pd(PPh$_3$)$_4$, Pd(PPh$_3$)$_2$Cl$_2$, or Pd$_2$(dba)$_3$, and with or without a copper (I) salt, affords intermediate 41 (see Knochel, et al. Chem. Rev. 1993, 93, 2117; and Weichert, et al. Syn. Lett. 1996, 473). This chemistry can also be extended to include a variety of alkylzinc and cycloalkylzinc reagents, which are available from the corresponding alkyl halides and cycloalkyl halides. The above intermediates can be deprotected as described above to afford compounds of Formula I.

SCHEME 17

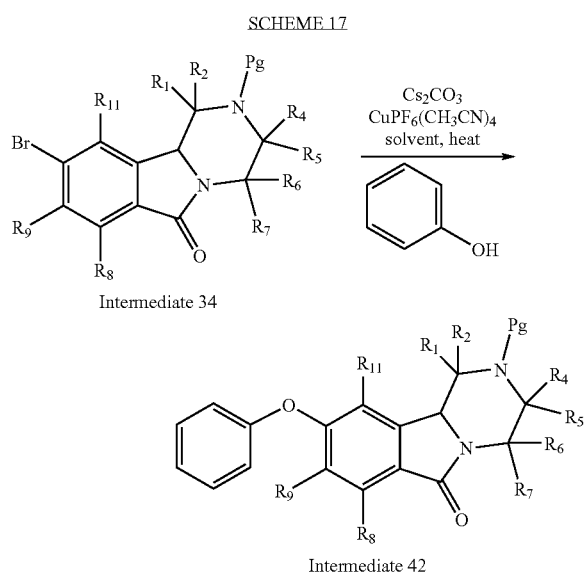

Intermediate 34

Intermediate 42

Compounds of Formula I with an arylhydroxy group attached to the aromatic ring can be synthesized by the procedures outlined in Scheme 17, as exemplified by the isoindoline core and it is understood that the aromatic substitution is shown for only one position on the aromatic ring and that similar transformations may be performed at R8, R9, R11. Intermediate 34 can be treated with various phenols in the presence of a base such as Cs$_2$CO$_3$, and a copper catalyst, such as CuPF$_6$(CH$_3$CN)$_4$, at elevated temperature to yield intermediate 42 (see Sawyer, Tetrahedron 2000, 56, 5045). The above intermediates can be deprotected as described above to afford compounds of Formula I.

In addition, there exists a wide range of procedures and protocols for functionalizing haloaromatics, aryldiazonium and aryltriflate compounds. These procedures are well known by those in the art and described, for example, by Stanforth, Tetrahedron, 1998, 263; Buchwald et al., J. Am. Chem. Soc., 1998, 9722; Stille, et al., J. Am. Chem. Soc., 1984, 7500. Among these procedures are biaryl couplings, alkylations, acylations, aminations, and amidations. The power of palladium catalyzed functionalization of aromatic cores has been explored in depth in the last decade. An excellent review of this field can be found in J. Tsuji, "Palladium Reagents and Catalysts, Innovations in Organic Synthesis", J. Wiley and Sons, New York, 1995.

Utilities and Combinations

Utilities

The compounds of the present invention are 5HT modulators, and include compounds which are, for example, agonists, partial agonists, antagonists or inverse agonists of the 5HT$_{2C}$ receptor. Accordingly, the compounds of the present invention may be useful for the treatment or prevention of diseases and disorders associated with 5HT receptor activity. Preferably, compounds of the present invention possess activity as agonists of the 5HT$_{2C}$ receptor, and may be used in the treatment of diseases or disorders associated with the activity of the 5HT$_{2C}$ receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, cholelithiasis and sleep disorders, dislipidemic conditions, bulimia nervosa and compulsive eating disorders); pain; sleep disorders and psychiatric disorders, such as substance abuse, depression, anxiety, psychosis, mania and schizophrenia.

These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-induced hypotension). These compounds could also be used for treatment of cardiac dysfunction (e.g., associated with valvular disease, myocardial infarction, cardiac hypertrophy or congestive heart failure); and improvement of the overall pulmonary function; transplant rejection; rheumatoid arthritis; osteoarthritis; fibromyalgia; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury. These compounds could also be used for treatment of sexual dysfunction and erectogenesis.

Compounds useful in the treatment of appetite or motivational disorders regulate desires to consume fats, sugars, carbohydrates, alcohol or drugs and more generally to regulate the consumption of ingredients with hedonic value. In the present description and in the claims, appetite disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a 5HT$_{2C}$ receptor agonist for the treatment of bulimia and obesity, including obesity associated with type II diabetes (non-insulin-dependent diabetes), or more generally any disease resulting in the patient becoming overweight. It may be due to any cause, whether genetic or environmental, including overeating and bulimia, polycystic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalants, nicotine, opioids, phencyclidine (or phencyclidine-like compounds), sedative-hypnotics or benzodiazepines, and other (or unknown) substances and combinations of the above. The terms "substance abuse disorders" also includes drug, nicotine or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Niemann-Pick's disease, Creutzfeld-Jakob disease, attention deficit-hyperactivity disorder, HIV, cardiovascular disease such as ischemia or stroke, and head trauma as well as age-related cognitive decline. Dementias are diseases that include memory loss and additional intellectual impairment separate from memory. $5HT_{2C}$ modulators may also be useful in treating cognitive impairments related to attentional deficits, such as attention deficit-hyperactivity disorders.

Compounds in the present invention may also be useful in treating diseases associated with dysfunction of brain dopaminergic systems, such as Parkinson's Disease and substance abuse disorders. Parkinsons's Disease is a neurogenerative movement disorder characterized by bradykinesia and tremor.

Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, cognition enhancing agents, agents used to treat neurodegeneration, agents used to treat respiratory conditions, agents used to treat bowel disorders, anti-inflammatory agents; anti-anxiety agents; anti-depressants; anti-psychotic agents; sedatives; hypnotics; anti-hypertensive agents; anti-tumor agents and analgesics.

Such other therapeutic agent(s) may be administered prior to, simultaneously with, or following the administration of the $5HT_{2C}$ modulators in accordance with the invention.

Examples of suitable anti-obesity agents for use in combination with the compounds of the present invention include leptin and leptin-sensitizing agents, melanocortin receptor (MC4R) agonists, agouti-related peptide (AGRP) antagonists, melanin-concentrating hormone receptor (MCHR) antagonists, growth hormone secretagogue receptor (GHSR) antagonists, orexin antagonists, CCK agonists, GLP-1 agonists, NPY1 or NPY5 antagonists, NPY2 modulators, corticotropin releasing factor agonists, histamine receptor-3 (H3) modulators, aP2 inhibitors, PPAR gamma modulators, PPAR delta modulators, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), leptinergics, adiponectin modulating agents, cannabinoid-1 receptor antagonists, such as rimonabant (Sanofi) or SLV-319 (Solvay), acetyl CoA carboxylase (ACC) inhibitors as disclosed in International patent application WO 03/072197 and monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), axokine (Regeneron).

Examples of suitable anti-diabetic agents for use in combination with the compounds of the present invention include: insulin, which may include short- and long-lasting forms as well as oral and inhaled forms, insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists such as muraglitizar described in Bristol-Myers Squibb U.S. Pat. No. 6,414,002, dipeptidyl peptidase IV (DP4) inhibitors such as BMS-477118 described in Bristol-Myers Squibb U.S. Pat. Nos. 6,395,767 and 6,573,287, SGLT2 inhibitors such as the compounds described in Bristol-Myers Squibb U.S. Pat. Nos. 6,414,126 and 6,515,117, glycogen phosphorylase inhibitors, and/or meglitinides, as well as insulin, and/or glucagon-like peptide-1 (GLP-1), and/or a PTP-1B inhibitor (protein tyrosine phosphatase-1B inhibitor).

The antidiabetic agent may be glucokinase inhibitors, 11 β HSD inhibitors or oral antihyperglycemic agents, which is preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's REZULIN, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi), preferably rosiglitazone and pioglitazone.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675.

The squalene synthetase inhibitors suitable for use herein include, but are not limited to, α-phosphono-sulfonates disclosed in U.S. Pat. No. 5,712,396, those disclosed by Biller et al., J. Med. Chem., 1988, Vol. 31, No. 10, pp 1869-1871, including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al., J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al., J.A.C.S., 1987, 109, 5544, cyclopropanes reported by Capson, T. L., Ph.D. dissertation, June, 1987, Dept. Med. Chem. U of Utah, Abstract, Table of Contents, pp 16, 17, 40-43, 48-51, Summary, pyrrolidine derivatives as disclosed by Sasyou, et al., WO 02/083636 and N-aryl-substituted cyclic amine derivatives disclosed by Okada et al., WO 02/076973.

Other hypolipidemic agents suitable for use herein include, but are not limited to, fibric acid derivatives, α PPAR agonists, such as fenofibrate, gemfibrozil, clofibrate, bezafibrate, ciprofibrate, clinofibrate and the like, probucol, and related compounds as disclosed in U.S. Pat. No. 3,674,836, probucol, phenylfibrate and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future 24, 9-15 (1999), (Avasimibe); "The ACAT inhibitor, Cl-1011 is effective in the prevention and regression of aortic fatty streak area in hamsters", Nicolosi et al., Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al., Bioorg. Med. Chem. Lett. (1996), 6(1), 47-50; "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al., Curr. Med. Chem. (1994), 1(3), 204-25; "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al., Chemtracts: Org. Chem. (1995), 8(6), 359-62, or TS-962 (Taisho Pharmaceutical Co. Ltd.), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in Atherosclerosis 115, 45-63 (1995) and J. Med. Chem. 41, 973 (1998).

The other lipid agent or lipid-modulating agent may be a cholesteryl transfer protein inhibitor (CETP) such as Pfizer's Torcetrapib® as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof, and inhibitors or lipid synthesis enzymes such as, for example, ACC, FAS, DGAT, MGAT, GPAT, AMP kinase, CPT1 and SCD1. Preferred dislipidemic agents are pravastatin, lovastatin, simvastatin, atorvastatin, fluvastatin, pitavastatin, rosuvastatin, fenofibrate and Pfizer's Torcetrapib® as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan, candasartan and talmisartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

5HT$_2$C modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor agonists, ML 1 B agonists. GABA A receptor agonists such as barbiturates (e.g., amobarbital, aprobarbital, butabarbital, mephobarbital, pentobarbital, phenobarbital, secobarbital and talbutal), benzodiazepines (e.g., diazepam, lorazepam, oxazepam, alprazolam, chlordiazepoxide, clonazepam, chlorazepate, halazepam and prazepam), also specifically including triazolam (Halcion). Other agents for treating sleep disorders include zolpidem (Ambien) and Neurocrine's indiplon.

5HT$_{2C}$ modulators may reduce or ameliorate substance abuse or addictive disorders. Therefore, combination of 5HT$_{2C}$ modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion and opiate antagonists.

5HT$_{2C}$ modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT$_{1A}$ receptor agonists (e.g., buspirone, flesinoxan, gepirone, ipsapirone and serzone), corticotropin releasing factor (CRF) antagonists and SSRI's.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine, citalopram and sertraline), monoamine oxidase inhibitors (MAOs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists (Bristol-Myers Squibb U.S. Pat. Nos. 6,642,230; 6,630,476; 6,589,952; 6,579,876; 6,525,056; 6,521,636; 6,518,271; 6,515,005; 6,448,261; 6,399,609; 6,362,180; and 6,358,950), alpha-adrenoreceptor antagonists, and atypical antidepressants (bupropion, lithium, nefazodone, trazodone and viloxazine).

The combination of a conventional antipsychotic drug with a 5HT$_{2C}$ modulator could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzapine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT$_{2A}$ receptor antagonists and 5HT$_{2A}$/dopamine receptor antagonists or partial agonists (e.g., olanzapine, aripiprazole, risperidone, ziprasidone).

The compounds described in the present invention could be used to enhance the effects of cognition-enhancing agents, such as acetylcholinesterase inhibitors (e.g., tacrine the active agent in Cognex®), ADHD agents (e.g. methyl-phenidate, atomoxetine the active agent in Strattera® and histamine 3 antagonists), muscarinic receptor-1 agonists (e.g., milameline), nicotinic agonists, glutamic acid receptor (AMPA and NMDA) modulators such as memantine, and nootropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6 receptor antagonists, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

The compounds described in the present invention could be used in combination with agents used to treat erectile dysfunction. Examples of suitable treatment for erectile dysfunction include sildenafil (Viagra), vardenafil (Levitra) and tadalafil (Cialis). Other compounds that could be used in combination for erectile dysfunction include yohimbine, phentolamine and papaverine.

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®, Arcoxia®, and Bextra®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1 inhibitor, tumor necrosis factor (TNF) antagonists (e.g., infliximab, OR1384, including TNF-alpha inhibitors, such as tenidap, anti-TNF antibodies or soluble TNF receptor such as etanercept (Enbrel®), Remicade®, rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with $5HT_{2C}$ modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., Et Al, "Cleavable CD40Ig Fusion Proteins and the Binding to Sgp39", J. Immunol. Methods (Netherlands), 188(1), pp. 1-7 (Dec. 15, 1995); Hollenbaugh, D., et al., "The Human T Cell Antigen Gp39, A Member of the TNF Gene Family, Is a Ligand for the CD40 Receptor: Expression of a Soluble Form of Gp39 with B Cell Co-Stimulatory Activity", EMBO J (England), 11(12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," New England J. of Medicine, 337(3), pp. 141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of formula I of the invention can be administered orally or parenterally, such as subcutaneously or intravenously, as well as by nasal application, transdermally, rectally or sublingually to various mammalian species known to be subject to such maladies, e.g., humans, in an effective amount within the dosage range of about 0.2 to 1000 mg, preferably from about 1 to 100 mg in a regimen of single, two or four divided daily doses.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intracisternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

Pharmacological Analysis

The pharmacological analysis of each compound for either antagonism or agonism of $5\text{-}HT_{2A}$, $5\text{-}HT_{2B}$ and $5\text{-}HT_{2C}$ receptors consisted of in vitro and in vivo studies. In vitro analyses included $K_i$ determinations at $5\text{-}HT_{2A}$, $5\text{-}HT_{2B}$ and $5\text{-}HT_{2C}$ receptors and an assessment of functional (i.e., agonism or antagonism) activity at each receptor class by calcium fluorescence and/or IP3 hydrolysis assays. Additional receptor assays were conducted to evaluate receptor specificity of $5\text{-}HT_{2C}$ receptors over monoamine and nuisance receptors (e.g. histamine, dopamine, and muscarinic). A compound is considered active as a $5\text{-}HT_2$ agonist if it has an $EC_{50}$ value or a $K_i$ value of less than about 50 micromolar; preferably less than about 1.0 micromolar; more preferably less than about 0.1 micromolar. Using the assays disclosed herein, compounds of the present invention have been shown to have an $EC_{50}$ value of less than about 50 micromolar for $5\text{-}HT_2$ agonism.

In vivo assays assessed compound activity in a variety of behavioral paradigms including acute and chronic feeding models, anxiety and depression models (learned-helplessness, elevated plus maze, Geller-Siefter, conditioned taste aversion, taste reactivity, satiety sequence). In aggregate, these models reflect activity as a $5\text{-}HT_{2C}$ agonist (feeding models, anxiety models, depression models) and provide some indication as to bioavailability, metabolism and pharmacokinetics.

Radioligand binding experiments were conducted on recombinant human $5\text{-}HT_{2A}$, $5\text{-}HT_{2B}$, and $5\text{-}HT_{2C}$ receptors expressed in HEK293E cells. The affinities of compounds of the present invention to bind at these receptors is determined by their capacity to compete for $[^{125}I]$-1-(2,5-dimethoxy-4-iodophenyl)-2-amino-propane (DOI) or $[^3H]$-lysergic acid diethylamide (LSD) binding at the $5\text{-}HT_{2A}$, $5\text{-}HT_{2B}$, or $5\text{-}HT_{2C}$ receptors. General references for binding assays include 1) Lucaites V L, Nelson D L, Wainscott D B, Baez M (1996) Receptor subtype and density determine the coupling repertoire of the $5\text{-}HT_2$ receptor subfamily. Life Sci., 59(13): 1081-95. Glennon R A, Seggel M R, Soine W H, Herrick-Davis K, Lyon R A, Titeler M (1988) [125I]-1-(2,5-dimethoxy-4-iodophenyl)-2-amino-propane: an iodinated radioligand that specifically labels the agonist high-affinity state of 5-HT2 serotonin receptors. J Med. Chem. (1988) 31(1):5-7 and 3 Leonhardt S, Gorospe E, Hoffman B J, Teitler M (1992) Molecular pharmacological differences in the interaction of serotonin with 5-hydroxytryptamine1C and 5-hydroxytryptamine2 receptors. Mol Pharmacol., 42(2):328-35.

The functional properties of compounds (efficacy and potency) were determined in whole cells expressing $5\text{-}HT_{2A}$, $5\text{-}HT_{2B}$, or $5\text{-}HT_{2C}$ receptors by assessing their ability to stimulate or inhibit receptor-mediated phosphoinositol hydrolysis and/or intracellular calcium release. The procedures used are described below.

In Vitro Binding Assays

Stable Expression of $5\text{-}HT_{2A}$, $5\text{-}HT_{2B}$ and $5\text{-}HT_{2C}$ Receptors in HEK293E Cells Stable cell lines were generated by transfecting 293EBNA cells with plasmids containing human $5\text{-}HT_{2A}$, $5\text{-}HT_{2B}$, or $5\text{-}HT_{2C}$ receptor (INI, INV, VNV or VGV RNA-edited isoforms) cDNA using calcium phosphate. These plasmids also contained the cytomegalovirus (CMV) immediate early promoter to drive receptor expression and EBV oriP for their maintenance as an extrachromosomal element, and the hph gene from E. Coli to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% $CO_2$) for 10 days. The $5\text{-}HT_{2A}$ cells were adapted to spinner culture for bulk processing whereas it was necessary to maintain the other lines as adherent cultures. On the day of harvest, cells were washed in phosphate-buffered saline (PBS), counted, and stored at −80° C.

Membrane Preparation

On the day of assay, pellets of whole cells (containing approximately $1\times10^8$ cells) expressing the $5\text{-}HT_{2A}$, $5\text{-}HT_{2B}$ or $5\text{-}HT_{2C}$ receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000×g for 10 min and the resulting pellet washed twice by repeated homogenization and centrifugation steps. The final pellet was resuspended in tissue buffer and protein determinations were made by the bichichoninic acid (BCA) assay (Pierce Co., IL) using bovine serum albumin as the standard.

Radioligand Binding Assays for the 5-HT$_{2A}$, 5-HT$_{2B}$ and 5-HT$_{2C}$ Receptors Radioligand binding studies were conducted to determine the binding affinities (Ki values) of compounds for the human recombinant 5-HT$_{2A}$, 5-HT$_{2B}$, and 5-HT$_{2C}$ receptors (Fitzgerald et al., 1999). Assays were conducted in disposable polypropylene 96-well plates (Costar Corp., Cambridge, Mass.) and were initiated by the addition of 5-HT$_{2A}$, 5-HT$_{2B}$, or 5-HT$_2$C membrane homogenate in tissue buffer (10-30 µg/well) to assay buffer (50 mM Tris HCl, 0.5 mM EDTA, 10 mM pargyline, 10 mM MgSO$_4$, 0.05% ascorbic acid, pH 7.5) containing [$^{125}$I]DOI for the 5-HT$_{2A}$ and 5-HT$_{2C}$ receptors (0.3-0.5 nM, final) or [$^3$H]LSD (1-2.0 nM, final) for the 5-HT$_{2B}$ receptor, with or without competing drug (i.e, newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (Packard cell harvester; Perkin-Elmer) over GFB glass-fiber filters that had been pre-soaked in 0.3% polyethyleneimine. Filters were washed in ice-cold 50 mM Tris HCl buffer (pH 7.5) and then counted on a Top Count (Packard).

Phosphoinositide Hydrolysis Studies

The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human 5-HT$_{2A}$, 5-HT$_{2B}$, or 5-HT$_{2C}$ receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 µg/ml hygromycin B, and 250 µg/ml G418. Following a 24-48 hr period, the growth media was removed and replaced with DMEM without fetal calf serum and inositol (Gibco BRL). The cells were then incubated with DMEM (without serum and inositol) containing a final concentration of 0.5 uCi/well myo-[$^3$H] inositol for 16-18 hr. Following this incubation, the cells were washed with DMEM (without serum or inositol) containing 10 mM LiCl and 10 µM pargyline and then incubated for 30 min with the same media but now containing one of several test compounds. Reactions were terminated by aspirating the media and lysing the cells by freeze-thaw. [$^3$H]phosphoinositides were extracted with chloroform/methanol (1:2 v/v), separated by anion exchange chromatography (Bio-Rad AG1-X8 resin), and counted by liquid scintillation spectroscopy as described previously (Egan et al., 1998).

Calcium Fluorescence Studies

The ability of newly synthesized compounds to stimulate calcium fluorescence was monitored in whole cells using a protocol described previously (Fitzgerald et al., 1999). HEK293E cells expressing the human 5-HT$_{2C}$, or 5-HT$_{2B}$ receptor were lifted with 0.5 mM EDTA and plated at a density of 50,000/well onto poly-D-lysine-coated 96-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 µg/ml hygromycin B, and 250 µg/ml G418. Following a 24 hr period, the cell plates are removed from the incubator and an equal volume of Loading Buffer (Hanks BSS with 200 mM HEPES, pH 5.98) containing the calcium dye reagent (Fluo-3) is added to each well (100 µL per well for 96-well plates and then incubated for 1 hour at 37 C.

Following the dye loading of the cells the plates are transferred to the FLIPR. Test compounds are added to the plate as a concentration response curve and the changes in fluorescence units due to calcium influx are monitored for a period of three seconds.

Data Analyses

The equilibrium apparent dissociation constants (Ki's) from the competition experiments were calculated using an iterative nonlinear regression curve-fitting program (Excelfit and TA Activity Base). For the PI hydrolysis and FLIPR experiments, EC50's were calculated using a one-site 'pseudo' Hill model: y=((Rmax−Rmin)/(1+R/EC50)nH))+Rmax where R=response (GraphPad Prism; San Diego, Calif.). Emax (maximal response) was derived from the fitted curve maxima (net IP stimulation) for each compound. Intrinsic activity (IA) was determined by expressing the Emax of a compound as a percentage of the Emax of 5-HT (IA=1.0).

Efficacy Models to Evaluate Food Consumption and Weight Loss

Acute overnight feeding assay. Compounds are assessed to for their ability to reduce food consumption during the dark cycle, which is the most active period of feeding in the rat. Sprague-Dawley rats are trained on a fixed ratio three (FR3) response paradigm which requires them to press a bar 3 consecutive times in order to obtain a food pellet. The number of bar presses occurring throughout the dark cycle can be monitored electronically as a measure of food intake by the animal. Rats are dosed orally or intraperitoneally with test compound 30 minutes prior to the onset of the dark cycle. The treated animals are then placed in individual operant boxes for 20 hours (12 hrs of dark cycle and the first 8 hours of the light cycle). Food intake in compound treated animals is compared to that of vehicle treated animals in order to determine percent reductions in food intake. Simultaneous measurements of water intake and locomotor activity are also measured during the period to assess for potential adverse effects.

Chronic Feeding Assay

Compounds are assessed for their long term impact on food intake and body weight in a three to fourteen week chronic treatment paradigm in Sprague-Dawley rats (starting weight ~450 g). Male Sprague-Dawley rats are pre-handled for one week prior to the onset of dosing during which time they are also assessed for food intake behavior. Rats are then assigned to treatment groups. Rats are dosed with vehicle or compound by oral gavage. The food intake and body weights are cumulatively assessed at the end of each treatment week and compared to vehicle treated animals. In some studies food intake is measured daily in order to assess the impact of reduced food consumption on pair-fed animals. At the end of the study period the animals are assessed for changes in body composition utilizing DEXA and are then sacrificed in order to examine changes in various blood plasma parameters.

REFERENCES

Arnt, J. Acta Pharmacol. et Toxicol. 1982: 51, 321-329.

Berridge M. J., Downes P. C., Hanley M. R. (1982) Lithium amplifies agonist-dependent phosphotidyinositol response in brain and salivary glands. Biochem. J., 206, 587-595.

Costall, B and Naylor, R J. Psychopharmacology. 1975: 43, 69-74.

Egan C. T., Herrick-Davis K., Miller K., Glennon R. A., and Teitler M. (1998) Agonist activity of LSD and lisuride at cloned 5-HT$_{2A}$ and 5-HT$_{2C}$ receptors. Psychopharmacology, 136, 409-414.

Fitzgerald L W, Conklin D S, Krause C M, Marshall A P, Patterson J P, Tran D P, Iyer G, Kostich W A, Largent B L, Hartig P R (1999) High-affinity agonist binding correlates with efficacy (intrinsic activity) at the human serotonin 5-HT$_{2A}$ and 5-HT$_{2C}$ receptors: evidence favoring the ternary complex and two-state models of agonist action. J. Neurochem., 72, 2127-2134.

Horlick, R. A., Sperle, K., Breth, L. A., Reid, C. C., Shen, E. S., Robbinds, A. K., Cooke, G. M., Largent, B. L. (1997) Rapid Generation of stable cell lines expressing corticotrophin-releasing hormone receptor for drug discovery. Protein Expr. Purif. 9, 301-308.

Dosage and Formulations

The serotonin agonist and serotonin antagonist compounds of this invention can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT2 receptors, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form. Further, they may also be administered by internasal delivery, transdermal delivery and suppository or depot delivery all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram (mg/kg) of body weight, with the preferred dose being about 0.01 to about 100 mg/kg; with the more preferred dose being about 0.01 to about 30 mg/kg. Advantageously, compounds of the present invention may be administered in a single daily dose, or the total daily dosage may be administered in divided doses of two, three, or four times daily.

Dosage forms of compositions suitable for administration contain from about 0.5 mg to about 100 mg of active ingredient per unit. In these pharmaceutical compositions the active ingredient will ordinarily be present in an amount of about 0.5-95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

EXAMPLES

Example 1

Preparation of (±)-1,3,4,10b-tetrahydro-7-trifluoromethoxy-pyrazino[2,1-a]isoindol-6(2H)-one

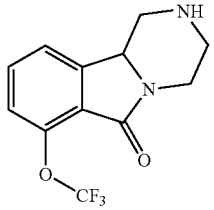

Step A. Preparation of N,N-diethyl-2-trifluoromethoxybenzamide

To a stirring solution of 2-trifluoromethoxybenzoic acid (3.6 g, 17.5 mmol, Avocado) in dry $CH_2Cl_2$ (150 mL) with DMF (0.5 mL) was added a 2M solution of oxalyl chloride in $CH_2Cl_2$ (17.5 mL) dropwise over 30 min. The reaction was stirred for 4 h and then conc. in vacuo to a white solid. The solid was dissolved in $CH_2Cl_2$ (150 mL) and reacted with diethylamine (3.2 g, 43.8 mmol, Aldrich) the reaction was stirred for 16 h and then conc. in vacuo to a yellow solid. The solid was purified by radial chromatography ($SiO_2$, 1:5, EtOAc:hexanes) to yield 4.3 grams (94%) of the product as a colorless oil. MS (ESI) 262 (M+H).

Step B. Preparation of N,N-diethyl-2-carboxaldehyde-6-trifluoromethoxybenzamide To a stirring solution of N,N-diethyl-2-trifluoromethoxybenzamide (2260 mg, 8.7 mmol) and N,N,N',N'-tetramethylethylenediamine (1410 mg, Aldrich) in dry THF (20 mL) at −78° C. under Ar was added 0.93 M s-butyllithium in hexanes (10.2 mL) dropwise. The reaction was stirred for 1 h and then DMF (2.0 mL) was added. The reaction was stirred for 1 h and then quenched with 1 M hydrochloric acid (15 mL). The reaction was extracted with EtOAc (3×15 mL). The organic layers were combined, dried over $Na_2SO_4$, and conc in vacuo to a yellow oil. The oil was purified by radial chromatography ($SiO_2$, 1:4, EtOAc:hexanes) to yield 2213 mg (88%) of the product as a colorless oil. MS (ESI) 290 (M+H).

Step C. Preparation of (±)-2-[2-[(benzyloxycarbonyl)amino]ethyl]-1-carbonitrile-1,3-dihydro-4-trifluoromethoxy-isoindol-3(1H)-one A stirring solution of N,N-diethyl-2-carboxaldehyde-6-trifluoromethoxybenzamide (2213 mg, 7.7 mmol) in 6 M hydrochloric acid (70 mL) was heated to reflux for 16 h. The reaction was cooled to room temperature and extracted with EtOAc (3×70 mL). The organic layers were combined, dried over $Na_2SO_4$, and conc in vacuo to a brown oil. The oil (1173 mg, 5.0 mmol) was added to a stirring solution of 1-(Benzyloxycarbonylamino)-2-aminoethane hydrochloride (1156 mg, 5.0 mmol, Aldrich) and sodium acetate (411 mg, 5.0 mmol, Aldrich) in ethanol (13.5 mL) and acetic acid (4.5 mL) followed by sodium cyamide (245 mg, 5.0 mmol, Aldrich). The reaction was stirred overnight and then conc in vacuo to a yellow solid. The solid was partioned between water (10 mL) and ethyl acetate (10 mL). The organic layer was separated and the aqueous layer was extracted with EtOAc (3×10 mL). The organic layers were combined, dried over $Na_2SO_4$, and conc in vacuo to a yellow oil. The oil was purified by radial chromatography (SiO2, 1:3, EtOAc:hexanes) to yield 1331 mg (63%) of the product as a colorless oil. MS (ESI) 420 (M+H).

Step D. Preparation of (±)-1,3,4,10b-tetrahydro-7-trifluoromethoxy-pyrazino[2,1-a]isoindol-6(2H)-one To a stirring solution of (±)-2-[2-[(benzyloxycarbonyl)amino]ethyl]-1-carbonitrile-1,3-dihydro-4-trifluoromethoxy-isoindol-3(1H)-one (1331 mg, 3.2 mmol) and 10% palladium on carbon (440 mg, Aldrich) in EtOH (9 mL) and HCl (1 mL) was added 80 psi of hydrogen. The reaction was stirred for 96 h. The reaction was filtered and the filtrate was conc. in vacuo to yield a white solid. The solid was partioned between 1 M aq. NaOH (10 mL) and ethyl acetate (10 mL). The organic layer was separated and the aqueous layer was extracted with EtOAc (3×10 mL). The organic layers were combined, dried over $Na_2SO_4$, and conc in vacuo to a pale yellow oil. The oil was purified by radial chromatography (SiO2, 98:2, $CH_2Cl_2$:MeOH with $NH_4OH$) to yield 432 mg (50%) of the product as a colorless oil. MS (ESI) 273 (M+H).

Example 2

Preparation of (R)-1,3,4,10b-tetrahydro-7-trifluoromethoxy-pyrazino[2,1-a]isoindol-6(2H)-one hydrochloric acid salt

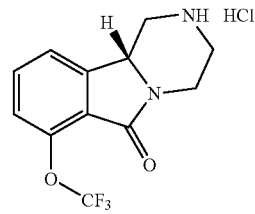

Step A. Preparation of N-(t-butoxycarbonyl)-(R)-1,3,4,10b-tetrahydro-7-trifluoromethoxy-pyrazino[2,1-a]isoindol-6(2H)-one To a stirring solution of (±)-1,3,4,10b-tetrahydro-7-trifluoromethoxy-pyrazino[2,1-a]isoindol-6(2H)-one (432 mg, 1.6 mmol) in dry $CH_2Cl_2$ (10 mL) was added di-t-butyl dicarbonate (383 mg, 1.8 mmol, Aldrich). The reaction was stirred for 4 h and then conc. in vacuo to a white solid. The solid was purified by radial chromatography (SiO2, 1:10, EtOAc:hexanes). The compound was then separated by chiral HPLC using an OD column with 80% heptane with 0.1% diethylamine and 20% 1:1 MeOH:EtOH with 0.1% diethylamine to yield 181 mg of the R enantiomer and 217 mg of the S enantiomer as white solids. MS (ESI) 373 (M+H).

Step B. Preparation of (R)-1,3,4,10b-tetrahydro-7-trifluoromethoxy-pyrazino[2,1-a]isoindol-6(2H)-one hydrochloride To a stirring solution of N-(t-butoxycarbonyl)-(R)-1,3,4,10b-tetrahydro-7-trifluoromethoxy-pyrazino[2,1-a]isoindol-6(2H)-one (181 mg, 0.5 mmol) in dry ether (5 mL) was added hydrochloric acid (1 mL). The reaction was stirred for 1 h and then conc. in vacuo to a white solid. The solid was dissolved in water and lyophilized to 147 mg of a white solid. MS (ESI) 309 (M−Cl).

Example 3

Preparation of (S)-1,3,4,10b-tetrahydro-7-trifluoromethoxy-pyrazino[2,1-a]isoindol-6(2H)-one hydrochloric acid salt

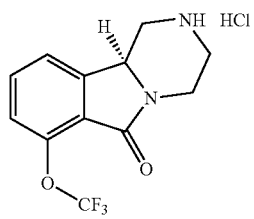

Prepared according to procedures described in Example 2 with substitution of N-(t-butoxycarbonyl)-(S)-1,3,4,10b-tetrahydro-7-trifluoromethoxy-pyrazino[2,1-a]isoindol-6(2H)-one for N-(t-butoxycarbonyl)-(R)-1,3,4,10b-tetrahydro-7-trifluoromethoxy-pyrazino[2,1-a]isoindol-6(2H)-one at Step B. MS (ESI) 309 (M−Cl).

Example 4

Preparation of (±)-1,3,4,10b-tetrahydro-7-methoxy-pyrazino[2,1-a]isoindol-6(2H)-one trifluoroacetic acid salt

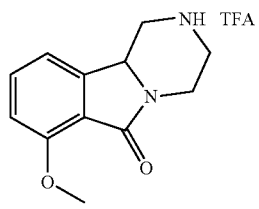

Prepared according to procedures described in Example 1 with substitution of 2-methoxybenzoic acid for 2-trifluoromethoxybenzoic acid at Step A. Final purification was accomplished by preparative LC/MS chromatography ($C_{18}$ column; 10-90% acetonitrile in water containing 0.05% trifluoroacetic acid). MS (ESI) 219.3 (M−$CF_3CO_2$).

Example 5

Preparation of (±)-1,3,4,10b-tetrahydro-7-fluoro-pyrazino[2,1-a]isoindol-6(2H)-one trifluoroacetic acid salt

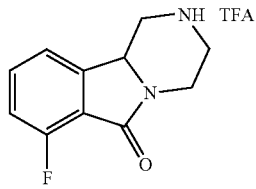

Prepared according to procedures described in Example 1 with substitution of 2-fluorobenzoic acid for 2-trifluoromethoxybenzoic acid at Step A. Final purification was accomplished as described in Example 4. MS (ESI) 207.2 (M−$CF_3CO_2$).

Example 6

Preparation of (±)-1,3,4,10b-tetrahydro-7-trifluoromethyl-pyrazino[2,1-a]isoindol-6(2H)-one

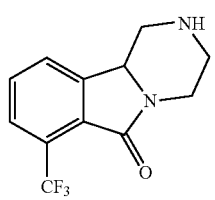

Prepared according to procedures described in Example 1 with substitution of 2-trifluoromethylbenzoic acid for 2-trifluoromethoxybenzoic acid at Step A. MS (ESI) 257.3 (M+H).

Example 7

Preparation of (R)-1,3,4,10b-tetrahydro-7-trifluoromethyl-pyrazino[2,1-a]isoindol-6(2H)-one hydrochloric acid salt

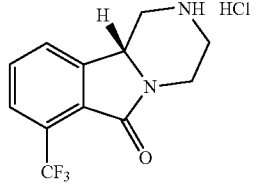

Prepared according to procedures described in Example 2 with substitution of (±)-1,3,4,10b-tetrahydro-7-trifluoromethyl-pyrazino[2,1-a]isoindol-6(2H)-one for (±)-1,3,4,10b-tetrahydro-7-trifluoromethoxy-pyrazino[2,1-a]isoindol-6(2H)-one at Step A. MS (ESI) 357.2 (M−Cl).

Example 8

Preparation of (S)-1,3,4,10b-tetrahydro-7-trifluoromethyl-pyrazino[2,1-a]isoindol-6(2H)-one hydrochloridic acid salt

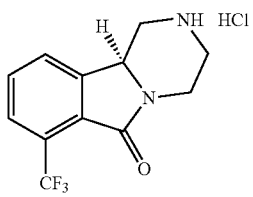

Prepared according to procedures described in Example 2 with substitution of (±)-1,3,4,10b-tetrahydro-7-trifluoromethyl-pyrazino[2,1-a]isoindol-6(2H)-one for (±)-1,3,4,10b-tetrahydro-7-trifluoromethoxy-pyrazino[2,1-a]isoindol-6(2H)-one at Step A. MS (ESI) 357.2 (M−Cl).

Example 9

Preparation of (±)-1,3,4,10b-tetrahydro-2-methyl-7-trifluoromethyl-pyrazino[2,1-a]isoindol-6(2H)-one

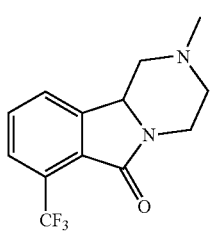

To a stirring solution of (±)-1,3,4,10b-tetrahydro-7-trifluoromethyl-pyrazino[2,1-a]isoindol-6(2H)-one (60 mg, 0.23 mmol) in water (1 mL) was added formic acid (0.22 mL, 5.9 mmol) and formaldehyde (190 mg, 2.3 mmol; 37% sol. in water). The reaction flask was sealed with a rubber septum (no nitrogen inlet) and warmed to 60° C. The reaction was maintained at this temperature for 24 h and was then cooled. The reaction was then diluted with saturated aqueous sodium bicarbonate, washed with ethyl acetate (3×50 mL), and the combined organic layers were dried over sodium sulfate, filtered, an concentrated. The resulting residue was purified by radial chromatography (2% ammonium hydroxide in 8% methanol in dichloromethane) to afford the desired product (33 mg, 52%) as a pale yellow residue.

MS (ESI) 271.6 (M+H).

Example 10

Preparation of (R)-1,3,4,10b-tetrahydro-7-trifluoromethyl-pyrazino[2,1-a]isoindole bis hydrochloric acid salt

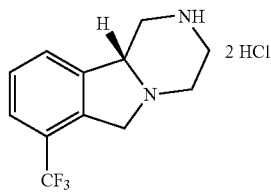

Step A. Preparation of N-(t-butoxycarbonyl)-(R)-1,3,4,10b-tetrahydro-7-trifluoromethyl-pyrazino[2,1-a]isoindole To a stirring solution of lithium aluminum hydride (1.12 mL, 1.12 mmol; 1.0 M in THF) in dry tetrahydrofuran (1.2 mL) at 0° C. was added dropwise sulfuric acid (0.50 mL, 0.50 mmol; 1.0 M in THF). After 1 h, N-(t-butoxycarbonyl)-(R)-1,3,4,10b-tetrahydro-7-trifluoromethyl-pyrazino[2,1-a]isoindol-6(2H)-one (100 mg, 0.28 mmol) was added dropwise as a solution in tetrahydrofuran (1.2 mL). The reaction was slowly allowed to warm to room temperature over a period of 1 h and was then quenched by the addition of water (2 mL) and 1N aqueous sodium hydroxide (0.30 mL). The mixture was extracted with ethyl acetate (×3), and the combined organic layers were dried over sodium sulfate, filtered, and concentrated. The resulting pale yellow residue was purified by radial chromatography (30-50% ethyl acetate in hexanes) to afford N-(t-butoxycarbonyl)-(R)-1,3,4,10b-tetrahydro-7-trifluoromethyl-pyrazino[2,1-a]isoindole (37 mg, 39%) as a clear residue. MS (ESI) 343.4 (M+H).

Step B. Preparation of (R)-1,3,4,10b-tetrahydro-7-trifluoromethyl-pyrazino[2,1-a]isoindole bis hydrochloric acid salt To N-(t-butoxycarbonyl)-(R)-1,3,4,10b-tetrahydro-7-trifluoromethyl-pyrazino[2,1-a]isoindole (37 mg, 0.11 mmol) was added concentrated aqueous hydrogen chloride (1 mL). After 15 min, the solution was concentrated, diluted with water, and lypholized to give (R)-1,3,4,10b-tetrahydro-7-trifluoromethyl-pyrazino[2,1-a]isoindole bis hydrochloric acid salt (33 mg, 99%) as an off white solid.

MS (ESI) 243.3 (M−HCl$_2$).

Example 11

Preparation of (R)-1,3,4,10b-tetrahydro-9-bromo-7-trifluoromethyl-pyrazino[2,1-a]isoindol-6(2H)-one hydrochloric acid salt

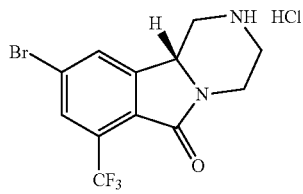

Step A. Preparation of N-(t-butoxycarbonyl)-(R)-1,3,4,10b-tetrahydro-9-bromo-7-trifluoromethyl-pyrazino[2,1-a]isoindol-6(2H)-one To a stirring solution of (R)-1,3,4,10b-tetrahydro-7-trifluoromethyl-pyrazino[2,1-a]isoindol-6(2H)-one hydrochloric acid salt (688 mg, 2.4 mmol) was added concentrated aqueous sulfuric acid (2.4 mL) and N-bromosuccinimide (420 mg, 2.4 mmol). The resulting brown solution was covered with aluminum foil and stirred in the dark for 24 h. The reaction was then diluted with ice water and basified with saturated aqueous sodium bicarbonate. The resulting mixture was diluted with tetrahydrofuran (30 mL) and treated with di-tert-butyl dicarbonate (567 mg, 2.6 mmol). After 4 h, the reaction washed with ethyl acetate (3×50 mL), and the combined organic layers were dried over sodium sulfate, filtered, and concentrated. The resulting residue was purified by radial chromatography (25% ethyl acetate in hexanes) to afford the desired Boc-carbamate (878 mg, 85%) as a white foamy solid.

MS (ESI) 435.2, 437.2 (M+H).

Step B. Preparation of (R)-1,3,4,10b-tetrahydro-9-bromo-7-trifluoromethyl-pyrazino[2,1-a]isoindol-6(2H)-one hydrochloric acid salt To N-(t-butoxycarbonyl)-(R)-1,3,4,10b-tetrahydro-9-bromo-7-trifluoromethyl-pyrazino[2,1-a]isoindol-6(2H)-one from Step A (105 mg, 0.24 mmol) was added diethyl ether (2 mL) and saturated aqueous hydrochloric acid (1 mL). After 15 min of stirring, the reaction was concentrated and treated with saturated aqueous ammonium hydroxide (2 mL). The solution was concentrated to dryness and the resulting residue was purified by radial chromatography (2% ammonium hydroxide in 4% methanol in dichloromethane) to give a clear residue. The residue was treated with 1N aqueous hydrogen chloride and lyophilized to afford the desired product (33 mg, 37%) as an off-white solid. MS (ESI) 335.2, 337.2 (M−Cl).

Example 12

Preparation of (R)-1,3,4,10b-tetrahydro-9-(2-methyl-4-trifluoromethoxyphenyl)-7-trifluoromethyl-pyrazino[2,1-a]isoindol-6(2H)-one hydrochloric acid salt

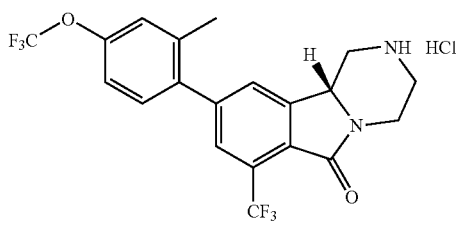

Step A. Preparation of N-(t-butoxycarbonyl)-(R)-1,3,4,10b-tetrahydro-9-(2-methyl-4-trifluoromethoxyphenyl)-7-trifluoromethyl-pyrazino[2,1-a]isoindol-6(2H)-one To an oven-dried flask was added toluene (1.4 mL) and tris(dibenzylideneacetone) dipalladium(0) (4.8 mg, 0.005 mmol). The resulting purple-red solution was degassed by exposing the reaction to vacuum and then an argon atmosphere (×3). Triphenylphosphine (9.7 mg, 0.037 mmol) was added and the reaction was again degassed. After 5 min, N-(t-butoxycarbonyl)-(R)-1,3,4,10b-tetrahydro-9-bromo-7-trifluoromethyl-pyrazino[2,1-a]isoindol-6(2H)-one (50 mg, 0.12 mmol) was added, and the resulting solution was degassed a third time. After 5 min, 2-methyl-4-trifluoromethoxyphenyl boronic acid (30 mg, 0.14 mmol) was added followed by aqueous sodium carbonate (0.267 mL; 2M). The resulting mixture was degassed a final time and warmed to reflux conditions. The reaction was maintained under reflux conditions for 14 h. The mixture was then cooled, diluted with ethyl acetate (10 mL) and water (10 mL), and the layers were separated. The aqueous layer washed with ethyl acetate (10 mL), and the combined organic extracts were dried over sodium sulfate, filtered, and concentrated. The resulting residue was purified by radial chromatography (20-30% ethyl acetate in hexanes) to give the desired Boc-carbamate (40 mg, 66%) as a clear residue. MS (ESI) 531.4 (M+H).

Step B. Preparation of (R)-1,3,4,10b-tetrahydro-9-(2-methyl-4-trifluoromethoxyphenyl)-7-trifluoromethyl-pyrazino[2,1-a]isoindol-6(2H)-one hydrochloric acid salt To N-(t-butoxycarbonyl)-(R)-1,3,4,10b-tetrahydro-9-(2-methyl-4-trifluoromethoxyphenyl)-7-trifluoromethyl-pyrazino[2,1-a]isoindol-6(2H)-one (11 mg, 0.022 mmol) was added diethyl ether (2 mL) and saturated aqueous hydrochloric acid (1 mL). After 15 min of stirring, the reaction was concentrated, diluted with water and lypholized to give (R)-1,3,4,10b-tetrahydro-9-(2-methyl-4-trifluoromethoxyphenyl)-7-trifluoromethyl-pyrazino[2,1-a]isoindol-6(2H)-one hydrochloric acid salt (9.7 mg, 97%) as a white solid. MS (ESI) 431.3 (M−Cl).

Example 13

Preparation of (R)-1,3,4,10b-tetrahydro-9-(4-methoxy-2-methylphenyl)-7-trifluoromethyl-pyrazino[2,1-a]isoindol-6(2H)-one hydrochloric acid salt

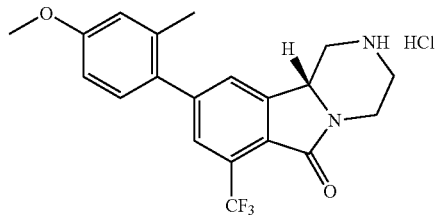

Prepared according to procedures described in Example 12 with substitution of 4-methoxy-2-methylphenyl boronic acid for 2-methyl-4-trifluoromethoxyphenyl boronic acid at Step A. MS (ESI) 377.4 (M−Cl).

Example 14

Preparation of (R)-1,3,4,10b-tetrahydro-9-(4-ethoxy-2-trifluoromethylphenyl)-7-trifluoromethyl-pyrazino[2,1-a]isoindol-6(2H)-one hydrochloric acid salt

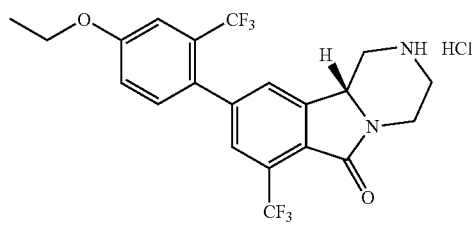

Prepared according to procedures described in Example 12 with substitution of 4-ethoxy-2-trifluoromethylphenyl boronic acid for 2-methyl-4-trifluoromethoxyphenyl boronic acid at Step A. MS (ESI) 445.3 (M–Cl).

Example 15

Preparation of (R)-1,3,4,10b-tetrahydro-9-(2,4-dichlorophenyl)-7-trifluoromethyl-pyrazino[2,1-a]isoindol-6(2H)-one hydrochloric acid salt

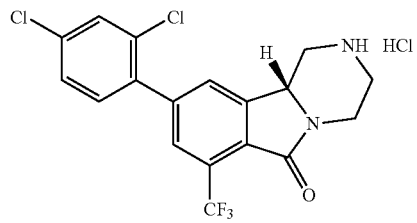

Prepared according to procedures described in Example 12 with substitution of 2,4-dichlorophenyl boronic acid for 2-methyl-4-trifluoromethoxyphenyl boronic acid at Step A. MS (ESI) 401.2, 403.2 (M–Cl).

Example 16

Preparation of (R)-1,3,4,10b-tetrahydro-9-(2-methyl-4-methylthiophenyl)-7-trifluoromethyl-pyrazino[2,1-a]isoindol-6(2H)-one hydrochloric acid salt

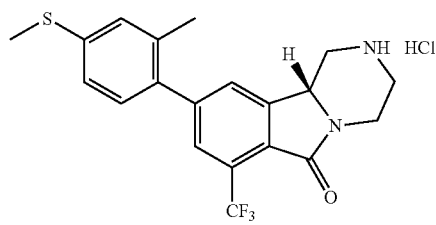

Prepared according to procedures described in Example 12 with substitution of 2-methyl-4-methylthiophenyl boronic acid for 2-methyl-4-trifluoromethoxyphenyl boronic acid at Step A. MS (ESI) 393.3 (M–Cl).

Example 17

Preparation of (R)-1,3,4,10b-tetrahydro-9-(2,4-ditrifluoromethylphenyl)-7-trifluoromethyl-pyrazino[2,1-a]isoindol-6(2H)-one hydrochloric acid salt

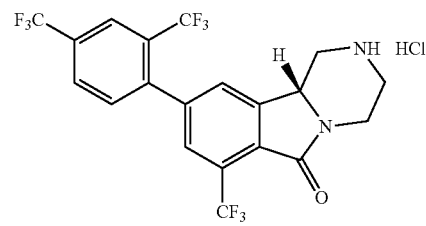

Prepared according to procedures described in Example 12 with substitution of 2,4-ditrifluoromethylphenyl boronic acid for 2-methyl-4-trifluoromethoxyphenyl boronic acid at Step A. MS (ESI) 469.2 (M–Cl).

Example 18

Preparation of (R)-1,3,4,10b-tetrahydro-9-phenyl-7-trifluoromethyl-pyrazino[2,1-a]isoindol-6(2H)-one trifluoroacetic acid salt

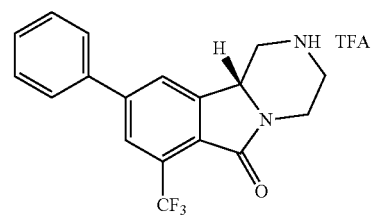

Prepared according to procedures described in Example 12 with substitution of phenyl boronic acid for 2-methyl-4-trifluoromethoxyphenyl boronic acid at Step A. Final purification was accomplished by preparative LC/MS chromatography ($C_{18}$ column; 10-90% acetonitrile in water containing 0.05% trifluoroacetic acid). MS (ESI) 333.3 (M+H).

Example 19

Preparation of (R)-1,3,4,10b-tetrahydro-9-(4-chlorophenyl)-7-trifluoromethyl-pyrazino[2,1-a]isoindol-6(2H)-one trifluoroacetic acid salt

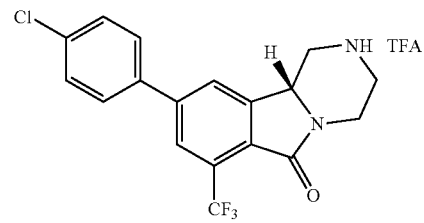

Prepared according to procedures described in Example 12 with substitution of 4-chlorophenyl boronic acid for 2-me-

Example 20

Preparation of (R)-1,3,4,10b-tetrahydro-9-(2-methyl-4-methylsulfonylphenyl)-7-trifluoromethyl-pyrazino[2,1-a]isoindol-6(2H)-one hydrochloric acid salt

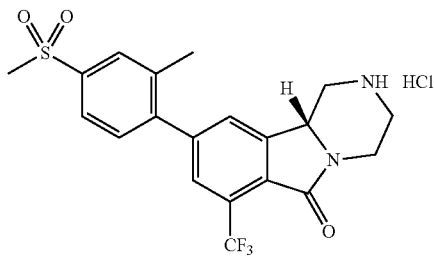

Prepared according to procedures described in Example 12 with substitution of 2-methyl-4-methylsulfonylphenyl boronic acid for 2-methyl-4-trifluoromethoxyphenyl boronic acid at Step A. MS (ESI) 425.3 (M–Cl).

Example 21

Preparation of (R)-1,3,4,10b-tetrahydro-9-(2-chlorophenyl)-7-trifluoromethyl-pyrazino[2,1-a]isoindol-6(2H)-one hydrochloric acid salt

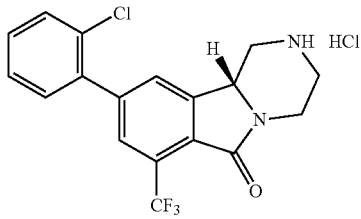

Prepared according to procedures described in Example 12 with substitution of 2-chlorophenyl boronic acid for 2-methyl-4-trifluoromethoxyphenyl boronic acid at Step A. MS (ESI) 367.3, 369.3 (M–Cl).

Example 22

Preparation of (R)-1,3,4,10b-tetrahydro-9-(3-chlorophenyl)-7-trifluoromethyl-pyrazino[2,1-a]isoindol-6(2H)-one hydrochloric acid salt

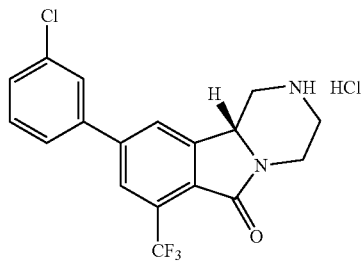

Prepared according to procedures described in Example 12 with substitution of 3-chlorophenyl boronic acid for 2-methyl-4-trifluoromethoxyphenyl boronic acid at Step A. MS (ESI) 367.2, 369.2 (M–Cl).

Example 23

Preparation of (R)-1,3,4,10b-tetrahydro-9-(2-methyl-4-trifluoromethoxyphenyl)-7-trifluoromethyl-pyrazino[2,1-a]isoindole bis hydrochloric acid salt

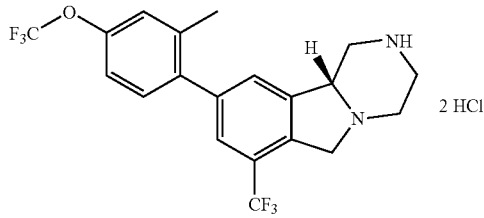

Prepared according to procedures described in Example 10 with substitution of N-(t-butoxycarbonyl)-(R)-1,3,4,10b-tetrahydro-9-(2-methyl-4-trifluoromethoxyphenyl)-7-trifluoromethyl-pyrazino[2,1-a]isoindol-6(2H)-one for N-(t-butoxycarbonyl)-(R)-1,3,4,10b-tetrahydro-7-trifluoromethyl-pyrazino[2,1-a]isoindol-6(2H)-one at Step A. MS (ESI) 417.3 (M–HCl$_2$).

Example 24

Preparation of (R)-1,3,4,10b-tetrahydro-9-(4-methoxy-2-methylphenyl)-7-trifluoromethyl-pyrazino[2,1-a]isoindole bis trifluoroacetic acid salt

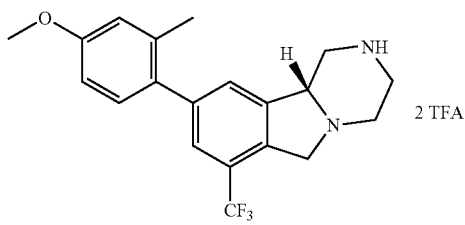

To a solution of (R)-1,3,4,10b-tetrahydro-9-(4-methoxy-2-methylphenyl)-7-trifluoromethyl-pyrazino[2,1-a]isoindol-6 (2H)-one hydrochloric acid salt (38 mg, 0.09 mmol) in dry tetrahydrofuran (1 mL) was added borane in dimethylsulfide (0.087 mL, 0.92 mmol) followed by dropwise addition of lithium aluminum hydride (0.092 mL, 0.092 mmol; 1.0 M in THF). After 30 min, the reaction was concentrated, quenched with aqueous hydrogen chloride (1N), and concentrated to dryness. The resulting residue was dissolved in water and basified with solid sodium carbonate. The mixture was then diluted with a 1:1 solution of acetone:methanol (10 mL) and filtered. The filtrate was concentrated and the residue was partially purified by radial chromatography (2% ammonium hydroxide in 4% methanol in dichloromethane).

The resulting impure free amine was dissolved in dichloromethane (10 mL); excess di-tert-butyl dicarbonate (100 mg, 0.46 mmol) was then added. After 30 min, the reaction was concentrated and the resulting yellow residue was partially purified by radial chromatography. The product was then treated with 12N aqueous hydrochloric acid (3 mL), concentrated, and finally purified by preparative LC/MS chromatography ($C_{18}$ column; 10-90% acetonitrile in water containing 0.05% trifluoroacetic acid) to give the desired product (8 mg, 30%) upon lypholization. MS (ESI) 363.4 ($M-CF_3CO_2-CF_3CO_2H$).

Example 25

Preparation of (R)-1,3,4,10b-tetrahydro-9-(2-methyl-4-methylthiophenyl)-7-trifluoromethyl-pyrazino[2,1-a]isoindole bis trifluoroacetic acid salt

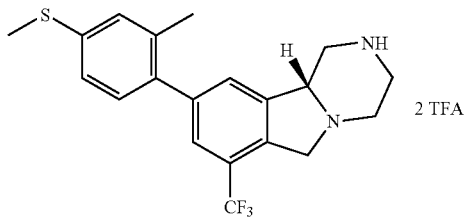

Prepared according to procedures described in Example 24 with substitution of (R)-1,3,4,10b-tetrahydro-9-(2-methyl-4-methylthiophenyl)-7-trifluoromethyl-pyrazino[2,1-a]isoindol-6(2H)-one hydrochloric acid salt for (R)-1,3,4,1-b-tetrahydro-9-(4-methoxy-2-methylphenyl)-7-trifluoromethyl-pyrazino[2,1-a]isoindol-6(2H)-one hydrochloric acid salt at Step A. MS (ESI) 379.3 ($M-CF_3CO_2-CF_3CO_2H$).

Example 26

Preparation of (R)-1,3,4,10b-tetrahydro-9-(2,4-difluorophenyl)amino-7-trifluoromethyl-pyrazino[2,1-a]isoindol-6(2H)-one trifluoroacetic acid salt

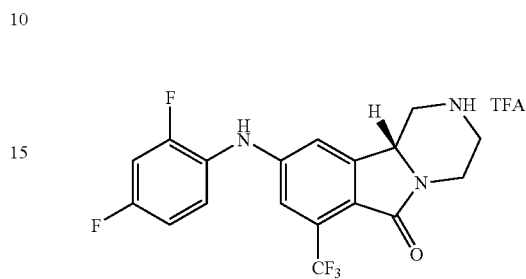

To a stirring solution of N-(t-butoxycarbonyl)-(R)-1,3,4,10b-tetrahydro-9-bromo-7-trifluoromethyl-pyrazino[2,1-a]isoindol-6(2H)-one (50 mg, 0.12 mmol) in toluene (2 mL) was added sequentially 2,4-difluoroaniline (0.035 mL, 0.35 mmol), sodium tert-butoxide (33 mg, 0.35 mmol), racemic BINAP (14 mg, 0.02 mmol), and tris(dibenzylideneacetone)dipalladium(0) (7 mg, 0.007 mmol). The resulting mixture was degassed by exposure to vacuum and then an argon atmosphere (×3) before being warmed to reflux conditions. The resulting brown-black mixture was maintained at reflux conditions for 14 h. The reaction was then cooled, diluted with ethyl acetate and saturated aqueous sodium chloride. The layers were separated and the aqueous layer washed with ethyl acetate. The combined organic layers were dried over sodium sulfate, filtered, and concentrated. The resulting residue was dissolved in trifluoroacetic acid (3 mL); after 20 min, the solution was concentrated and purified by preparative LC/MS chromatography ($C_{18}$ column; 10-90% acetonitrile in water containing 0.05% trifluoroacetic acid) to give the desired product (4.5 mg, 6.4%) as a pale yellow solid. MS (ESI) 384.3 ($M-CF_3CO_2$).

Example 27

Preparation of (R)-1,3,4,10b-tetrahydro-9-(2-methoxyphenyl)amino-7-trifluoromethyl-pyrazino[2,1-a]isoindol-6(2H)-one trifluoroacetic acid salt

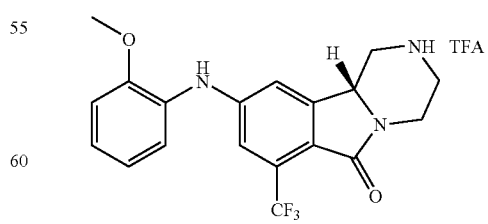

Prepared according to procedures described in Example 26 with substitution of 2-methoxyaniline for 2,4-difluoroaniline at Step A. MS (ESI) 378.4 ($M-CF_3CO_2$).

Example 28

Preparation of (R)-1,3,4,10b-tetrahydro-9-(2,4-dimethoxyphenyl)amino-7-trifluoromethyl-pyrazino[2,1-a]isoindol-6(2H)-one trifluoroacetic acid salt

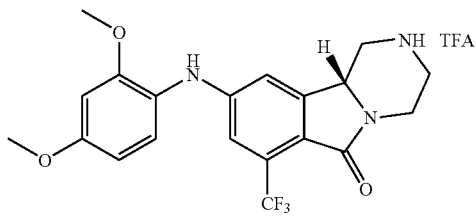

Prepared according to procedures described in Example 26 with substitution of 2,4-dimethoxyaniline for 2,4-difluoroaniline at Step A. MS (ESI) 408.3 (M–CF$_3$CO$_2$).

Example 29

Preparation of (R)-1,3,4,10b-tetrahydro-9-(2-furyl)-7-trifluoromethyl-pyrazino[2,1-a]isoindole hydrochloric acid salt

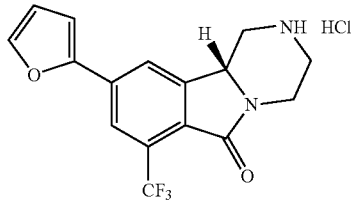

Step A. Preparation of N-(t-butoxycarbonyl)-(R)-1,3,4,10b-tetrahydro-9-(2-furyl)-7-trifluoromethyl-pyrazino[2,1-a]isoindol-6(2H)-one To a degassed solution of tetrakis(triphenylphosphine)palladium(0) (3 mg, 0.002 mmol) in toluene (2 mL) was added N-(t-butoxycarbonyl)-(R)-1,3,4,10b-tetrahydro-9-bromo-7-trifluoromethyl-pyrazino[2,1-a]isoindol-6(2H)-one (50 mg, 0.12 mmol). The resulting solution was degassed by exposure to vacuum and then an argon atmosphere (×3). To this solution was added 2-(tributylstannyl)furan (0.038 mL, 0.12 mmol). The resulting solution was degassed a final time and was then warmed to reflux conditions. The light yellow solution was maintained at reflux conditions for 14 h and became gray in color. The reaction was cooled, diluted with ethyl acetate, aqueous hydrogen chloride (1N), and saturated aqueous sodium chloride. The layers were separated and the aqueous layer washed with ethyl acetate. The combined organic layers were dried over sodium sulfate, filtered, and concentrated. The resulting residue was purified by radial chromatography (10-30% ethyl acetate in hexanes) to give the desired product as a clear residue (44 mg, 90%).

MS (ESI) 423.3 (M+H).

Step B. Preparation of (R)-1,3,4,10b-tetrahydro-9-(2-furyl)-7-trifluoromethyl-pyrazino[2,1-a]isoindol-6(2H)-one hydrochloric acid salt.

A stirring solution of N-(t-butoxycarbonyl)-(R)-1,3,4,10b-tetrahydro-9-(2-furyl)-7-trifluoromethyl-pyrazino[2,1-a]isoindol-6(2H)-one (44 mg, 0.10 mmol) in diethyl ether (2 mL) was treated with concentrated aqueous hydrogen chloride (1 mL). The resulting mixture was stirred vigorously for 15 min and was then concentrated. Saturated aqueous ammonium hydroxide (2 mL) was added, and the white mixture was concentrated. The resulting residue was purified by radial chromatography (2% ammonium hydroxide in 8% methanol in dichloromethane); the product was then treated with aqueous hydrogen chloride (1N) and lyophilized to give the desired hydrochloric acid salt as a white solid (28 mg, 68%). MS (ESI) 323.3 (M–Cl).

Example 30

Preparation of (±)-1,3,4,10b-tetrahydro-3,3-dimethyl-7-trifluoromethyl-pyrazino[2,1-a]isoindol-6(2H)-one

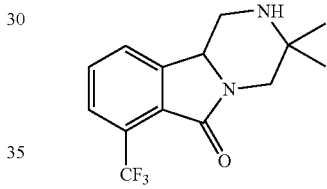

Prepared according to procedures described in Example 1 from Step C with the substitution of 1-amino-2-(benzyloxycarbonylamino)-2-methylpropane hydrochloride for 1-(benzyloxycarbonylamino)-2-aminoethane hydrochloride and 3-hydroxy-7-trifluoromethyl-3H-isobenzofuran-1-one for 3-hydroxy-7-trifluoromethoxy-3H-isobenzofuran-1-one. MS (ESI) 285 (M+H).

Examples 31 and 32

Preparation of (3S,10bR)-1,3,4,10b-tetrahydro-3-methyl-7-trifluoromethyl-pyrazino[2,1-a]isoindol-6(2H)-one hydrochloric acid salt and (3S,10bS)-1,3,4,10b-tetrahydro-3-methyl-7-trifluoromethyl-pyrazino[2,1-a]isoindol-6(2H)-one hydrochloric acid salt

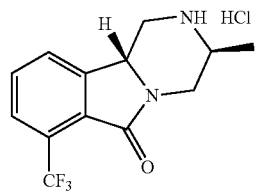

-continued

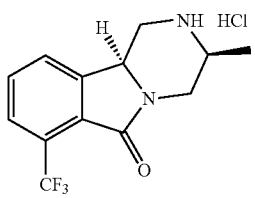

Prepared according to procedures described in Example 1 from Step C with the substitution of (S)-1-amino-2-(benzyloxycarbonylamino)propane hydrochloride for 1-(benzyloxycarbonylamino)-2-aminoethane hydrochloride and 3-hydroxy-7-trifluoromethyl-3H-isobenzofuran-1-one for 3-hydroxy-7-trifluoromethoxy-3H-isobenzofuran-1-one with separation of the diastereomers at the last step during purification. MS (ESI) 271 (M−Cl).

Examples 33 and 34

Preparation of (3R,10bR)-1,3,4,10b-tetrahydro-3-methyl-7-trifluoromethyl-pyrazino[2,1-a]isoindol-6 (2H)-one hydrochloric acid salt and (3R,10bS)-1,3,4,10b-tetrahydro-3-methyl-7-trifluoromethyl-pyrazino[2,1-a]isoindol-6(2H)-one hydrochloric acid salt

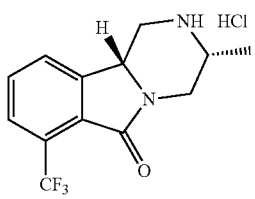

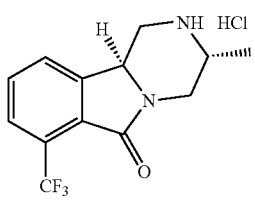

Prepared according to procedures described in Example 1 from Step C with the substitution of (R)-1-amino-2-(benzyloxycarbonylamino)propane hydrochloride for 1-(benzyloxycarbonylamino)-2-aminoethane hydrochloride and 3-hydroxy-7-trifluoromethyl-3H-isobenzofuran-1-one for 3-hydroxy-7-trifluoromethoxy-3H-isobenzofuran-1-one with separation of the diastereomers at the last step during purification. MS (ESI) 271 (M−Cl).

Example 35

Preparation of (R)-1,3,4,10b-tetrahydro-9-phenylamino-7-trifluoromethyl-pyrazino[2,1-a]isoindol-6 (2H)-one trifluoroacetic acid salt

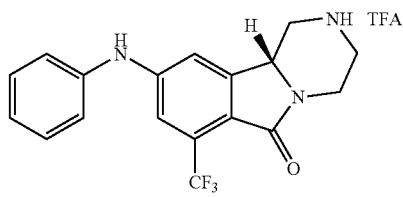

Step A. Preparation of N-(t-butoxycarbonyl)-(R)-1,3,4,10b-tetrahydro-9-phenylamino-7-trifluoromethyl-pyrazino[2,1-a]isoindol-6(2H)-one To a degassed solution of tris(dibenzylideneacetone) dipalladium(0) (7 mg, 0.007 mmol) and 2-(di-tert-butylphosphino)biphenyl (6 mg, 0.021 mmol) in toluene (2 mL) was added N-(t-butoxycarbonyl)-(R)-1,3,4,10b-tetrahydro-9-bromo-7-trifluoromethyl-pyrazino[2,1-a]isoindol-6(2H)-one (50 mg, 0.115 mmol). The mixture was degassed (alternating vacuum and argon) and aniline (0.031 mL, 0.345 mmol) and sodium tert-butoxide (33 mg, 0.345 mmol) were added. The mixture was degassed a final time and then subjected to microwave conditions (150° C., 1800 sec). The mixture was diluted with saturated aqueous sodium chloride and ethyl acetate, and the layers were separated. The aqueous layer washed with ethyl acetate (×2) and the combined organic layers were dried over sodium sulfate, filtered, and concentrated. The resulting residue was purified by radial chromatography (10-20% ethyl acetate in hexanes) to give 28 mg (55%) of a pale yellow residue. MS (ESI) 448 (M+H).

Step B. Preparation of (R)-1,3,4,10b-tetrahydro-9-phenylamino-7-trifluoromethyl-pyrazino[2,1-a]isoindol-6(2H)-one trifluoroacetic acid salt The product from Step A was dissolved in trifluoroacetic acid (3 mL); after 20 min, the solution was concentrated and purified by preparative LC/MS chromatography ($C_{18}$ column; 10-90% acetonitrile in water containing 0.05% trifluoroacetic acid) to give the desired product (16 mg, 50%) as a pale yellow solid upon lypholization. MS (ESI) 348 (M−$CF_3CO_2$).

Example 36

Preparation of (R)-1,3,4,10b-tetrahydro-9-(2-chloro-5-trifluoromethylphenyl)amino-7-trifluoromethyl-pyrazino[2,1-a]isoindol-6(2H)-one trifluoroacetic acid salt

Prepared according to procedures described in Example 35 from Step A with the substitution of 2-chloro-5-trifluoromethylaniline for aniline. MS (ESI) 450.3, 452.3 (M–CF$_3$CO$_2$).

Example 37

Preparation of (R)-1,3,4,10b-tetrahydro-9-(4-trifluoromethoxyphenyl)amino-7-trifluoromethyl-pyrazino[2,1-a]isoindol-6(2H)-one trifluoroacetic acid salt

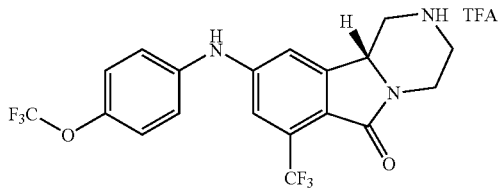

Prepared according to procedures described in Example 35 from Step A with the substitution of 4-trifluoromethoxyaniline for aniline. MS (ESI) 432 (M–CF$_3$CO$_2$).

Example 38

Preparation of (R)-1,3,4,10b-tetrahydro-9-(ethenyl)-7-trifluoromethyl-pyrazino[2,1-a]isoindol-6(2H)-one hydrochloric acid salt

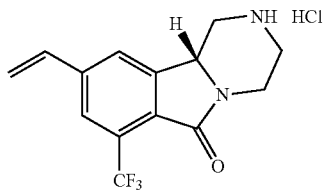

Prepared according to procedures described in Example 29 from Step A with the substitution of tributyl(vinyl)tin for 2-(tributylstannyl)furan. MS (ESI) 283 (M–Cl).

Example 39

Preparation of (R)-1,3,4,10b-tetrahydro-9-acetyl-7-trifluoromethyl-pyrazino[2,1-a]isoindol-6(2H)-one hydrochloric acid salt

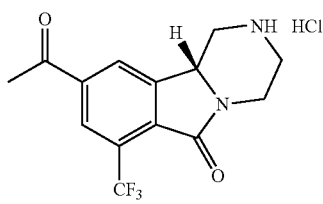

Prepared according to procedures described in Example 29 from Step A with the substitution of tributyl(1-ethoxyvinyl)tin for 2-(tributylstannyl)furan. MS (ESI) 299 (M–Cl).

Example 40

Preparation of (R)-1,3,4,10b-tetrahydro-9-ethyl-7-trifluoromethyl-pyrazino[2,1-a]isoindol-6(2H)-one trifluoroacetic acid salt

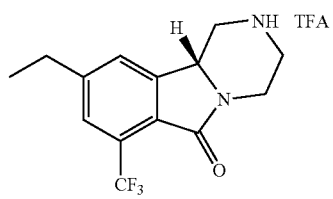

To N-(t-butoxycarbonyl)-(R)-1,3,4,10b-tetrahydro-9-ethenyl-7-trifluoromethyl-pyrazino[2,1-a]isoindol-6(2H)-one (20 mg, 0.052) from Example 38 was added methanol (2 mL) and the resulting solution was degassed via alternating exposure to vacuum and argon. To this solution was added 10% palladium on carbon (10 mg, Aldrich) and the black suspension was subjected a hydrogen atmosphere (1 atm). After 1 h, the reaction was filtered, concentrated and the resulting yellow residue was treated with concentrated aqueous hydrogen chloride (1 mL). After 15 minutes of vigorous stirring, the reaction mixture was concentrated. Saturated aqueous ammonium hydroxide (2 mL) was added, and the white mixture was concentrated. The resulting residue was purified by radial chromatography (2% ammonium hydroxide in 8% methanol in dichloromethane) to give a clear residue. This residue was further purified by preparative LC/MS chromatography (C$_{18}$ column; 10-90% acetonitrile in water containing 0.05% trifluoroacetic acid) to give the desired product (9 mg, 44%) as a pale yellow solid upon lypholization. MS (ESI) 285 (M–CF$_3$CO$_2$).

Example 41

Preparation of (R)-1,3,4,10b-tetrahydro-9-(4-isopropoxy-2-trifluoromethylphenyl)-7-trifluoromethyl-pyrazino[2,1-a]isoindol-6(2H)-one hydrochloric acid salt

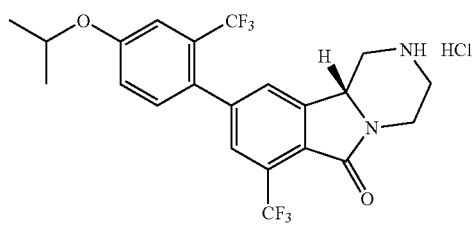

Step A. Preparation of N-(t-butoxycarbonyl)-(R)-1,3,4,10b-tetrahydro-9-(4-isopropoxy-2-(trifluoromethyl)phenyl)-7-trifluoromethyl-pyrazino[2,1-a]isoindol-6(2H)-one To an oven-dried flask was added toluene (2 mL) and tetrakis(triphenylphosphine)palladium(0) (6 mg, 0.006 mmol). The resulting yellow solution was degassed by exposing the reaction to vacuum and then an argon atmosphere (×3). After 5 min, N-(t-butoxycarbonyl)-(R)-1,3,4,10b-tetrahydro-9-bromo-7-trifluoromethyl-pyrazino[2,1-a]isoindol-6(2H)-one (50 mg, 0.12 mmol) was added, and the resulting solution was degassed again. After 5 min, 4-isopropoxy-2-(trifluoromethyl)phenyl boronic acid (31 mg, 0.13 mmol) was added followed by aqueous sodium carbonate (0.267 mL; 2M). The resulting mixture was degassed a final time and warmed to reflux conditions. The reaction was maintained under reflux conditions for 14 h. The mixture was then cooled, diluted with ethyl acetate (10 mL) and water (10 mL), and the layers were separated. The aqueous layer washed with ethyl acetate (10 mL), and the combined organic extracts were dried over sodium sulfate, filtered, and concentrated. The resulting residue was purified by radial chromatography (20-30% ethyl acetate in hexanes) to give the desired Boc-carbamate (28 mg, 44%) as a clear residue. MS (ESI) 559.4 (M+H).

Step B. Preparation of (R)-1,3,4,10b-tetrahydro-9-(4-isopropoxy-2-trifluoromethylphenyl)-7-trifluoromethyl-pyrazino[2,1-a]isoindol-6(2H)-one hydrochloric acid salt To N-(t-butoxycarbonyl)-(R)-1,3,4,10b-tetrahydro-9-(2-methyl-4-trifluoromethoxyphenyl)-7-trifluoromethyl-pyrazino[2,1-a]isoindol-6(2H)-one (28 mg, 0.05 mmol) was added diethyl ether (2 mL) and saturated aqueous hydrochloric acid (1 mL). After 15 minutes of vigorous stirring, the reaction mixture was concentrated. Saturated aqueous ammonium hydroxide (2 mL) was added, and the white mixture was concentrated. The resulting residue was purified by radial chromatography (2% ammonium hydroxide in 8% methanol in dichloromethane) to give a clear residue. This residue was treated with aqueous hydrogen chloride (1 mL; 1N) and lypholized to give (R)-1,3,4,10b-tetrahydro-9-(4-isopropoxy-2-trifluoromethylphenyl)-7-trifluoromethyl-pyrazino[2,1-a]isoindol-6(2H)-one hydrochloric acid salt (20 mg, 80%) as a white solid. MS (ESI) 459 (M−Cl).

Example 42

Preparation of (S)-1,3,4,10b-tetrahydro-7-trifluoromethyl-pyrazino[2,1-a]isoindole bis hydrochloric acid salt

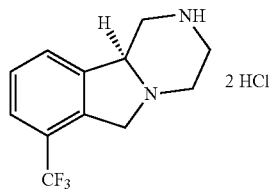

Prepared according to procedures described in Example 10 from Step A with the substitution of N-(t-butoxycarbonyl)-(S)-1,3,4,10b-tetrahydro-7-trifluoromethyl-pyrazino[2,1-a]isoindol-6(2H)-one for N-(t-butoxycarbonyl)-(R)-1,3,4,10b-tetrahydro-7-trifluoromethyl-pyrazino[2,1-a]isoindol-6(2H)-one. MS (ESI) 243.3 (M−HCl$_2$).

Example 43

Preparation of (±)-1,3,4,10b-tetrahydro-7-chloro-pyrazino[2,1-a]isoindol-6(2H)-one hydrochloric acid salt

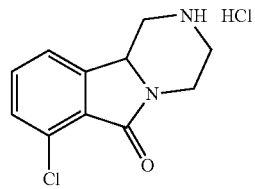

Step A. Preparation of (±)-2-(2,2-diethoxyethyl)-1-carbonitrile-1,3-dihydro-4-chloro-isoindol-3(1H)-one Prepared according to the procedures described in Example 1, Step A-C, with the substitution of 2-chlorobenzoic acid for 2-trifluoromethoxybenzoic acid in Step A and aminoacetaldehyde diethyl acetal for 1-(benzyloxycarbonylamino)-2-aminoethane hydrochloride in Step C. MS (ESI) 263.3, 265.3 (M+H).

Step B. Preparation of (±)-2-(2,2-diethoxyethyl)-1-(aminomethyl)-1,3-dihydro-4-chloro-isoindol-3(1H)-one To (±)-2-(2,2-diethoxyethyl)-1-carbonitrile-1,3-dihydro-4-chloro-isoindol-3(1H)-one (1.0 g, 3.25 mmol) in ethanol (30 mL) was added Raney 2400 Nickel (1 mL; Aldrich, slurry in water). The mixture was degassed and the reaction vessel was fitted with a hydrogen balloon. After 4 h, the mixture was filtered (with a water wash), concentrated, and purified by radial chromatography (2% ammonium hydroxide in 4% methanol in dichloromethane) to give the desired amino acetal as a yellow oil (640 mg, 63%). MS (ESI) 267.3, 269.2 (M+H).

Step C. Preparation of (±)-N-(t-butoxycarbonyl)-1,3,4,10b-tetrahydro-7-chloropyrazino[2,1-a]isoindol-6(2H)-one To (±)-2-(2,2-diethoxyethyl)-1-(aminomethyl)-1,3-dihydro-4-chloro-isoindol-3(1H)-one (400 mg, 1.3 mmol) was added aqueous hydrogen chloride (50 mL, 1N). The resulting mixture was stirred for 48 h. Half of this mixture (25 mL) was basified with sodium carbonate and then washed with 1,2-dichloroethane (×6). The combined organic layers were dried over sodium sulfate, filtered, and concentrated to a volume of approximately 50 mL. To this yellow solution was added sodium triacetoxyborohydride (270 mg, 1.3 mmol), and the resulting mixture was stirred for 24 h before being quenched with aqueous hydrogen chloride (1N). The mixture was then basified with sodium carbonate, diluted with tetrahydrofuran (100 mL) and treated with excess di-tert-butyl dicarbonate (400 mg). The resulting mixture was stirred for 1 h and was then washed with dichloromethane (×3). The combined organic layers were dried over sodium sulfate, filtered, concentrated, and the resulting yellow residue was purified by radial chromatography (30-50% ethyl acetate in hexanes) to give the desired (±)-N-(t-butoxycarbonyl)-1,3,4,10b-tetrahydro-7-chloro-pyrazino[2,1-a]isoindol-6(2H)-one as a white solid (32 mg, 23%). MS (ESI) 323.3, 325.3 (M+H).

Step D. Preparation of (±)-1,3,4,10b-tetrahydro-7-chloro-pyrazino[2,1-a]isoindol-6(2H)-one hydrochloric acid salt To (±)-N-(t-butoxycarbonyl)-1,3,4,10b-tetrahydro-7-chloropyrazino[2,1-a]isoindol-6(2H)-one (15 mg, 0.05 mmol) was added concentrated hydrochloric acid (1 mL). After 15 min, the resulting solution was concentrated, diluted with water, and lypholized to give (±)-1,3,4,10b-tetrahydro-7-chloro-pyrazino[2,1-a]isoindol-6(2H)-one hydrochloric acid salt as an off-white solid (12 mg, 100%). MS (ESI) 223.2, 225.2 (M–Cl).

Example 44

Preparation of (R)-1,3,4,10b-tetrahydro-9-ethyl-7-trifluoromethyl-pyrazino[2,1-a]isoindole bis hydrochloric acid salt

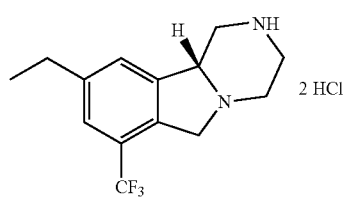

Prepared according to procedures described in Example 10 from Step A with the substitution of N-(t-butoxycarbonyl)-(R)-1,3,4,10b-tetrahydro-9-ethyl-7-trifluoromethyl-pyrazino[2,1-a]isoindol-6(2H)-one for N-(t-butoxycarbonyl)-(R)-1,3,4,10b-tetrahydro-7-trifluoromethyl-pyrazino[2,1-a]isoindol-6(2H)-one. MS (ESI) 285.3 (M–HCl$_2$).

Example 45

Preparation of (±)-1,3,4,10b-tetrahydro-7-methylthio-pyrazino[2,1-a]isoindol-6(2H)-one hydrochloric acid salt

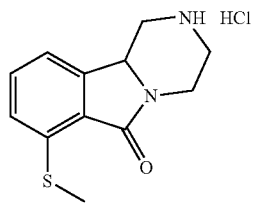

Prepared according to procedures described in Example 43 with the substitution of 2-(methylthio)benzoic acid for 2-chlorobenzoic acid in step A. MS (ESI) 235.2 (M–Cl).

Examples 46 and 47

Preparation of (R)-1,3,4,9a-tetrahydro-2H-9-oxa-2,4-a-diaza-anthracen-10-one and (S)-1,3,4,9a-tetrahydro-2H-9-oxa-2,4-a-diaza-anthracen-10-one

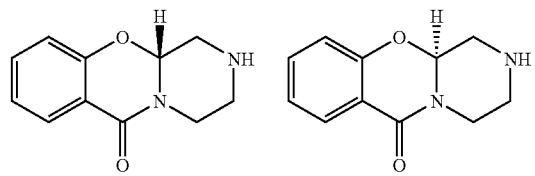

Step A. Preparation of [2-(2-hydroxy-benzoylamino)-ethyl]-carbamic acid tert-butyl ester To a stirring solution of salicylic acid (2.0 g, 14.5 mmol) and t-butyl N-(2-aminoethyl)carbamate (2.32 g, 14.5 mmol) in dry THF (15 mL) was added a solution of 1,3-dicyclocarbodiimide (3.29 g, 16.0 mmol) in CH$_2$Cl$_2$ (5 mL) dropwise at 0° C. The reaction was stirred for 18 h and then filtered. The filtrate was conc in vacuo. The residue was dissolved in EtOAc (50 mL), washed with 5% NaHCO$_3$, dried with MgSO$_4$, and conc in vacuo to a white solid. The solid purified by silica gel chromatography (gradient: 0-70% EtOAc in hexanes) to yield 2.88 grams (71%) of the product as white solid.

Step B. Preparation of N-(2-aminoethyl)-2-hydroxybenzamide

To a stirring solution of [2-(2-hydroxy-benzoylamino)-ethyl]-carbamic acid tert-butyl ester (1.0 g, 3.57 mmol) in CH$_2$Cl$_2$ (20 mL) was added 2 M HCl (10.71 mL, 21.42 mmol). The reaction was stirred for 30 min and then conc in vacuo to yield a white solid. The solid was rinsed with Et$_2$O and dissolved in 20 mL of MeOH. To the solution was added DiaionWaz21 J resin (5 g, Supelco). The solution was stirred for 30 min and then filtered. The filtrate was conc in vacuo to yield 629 mg (98%) of the product as a colorless oil. MS (ESI): 181 (M+H).

Step C. Preparation of N-[2-(2,2-dimethoxy-ethylamino)-ethyl]-2-hydroxy-benzamide To a solution of N-(2-aminoethyl)-2-hydroxybenzamide (332 mg, 1.85 mmol), dimethoxyacetaldehyde (0.475 mL, 1.85 mmol) in CH$_2$Cl$_2$ (10 mL) was added sodium triacetoxyboro hydrid (588 mg, 2.80 mmol). The resulting mixture was stirred overnight, then diluted with EtOAc (50 mL), washed with 10 mL of water and then brine, dried over MgSO$_4$, and conc in vacuo to yield 441 mg (97%) of the product as a colorless oil. MS (ESI) 269 (M+H).

Step D. Preparation of (±)-1,3,4,9a-tetrahydro-2H-9-oxa-2,4-a-diaza-anthracen-10-one To a stirring solution of N-[2-(2,2-dimethoxy-ethylamino)-ethyl]-2-hydroxy benzamide (300 mg, 1.11 mmol) in CHCl$_3$ (100 mL) was added conc H$_2$SO$_4$ (2 mL). The reaction was refluxed overnight, then cooled to room temperature then poured into a mixture of ice-saturated NaHCO$_3$ solution. The mixture was extracted with EtOAc (3×50 mL). The organic layers were combined, washed with brine, dried on MgSO₄, and conc in vacuo to yield a yellowish oil. The oil was then purified by chiral HPLC using an OD column with 10% iPrOH in heptane to yield 50 mg of the R enantiomer as white solid, MS (ESI) 205 (M+H), and 56 mg of the S enantiomer as white solid, MS (ESI) 205 (M+H).

Example 59

Preparation of (±)-1,3,4,10b-tetrahydro-7-chloro-9-methoxy-pyrazino[2,1-a]isoindol-6(2H)-one hydrochloric acid salt

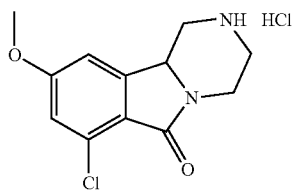

Step A. Preparation of 2-chloro-4-methoxybenzoic acid

To a solution of 2-chloro-4-hydroxybenzoic acid hydrate (2.0 g, 12 mmol), iodomethane (2.9 mL, 46 mmol) and N,N-dimethylformamide (50 mL) was added sodium hydride (1.9 g, 46 mmol; 60% dispersion in mineral oil) in one portion. After stirring the mixture vigorously for 16 h, the reaction was quenched with water and washed with ethyl acetate. The aqueous layer was then acidified with aqueous hydrogen chloride (6N) to give a white precipitate. The mixture was filtered, washed with water, and the filter cake was dried in a vacuum oven to give the desired acid as an off-white solid (1.4 g, 65%). MS (ESI) 187.1, 189.1 (M+H).

Step B. Preparation of (±)-2-(2,2-diethoxyethyl)-1-carbonitrile-1,3-dihydro-4-chloro-6-methoxy-isoindol-3(1H)-one Prepared according to the procedure described in Example 43, Step A, with the substitution of 2-chloro-4-methoxybenzoic acid for 2-chlorobenzoic acid.
MS (ESI) 293.2, 295.1 (M−OEt).

Step C. Preparation of (±)-N-(t-butoxycarbonyl)-2-(2,2-diethoxyethyl)-1-(aminomethyl)-1,3-dihydro-4-chloro-6-methoxy-isoindol-3(1H)-one To (±)-2-(2,2-diethoxyethyl)-1-carbonitrile-1,3-dihydro-4-chloro-6-methoxy-isoindol-3(1H)-one (150 mg, 0.45 mmol) in ethanol (5 mL) was added Raney 2400 Nickel (0.1 mL; Aldrich, slurry in water). The mixture was degassed and the reaction vessel was fitted with a hydrogen balloon. After 14 h, the mixture was filtered (with a water wash), concentrated, and the resulting residue was redissolved in tetrahydrofuran (5 mL). Di-tert-butyl dicarbonate (150 mg, 0.68 mmol) was added in one portion. After 1.5 h, the reaction was concentrated and purified by flash column chromatography (0-50% ethyl acetate in hexanes) to give the desired carbamate as a yellow residue (193 mg, 97%). MS (ESI) 443.3, 445.3 (M+H).

Step D. Preparation of (±)-N-(t-butoxycarbonyl)-1,3,4,10b-tetrahydro-7-chloro-9-methoxy-pyrazino[2,1-a]isoindol-6(2H)-one To (±)-2-(2,2-diethoxyethyl)-1-(aminomethyl)-1,3-dihydro-4-chloro-6-methoxy-isoindol-3(1H)-one (190 mg, 0.44 mmol) was added aqueous hydrogen chloride (5 mL, 12N). After 5 min, the solution was concentrated. The resulting residue was treated with 1,2-dichloroethane (5 mL) and sodium triacetoxyborohydride (203 mg, 0.96 mmol). Methanol (1 mL) was added to dissolve the imine salt. After 14 h, the reaction was concentrated, treated with aqueous hydrogen chloride (2.0 mL, 1N), and diluted with tetrahydrofuran (5 mL). Di-tert-butyl dicarbonate (190 mg, 0.87 mmol) was added in one portion, and the resulting mixture was basified with excess solid sodium carbonate. After stirring the resulting mixture vigorously for 1.5 h, the reaction was extracted with ethyl acetate (×3), and the combined organic layers were dried over sodium sulfate, filtered, and concentrated. The resulting residue was purified by flash column chromatography (30% ethyl acetate in hexanes) to give the desired product as a white solid (78 mg, 51%). MS (ESI) 353.2, 355.2 (M+H).

Step E. Preparation of (±)-1,3,4,10b-tetrahydro-7-chloro-9-methoxy-pyrazino[2,1-a]isoindol-6(2H)-one hydrochloric acid salt To (±)-N-(t-butoxycarbonyl)-1,3,4,10b-tetrahydro-7-chloro-9-methoxy-pyrazino[2,1-a]isoindol-6(2H)-one (20 mg, 0.06 mmol) was added concentrated hydrochloric acid (1 mL). After 15 min, the resulting solution was concentrated, diluted with water, and lypholized to give (±)-1,3,4,10b-tetrahydro-7-chloro-9-methoxy-pyrazino[2,1-a]isoindol-6(2H)-one hydrochloric acid salt as an off-white solid (15 mg, 91%). MS (ESI) 253.1, 255.1 (M−Cl)

Example 60

Preparation of (R)-1,3,4,10b-tetrahydro-7-chloro-9-methoxy-pyrazino[2,1-a]isoindol-6(2H)-one hydrochloric acid salt

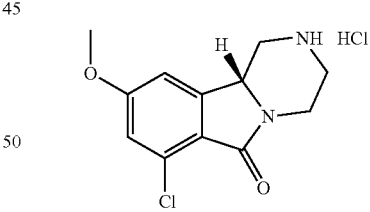

Step A. Preparation of N-(t-butoxycarbonyl)-(R)-1,3,4,10b-tetrahydro-7-chloro-9-methoxy-pyrazino[2,1-a]isoindol-6(2H)-one (±)-N-(t-butoxycarbonyl)-1,3,4,10b-tetrahydro-7-chloro-9-methoxy-pyrazino[2,1-a]isoindol-6(2H)-one (55 mg, 0.16 mmol) from Example 59, Step C, was separated by chiral HPLC using an OD column with 80% heptane with 0.1% diethylamine and 20% 1:1 MeOH:EtOH with 0.1% diethylamine to yield 16 mg (29%) of the R enantiomer and 17 mg (31%) of the S enantiomer as white solids. MS (ESI) 353.3, 355.3 (M+H).

Step B. Preparation of (R)-1,3,4,10b-tetrahydro-7-chloro-9-methoxy-pyrazino[2,1-a]isoindol-6(2H)-one hydrochloride To N-(t-butoxycarbonyl)-(R)-1,3,4,10b-tetrahydro-7-chloro-9-methoxy-pyrazino[2,1-a]isoindol-6(2H)-one (16 mg, 0.05 mmol) was added concentrated aqueous hydrochloric acid (1 mL, 12N). After 1 min, the solution was concentrated, diluted with water, and lypholized to give a white solid (13 mg, quant). MS (ESI) 253.2, 255.2 (M−Cl).

Example 61

Preparation of (S)-1,3,4,10b-tetrahydro-7-chloro-9-methoxy-pyrazino[2,1-a]isoindol-6(2H)-one hydrochloric acid salt

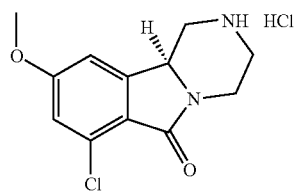

Prepared according to procedures described in Example 60, Step B, with substitution of N-(t-butoxycarbonyl)-(S)-1,3,4,10b-tetrahydro-7-chloro-9-methoxy-pyrazino[2,1-a]isoindol-6(2H)-one for N-(t-butoxycarbonyl)-(R)-1,3,4,10b-tetrahydro-7-chloro-9-methoxy-pyrazino[2,1-a]isoindol-6(2H)-one. MS (ESI) 253.2, 255.2 (M−Cl).

Example 62

Preparation of (R)-1,3,4,10b-tetrahydro-7-chloro-pyrazino[2,1-a]isoindol-6(2H)-one hydrochloric acid salt

Prepared according to procedures described in Example 60 with substitution of (±)-N-(t-butoxycarbonyl)-1,3,4,10b-tetrahydro-7-chloro-pyrazino[2,1-a]isoindol-6(2H)-one (Example 43, Step C) for (±)-N-(t-butoxycarbonyl)-1,3,4,10b-tetrahydro-7-chloro-9-methoxy-pyrazino[2,1-a]isoindol-6(2H)-one at Step A. MS (ESI) 223.2, 225.2 (M−Cl).

Example 63

Preparation of (S)-1,3,4,10b-tetrahydro-7-chloro-pyrazino[2,1-a]isoindol-6(2H)-one hydrochloric acid salt

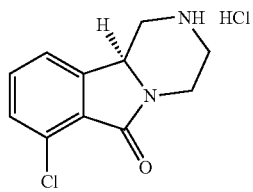

Prepared according to the procedure described in Example 61 with substitution of N-(t-butoxycarbonyl)-(S)-1,3,4,10b-tetrahydro-7-chloro-pyrazino[2,1-a]isoindol-6(2H)-one for N-(t-butoxycarbonyl)-(S)-1,3,4,10b-tetrahydro-7-chloro-9-methoxy-pyrazino[2,1-a]isoindol-6(2H)-one. MS (ESI) 223.2, 225.1 (M−Cl).

Example 64

Preparation of (R)-1,3,4,10b-tetrahydro-7-methylthio-pyrazino[2,1-a]isoindol-6(2H)-one hydrochloric acid salt

Prepared according to procedures described in Examples 59 and 60 with substitution of 2-(methylthio)benzoic acid for 2-chloro-4-hydroxybenzoic acid hydrate in Example 59, Step A, and (±)-N-(t-butoxycarbonyl)-1,3,4,10b-tetrahydro-7-methylthio-pyrazino[2,1-a]isoindol-6(2H)-one (Example 45) for (±)-N-(t-butoxycarbonyl)-1,3,4,10b-tetrahydro-7-chloro-9-methoxy-pyrazino[2,1-a]isoindol-6(2H)-one in Example 60, Step A. MS (ESI) 235.2 (M−Cl).

Example 65

Preparation of (S)-1,3,4,10b-tetrahydro-7-thiomethoxy-pyrazino[2,1-a]isoindol-6(2H)-one hydrochloric acid salt

Prepared according to procedures described in Examples 59 and 61 with substitution of 2-(methylthio)benzoic acid for 2-chloro-4-hydroxybenzoic acid hydrate in Example 59, Step A, and N-(t-butoxycarbonyl)-(S)-1,3,4,10b-tetrahydro-7-thiomethoxy-pyrazino[2,1-a]isoindol-6(2H)-one for N-(t-butoxycarbonyl)-(S)-1,3,4,10b-tetrahydro-7-chloro-9-methoxy-pyrazino[2,1-a]isoindol-6(2H)-one in Example 61. MS (ESI) 235.2 (M−Cl).

Example 66

Preparation of (R)-1,3,4,10b-tetrahydro-7-chloro-pyrazino[2,1-a]isoindole bis hydrochloric acid salt

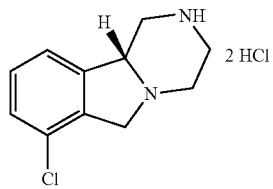

Prepared according to procedures described in Example 10 from Step A with the substitution of N-(t-butoxycarbonyl)-(R)-1,3,4,10b-tetrahydro-7-chloro-pyrazino[2,1-a]isoindol-6(2H)-one for N-(t-butoxycarbonyl)-(R)-1,3,4,10b-tetrahydro-7-trifluoromethyl-pyrazino[2,1-a]isoindol-6(2H)-one. MS (ESI) 209.1, 211.2 (M−HCl$_2$).

Example 67

Preparation of (R)-1,3,4,10b-tetrahydro-9-nitrile-7-trifluoromethyl-pyrazino[2,1-a]isoindol-6(2H)-one hydrochloric acid salt

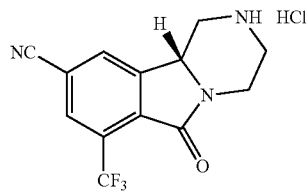

Step A. Preparation of N-(t-butoxycarbonyl)-(R)-1,3,4,10b-tetrahydro-9-nitrile-7-trifluoromethyl-pyrazino[2,1-a]isoindol-6(2H)-one Zinc cyamide (8 mg, 0.07 mmol) was added to a degassed solution of N-(t-butoxycarbonyl)-(R)-1,3,4,10b-tetrahydro-9-bromo-7-trifluoromethyl-pyrazino[2,1-a]isoindol-6(2H)-one (Example 11, Step A), tetrakis(triphenylphosphine)palladium(0) (8 mg, 0.007 mmol), and N,N-dimethylformamide (1 mL). The mixture was degassed again via exposure to alternating vacuum and argon (×3) and was then subjected to microwave conditions (150° C., 30 min; 300 W). The reaction was cooled, diluted with ethyl acetate, and the reaction washed with 50% saturated aqueous sodium chloride. The aqueous layer washed with ethyl acetate (×2), and the combined organic layers were dried over sodium sulfate, filtered, and concentrated. The resulting residue was purified by radial chromatography (20% ethyl acetate in hexanes) to give the desired product as a clear residue (21 mg, 81%). MS (ESI) 382.2 (M+H).

Step B. Preparation of (R)-1,3,4,10b-tetrahydro-9-nitrile-7-trifluoromethyl-pyrazino[2,1-a]isoindol-6(2H)-one hydrochloric acid salt N-(t-butoxycarbonyl)-(R)-1,3,4,10b-tetrahydro-9-nitrile-7-trifluoromethyl-pyrazino[2,1-a]isoindol-6(2H)-one was dissolved in diethyl ether (1 mL) and treated with concentrated aqueous hydrogen chloride (1 mL). After 1 h, the reaction was concentrated, diluted with water, and lypholized to give the desired product as an off-white flaky solid (14 mg, 88%). MS (ESI) 282.2 (M−Cl).

Example 68

Preparation of (±)-1,3,4,10b-tetrahydro-7-nitrile-pyrazino[2,1-a]isoindol-6(2H)-one hydrochloric acid salt

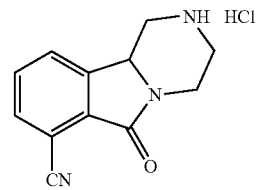

Step A. Preparation of N-(t-butoxycarbonyl)-(±)-1,3,4,10b-tetrahydro-7-nitrile-pyrazino[2,1-a]isoindol-6(2H)-one To N-(t-butoxycarbonyl)-(±)-1,3,4,10b-tetrahydro-7-chloro-pyrazino[2,1-a]isoindol-6(2H)-one (25 mg, 0.08 mmol; Example 43, Step C) in a round-bottom flask was added zinc cyamide (5 mg, 0.05 mmol), tris(dibenzylideneacetone)dipalladium(0) (1.4 mg, 0.002 mmol), and 1,1'-bis(diphenylphosphino)ferrocene (1.7 mg, 0.003 mmol). To these reagents was added N,N-dimethylacetamide (1 mL), and the resulting mixture was degassed. The reaction was then subjected to microwave conditions (130° C., 30 min; 300 W); the reaction was then cooled, and additional zinc cyamide (0.05 mmol), tris(dibenzylideneacetone)dipalladium(0) (0.002 mmol), and 1,1'-bis(diphenylphosphino)ferrocene (0.003 mmol) were added. The reaction was again subjected to microwave conditions (160° C., 60 min; 300 W). The resulting black mixture was then subjected to microwave conditions for a final time (220° C., 60 min; 300 W) before being diluted with tetrahydrofuran (2 mL) and treated with excess di-tert-butyl dicarbonate. After 1 h, the reaction was diluted with ethyl acetate and the mixture washed with saturated aqueous ammonium hydroxide and saturated aqueous sodium chloride. The organic layer was then dried over sodium sulfate, filtered, and concentrated. The resulting residue was purified by radial chromatography (30-50% ethyl acetate in hexanes) to give the desired product as a clear residue (7 mg, 29%). MS (ESI) 314.3 (M+H).

Step B. Preparation of (±)-1,3,4,10b-tetrahydro-7-nitrile-pyrazino[2,1-a]isoindol-6(2H)-one hydrochloric acid salt Concentrated aqueous hydrogen chloride (1 mL) was added to N-(t-butoxycarbonyl)-(±)-1,3,4,10b-tetrahydro-7-nitrile-pyrazino[2,1-a]isoindol-6(2H)-one (7 mg, 0.02 mmol). After 1 min, the solution was concentrated, diluted with water, and lypholized to a white residue (1.0 mg, 18%). MS (ESI) 214.3 (M−Cl).

Example 69

Preparation of (R)-1,3,4,10b-tetrahydro-9-(2-propenyl)-7-trifluoromethyl-pyrazino[2,1-a]isoindol-6 (2H)-one hydrochloric acid salt

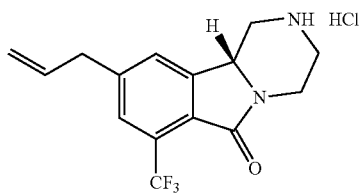

Prepared according to the procedures of Example 29, Steps A-B, substituting allyltributyltin for 2-(tributylstannyl)furan in Step A. MS (ESI) 297.3 (M−Cl).

Example 70

Preparation of (R)-1,3,4,10b-tetrahydro-9-(propyl)-7-trifluoromethyl-pyrazino[2,1-a]isoindol-6(2H)-one hydrochloric acid salt

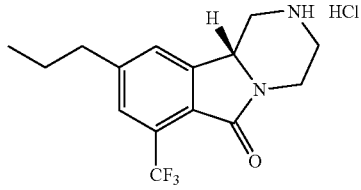

Step A. Preparation of N-(t-butoxycarbonyl)-(R)-1,3,4,10b-tetrahydro-9-propyl-7-trifluoromethyl-pyrazino[2,1-a]isoindol-6(2H)-one A mixture of N-(t-butoxycarbonyl)-(R)-1,3,4,10b-tetrahydro-9-(2-propenyl)-7-trifluoromethyl-pyrazino[2,1-a]isoindol-6(2H)-one (27 mg, 0.07 mmol) and palladium on carbon (10 mg, 10 wt %; Aldrich) in methanol (1 mL) was subjected to 1 atmosphere of hydrogen for 50 min. The reaction was then filtered, concentrated, and the resulting residue was purified by radial chromatography (30% ethyl acetate in hexanes) to give the desired product as a clear residue (25 mg, 91%). MS (ESI) 399.4 (M+H).

Step B. Preparation of (R)-1,3,4,10b-tetrahydro-9-propyl-7-trifluoromethyl-pyrazino[2,1-a]isoindol-6 (2H)-one hydrochloric acid salt To N-(t-butoxycarbonyl)-(R)-1,3,4,10b-tetrahydro-9-propyl-7-trifluoromethyl-pyrazino[2,1-a]isoindol-6(2H)-one (25 mg, 0.06 mmol) was added concentrated aqueous hydrogen chloride (1 mL). After 5 min, the solution was concentrated, diluted with water, and lypholized to give the desired product as an off-white solid (19 mg, 89%). %). MS (ESI) 299.3 (M−Cl).

Example 71

Preparation of (R)-1,3,4,10b-tetrahydro-9-(1-propynyl)-7-trifluoromethyl-pyrazino[2,1-a]isoindol-6 (2H)-one hydrochloric acid salt

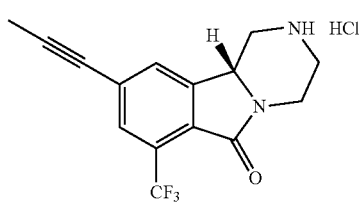

Prepared according to the procedures of Example 29, Steps A-B, substituting tributyl(1-propynyl)tin for 2-(tributylstannyl)furan in Step A. MS (ESI) 297.3 (M−Cl).

Example 72

Preparation of (±)-1,3,4,10b-tetrahydro-7-hydroxy-pyrazino[2,1-a]isoindol-6(2H)-one hydrochloric acid salt

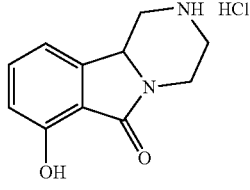

Step A. Preparation of N-(t-butoxycarbonyl)-(±)-1,3,4,10b-tetrahydro-7-methoxy-pyrazino[2,1-a]isoindol-6(2H)-one To a solution of (±)-1,3,4,10b-tetrahydro-7-methoxy-pyrazino[2,1-a]isoindol-6(2H)-one (1.7 g, 0.008 mmol) prepared according to the procedures of Example 1, Steps A-D, substituting 2-methoxybenzoic acid for 2-trifluoromethoxybenzoic acid at Step A, in tetrahydrofuran (20 mL) was added di-tert-butyl dicarbonate (2.5 g, 0.012 mmol). After 2 h, the solution was concentrated and purified by flash column chromatography (50-100% ethyl acetate in hexanes) to give the desired product as a white solid (2.4 g, quant). MS (ESI) 319.3 (M+H).

Step B. Preparation of N-(t-butoxycarbonyl)-(±)-1,3,4,10b-tetrahydro-7-hydroxy-pyrazino[2,1-a]isoindol-6(2H)-one To a solution of N-(t-butoxycarbonyl)-(±)-1,3,4,10b-tetrahydro-7-methoxy-pyrazino[2,1-a]isoindol-6(2H)-one (100 mg, 0.31 mmol) in dichloromethane (3 mL) at −78° C. was added dropwise boron tribromide (0.79 mL, 0.79 mmol; 1.0M in $CH_2Cl_2$). After 5 min, the reaction was warmed to 0° C. and an additional 0.2 mL of boron tribromide (1.0 M in $CH_2Cl_2$) was added. After 2 h, the yellow mixture was recooled to −78° C. and quenched with water. The reaction was warmed to room temperature and stirred for 14 h. The mixture was then concentrated, quenched again with aqueous hydrogen chloride (3M), and the resulting yellow solution was concentrated to dryness. The residue was diluted with tetrahydrofuran (10 mL) and saturated aqueous sodium bicarbonate (1 mL). Di-tert-butyl dicarbonate (69 mg, 0.31 mmol) was added, and the mixture was stirred for 1 h. The reaction was then diluted with ethyl acetate and the layers were separated. The organic layer was then dried over sodium sulfate, filtered, and concentrated. The resulting residue was purified by radial chromatography (20% ethyl acetate in hexanes) to give the desired product as an off-white solid (86 mg, 90%). MS (ESI) 305.3 (M+H).

Step C. Preparation of (±)-1,3,4,10b-tetrahydro-7-hydroxy-pyrazino[2,1-a]isoindol-6(2H)-one hydrochloric acid salt To N-(t-butoxycarbonyl)-(±)-1,3,4,10b-tetrahydro-7-hydroxy-pyrazino[2,1-a]isoindol-6(2H)-one (24 mg, 0.08 mmol) was added concentrated aqueous hydrogen chloride (1 mL). After 5 min, the solution was concentrated, diluted with water, and lypholized to give the desired product as an off-white solid (8 mg, 42%). MS (ESI) 205.2 (M−Cl).

Example 73

Preparation of (±)-1,3,4,10b-tetrahydro-7-benzyloxy-pyrazino[2,1-a]isoindol-6(2H)-one hydrochloric acid salt

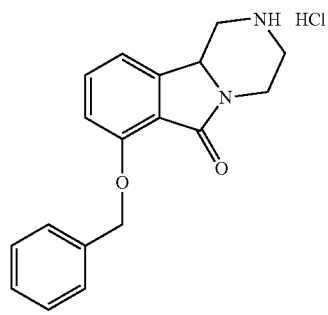

Step A. Preparation of N-(t-butoxycarbonyl)-(±)-1,3,4,10b-tetrahydro-7-benzyloxy-pyrazino[2,1-a]isoindol-6(2H)-one To a solution of N-(t-butoxycarbonyl)-(±)-1,3,4,10b-tetrahydro-7-hydroxy-pyrazino[2,1-a]isoindol-6(2H)-one (30 mg, 0.10 mmol) from Example 72, Step B, in N,N-dimethylformamide (1.5 mL) was added benzyl bromide (0.017 mL, 0.15 mmol) and potassium carbonate (41 mg, 0.29 mmol). The resulting mixture was warmed to 80° C. After 4 h the reaction was cooled to room temperature, diluted with ethyl acetate, washed with 50% saturated aqueous sodium chloride, and the organic layer was dried over sodium sulfate, filtered, and concentrated. The resulting residue was purified by radial chromatography (30% ethyl acetate in hexanes) to give the desired product as a clear residue (31 mg, 80%). MS (ESI) 395.4 (M+H).

Step B. Preparation of (±)-1,3,4,10b-tetrahydro-7-benzyloxy-pyrazino[2,1-a]isoindol-6(2H)-one hydrochloric acid salt To N-(t-butoxycarbonyl)-(±)-1,3,4,10b-tetrahydro-7-benzyloxy-pyrazino[2,1-a]isoindol-6(2H)-one (31 mg, 0.08 mmol) was added concentrated aqueous hydrogen chloride (1 mL). After 5 min, the solution was concentrated, treated with saturated aqueous ammonium chloride, and reconcentrated. The resulting mixture was purified via radial chromatography (8% methanol in dichloromethane containing 2% ammonium hydroxide) to give (±)-1,3,4,10b-tetrahydro-7-benzyloxy-pyrazino[2,1-a]isoindol-6(2H)-one. This material was treated with aqueous hydrogen chloride (1N), concentrated, diluted with water, and lypholized to give the desired product as an off-white solid (19 mg, 72%). MS (ESI) 295.3 (M−Cl).

Example 74

Preparation of (±)-1,3,4,10b-tetrahydro-7-isopropoxy-pyrazino[2,1-a]isoindol-6(2H)-one hydrochloric acid salt

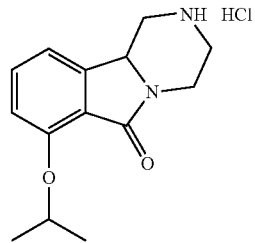

Prepared according to the procedures of Example 73, Steps A-B, substituting 2-iodopropane for benzyl bromide in Step A. MS (ESI) 247.3 (M−Cl).

Example 75

Preparation of (±)-1,3,4,10b-tetrahydro-7-(2-methylpropyloxy)-pyrazino[2,1-a]isoindol-6(2H)-one hydrochloric acid salt

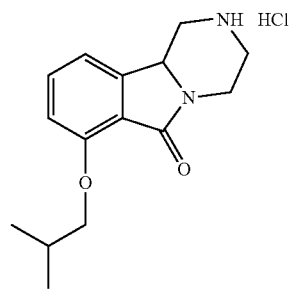

Prepared according to the procedures of Example 73, Steps A-B, substituting 1-iodo-2-methylpropane for benzyl bromide in Step A. MS (ESI) 261.3 (M−Cl).

Example 76

Preparation of (R)-1,3,4,10b-tetrahydro-9-(2-ethoxyphenyl)amino-7-trifluoromethyl-pyrazino[2,1-a]isoindol-6(2H)-one

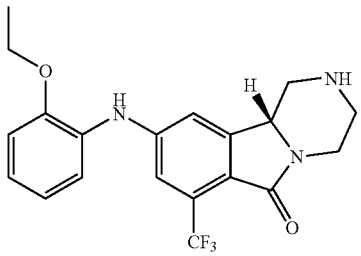

A solution of tris(dibenzylideneacetone)dipalladium(0) (12 mg, 13 μmol) and 2-(di-tert-butylphosphino)biphenyl (12.0 mg, 40 μmol) in anhydrous toluene (5 mL) was degassed with argon for 15 min at room temperature, then N-(t-butoxycarbonyl)-(R)-1,3,4,10b-tetrahydro-9-bromo-7-trifluoromethyl-pyrazino[2,1-a]isoindol-6(2H)-one (93 mg, 0.21 mmol) was added. Upon further degassing, 2-ethoxyaniline (88 mg, 0.64 mmol) and sodium tert-butoxide (61 mg, 0.64 mmol) were added. The mixture was degassed a final time and then subjected to microwave conditions (150 W, 150° C.) for 1 h. Upon cooling to room temperature, the mixture was filtered through a bilayer pad of diatomaceous earth and silica gel using 1:1 hexanes/EtOAc (500 mL) to wash the pad. The filtrate was concentrated in vacuo and the residue was purified by flash column chromatography (silica gel, 5-60% Et$_2$O/hexanes) to provide the corresponding N-linked oxoisoindole (55 mg) in 52% yield. A solution of the Boc-protected oxoisoindole in CH$_2$Cl$_2$ (10 mL) at −10° C. was treated with TFA (3 mL) and stirred for 3 h. Upon concentration in vacuo, the residue was partitioned between CH$_2$Cl$_2$ (50 mL) and satd NaHCO$_3$ (50 mL). The aqueous phase was extracted with CH$_2$Cl$_2$ (4×75 mL). The combined organic phases were dried over Na$_2$SO$_4$, filtered, and concentrated in vacuo. The residue was purified by flash column chromatography [silica gel, 5-33% (80:18:2 CHCl$_3$/MeOH/concd NH$_4$OH)/CH$_2$Cl$_2$] and trituration with CH$_2$Cl$_2$/Et$_2$O/hexanes to provide the desired product (24 mg, 63%) as a white solid. MS (APCI) 392 (M+H).

Example 77

Preparation of (R)-1,3,4,10b-tetrahydro-9-(4-fluoro-3-methylphenyl)amino-7-trifluoromethyl-pyrazino[2,1-a]isoindol-6(2H)-one

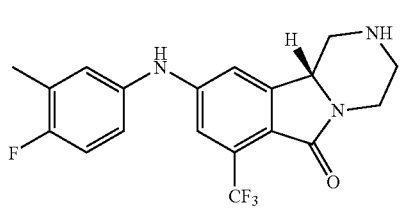

Prepared according to procedures described in Example 76 with substitution of 4-fluoro-2-methylaniline for 2-ethoxyaniline. MS (APCI) 380 (M+H).

Example 78

Preparation of (R)-1,3,4,10b-tetrahydro-9-(2,5-dichlorophenyl)amino-7-trifluoromethyl-pyrazino[2,1-a]isoindol-6(2H)-one

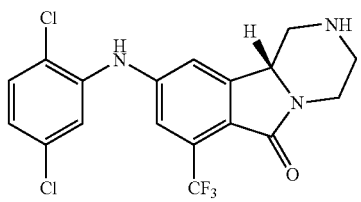

Prepared according to procedures described in Example 76 with substitution of 2,5-dichloroaniline for 2-ethoxyaniline. MS (APCI) 416 (M+H).

Example 79

Preparation of (R)-1,3,4,10b-tetrahydro-9-(2-fluorophenyl)amino-7-trifluoromethyl-pyrazino[2,1-a]isoindol-6(2H)-one

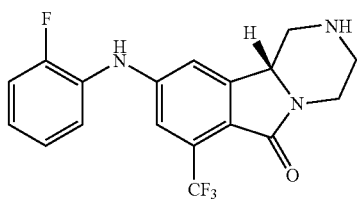

Prepared according to procedures described in Example 76 with substitution of 2-fluoroaniline for 2-ethoxyaniline. MS (APCI) 366 (M+H).

Example 80

Preparation of (R)-1,3,4,10b-tetrahydro-9-(2,3-difluorophenyl)amino-7-trifluoromethyl-pyrazino[2,1-a]isoindol-6(2H)-one

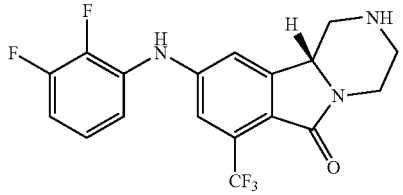

Prepared according to procedures described in Example 76 with substitution of 2,3-difluoroaniline for 2-ethoxyaniline. MS (APCI) 384 (M+H).

Example 81

Preparation of (R)-1,3,4,10b-tetrahydro-9-(2-fluoro-4-methoxyphenyl)amino-7-trifluoromethyl-pyrazino[2,1-a]isoindol-6(2H)-one

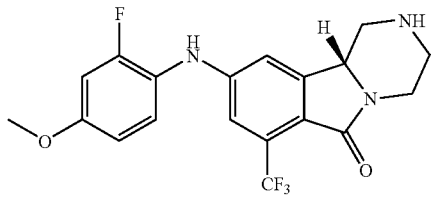

Prepared according to procedures described in Example 76 with substitution of 2-fluoro-4-methoxyaniline for 2-ethoxyaniline. MS (APCI) 396 (M+H).

Example 82

Preparation of (R)-1,3,4,10b-tetrahydro-9-(2-methoxy-3-pyridinyl)amino-7-trifluoromethyl-pyrazino[2,1-a]isoindol-6(2H)-one

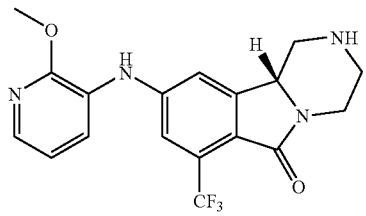

Prepared according to procedures described in Example 76 with substitution of 3-amino-2-methoxypyridine for 2-ethoxyaniline. MS (APCI) 379 (M+H).

Example 83

Preparation of (R)-1,3,4,10b-tetrahydro-9-(4-fluoro-5-methyl-3-pyridinyl)amino-7-trifluoromethyl-pyrazino[2,1-a]isoindol-6(2H)-one

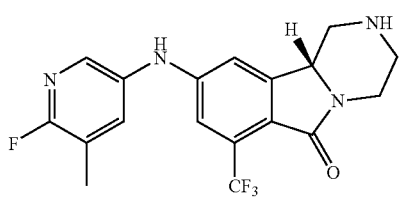

Prepared according to procedures described in Example 76 with substitution of 5-amino-2-fluoro-3-methylpyridine for 2-ethoxyaniline at Step A. MS (APCI) 381 (M+H).

Example 84

Preparation of (R)-1,3,4,10b-tetrahydro-9-(2-ethoxy-3-pyridinyl)amino-7-trifluoromethyl-pyrazino[2,1-a]isoindol-6(2H)-one

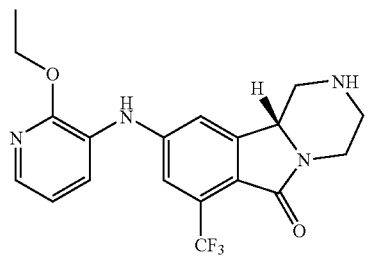

Step A. Preparation of N-(t-butoxycarbonyl)-(R)-1,3,4,10b-tetrahydro-9-amino-7-trifluoromethyl-pyrazino[2,1-a]isoindol-6(2H)-one A solution of tris(dibenzylideneacetone)dipalladium(0) (14 mg, 15 μmol) and 2-(di-tert-butylphosphino)biphenyl (14.0 mg, 46 μmol) in anhydrous toluene (5.5 mL) was degassed with argon for 15 min at room temperature, then N-(t-butoxycarbonyl)-(R)-1,3,4,10b-tetrahydro-9-bromo-7-trifluoromethyl-pyrazino[2,1-a]isoindol-6(2H)-one (110 mg, 0.25 mmol) was added. Upon further degassing, benzophenone imine (0.14 mg, 0.75 mmol) and sodium tert-butoxide (73 mg, 0.75 mmol) were added. The mixture was degassed a final time and then subjected to microwave conditions (150 W, 150° C.) for 1 h. Upon cooling to room temperature, the mixture was filtered through a pad of diatomaceous earth and the pad washed with EtOAc (100 mL). The filtrate was concentrated in vacuo and the residue was dissolved in MeOH (10 mL) and cooled to 0° C. To this solution was added sodium acetate (95 mg, 1.4 mmol) and hydroxylamine hydrochloride (150 mg, 1.8 mmol). The reaction was warmed to room temperature and stirred for 1.5 h. Additional amounts of sodium acetate (95 mg, 1.4 mmol) and hydroxylamine hydrochloride (150 mg, 1.8 mmol) were added at 0° C. and the reaction was stirred at room temperature for an additional 2.5 h. The solution was concentrated in vacuo and the residue was partitioned between $CH_2Cl_2$ (50 mL) and 1 N NaOH (50 mL). The aqueous phase was extracted with $CH_2Cl_2$ (4×75 mL). The combined organic phases were dried over $Na_2SO_4$, filtered, and concentrated in vacuo. The residue was purified by flash column chromatography (silica gel, 5-33% EtOAc/hexanes) to provide the product (47 mg) in 50% yield. MS (APCI) 372 (M+H).

Step B. Preparation of (R)-1,3,4,10b-tetrahydro-9-(2-ethoxy-3-pyridinyl)amino-7-trifluoromethyl-pyrazino[2,1-a]isoindol-6(2H)-one A solution of tris(dibenzylideneacetone)dipalladium(0) (12 mg, 13 μmol) and 2-(di-tert-butylphosphino)biphenyl (12.0 mg, 40 μmol) in anhydrous toluene (5 mL) was degassed with argon for 15 min at room temperature, then 3-bromo-2-ethoxypyridine (33 mg, 0.16 mmol) was added.

Upon further degassing, N-(t-butoxycarbonyl)-(R)-1,3,4,10b-tetrahydro-9-amino-7-trifluoromethyl-pyrazino[2,1-a]isoindol-6(2H)-one (66 mg, 0.18 mmol) and sodium tert-butoxide (26 mg, 0.27 mmol) were added. The mixture was degassed a final time and then subjected to microwave conditions (150 W, 150° C.) for 1 h. Upon cooling to room temperature, the mixture was filtered through a pad of diatomaceous earth and the pad washed with EtOAc (100 mL). The filtrate was concentrated in vacuo and the residue was purified by flash column chromatography (silica gel, 5-60% $Et_2O$/hexanes) to provide the corresponding N-linked oxoisoindole (35 mg) in 44% yield. A solution of the Boc-protected oxoisoindole in $CH_2Cl_2$ (10 mL) at −10° C. was treated with TFA (3 mL) and stirred for 2.5 h. Upon concentration in vacuo, the residue was purified by preparative HPLC (Varian Dynamax C18 column, 10-100% $CH_3CN/H_2O$ with 0.05% TFA) followed by trituration of the combined fractions with $CH_2Cl_2/Et_2O$/hexanes to provide the product (9 mg, 25%) as a yellow solid: MS (APCI) 393 (M+H).

Example 85

Preparation of (R)-1,3,4,10b-tetrahydro-9-(2-isopropoxy-5-methyl-3-pyridinyl)amino-7-trifluoromethyl-pyrazino[2,1-a]isoindol-6(2H)-one

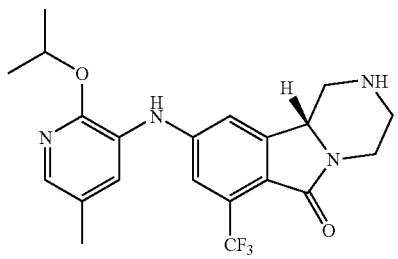

Prepared according to procedures described in Example 84 with substitution of 3-bromo-2-isopropoxy-5-methylpyridine for 3-bromo-2-ethoxypyridine at Step B. MS (APCI) 421 (M+H).

Example 86

Preparation of (R)-1,3,4,10b-tetrahydro-9-(2-isopropoxy-4-methyl-3-pyridinyl)amino-7-trifluoromethyl-pyrazino[2,1-a]isoindol-6(2H)-one

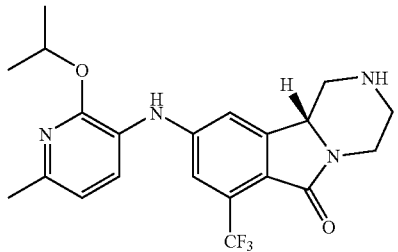

Prepared according to procedures described in Example 84 with substitution of 3-bromo-2-isopropoxy-4-methylpyridine for 3-bromo-2-ethoxypyridine at Step B. MS (APCI) 421 (M+H).

Example 87

Preparation of (R)-1,3,4,10b-tetrahydro-9-(2-ethoxy-5-methyl-3-pyridinyl)amino-7-trifluoromethyl-pyrazino[2,1-a]isoindol-6(2H)-one

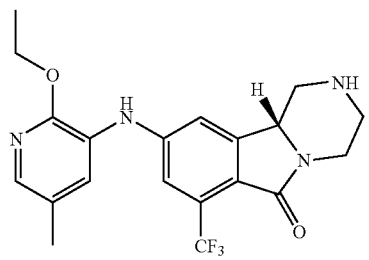

Prepared according to procedures described in Example 84 with substitution of 3-bromo-2-ethoxy-5-methylpyridine for 3-bromo-2-ethoxypyridine at Step B. MS (APCI) 421 (M+H).

Example 88

Preparation of (4R,10bR)-1,3,4,10b-tetrahydro-4-methyl-7-trifluoromethyl-pyrazino[2,1-a]isoindol-6(2H)-one hydrochloric acid salt

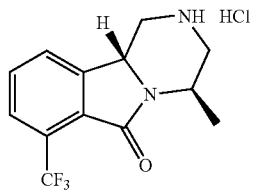

Step A. Preparation of 2-(1-cyano-3-oxo-4-trifluoromethyl-1,3-dihydro-isoindol-2-yl)-propionic acid tert-butyl ester To a stirring solution of 3-hydroxy-7-trifluoromethyl-3H-isobenzofuran-1-one (436 mg, 2 mmol) and sodium acetate (164 mg, 2 mmol) in ethanol (6 mL) and acetic acid (2 mL) was added R-tert-butyl 2-aminopropanoate hydrochloride (363 mg, 2 mmol) and sodium cyamide (98 mg, 2 mmol). The reaction was stirred overnight and then conc in vacuo to a yellow solid. The solid was partioned between water and ethyl acetate. The organic layer was separated and the aqueous phase was extracted with ethyl acetate (2×10 mL). The organic layers were combined, dried over $Na_2SO_4$, and conc. in vacuo to a yellow oil. The oil was purified by radial chromatography (silica gel, 3:1 hexanes:EtOAc) to give 390 mg of the desired product as a pale yellow oil.

MS (ESI) 355 (M+H).

Step B. Preparation of 2-(1-aminomethyl-3-oxo-4-trifluoromethyl-1,3-dihydro-isoindol-2-yl)-propionic acid hydrochloride A stirring degassed solution of 2-(1-cyano-3-oxo-4-trifluoromethyl-1,3-dihydro-isoindol-2-yl)-propionic acid tert-butyl ester (390 mg, 1.1 mmol) and 10% palladium on carbon (20 mg) in methanol (10 mL) and conc. hydrochloric acid (1 mL) was added 80 psi of hydrogen. The reaction was stirred for 4 h and then filtered. The filtrated was conc. in vacuo to a white solid. The solid was dissolved in water and lypholized to give 352 mg of the desired product as a white solid. MS (ESI) 303 (M−Cl).

Step C. Preparation of (4R,10bS)-1,3,4,10b-tetrahydro-4-methyl-3-oxo-7-trifluoromethoxy-pyrazino[2,1-a]isoindol-6(2H)-one and (4R,10bR)-1,3,4,10b-tetrahydro-4-methyl-3-oxo-7-trifluoromethoxy-pyrazino[2,1-a]isoindol-6(2H)-one A stirring solution of 2-(1-aminomethyl-3-oxo-4-trifluoromethyl-1,3-dihydro-isoindol-2-yl)-propionic acid hydrochloride (185 mg, 0.55 mmol) and triethylamine (268 mg, 2.65 mmol) in dry DMF (10 mL) was added benzotriazol-1-yloxy-tris(pyrrolidinyl)-phosphonium hexafluorophosphate (354 mg, 0.68 mmol). The reaction was stirred for 4 h and then conc. in vacuo to a yellow oil. The oil was partioned between water and ethyl acetate. The organic layer was separated, dried over $Na_2SO_4$, and conc. in vacuo to a yellow solid. The solid was purified by radial chromatography (silica gel, EtOAc) to give 84 mg of the desired product as a white solid. MS (ESI) 285 (M+H).

Step D. Preparation of N-(t-butoxycarbonyl)-(4R,10bR)-1,3,4,10b-tetrahydro-4-methyl-7-trifluoromethoxy-pyrazino[2,1-a]isoindol-6(2H)-one A stirring solution of (4R,10bS)-1,3,4,10b-tetrahydro-4-methyl-3-oxo-7-trifluoromethoxy-pyrazino[2,1-a]isoindol-6(2H)-one and (4R,10bR)-1,3,4,10b-tetrahydro-4-methyl-3-oxo-7-trifluoromethoxy-pyrazino[2,1-a]isoindol-6(2H)-one (84 mg, 0.3 mmol) in dry THF (3 mL) was added 1 M borane in THF (1.5 mL). The reaction was heated to reflux for 16 h and then cooled to room temperature. The reaction was quenched with conc. hydrochloric acid (1 mL) and heated to reflux for 1 h. The reaction was conc. in vacuo to a white solid. The solid was dissovled in THF and made basic with 1 M aq NaOH. The reaction was then treated with di-tert-butyl dicarbonate (87 mg, 0.4 mmol) for 3 h. The reaction was extracted with EtOAc (3×5 mL). The organic layers were combined, dried over $Na_2SO_4$, and conc. in vacuo to a colorless oil. The oil was purified by radial chromatography (silica gel, 7:1 hexanes:EtOAc) to give 32 mg of the desired product as a white solid and 32 mg of N-(t-butoxycarbonyl)-(4R,10bS)-1,3,4,10b-tetrahydro-4-methyl-7-trifluoromethoxy-pyrazino[2,1-a]isoindol-6(2H)-one as a colorless oil. MS (ESI) 371 (M+H).

Step E. Preparation of (4R,10bR)-1,3,4,10b-tetrahydro-4-methyl-7-trifluoromethoxy-pyrazino[2,1-a]isoindol-6(2H)-one hydrochloric acid salt To a stirring solution of N-(t-butoxycarbonyl)-(4R,10bR)-1,3,4,10b-tetrahydro-4-methyl-7-trifluoromethoxy-pyrazino[2,1-a]isoindol-6(2H)-one (30 mg, 0.08 mmol) in dry ether (2 mL) was added hydrochloric acid (1 mL). The reaction was stirred for 1 h and then conc. in vacuo to a white solid. The solid was dissolved in water and lyophilized to 21 mg of a white solid. MS (ESI) 271 (M−Cl).

Example 89

Preparation of (4R,10bS)-1,3,4,10b-tetrahydro-4-methyl-7-trifluoromethyl-pyrazino[2,1-a]isoindol-6(2H)-one hydrochloric acid salt

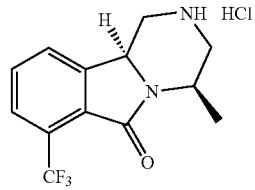

Prepared according to procedures described in Example 88 with substitution of N-(t-butoxycarbonyl)-(4R,10bS)-1,3,4,10b-tetrahydro-4-methyl-7-trifluoromethoxy-pyrazino[2,1-a]isoindol-6(2H)-one at Step E. MS (ESI) 271 (M−Cl).

Example 90

Preparation of (4S,10bS)-1,3,4,10b-tetrahydro-4-methyl-7-trifluoromethyl-pyrazino[2,1-a]isoindol-6(2H)-one hydrochloric acid salt

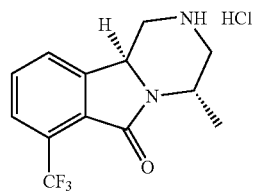

Prepared according to procedures described in Example 88 with substitution of S-tert-butyl 2-aminopropanoate hydrochloride for R-tert-butyl 2-aminopropanoate hydrochloride at Step A. MS (ESI) 271 (M−Cl).

Example 91

Preparation of (4S,10bR)-1,3,4,10b-tetrahydro-4-methyl-7-trifluoromethyl-pyrazino[2,1-a]isoindol-6(2H)-one hydrochloric acid salt

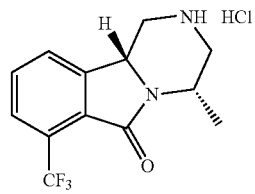

Prepared according to procedures described in Example 88 with substitution of S-tert-butyl 2-aminopropanoate hydrochloride for R-tert-butyl 2-aminopropanoate hydrochloride at Step A. MS (ESI) 271 (M−Cl).

Example 92

Preparation of (4S,10bS)-1,3,4,10b-tetrahydro-4-isopropyl-7-trifluoromethyl-pyrazino[2,1-a]isoindol-6(2H)-one hydrochloric acid salt

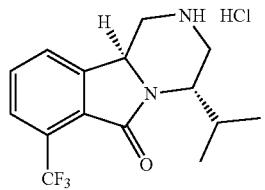

Prepared according to procedures described in Example 88 with substitution of S-tert-butyl 2-amino-3-methylbutanoate hydrochloride for R-tert-butyl 2-aminopropanoate hydrochloride at Step A. MS (ESI) 299 (M−Cl).

Example 93

Preparation of (4S,10bR)-1,3,4,10b-tetrahydro-4-isopropyl-7-trifluoromethyl-pyrazino[2,1-a]isoindol-6(2H)-one hydrochloric acid salt

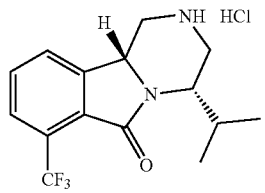

Prepared according to procedures described in Example 88 with substitution of S-tert-butyl 2-amino-3-methylbutanoate hydrochloride for R-tert-butyl 2-aminopropanoate hydrochloride at Step A. MS (ESI) 299 (M−Cl).

Example 94

Preparation of (4S,10bS)-1,3,4,10b-tetrahydro-4-(2-methylpropyl)-7-trifluoromethyl-pyrazino[2,1-a]isoindol-6(2H)-one hydrochloric acid salt

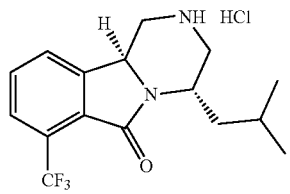

Prepared according to procedures described in Example 88 with substitution of S-tert-butyl 2-amino-4-methylpentanoate hydrochloride for R-tert-butyl 2-aminopropanoate hydrochloride at Step A. MS (ESI) 313 (M−Cl).

Example 95

Preparation of (4S,10bR)-1,3,4,10b-tetrahydro-4-(2-methylpropyl)-7-trifluoromethyl-pyrazino[2,1-a]isoindol-6(2H)-one hydrochloric acid salt

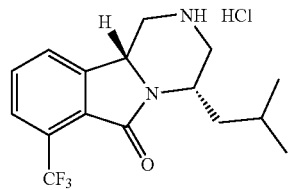

Prepared according to procedures described in Example 88 with substitution of S-tert-butyl 2-amino-4-methylpentanoate hydrochloride for R-tert-butyl 2-aminopropanoate hydrochloride at Step A. MS (ESI) 313 (M−Cl).

Example 96

Preparation of (4S,10bS)-1,3,4,10b-tetrahydro-4-(phenylmethyl)-7-trifluoromethyl-pyrazino[2,1-a]isoindol-6(2H)-one hydrochloric acid salt

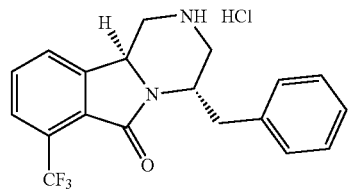

Prepared according to procedures described in Example 88 with substitution of S-tert-butyl 2-amino-3-phenylpropanoate hydrochloride for R-tert-butyl 2-aminopropanoate hydrochloride at Step A. MS (ESI) 347 (M−Cl).

Example 97

Preparation of (4S,10bR)-1,3,4,10b-tetrahydro-4-(phenylmethyl)-7-trifluoromethyl-pyrazino[2,1-a]isoindol-6(2H)-one hydrochloric acid salt

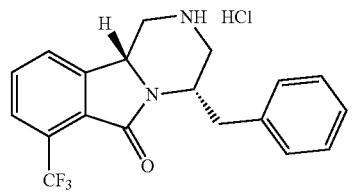

Prepared according to procedures described in Example 88 with substitution of S-tert-butyl 2-amino-3-phenylpropanoate hydrochloride for R-tert-butyl 2-aminopropanoate hydrochloride at Step A. MS (ESI) 347 (M−Cl).

Example 98

Preparation of (R)-1,3,4,10b-tetrahydro-9-(cis-1-propenyl)-7-trifluoromethyl-pyrazino[2,1-a]isoindol-6(2H)-one hydrochloric acid salt

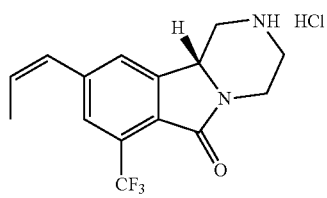

Step A. Preparation of N-(t-butoxycarbonyl)-(R)-1,3,4,10b-tetrahydro-9-(cis-1-propenyl)-7-trifluoromethyl-pyrazino[2,1-a]isoindol-6(2H)-one To a stirring degassed solution of N-(t-butoxycarbonyl)-(R)-1,3,4,10b-tetrahydro-9-bromo-7-trifluoromethyl-pyrazino[2,1-a]isoindol-6(2H)-one (54 mg, 0.12 mmol) in DME (1.2 mL) was added tetrakis(triphenylphosphine)palladium(0) (1.7 mg, 0.0015 mmol). After 15 min., cis-1-propenylboronic acid (31 mg, 0.37 mmol), potassium carbonate (17 mg, 0.12 mmol), and water (0.3 mL) were added. The reaction was heated to reflux for 3 h and then cooled to room temp. The reaction was diluted with brine and extracted with EtOAc (3×5 mL). The organic layers were combined, dried over $Na_2SO_4$, and conc. in vacuo to a yellow oil. The oil was purified by flash chromatography (silica gel, 0-50% EtOAc in hexanes) to give 42 mg of the desired product as a colorless oil. MS (ESI) 397 (M+H).

Step B. Preparation of (R)-1,3,4,10b-tetrahydro-9-(cis-1-propenyl)-7-trifluoromethyl-pyrazino[2,1-a]isoindol-6(2H)-one hydrochloric acid salt To a stirring solution of N-(t-butoxycarbonyl)-(R)-1,3,4,10b-tetrahydro-9-(cis-1-propenyl)-7-trifluoromethyl-pyrazino[2,1-a]isoindol-6(2H)-one (40 mg, 0.1 mmol) in dry ether (2 mL) was added hydrochloric acid (1 mL). The reaction was stirred for 1 h and then conc. in vacuo to a white solid. The solid was dissolved in water and lyophilized to 24 mg of a white solid. MS (ESI) 297 (M−Cl).

Example 99

Preparation of (R)-1,3,4,10b-tetrahydro-9-(2-methyl-1-propenyl)-7-trifluoromethyl-pyrazino[2,1-a]isoindol-6(2H)-one hydrochloric acid salt

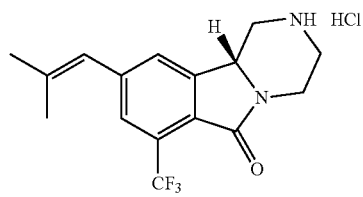

Prepared according to procedures described in Example 98 with substitution of 2-methyl-propenylboronic acid for cis-1-propenylboronic acid at Step A. MS (ESI) 311 (M−Cl).

Example 100

Preparation of (R)-1,3,4,10b-tetrahydro-9-(2-methylpropyl)-7-trifluoromethyl-pyrazino[2,1-a]isoindol-6(2H)-one hydrochloric acid salt

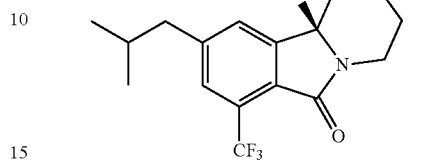

Step A. Preparation of N-(t-butoxycarbonyl)-(R)-1,3,4,10b-tetrahydro-9-(2-methylpropyl)-7-trifluoromethyl-pyrazino[2,1-a]isoindol-6(2H)-one To a stirring degassed solution of N-(t-butoxycarbonyl)-(R)-1,3,4,10b-tetrahydro-9-(2-methyl-1-propenyl)-7-trifluoromethyl-pyrazino[2,1-a]isoindol-6(2H)-one (60 mg, 0.15 mmol) and 10% palladium on carbon (5 mg) in MeOH (2 mL) was added hydrogen (1 atm). After 2 h, the reaction was filter and the solid washed with methanol. The organic layers were combined and conc. in vacuo to a colorless oil. The oil was purified by flash chromatography (silica gel, 0-50% EtOAc in hexanes) to give 28 mg of the desired product as a white solid. MS (ESI) 413 (M+H).

Step B. Preparation of (R)-1,3,4,10b-tetrahydro-9-(2-methylpropyl)-7-trifluoromethyl-pyrazino[2,1-a]isoindol-6(2H)-one hydrochloric acid salt To a stirring solution of N-(t-butoxycarbonyl)-(R)-1,3,4,10b-tetrahydro-9-(2-methylpropyl)-7-trifluoromethyl-pyrazino[2,1-a]isoindol-6(2H)-one (25 mg, 0.06 mmol) in dry ether (2 mL) was added hydrochloric acid (1 mL). The reaction was stirred for 1 h and then conc. in vacuo to a white solid. The solid was dissolved in water and lyophilized to 16 mg of a white solid. MS (ESI) 313 (M−Cl).

Example 101

Preparation of (R)-1,3,4,10b-tetrahydro-9-methylthio-7-trifluoromethyl-pyrazino[2,1-a]isoindol-6(2H)-one hydrochloric acid salt

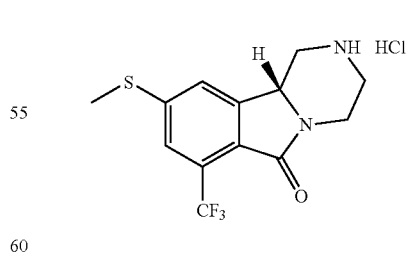

Step A. Preparation of N-(t-butoxycarbonyl)-(R)-1,3,4,10b-tetrahydro-9-methylthio-7-trifluoromethyl-pyrazino[2,1-a]isoindol-6(2H)-one To a stirring solution of N-(t-butoxycarbonyl)-(R)-1,3,4,10b-tetrahydro-9-bromo-7-trifluoromethyl-pyrazino[2,1-a]

isoindol-6(2H)-one (56 mg, 0.13 mmol) in dry DMF (1 mL) at 60° C. was added sodium methanethiolate (9.9 mg, 0.14 mmol). The reaction was heated to reflux for 30 min and then cooled to room temperature. The reaction was quenched with 1M aq. NaOH and extracted with EtOAc (3×5 mL). The organic layers were combined, dried over $Na_2SO_4$, and conc. in vacuo to a yellow oil. The oil was purified by flash chromatography (silica gel, 0-33% EtOAc in hexanes) to give 34 mg of the desired product as a colorless oil. MS (ESI) 403 (M+H).

Step B. Preparation of (R)-1,3,4,10b-tetrahydro-9-methylthio-7-trifluoromethyl-pyrazino[2,1-a]isoindol-6(2H)-one hydrochloric acid salt To a stirring solution of N-(t-butoxycarbonyl)-(R)-1,3,4,10b-tetrahydro-9-methylthio-7-trifluoromethyl-pyrazino[2,1-a]isoindol-6(2H)-one (34 mg, 0.08 mmol) in dry ether (2 mL) was added hydrochloric acid (1 mL). The reaction was stirred for 1 h and then conc. in vacuo to a white solid. The solid was dissolved in water and lyophilized to yield 21 mg of a white solid. MS (ESI) 303 (M−Cl).

Example 102

Preparation of (R)-1,3,4,10b-tetrahydro-9-ethylthio7-trifluoromethyl-pyrazino[2,1-a]isoindol-6(2H)-one hydrochloric acid salt

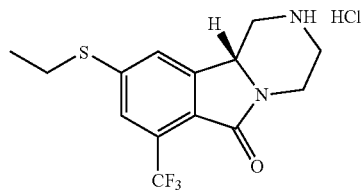

Prepared according to procedures described in Example 101 with substitution of sodium ethanethiolate for sodium methanethiolate at Step A. MS (ESI) 317 (M−Cl).

Example 103

Preparation of (R)-1,3,4,10b-tetrahydro-9-isopropylthio-7-trifluoromethyl-pyrazino[2,1-a]isoindol-6(2H)-one hydrochloric acid salt

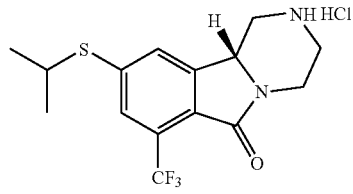

Prepared according to procedures described in Example 101 with substitution of sodium 2-propanethiolate for sodium ethanethiolate at Step A. MS (ESI) 331 (M−Cl).

Example 104

Preparation of (R)-1,3,4,10b-tetrahydro-9-butyl-7-trifluoromethyl-pyrazino[2,1-a]isoindol-6(2H)-one hydrochloric acid salt

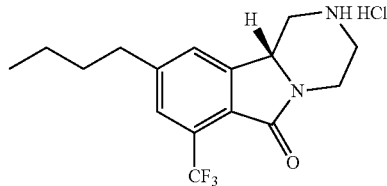

Prepared according to procedures described in Example 98 with substitution of butylboronic acid for cis-1-propenylboronic acid and 1,1'-bis(diphenylphosphino)ferrocene palladium(II) dichloride dichloromethane complex for tetrakis(triphenylphosphine)-palladium(0) at Step A. MS (ESI) 313 (M−Cl).

Example 105

Preparation of (R)-1,3,4,10b-tetrahydro-9-(1-cyclohexenyl)-7-trifluoromethyl-pyrazino[2,1-a]isoindol-6(2H)-one hydrochloric acid salt

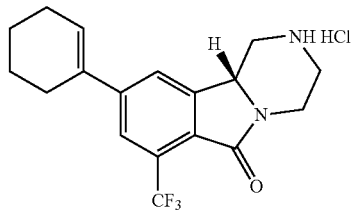

Prepared according to procedures described in Example 104 with substitution of 2-(1-cyclohexenyl)-4,4,5,5-tetramethyl-1,3,2-dioxaborolane acid for butylboronic acid. MS (ESI) 337 (M−Cl).

Example 106

Preparation of (R)-1,3,4,10b-tetrahydro-9-(3-pentyl)-7-trifluoromethyl-pyrazino[2,1-a]isoindol-6(2H)-one hydrochloric acid salt

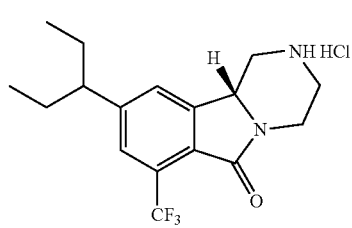

Step A. Preparation of N-(t-butoxycarbonyl)-(R)-1,3,4,10b-tetrahydro-9-(3-pentyl)-7-trifluoromethyl-pyrazino[2,1-a]isoindol-6(2H)-one To a stirring degassed solution of N-(t-butoxycarbonyl)-(R)-1,3,4,10b-tetrahydro-9-bromo-7-trifluoromethyl-pyrazino[2,1-a]isoindol-6(2H)-one (66 mg, 0.15 mmol) and potassium carbonate (105 mg, 0.76 mmol) in DMF (1.0 mL) was added 1,1'-bis(diphenylphosphino)ferrocene palladium (II) dichloride dichloromethane complex (12 mg, 0.015 mmol). After 15 min., 0.5 M THF solution of 3-propenylzinc bromide (0.45 mL, 0.9 mmol) was added. The reaction was heated to reflux for 15 min and then cooled to room temp. The reaction was quenched with 1M aq. NaOH and extracted with EtOAc (3×10 mL). The organic layers were combined, dried over Na$_2$SO$_4$, and conc. in vacuo to a black oil. The oil was purified by flash chromatography (silica gel, 0-50% EtOAc in hexanes) to give 36 mg of the desired product as a colorless oil. MS (ESI) 427 (M+H).

Step B. Preparation of (R)-1,3,4,10b-tetrahydro-9-(3-pentyl)-7-trifluoromethyl-pyrazino[2,1-a]isoindol-6(2H)-one hydrochloric acid salt To a stirring solution of N-(t-butoxycarbonyl)-(R)-1,3,4,10b-tetrahydro-9-(3-pentyl)-7-trifluoromethyl-pyrazino[2,1-a]isoindol-6(2H)-one (35 mg, 0.08 mmol) in dry ether (2 mL) was added hydrochloric acid (1 mL). The reaction was stirred for 1 h and then conc. in vacuo to a white solid. The solid was dissolved in water and lyophilized to 25 mg of a white solid. MS (ESI) 327 (M−Cl).

Example 107

Preparation of (R)-1,3,4,10b-tetrahydro-9-cyclopentyl-7-trifluoromethyl-pyrazino[2,1-a]isoindol-6(2H)-one hydrochloric acid salt

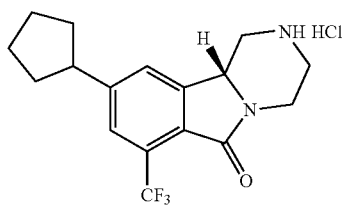

Prepared according to procedures described in Example 106 with substitution of cyclopentylzinc bromide for 3-propenylzinc bromide in Step A. MS (ESI) 325 (M−Cl).

Example 108

Preparation of (R)-1,3,4,10b-tetrahydro-9-(1-cyclohexyl)-7-trifluoromethyl-pyrazino[2,1-a]isoindol-6(2H)-one hydrochloric acid salt

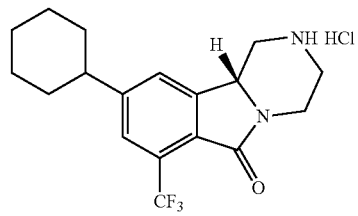

Prepared according to procedures described in Example 100 with substitution of N-(t-butoxycarbonyl)-(R)-1,3,4,10b-tetrahydro-9-(1-cyclohexenyl)-7-trifluoromethyl-pyrazino[2,1-a] isoindol-6(2H)-one for N-(t-butoxycarbonyl)-(R)-1,3,4,10b-tetrahydro-9-(2-methyl-1-propenyl)-7-trifluoromethyl-pyrazino[2,1-a]isoindol-6(2H)-one in Step A. MS (ESI) 339 (M−Cl).

Example 109

Preparation of (R)-1,3,4,10b-tetrahydro-9-isopropyl-7-trifluoromethyl-pyrazino[2,1-a]isoindol-6(2H)-one hydrochloric acid salt

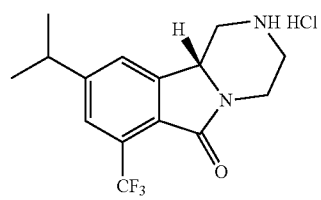

Prepared according to procedures described in Example 98 with isopropylboronic acid for cis-1-propenylboronic acid in Step A followed by the procedures described in Example 100. MS (ESI) 299 (M−Cl).

Example 110

Preparation of (R)-1,3,4,10b-tetrahydro-9-cyclopropyl-7-trifluoromethyl-pyrazino[2,1-a]isoindol-6(2H)-one hydrochloric acid salt

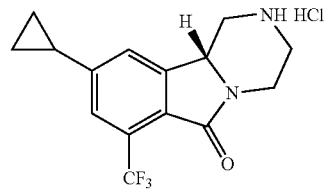

Prepared according to procedures described in Example 104 with substitution of 2-cyclopropyl-4,4,5,5-tetramethyl-1,3,2-dioxaborolane for butylboronic acid. MS (ESI) 297 (M−Cl).

Example 111

Preparation of (R)-1,3,4,10b-tetrahydro-9-hydroxymethyl-7-trifluoromethyl-pyrazino[2,1-a]isoindol-6(2H)-one hydrochloric acid salt

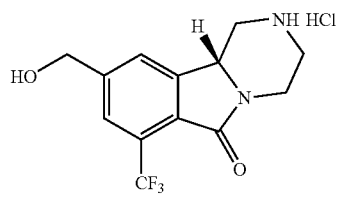

Step A. Preparation of N-(t-butoxycarbonyl)-(R)-1,3,4,10b-tetrahydro-9-hydroxymethyl-7-trifluoromethyl-pyrazino[2,1-a]isoindol-6(2H)-one To a stirring solution of N-(t-butoxycarbonyl)-(R)-1,3,4,10b-tetrahydro-9-(cis-1-propenyl)-7-trifluoromethyl-pyrazino[2,1-a]isoindol-6(2H)-one (182 mg, 0.46 mmol) in MeOH (5.0 mL) at −78° C. was bubbled ozone for 5 min. until the reaction turned a light blue color. After 5 min., sodium borohydride (23 mg, 0.6 mmol) was added. The reaction was stir for 1 hr and then warmed to room temp. The reaction was conc. in vacuo to a white solid and then dissolved in 1M aq. HCl. After 15 min, the reaction was diluted with EtOAc, basified with NaHCO₃, and treated with di-t-butyl dicarbonate (125 mg, 0.58 mmol). After 1 h, the reaction was extracted with EtOAc (3×5 mL). The organic layers were combined, dried over Na₂SO₄, and conc. in vacuo to a colorless oil. The oil was purified by flash chromatography (silica gel, 0-50% EtOAc in hexanes) to give 141 mg of the desired product as a white solid. MS (ESI) 387 (M+H).

Step B. Preparation of (R)-1,3,4,10b-tetrahydro-9-hydroxymethyl-7-trifluoromethyl-pyrazino[2,1-a]isoindol-6(2H)-one hydrochloric acid salt To a stirring solution of N-(t-butoxycarbonyl)-(R)-1,3,4,10b-tetrahydro-9-hydroxymethyl-7-trifluoromethyl-pyrazino[2,1-a]isoindol-6(2H)-one (14 mg, 0.04 mmol) in dry ether (2 mL) was added hydrochloric acid (1 mL). The reaction was stirred for 1 h and then conc. in vacuo to a white solid. The solid was dissolved in water and lyophilized to 10 mg of a white solid. MS (ESI) 287 (M−Cl).

Example 112

Preparation of (R)-1,3,4,10b-tetrahydro-9-methyl-7-trifluoromethyl-pyrazino[2,1-a]isoindol-6(2H)-one hydrochloric acid salt

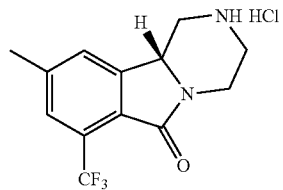

Prepared according to procedures described in Example 100 with substitution of N-(t-butoxycarbonyl)-(R)-1,3,4,10b-tetrahydro-9-hydroxymethyl-7-trifluoromethyl-pyrazino[2,1-a] isoindol-6(2H)-one for N-(t-butoxycarbonyl)-(R)-1,3,4,10b-tetrahydro-9-(2-methyl-1-propenyl)-7-trifluoromethyl-pyrazino[2,1-a]isoindol-6(2H) one in Step A. MS (ESI) 271 (M−Cl).

Example 113

Preparation of (R)-1,3,4,10b-tetrahydro-9-methoxymethyl-7-trifluoromethyl-pyrazino[2,1-a]isoindol-6(2H)-one hydrochloric acid salt

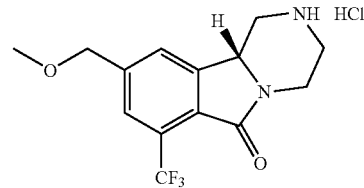

Step A. Preparation of N-(t-butoxycarbonyl)-(R)-1,3,4,10b-tetrahydro-9-methoxymethyl-7-trifluoromethyl-pyrazino[2,1-a]isoindol-6(2H)-one To a stirring solution of N-(t-butoxycarbonyl)-(R)-1,3,4,10b-tetrahydro-9-hydroxymethyl-7-trifluoromethyl-pyrazino[2,1-a]isoindol-6(2H)-one (30 mg, 0.08 mmol) and proton sponge (26 mg, 0.12 mmol) in dry CH₂Cl₂ (1.0 mL) was added trimethyloxonium tetrafluoroborate (11.5 mg, 0.08 mmol). The reaction was stir for 16 hr and then quenched with 1M aq. HCl. The reaction was extracted with EtOAc (3×10 mL). The organic layers were combined, dried over Na₂SO₄, and conc. in vacuo to a pink oil. The oil was purified by flash chromatography (silica gel, 0-40% EtOAc in hexanes) to yield 13 mg of the desired product as a colorless oil. MS (ESI) 401 (M+H).

Step B. Preparation of (R)-1,3,4,10b-tetrahydro-9-methoxymethyl-7-trifluoromethyl-pyrazino[2,1-a] isoindol-6(2H)-one hydrochloric acid salt To a stirring solution of N-(t-butoxycarbonyl)-(R)-1,3,4,10b-tetrahydro-9-methoxymethyl-7-trifluoromethyl-pyrazino[2,1-a]isoindol-6(2H)-one (12 mg, 0.03 mmol) in dry ether (2 mL) was added hydrochloric acid (1 mL). The reaction was stirred for 1 h and then conc. in vacuo to a white solid. The solid was dissolved in water and lyophilized to 10 mg of a white solid. MS (ESI) 301 (M−Cl).

Example 114

Preparation of (R)-1,3,4,10b-tetrahydro-9-hydroxy-7-trifluoromethyl-pyrazino[2,1-a]isoindol-6(2H)-one hydrochloric acid salt

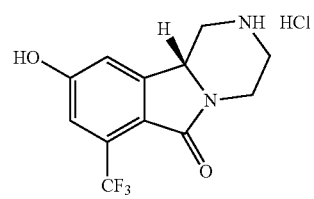

Step A. Preparation of N-(t-butoxycarbonyl)-(R)-1,3,4,10b-tetrahydro-9-hydroxy-7-trifluoromethyl-pyrazino[2,1-a]isoindol-6(2H)-one To a stirring degassed solution of N-(t-butoxycarbonyl)-(R)-1,3,4,10b-tetrahydro-9-bromo-7-trifluoromethyl-pyrazino[2,1-a]isoindol-6(2H)-one (435 mg, 1.0 mmol), bis(pinacolato)diboron (279 mg, 1.1 mmol), and potassium acetate (294 mg, 3.0 mmol) in dry DMF (5.0 mL) was added palladium(II) acetate (6.7 mg, 0.03 mmol). The reaction was heated to 80° C. for 2 h and then cooled to room temp. The reaction was quenched with water and extracted with EtOAc (3×5 mL). The organic layers were combined, dried over $Na_2SO_4$, and conc. in vacuo to a brown oil. The oil was dissolved in THF (5 mL) and acetic acid (0.05 mL) and treated with hydrogen peroxide (0.25 mL). The reaction was stirred for 15 min and then quenched with st. aq. $NaHSO_3$. The reaction was extracted with EtOAc (3×5 mL). The organic layers were combined, dried over $Na_2SO_4$, and conc. in vacuo to a brown oil. The oil was purified by flash chromatography (silica gel, 0-70% EtOAc in hexanes) to give 347 mg of the desired product as a pale yellow solid. MS (ESI) 373 (M+H).

Step B. Preparation of (R)-1,3,4,10b-tetrahydro-9-hydroxy-7-trifluoromethyl-pyrazino[2,1-a]isoindol-6(2H)-one hydrochloric acid salt To a stirring solution of N-(t-butoxycarbonyl)-(R)-1,3,4,10b-tetrahydro-9-hydroxy-7-trifluoromethyl-pyrazino[2,1-a]isoindol-6(2H)-one (14 mg, 0.04 mmol) in dry ether (2 mL) was added hydrochloric acid (1 mL). The reaction was stirred for 1 h and then conc. in vacuo to a white solid. The solid was dissolved in water and lyophilized to 10 mg of a white solid. MS (ESI) 273 (M−Cl).

Example 115

Preparation of (R)-1,3,4,10b-tetrahydro-9-methoxy-7-trifluoromethyl-pyrazino[2,1-a]isoindol-6(2H)-one hydrochloric acid salt

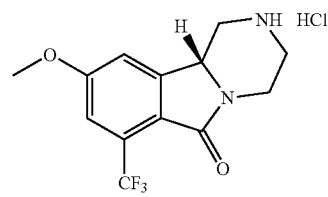

Step A. Preparation of N-(t-butoxycarbonyl)-(R)-1,3,4,10b-tetrahydro-9-methoxy-7-trifluoromethyl-pyrazino[2,1-a]isoindol-6(2H)-one To a stirring degassed solution of N-(t-butoxycarbonyl)-(R)-1,3,4,10b-tetrahydro-9-methoxy-7-trifluoromethyl-pyrazino[2,1-a]isoindol-6(2H)-one (58 mg, 0.16 mmol), and potassium carbonate (33 mg, 0.24 mmol) in dry DMF (1.0 mL) was added methyl iodide (24 mg, 0.17 mmol). The reaction was stirred for 2 h and then quenched with brine. The reaction was extracted with EtOAc (3×5 mL). The organic layers were combined, dried over $Na_2SO_4$, and conc. in vacuo to a pale yellow oil. The oil was purified by flash chromatography (silica gel, 0-50% EtOAc in hexanes) to give 41 mg of the desired product as a colorless oil. MS (ESI) 387 (M+H).

Step B. Preparation of (R)-1,3,4,10b-tetrahydro-9-methoxy-7-trifluoromethyl-pyrazino[2,1-a]isoindol-6(2H)-one hydrochloric acid salt To a stirring solution of N-(t-butoxycarbonyl)-(R)-1,3,4,10b-tetrahydro-9-methoxy-7-trifluoromethyl-pyrazino[2,1-a]isoindol-6(2H)-one (40 mg, 0.1 mmol) in dry ether (2 mL) was added hydrochloric acid (1 mL). The reaction was stirred for 1 h and then conc. in vacuo to a white solid. The solid was dissolved in water and lyophilized to 10 mg of a white solid. MS (ESI) 287 (M−Cl).

Example 116

Preparation of (R)-1,3,4,10b-tetrahydro-9-ethoxy-7-trifluoromethyl-pyrazino[2,1-a]isoindol-6(2H)-one hydrochloric acid salt

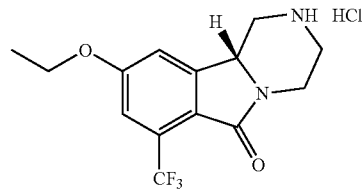

Prepared according to procedures described in Example 115 with substitution of ethyl iodide for methyl iodide in Step A. MS (ESI) 301 (M−Cl).

Example 117

Preparation of (R)-1,3,4,10b-tetrahydro-9-isopropoxy-7-trifluoromethyl-pyrazino[2,1-a]isoindol-6(2H)-one hydrochloric acid salt

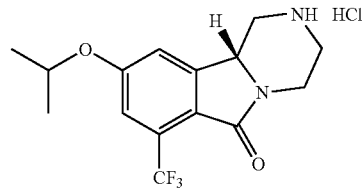

Prepared according to procedures described in Example 115 with substitution of isopropyl iodide for methyl iodide in Step A. MS (ESI) 315 (M−Cl).

Example 118

Preparation of (R)-1,3,4,10b-tetrahydro-9-cyclobutylmethoxy-7-trifluoromethyl-pyrazino[2,1-a]isoindol-6(2H)-one hydrochloric acid salt

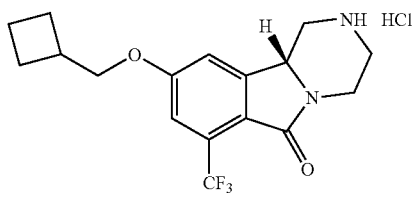

Prepared according to procedures described in Example 115 with substitution of cyclobutylmethyl iodide for methyl iodide in Step A. MS (ESI) 341 (M−Cl).

Example 119

Preparation of (R)-1,3,4,10b-tetrahydro-9-isopropoxy-7-trifluoromethyl-pyrazino[2,1-a]isoindole bishydrochloric acid salt

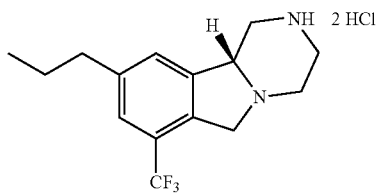

Prepared according to procedures described in Example 10 with substitution of N-(t-butoxycarbonyl)-(R)-1,3,4,10b-tetrahydro-9-isopropoxy-7-trifluoromethyl-pyrazino[2,1-a]isoindol-6(2H)-one for N-(t-butoxycarbonyl)-(R)-1,3,4,10b-tetrahydro-7-trifluoromethyl-pyrazino[2,1-a]isoindol-6(2H)-one in Step A.
MS (ESI) 315 (M−HCl$_2$).

Example 120

Preparation of (R)-1,3,4,10b-tetrahydro-9-ethynyl-7-trifluoromethyl-pyrazino[2,1-a]isoindol-6(2H)-one hydrochloric acid salt

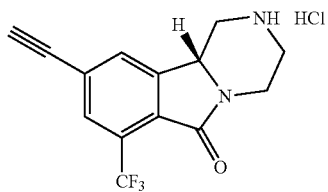

Step A. Preparation of N-(t-butoxycarbonyl)-(R)-1,3,4,10b-tetrahydro-9-ethynyl-7-trifluoromethyl-pyrazino[2,1-a]isoindol-6(2H)-one To a stirring solution of N-(t-butoxycarbonyl)-(R)-1,3,4,10b-tetrahydro-9-trimethylsilylethynyl-7-trifluoromethyl-pyrazino[2,1-a]isoindol-6(2H)-one, prepared according to procedures described in Example 29 with substitution of tributyl(trimethylsilylethynyl)tin for 2-(tributylstannyl)furan (44 mg, 0.1 mmol in MeOH (1.0 mL) was added potassium carbonate (13 mg, 0.1 mmol). The reaction was stirred for 5 min and then quenched with brine. The reaction was extracted with EtOAc (2×5 mL). The organic layers were combined, dried over Na$_2$SO$_4$, and conc. in vacuo to a pale yellow oil. The oil was purified by radial chromatography (silica gel, 30% EtOAc in hexanes) to give 27 mg of the desired product as a pale yellow oil.
MS (ESI) 381 (M+H).

Step B. Preparation of (R)-1,3,4,10b-tetrahydro-9-ethynyl-7-trifluoromethyl-pyrazino[2,1-a]isoindol-6(2H)-one hydrochloric acid salt To a stirring solution of N-(t-butoxycarbonyl)-(R)-1,3,4,10b-tetrahydro-9-ethynyl-7-trifluoromethyl-pyrazino[2,1-a]isoindol-6(2H)-one (27 mg, 0.8 mmol) in dry ether (2 mL) was added hydrochloric acid (1 mL). The reaction was stirred for 1 h and then conc. in vacuo to a white solid. The solid was dissolved in water and lyophilized to 22 mg of a white solid.
MS (ESI) 281 (M−Cl).

Example 121

Preparation of (R)-1,3,4,10b-tetrahydro-9-(trans-1-propenyl)-7-trifluoromethyl-pyrazino[2,1-a]isoindol-6(2H)-one hydrochloric acid salt

Prepared according to procedures described in Example 98 with substitution of trans-1-propenylboronic acid for cis-1-propenylboronic acid at Step A.
MS (ESI) 297 (M−Cl).

Examples 122 and 123

Preparation of (R)-1,3,4,10b-tetrahydro-9-ethyl-7-trifluoromethoxy-pyrazino[2,1-a]isoindol-6(2H)-one hydrochloric acid salt and (S)-1,3,4,10b-tetrahydro-9-ethyl-7-trifluoromethoxy-pyrazino[2,1-a]isoindol-6(2H)-one hydrochloric acid salt

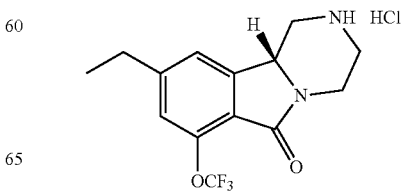

-continued

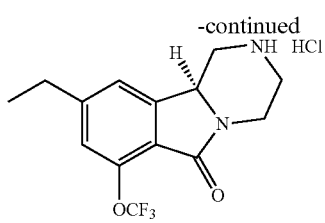

Step A. Preparation of N,N-diethyl-4-bromo-2-(trifluoromethoxy)benzamide

To a stirring solution of 4-bromo-1-iodo-2-(trifluoromethoxy)benzene (11600 mg, 32 mmol) in dry THF (300 mL) at −78° C. under Ar was added 2.5M n-butyllithium in hexanes (25 mL) dropwise. The reaction was stirred for 1.5 h and then quenched with crushed dry ice. The reaction was stirred for 30 min and then slowly warmed to room temperature. The reaction was partioned between 1 M hydrochloric acid in brine EtOAc. The organic layers were separated, washed with sat. aq. NaHSO$_3$, dried over Na$_2$SO$_4$, and conc in vacuo to a brown oil. The oil was dissolved in dry CH$_2$Cl$_2$ (300 mL) with dry DMF (0.2 mL) and then treated with oxalyl chloride in CH$_2$Cl$_2$ (32 mL) dropwise. The reaction was stirred for 4 h and then conc in vacuo to a brown oil. The oil was dissolved in dry CH$_2$Cl$_2$ (300 mL) and then treated with diethylamine (5767 mg, 79 mmol) dropwise. The reaction was stirred for 48 h and then conc in vacuo to a brown oil. The oil was purified by flash chromatography (SiO$_2$, 1:2, EtOAc:hexanes) to yield 8500 mg of the product as a colorless oil. MS (ESI) 341 (M+H).

Step B. Preparation of N,N-diethyl-4-ethenyl-2-(trifluoromethoxy)benzamide

To a stirring degassed solution of N,N-diethyl-4-bromo-2-(trifluoromethoxy)benzamide (2373 mg, 7 mmol) in THF (40 mL) was added tetrakis(triphenylphosphine)palladium(0) (97 mg, 0.08 mmol). After 15 min., potassium carbonate (2898 mg, 21 mmol), 2,4,6-trivinylcyclotriboroxane pyridine complex (2663 mg, 7 mmol), and water (8 mL). The reaction was heated to reflux for 3 h and then cooled to room temperature. The reaction was diluted with brine and extracted with EtOAc (3×25 mL). The organic layers were combined, dried over Na$_2$SO$_4$, and conc. in vacuo to a pale yellow oil. The oil was purified by flash chromatography (SiO$_2$, 0-50% EtOAc in hexanes) to give 1783 mg of the desired product as a colorless oil. MS (ESI) 288 (M+H).

Step C. Preparation of N,N-diethyl-4-ethyl-2-(trifluoromethoxy)benzamide

To a stirring degassed solution of N,N-diethyl-4-ethenyl-2-(trifluoromethoxy)benzamide (1783 mg, 6.2 mmol) and 10% palladium on carbon (50 mg) in MeOH (30 mL) was added hydrogen (1 atm). The reaction was stirred for 1 h and then filtered. The filtrate was conc. in vacuo to a colorless oil. The oil was purified by flash chromatography (SiO$_2$, 0-50% EtOAc in hexanes) to give 1489 mg of the desired product as a colorless oil. MS (ESI) 290 (M+H).

Step D. Preparation of (R)-1,3,4,10b-tetrahydro-9-ethyl-7-trifluoromethoxy-pyrazino[2,1-a]isoindol-6(2H)-one hydrochloric acid salt and (S)-1,3,4,10b-tetrahydro-9-ethyl-7-trifluoromethoxy-pyrazino[2,1-a]isoindol-6(2H)-one hydrochloric acid salt Prepared according to procedures described in Example 1, Steps B-D with substitution of N,N-diethyl-4-ethyl-2-(trifluoromethoxy)benzamide for N,N-diethyl-2-(trifluoromethoxy)benzamide at Step B. Followed by separation of enantiomers by the procedures described in Example 2 with the modification of 35% 1:1 MeOH:EtOH for 20% 1:1 MeOH:EtOH. MS (ESI) 301 (M−Cl).

Examples 124 and 125

Preparation of (R)-1,3,4,10b-tetrahydro-9-propyl-7-trifluoromethoxy-pyrazino[2,1-a]isoindol-6(2H)-one hydrochloric acid salt and (S)-1,3,4,10b-tetrahydro-9-propyl-7-trifluoromethoxy-pyrazino[2,1-a]isoindol-6(2H)-one hydrochloric acid salt

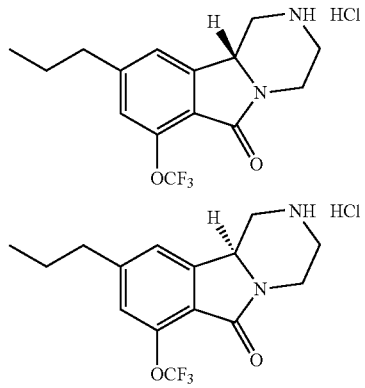

Prepared according to procedures described in Example 122 with substitution of cis-1-propenylboronic acid for 2,4,6-trivinylcyclotriboroxane pyridine complex at Step B. MS (ESI) 315 (M−Cl).

Examples 126 and 127

Preparation of (R)-1,3,4,10b-tetrahydro-9-methoxy-7-trifluoromethoxy-pyrazino[2,1-a]isoindol-6(2H)-one hydrochloric acid salt and (S)-1,3,4,10b-tetrahydro-9-methoxy-7-trifluoromethoxy-pyrazino[2,1-a]isoindol-6(2H)-one hydrochloric acid salt

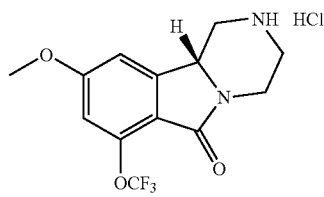

-continued

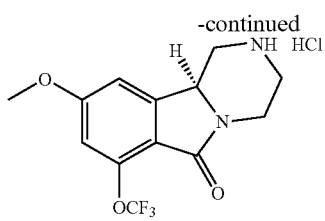

Step A. Preparation N,N-diethyl-4-hydroxy-2-(trifluoromethoxy)benzamide

To a stirring degassed solution of N,N-diethyl-4-bromo-2-(trifluoromethoxy)benzamide (2768 mg, 8.2 mmol), bis(pinacolato)diboron (2281 mg, 9.0 mmol), and potassium acetate (2402 mg, 24.5 mmol) in dry DMF (60 mL) was added palladium(II) acetate (55 mg, 0.25 mmol). The reaction was heated to 80° C. for 2 h and then cooled to room temp. The reaction was quenched with water and extracted with EtOAc (3×75 mL). The organic layers were combined, dried over $Na_2SO_4$, and conc. in vacuo to a brown oil. The oil was dissolved in THF (40 mL) and acetic acid (2.0 mL) and treated with hydrogen peroxide (8 mL). The reaction was stirred for 15 min and then quenched with st. aq. $NaHSO_3$. The reaction was extracted with EtOAc (3×40 mL). The organic layers were combined, dried over $Na_2SO_4$, and conc. in vacuo to a brown oil. The oil was purified by flash chromatography (silica gel, 20-70% EtOAc in hexanes) to give 1876 mg of the desired product as a white solid. MS (ESI) 278 (M+H).

Step B. Preparation N,N-diethyl-4-[(1,1-dimethylethyl)dimethylsilyl]oxy-2-(trifluoromethoxy)benzamide To a stirring solution of N,N-diethyl-4-hydroxy-2-(trifluoromethoxy)benzamide (1876 mg, 6.8 mmol) and diisopropylethylamine (1747 mg, 13.5 mmol) in dry DMF (60 mL) was added chloro(1,1-dimethylethyl)dimethylsilane (1123 mg, 7.5 mmol). The reaction was stirred for 16 h and then quenched with 1M HCl. The reaction was extracted with EtOAc (3×50 mL). The organic layers were combined, dried over $Na_2SO_4$, and conc. in vacuo to a pale yellow oil. The oil was purified by flash chromatography (silica gel, 0-40% EtOAc in hexanes) to give 1941 mg of the desired product as a colorless oil. MS (ESI) 392 (M+H).

Step C. Preparation N,N-diethyl-6-carboxaldehyde-4-hydroxy-2-(trifluoromethoxy)benzamide To a stirring solution of N,N-diethyl-4-[(1,1-dimethylethyl)dimethylsilyl]oxy-2-(trifluoromethoxy)benzamide (915 mg, 2.3 mmol) and N,N,N',N'-tetramethylethylenediamine (433 mg, 2.9 mmol) in dry THF (6 mL) at −78° C. under Ar was added 1.1 M s-butyllithium in hexanes (2.66 mL) dropwise. The reaction was stirred for 30 min and then DMF (0.55 mL) was added. The reaction was stirred for 15 min and then quenched with methanol (1 mL). After 10 min, the reaction was warmed to room temperature and 1M NaOH was added. After 15 min, the reaction was acidified with 1M HCl and extracted with EtOAc (3×15 mL). The organic layers were combined, dried over $Na_2SO_4$, and conc in vacuo to a pale yellow oil. The oil was purified by flash chromatography (SiO2, 0-60% EtOAc in hexanes) to yield 668 mg of the desired product as a white solid. MS (ESI) 306 (M+H).

Step D. Preparation N,N-diethyl-6-carboxaldehyde-4-methoxy-2-(trifluoromethoxy)benzamide To a stirring solution of N,N-diethyl-6-carboxaldehyde-4-hydroxy-2-(trifluoromethoxy)benzamide (650 mg, 2.1 mmol) and potassium carbonate (552 mg, 4 mmol) in dry DMF (20 mL) was added iodomethane (378 mg, 2.66 mmol). The reaction was stirred for 16 h and then quenched with water. The reaction was extracted with EtOAc (3×25 mL). The organic layers were combined, dried over $Na_2SO_4$, and conc in vacuo to a yellow oil. The oil was purified by flash chromatography (SiO2, 0-60% EtOAc in hexanes) to yield 675 mg of the desired product as a colorless oil. MS (ESI) 320 (M+H).

Step E. Preparation of (R)-1,3,4,10b-tetrahydro-9-methoxy-7-trifluoromethoxy-pyrazino[2,1-a]isoindol-6(2H)-one hydrochloric acid salt and (S)-1,3,4,10b-tetrahydro-9-methoxy-7-trifluoromethoxy-pyrazino[2,1-a]isoindol-6(2H)-one hydrochloric acid salt Prepared according to procedures described in Example 1, Steps C-D with substitution of N,N-diethyl-6-carboxaldehyde-4-methoxy-2-(trifluoromethoxy)benzamide for N,N-diethyl-6-carboxaldehyde-2-(trifluoromethoxy)benzamide at Step C. Followed by separation of enantiomers by the procedures described in Example 2 with the modification of 35% 1:1 MeOH:EtOH for 20% 1:1 MeOH:EtOH. MS (ESI) 303 (M−Cl).

Examples 128 and 129

Preparation of (R)-1,3,4,10b-tetrahydro-9-cyclopropyl-7-trifluoromethoxy-pyrazino[2,1-a]isoindol-6(2H)-one hydrochloric acid salt and (S)-1,3,4,10b-tetrahydro-9-cyclopropyl-7-trifluoromethoxy-pyrazino[2,1-a]isoindol-6(2H)-one hydrochloric acid salt

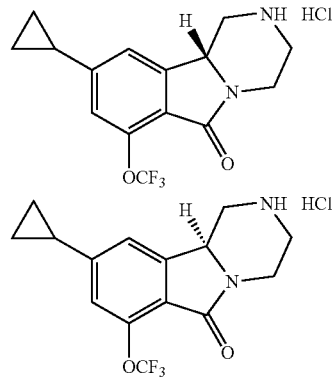

Step A. Preparation of N-(t-butoxycarbonyl)-(±)-1,3,4,10b-tetrahydro-9-hydroxy-7-trifluoromethoxy-pyrazino[2,1-a]isoindol-6(2H)-one To a stirring solution of N-(t-butoxycarbonyl)-(±)-1,3,4,10b-tetrahydro-9-methoxy-7-trifluoromethoxy-pyrazino[2,1-a]isoindol-6(2H)-one (201 mg, 0.5 mmol) in dry $CH_2Cl_2$ (3 mL) at −78° C. under Ar was added lM boron tribromide in CH$_2$Cl$_2$ (1.75 mL). The reaction was stirred for 1 h and then warmed to room temperature for 18 h. The reaction was refluxed for 24 h and then quenched with water. The reaction was stirred for 30 min and then conc. in vacuo to a brown solid. The solid was treated with 6M HCl. After 1 h, the reaction was conc. in vacuo to a brown solid. The solid was partioned between water and EtOAc, basified with sodium bicarbonate, and treated with di-t-butyl dicarbonate (109 mg, 0.5 mmol). The reaction was stirred for 1 h and extracted with EtOAc (3×10 mL). The organic layers were combined, dried over MgSO$_4$, and conc. in vacuo to a brown solid. The solid was purified by trituration with chloroform to yield 103 mg of the desired product as a white solid. MS (ESI) 389 (M+H).

Step B. Preparation of N-(t-butoxycarbonyl)-(±)-1,3,4,10b-tetrahydro-9-trifluoromethylsulfonyloxy-7-trifluoromethoxy-pyrazino[2,1-a]isoindol-6(2H)-one To a stirring solution of N-(t-butoxycarbonyl)-(±)-1,3,4,10b-tetrahydro-9-hydroxy-7-trifluoromethoxy-pyrazino[2,1-a]isoindol-6(2H)-one (100 mg, 0.26 mmol) and 2,6-lutidine (139 mg, 1.3 mmol) in dry CH$_2$Cl$_2$ (3 mL) at 0° C. was added trifluoromethanesulfonic anhydride (109 mg, 0.39 mmol). The reaction was stirred for 30 min and then quenched with methanol. The reaction was conc. in vacuo to a brown oil. The oil was purified by flash chromatography (SiO2, 0-50% EtOAc in hexanes) to yield 101 mg of the desired product as a white solid. MS (ESI) 521 (M+H).

Step C. Preparation of N-(t-butoxycarbonyl)-(±)-1,3,4,10b-tetrahydro-9-cyclopropyl-7-trifluoromethoxy-pyrazino[2,1-a]isoindol-6(2H)-one To a stirring degassed solution of N-(t-butoxycarbonyl)-(±)-1,3,4,10b-tetrahydro-9-trifluoromethylsulfonyloxy-7-trifluoromethoxy-pyrazino[2,1-a]isoindol-6(2H)-one (100 mg, 0.19 mmol), 2-cyclopropyl-4,4,5,5-tetramethyl-1,3,2-dioxaborolane (101 mg, 0.6 mmol), and potassium carbonate (138 mg, 1.0 mmol) in DME (2 mL) under Ar was added bis(diphenylphosphino)ferrocene palladium(II) dichloride dichloromethane complex (5 mg, 0.006 mmol) and water (0.2 mL). The reaction was heated to reflux for 3 h and then cooled to room temperature. The reaction was quenched with 1M NaOH and extracted with EtOAc (3×5 mL). The organic layers were combined, dried over Na$_2$SO$_4$, and conc in vacuo to a brown oil. The oil was purified by flash chromatography (SiO2, 0-50% EtOAc in hexanes) to yield 70 mg of the desired product as a white solid. MS (ESI) 413 (M+H).

Step D. Preparation of (R)-1,3,4,10b-tetrahydro-9-cyclopropyl-7-trifluoromethoxy-pyrazino[2,1-a]isoindol-6(2H)-one hydrochloric acid salt and (S)-1,3,4,10b-tetrahydro-9-cyclopropyl-7-trifluoromethoxy-pyrazino[2,1-a]isoindol-6(2H)-one hydrochloric acid salt The compounds were separated by chiral HPLC using an OD column with 65% heptane with 0.1% diethylamine and 35% 1:1 MeOH:EtOH with 0.1% diethylamine to yield 25 mg of the R enantiomer and 24 mg of the S enantiomer as white solids. The solids were individually dissolved in dry ether (1 mL) and the treated with hydrochloric acid (1 mL). The reaction was stirred for 1 h and then conc. in vacuo to a white solid. The solid was dissolved in water and lyophilized to yield 20 mg of the R enantiomer and 20 mg of the S enantiomer as white solids. MS (ESI) 313 (M–Cl).

Examples 130 and 131

Preparation of (R)-1,3,4,10b-tetrahydro-9-isopropyl-7-trifluoromethoxy-pyrazino[2,1-a]isoindol-6(2H)-one hydrochloric acid salt and (S)-1,3,4,10b-tetrahydro-9-isopropyl-7-trifluoromethoxy-pyrazino[2,1-a]isoindol-6(2H)-one hydrochloric acid salt

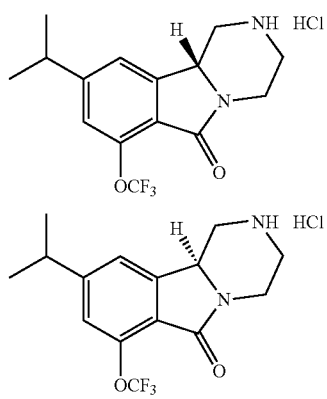

Step A. Preparation of N-(t-butoxycarbonyl)-(±)-1,3,4,10b-tetrahydro-9-isopropenyl-7-trifluoromethoxy-pyrazino[2,1-a]isoindol-6(2H)-one To a stirring degassed solution of N-(t-butoxycarbonyl)-(±)-1,3,4,10b-tetrahydro-9-trifluoromethylsulfonyloxy-7-trifluoromethoxy-pyrazino[2,1-a]isoindol-6(2H)-one (111 mg, 0.21 mmol), isopropenylboronic acid (55 mg, 0.64 mmol), and potassium carbonate (145 mg, 1.1 mmol) in DME (2 mL) under Ar was added tetrakis(triphenylphosphine)-palladium(0) (7 mg, 0.006 mmol) and water (0.2 mL). The reaction was heated to reflux for 3 h and then cooled to room temperature. The reaction was quenched with 1M NaOH and extracted with EtOAc (3×5 mL). The organic layers were combined, dried over Na$_2$SO$_4$, and conc in vacuo to a brown oil. The oil was purified by flash chromatography (SiO2, 0-50% EtOAc in hexanes) to yield 68 mg of the desired product as a colorless oil. MS (ESI) 413 (M+H).

Step B. Preparation of N-(t-butoxycarbonyl)-(±)-1,3,4,10b-tetrahydro-9-isopropyl-7-trifluoromethoxy-pyrazino[2,1-a]isoindol-6(2H)-one To a stirring degassed solution of N-(t-butoxycarbonyl)-(±)-1,3,4,10b-tetrahydro-9-isopropenyl-7-trifluoromethoxy-pyrazino[2,1-a]isoindol-6(2H)-one (67 mg, 0.16 mmol) and 10% palladium on carbon (5 mg) in MeOH (3 mL) was added hydrogen (1 atm). The reaction was stirred for 2 h and then filtered. The filtrate was conc in vacuo to a colorless oil. The oil was purified by flash chromatography (SiO2, 0-50% EtOAc in hexanes) to yield 67 mg of the desired product as a colorless oil. MS (ESI) 415 (M+H).

Step C. Preparation of (R)-1,3,4,10b-tetrahydro-9-isopropyl-7-trifluoromethoxy-pyrazino[2,1-a]isoindol-6(2H)-one hydrochloric acid salt and (S)-1,3,4,10b-tetrahydro-9-isopropyl-7-trifluoromethoxy-pyrazino[2,1-a]isoindol-6(2H)-one hydrochloric acid salt The compounds were separated by chiral HPLC using an OD column with 65% heptane with 0.1% diethylamine and 35% 1:1 MeOH:EtOH with 0.1% diethylamine to yield 29 mg of the R enantiomer and 27 mg of the S enantiomer as colorless oils. The oils were individually dissolved in dry ether (1 mL) and the treated with hydrochloric acid (1 mL). The reaction was stirred for 1 h and then conc. in vacuo to a white solid. The solid was dissolved in water and lyophilized to yield 18 mg of the R enantiomer and 17 mg of the S enantiomer as white solids. MS (ESI) 315 (M–Cl).

Example 132

Preparation of a mixture of (1S,2R,10bR)-1,3,4,10b-tetrahydro-9-(2-methylcyclopropyl)-7-trifluoromethyl-pyrazino[2,1-a]isoindol-6(2H)-one hydrochloric acid salt and (1R,2S,10bR)-1,3,4,10b-tetrahydro-9-(2-methylcyclopropyl)-7-trifluoromethyl-pyrazino[2,1-a]isoindol-6(2H)-one hydrochloric acid salt

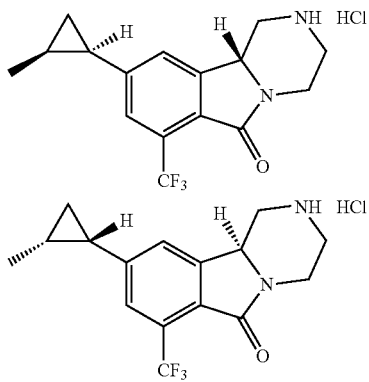

Step A. Preparation of a mixture of N-(t-butoxycarbonyl)-(1S,2R,10bR)-1,3,4,10b-tetrahydro-9-(2-methylcyclopropyl)-7-trifluoromethyl-pyrazino[2,1-a]isoindol-6(2H)-one hydrochloric acid salt and N-(t-butoxycarbonyl)-(1R,2S,10bR)-1,3,4,10b-tetrahydro-9-(2-methylcyclopropyl)-7-trifluoromethyl-pyrazino[2,1-a]isoindol-6(2H)-one hydrochloric acid salt To a stirring degassed solution of N-(t-butoxycarbonyl)-(R)-1,3,4,10b-tetrahydro-9-(cis-1-propenyl)-7-trifluoromethyl-pyrazino[2,1-a]isoindol-6(2H)-one (75 mg, 0.19 mmol) and palladium(II) acetate (1 mg, 0.004 mmol) in CH$_2$Cl$_2$ (1 mL) under Ar was added a 0.5M solution of diazomethane in ether (2.6 mL). After 1 h, the reaction was warmed to room temperature for 16 h. The addition of diazomethane was repeated twice more. The reaction was filtered and then conc. in vacuo to a pale yellow oil. The oil was dissolved in acetone (2 mL) and treated with 4-methylmorpholine N-oxide (26 mg, 0.22 mmole) and osmium tetraoxide in water (1.0 mg in 0.16 mL). The reaction was stirred for 1 h and then quenched with sat. aq. Na$_2$SO$_3$. The reaction was extracted with EtOAc (3×10 mL). The organic layers were combined, dried over MgSO$_4$, and conc in vacuo to a pale yellow oil. The oil was purified by flash chromatography (SiO2, 0-50% EtOAc in hexanes) to yield 28 mg of the desired product as a colorless oil. MS (ESI) 411 (M+H).

Step B. Preparation of a mixture of (1S,2R,10bR)-1,3,4,10b-tetrahydro-9-(2-methylcyclopropyl)-7-trifluoromethyl-pyrazino[2,1-a]isoindol-6(2H)-one hydrochloric acid salt and (1R,2S,10bR)-1,3,4,10b-tetrahydro-9-(2-methylcyclopropyl)-7-trifluoromethyl-pyrazino[2,1-a]isoindol-6(2H)-one hydrochloric acid salt To a stirring solution of N-(t-butoxycarbonyl)-(10bR)-1,3,4,10b-tetrahydro-9-[(1S,2R)-2-methylcyclopropyl)-7-trifluoromethyl-pyrazino[2,1-a]isoindol-6(2H)-one and N-(t-butoxycarbonyl)-(10bR)-1,3,4,10b-tetrahydro-9-[(1R,2S)-2-methylcyclopropyl)-7-trifluoromethyl-pyrazino[2,1-a]isoindol-6(2H)-one (22 mg, 0.05 mmol) in dry ether (2 mL) was added hydrochloric acid (1 mL). The reaction was stirred for 1 h and then conc. in vacuo to a white solid. The solid was dissolved in water and lyophilized to 15 mg of a white solid. MS (ESI) 311 (M–Cl).

Example 133

Preparation of a mixture of (1S,2S,10bR)-1,3,4,10b-tetrahydro-9-(2-methylcyclopropyl)-7-trifluoromethyl-pyrazino[2,1-a]isoindol-6(2H)-one hydrochloric acid salt and (1R,2R,10bR)-1,3,4,10b-tetrahydro-9-(2-methylcyclopropyl)-7-trifluoromethyl-pyrazino[2,1-a]isoindol-6(2H)-one hydrochlori acid salt

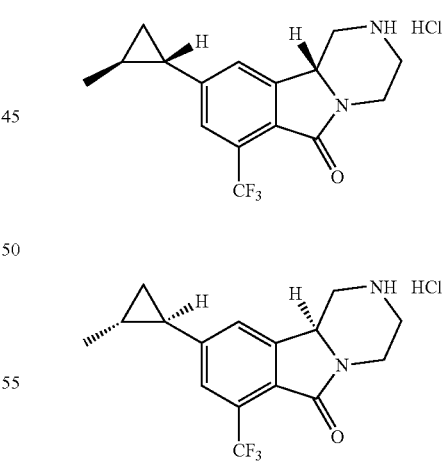

Prepared according to procedures described in Example 132 with substitution of N-(t-butoxycarbonyl)-(R)-1,3,4,10b-tetrahydro-9-(trans-1-propenyl)-7-trifluoromethyl-pyrazino[2,1-a]isoindol-6(2H)-one for N-(t-butoxycarbonyl)-(R)-1,3,4,10b-tetrahydro-9-(cis-1-propenyl)-7-trifluoromethyl-pyrazino[2,1-a]isoindol-6(2H)-one at Step A. MS (ESI) 311 (M–Cl).

Example 134

Preparation of a mixture of (R)-1,3,4,10b-tetrahydro-9-(1-methylcyclopropyl)-7-trifluoromethyl-pyrazino[2,1-a]isoindol-6(2H)-one hydrochloric acid salt

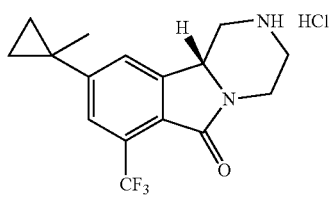

Prepared according to procedures described in Example 132 with substitution of N-(t-butoxycarbonyl)-(R)-1,3,4,10b-tetrahydro-9-(isopropenyl)-7-trifluoromethyl-pyrazino[2,1-a]isoindol-6(2H)-one for N-(t-butoxycarbonyl)-(R)-1,3,4,10b-tetrahydro-9-(cis-1-propenyl)-7-trifluoromethyl-pyrazino[2,1-a]isoindol-6(2H)-one at Step A. MS (ESI) 311 (M−Cl).

Examples 135 and 136

Preparation of (R)-1,3,4,10b-tetrahydro-9-difluoromethyl-7-trifluoromethyl-pyrazino[2,1-a]isoindol-6(2H)-one hydrochloric acid and (S)-1,3,4,10b-tetrahydro-9-difluoromethyl-7-trifluoromethyl-pyrazino[2,1-a]isoindol-6(2H)-oe hydrochloric acid

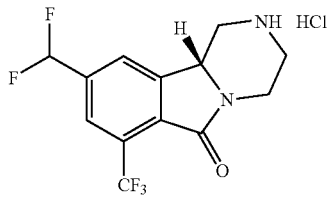

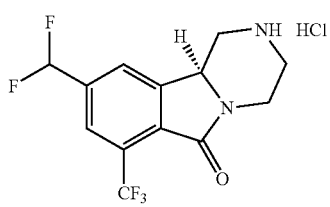

Step A. Preparation of N-(t-butoxycarbonyl)-(±)-1,3,4,10b-tetrahydro-9-carboxaldehyde-7-trifluoromethyl-pyrazino[2,1-a]isoindol-6(2H)-one To a stirring degassed solution of N-(t-butoxycarbonyl)-(±)-1,3,4,10b-tetrahydro-9-vinyl-7-trifluoromethyl-pyrazino[2,1-a]isoindol-6(2H)-one (408 mg, 1.1 mmol) in MeOH (5.0 mL) at −78° C. was bubbled ozone for 5 min. until the reaction turned a light blue color. After 5 min., nitrogen was bubbled thru the reaction for 5 min and then triphenylphosphine (308 mg, 1.2 mmol) was added. After 15 min, the reaction was conc. in vacuo to a yellow oil. The oil was purified by flash chromatography (SiO2, 0-50% EtOAc in hexanes) to yield 321 mg of the desired product as a white solid. MS (ESI) 383 (M+H).

Step B. Preparation of N-(t-butoxycarbonyl)-(±)-1,3,4,10b-tetrahydro-9-difluoromethyl-7-trifluoromethyl-pyrazino[2,1-a]isoindol-6(2H)-one To a stirring solution of N-(t-butoxycarbonyl)-(±)-1,3,4,10b-tetrahydro-9-carboxaldehyde-7-trifluoromethyl-pyrazino[2,1-a]isoindol-6(2H)-one (124 mg, 0.32 mmol) in $CH_2Cl_2$ (3.0 mL) at −78° C. in a teflon vial was added [bis(2-methoxyethyl)amino]sulfur trifluoride (122 mg, 0.55 mmol). After 30 min, the reaction was warmed to room temperature for 30 min. The reaction was quenched with sat aq $NaHCO_3$. The reaction was extracted with $CH_2Cl_2$ (3×5 mL). The organic layers were combined, dried over $Na_2SO_4$, and conc in vacuo to a yellow oil. The oil was purified by flash chromatography (SiO2, 0-50% EtOAc in hexanes) to yield 121 mg of the desired product as a colorless oil. MS (ESI) 407 (M+H).

Step C. Preparation of (R)-1,3,4,10b-tetrahydro-9-difluoromethyl-7-trifluoromethoxy-pyrazino[2,1-a]isoindol-6(2H)-one hydrochloric acid salt and (S)-1,3,4,10b-tetrahydro-9-difluoromethyl-7-trifluoromethoxy-pyrazino[2,1-a]isoindol-6(2H)-one hydrochloric acid salt Prepared according to procedures described in Examples 130 and 131 at Step C. MS (ESI) 307 (M−Cl).

Examples 137 and 138

Preparation of (R)-1,3,4,10b-tetrahydro-7-chloro-9-ethyl-pyrazino[2,1-a]isoindol-6(2H)-one hydrochloric acid and (S)-1,3,4,10b-tetrahydro-7-chloro-9-ethyl-pyrazino[2,1-a]isoindol-6(2H)-one hydrochloric acid

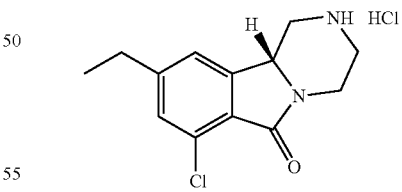

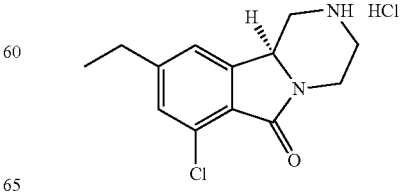

Step A. Preparation of N,N-diethyl-4-bromo-2-chlorobenzamide

Prepared according to procedures described in Example 1 with substitution of 4-bromo-2-chlorobenzoic acid for 2-trifluoromethoxybenzoic acid at Step A. MS (ESI) 290 (M+H).

Step B. Preparation of N,N-diethyl-2-chloro-4-ethenylbenzamide

Prepared according to procedures described in Example 122 Step B with substitution of N,N-diethyl-4-bromo-2-chlorobenzamide for N,N-diethyl-4-bromo-2-trifluoromethoxybenzamide. MS (ESI) 238 (M+H).

Step C. Preparation of N,N-diethyl-2-chloro-4-ethylbenzamide

Prepared according to procedures described in Example 100 Step A. MS (ESI) 240 (M−Cl).

Step D. Preparation of (R)-1,3,4,10b-tetrahydro-7-chloro-9-ethyl-pyrazino[2,1-a]isoindol-6(2H)-one hydrochloric acid and (S)-1,3,4,10b-tetrahydro-7-chloro-9-ethyl-pyrazino[2,1-a]isoindol-6(2H)-one hydrochloric acid Prepared according to procedures described in Example 43 with substitution of N,N-diethyl-2-chloro-4-ethylbenzamide for N,N-diethyl-2-chlorobenzamide at Step A followed by the separation of enantiomers according to the procedures described in Example 128 Step D. MS (ESI) 251 (M−Cl).

Examples 139 and 140

Preparation of (R)-1,3,4,10b-tetrahydro-7-chloro-9-propyl-pyrazino[2,1-a]isoindol-6(2H)-one hydrochloric acid and (S)-1,3,4,10b-tetrahydro-7-chloro-9-propyl-pyrazino[2,1-a]isoindol-6(2H)-one hydrochloric acid

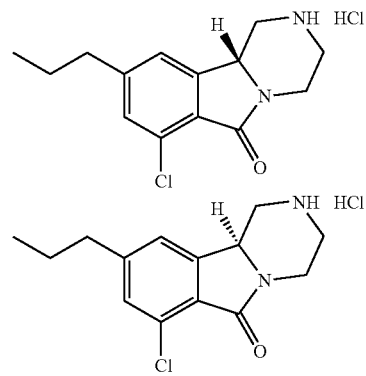

Prepared according to procedures described in Example 137 with substitution of 1-cis-propenylboronic acid for 2,4,6-trivinylcyclotriboroxane pyridine complex at Step B. MS (ESI) 265 (M−Cl).

Examples 141 and 142

Preparation of (R)-1,3,4,10b-tetrahydro-7-methylthio-9-propyl-pyrazino[2,1-a]isoindol-6(2H)-one hydrochloric acid and (S)-1,3,4,10b-tetrahydro-7-methylthio-9-propyl-pyrazino[2,1-a]isoindol-6(2H)-one hydrochloric acid

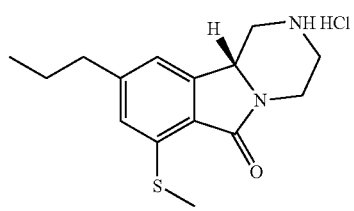

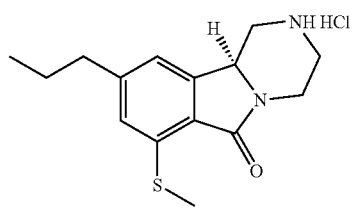

Step A. Preparation of N,N-diethyl-2-methylthio-4-propylbenzamide

To a stirring solution of N,N-diethyl-4-propylbenzamide (2.0 g, 9.3 mmol) and N,N,N',N'-tetramethylethylenediamine (1085 mg, 9.4 mmol) in dry THF (93 mL) at −78° C. under Ar was added 0.78 M s-butyllithium in hexanes (12 mL). The reaction was stirred for 30 min and then methyl disulfide (1936 mg, 12.1 mmol) was added. The reaction was stirred for 5 min and then quenched with MeOH (1 mL) and brine. The reaction was extracted with EtOAc (3×50 mL). The organic layers were combined, dried over $Na_2SO_4$, and conc in vacuo to a yellow oil. The oil was purified by flash chromatography (SiO2, 0-30% EtOAc in hexanes) to yield 2.1 g (86%) of the product as a yellow oil. MS (ESI) 266 (M+H).

Step B. Preparation of (R)-1,3,4,10b-tetrahydro-7-methylthio-9-propyl-pyrazino[2,1-a]isoindol-6(2H)-one hydrochloric acid and (S)-1,3,4,10b-tetrahydro-7-methylthio-9-propyl-pyrazino[2,1-a]isoindol-6(2H)-one hydrochloric acid Prepared according to procedures described in Example 43 with substitution of N,N-diethyl-2-methylthio-4-propylbenzamide for N,N-diethyl-2-chlorobenzamide at Step A followed by the separation of enantiomers according to the procedures described in Example 128 Step D. MS (ESI) 277 (M−Cl).

Examples 143 and 144

Preparation of (R)-1,3,4,10b-tetrahydro-9-ethyl-7-methylthio-pyrazino[2,1-a]isoindol-6(2H)-one hydrochloric acid and (S)-1,3,4,10b-tetrahydro-9-ethyl-7-methylthio-pyrazino[2,1-a]isoindol-6(2H)-one hydrochloric acid

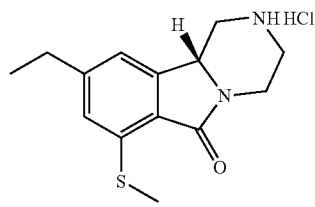

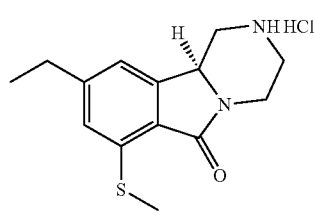

Prepared according to procedures described in Example 141 with substitution of N,N-diethyl-4-ethylbenzamide for N,N-diethyl-4-propylbenzamide at Step A. MS (ESI) 263 (M−Cl).

Examples 145 and 146

Preparation of (R)-1,3,4,10b-tetrahydro-9-ethyl-7-isopropylthio-pyrazino[2,1-a]isoindol-6(2H)-one hydrochloric acid and (S)-1,3,4,10b-tetrahydro-9-ethyl-7-methylthio-pyrazino[2,1-a]isoindol-6(2H)-one hydrochloric acid

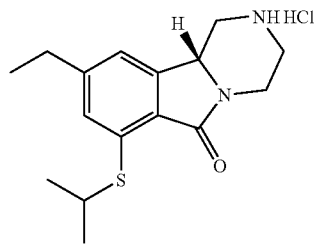

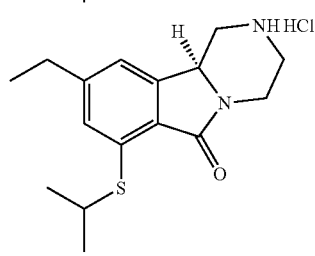

Prepared according to procedures described in Example 141 with substitution of N,N-diethyl-4-ethylbenzamide for N,N-diethyl-4-propylbenzamide and isopropyl disulfide for methyl disulfide at Step A. MS (ESI) 291 (M−Cl).

Examples 147 and 148

Preparation of (R)-1,3,4,10b-tetrahydro-9-ethyl-7-ethylthio-pyrazino[2,1-a]isoindol-6(2H)-one hydrochloric acid and (S)-1,3,4,10b-tetrahydro-9-ethyl-7-ethylthio-pyrazino[2,1-a]isoindol-6(2H)-one hydrochloric acid

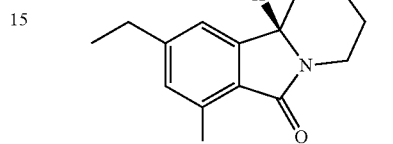

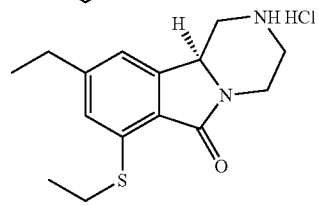

Prepared according to procedures described in Example 141 with substitution of N,N-diethyl-4-ethylbenzamide for N,N-diethyl-4-propylbenzamide and ethyl disulfide for methyl disulfide at Step A. MS (ESI) 277 (M−Cl).

Example 149

Preparation of (R)-1,3,4,10b-tetrahydro-9-ethyl-7-methylsulfonyl-pyrazino[2,1-a]isoindol-6(2H)-one hydrochloric acid

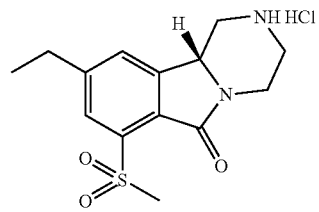

Step A. Preparation of N-(t-butoxycarbonyl)-(R)-1,3,4,10b-tetrahydro-9-ethyl-7-methylsulfonyl-pyrazino[2,1-a]isoindol-6(2H)-one To a stirring solution of N-(t-butoxycarbonyl)-(R)-1,3,4,10b-tetrahydro-9-ethyl-7-methylthio-pyrazino[2,1-a]isoindol-6(2H)-one (42 mg, 0.12 mmol) in dry MeOH (0.75 mL) and water (0.75 mL) was added oxone (93 mg, 0.15 mmol). The reaction was stirred for 4 h and then diluted with water. The reaction was extracted with EtOAc (3×5 mL). The organic layers were combined, dried over $Na_2SO_4$, and conc in vacuo to a yellow oil. The oil was purified by flash chromatography (SiO2, 0-50% EtOAc in hexanes) to yield 38 mg (84%) of the product as a colorless oil. MS (ESI) 395 (M+H).

Step B. Preparation of (R)-1,3,4,10b-tetrahydro-9-ethyl-7-methylsulfonyl-pyrazino[2,1-a]isoindol-6(2H)-one hydrochloric acid Prepared according to procedures described in Example 10 in Step B. MS (ESI) 295 (M–Cl).

Example 150

Preparation of (R)-1,3,4,10b-tetrahydro-7-chloro-9-hydroxy-pyrazino[2,1-a]isoindol-6(2H)-one hydrochloric acid

Prepared according to procedures described in Example 128 Step A with substitution of N-(t-butoxycarbonyl)-(R)-1,3,4,10b-tetrahydro-7-chloro-9-methoxy-pyrazino[2,1-a]isoindol-6(2H)-one, produced by procedures described in Example 126 with the substitution of N,N-diethyl-4-bromo-2-chlorobenzamide for N,N-diethyl-4-bromo-2-trifluoromethoxybenzamide, for N-(t-butoxycarbonyl)-(±)-1,3,4,10b-tetrahydro-9-methoxy-7-trifluoromethoxy-pyrazino[2,1-a] isoindol-6(2H)-one. Followed by the separation of enantiomers according to the procedures described in Example 128 Step D. MS (ESI) 239 (M–Cl).

Example 151

Preparation of (R)-1,3,4,10b-tetrahydro-7-chloro-9-cyclopropyl-pyrazino[2,1-a]isoindol-6(2H)-one hydrochloric acid

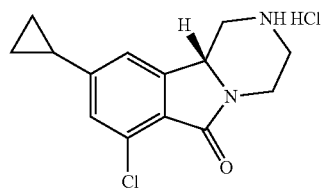

Prepared according to procedures described in Example 128 Steps B-D with substitution of N-(t-butoxycarbonyl)-(R)-1,3,4,10b-tetrahydro-7-chloro-9-hydroxy-pyrazino[2,1-a]isoindol-6(2H)-one for N-(t-butoxycarbonyl)-(±)-1,3,4,10b-tetrahydro-9-hydroxy-7-trifluoromethoxy-pyrazino[2,1-a]isoindol-6(2H)-one in Step B. MS (ESI) 263 (M–Cl).

Example 152

Preparation of (R)-1,3,4,10b-tetrahydro-7-chloro-9-ethenyl-pyrazino[2,1-a]isoindol-6(2H)-one hydrochloric acid

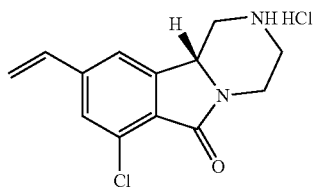

Prepared according to procedures described in Example 151 with substitution of 2,4,6-trivinylcyclotriboroxane pyridine complex for 2-cyclopropyl-4,4,5,5-tetramethyl-1,3,2-dioxaborolane in Step B. MS (ESI) 249 (M–Cl).

Example 153

Preparation of (R)-1,3,4,10b-tetrahydro-7-chloro-9-methyl-pyrazino[2,1-a]isoindol-6(2H)-one hydrochloric acid

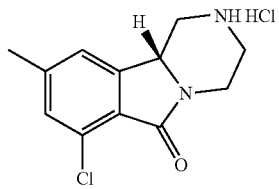

Prepared according to procedures described in Example 151 with substitution of 2,4,6-trimethylcyclotriboroxane pyridine complex for 2-cyclopropyl-4,4,5,5-tetramethyl-1,3,2-dioxaborolane in Step B. MS (ESI) 237 (M–Cl).

Example 154

Preparation of (R)-1,3,4,10b-tetrahydro-7-chloro-9-isopropyl-pyrazino[2,1-a]isoindol-6(2H)-one hydrochloric acid

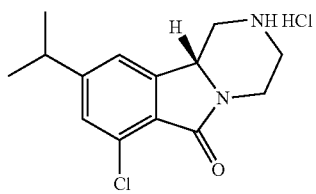

Prepared according to procedures described in Example 130 with substitution of N-(t-butoxycarbonyl)-(R)-1,3,4,10b-tetrahydro-7-chloro-9-trifluoromethylsulfonyloxy-pyrazino[2,1-a]isoindol-6(2H)-one for N-(t-butoxycarbonyl)-(±)-1,3,4,10b-tetrahydro-7-trifluoromethoxy-9-trifluoromethylsulfonyloxy-pyrazino[2,1-a]isoindol-6(2H)-one in Step A. MS (ESI) 265 (M–Cl).

Example 155

Preparation of (R)-1,3,4,10b-tetrahydro-7-chloro-9-ethoxy-pyrazino[2,1-a]isoindol-6(2H)-one hydrochloric acid

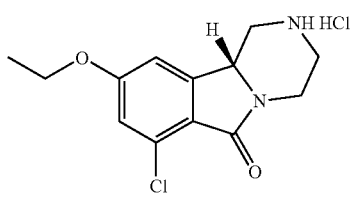

Prepared according to procedures described in Example 115 with substitution of N-(t-butoxycarbonyl)-(R)-1,3,4,10b-tetrahydro-7-chloro-9-hydroxy-pyrazino[2,1-a]isoindol-6(2H)-one for N-(t-butoxycarbonyl)-(R)-1,3,4,10b-tetrahydro-9-hydroxy-7-trifluoromethyl-pyrazino[2,1-a]isoindol-6(2H)-one and ethyl iodide for methyl iodide in Step A. MS (ESI) 267 (M–Cl).

Example 156

Preparation of (R)-1,3,4,10b-tetrahydro-7-chloro-9-cyclobutylmethoxy-pyrazino[2,1-a]isoindol-6(2H)-one hydrochloric acid

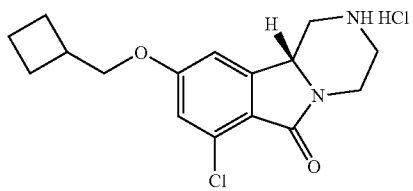

Prepared according to procedures described in Example 115 with substitution of N-(t-butoxycarbonyl)-(R)-1,3,4,10b-tetrahydro-7-chloro-9-hydroxy-pyrazino[2,1-a]isoindol-6(2H)-one for N-(t-butoxycarbonyl)-(R)-1,3,4,10b-tetrahydro-9-hydroxy-7-trifluoromethyl-pyrazino[2,1-a]isoindol-6(2H)-one and cyclobutylmethyl iodide for methyl iodide in Step A. MS (ESI) 307 (M–Cl).

Example 157

Preparation of (R)-1,3,4,10b-tetrahydro-7-chloro-9-cyclopropylmethoxy-pyrazino[2,1-a]isoindol-6(2H)-one hydrochloric acid

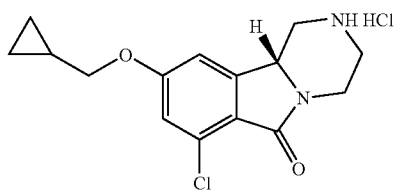

Prepared according to procedures described in Example 115 with substitution of N-(t-butoxycarbonyl)-(R)-1,3,4,10b-tetrahydro-7-chloro-9-hydroxy-pyrazino[2,1-a]isoindol-6(2H)-one for N-(t-butoxycarbonyl)-(R)-1,3,4,10b-tetrahydro-9-hydroxy-7-trifluoromethyl-pyrazino[2,1-a]isoindol-6(2H)-one and cyclopropylmethyl iodide for methyl iodide in Step A. MS (ESI) 293 (M–Cl).

Examples 158 and 159

Preparation of (R)-1,3,4,10b-tetrahydro-9-ethyl-7-methoxy-pyrazino[2,1-a]isoindol-6(2H)-one hydrochloric acid and (S)-1,3,4,10b-tetrahydro-9-ethyl-7-methoxy-pyrazino[2,1-a]isoindol-6(2H)-one hydrochloric acid

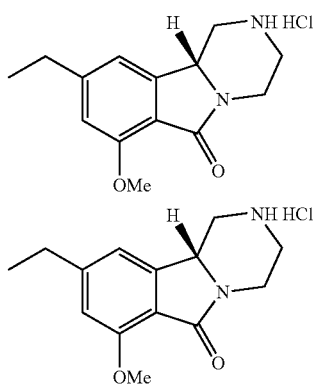

Step A. Preparation of N,N-diethyl-4-chloro-2-methoxybenzamide

Prepared according to procedures described in Example 1 Step A with substitution of 4-chloro-2-methoxybenzoic acid for 2-trifluoromethoxybenzoic acid.

MS (ESI) 290 (M+H).

Step B. Preparation of N,N-diethyl-4-ethenyl-2-methoxybenzamide

To a stirring degassed solution of N,N-diethyl-4-chloro-2-methoxybenzamide (65 mg, 0.35 mmol), potassium fluoride (134 mg, 2.3 mmol), and 2,4,6-trivinylcyclotriboroxane pyridine complex (132 mg, 0.35 mmol) in 1,4-dioxane (3 mL) was added bis(tri-t-butylphosphine)palladium (5 mg, 0.01 mmol). The reaction was heated to reflux for 5 h and then cooled to room temperature. The reaction was diluted with brine and extracted with EtOAc (3×5 mL). The organic layers were combined, dried over $Na_2SO_4$, and conc. in vacuo to a pale yellow oil. The oil was purified by flash chromatography ($SiO_2$, 0-50% EtOAc in hexanes) to give 40 mg of the desired product as a colorless oil. MS (ESI) 234 (M+H).

Step C. Preparation of N,N-diethyl-4-ethyl-2-methoxybenzamide

Prepared according to procedures described in Example 100 at Step A. MS (ESI) 240 (M–Cl).

Step D. Preparation of (R)-1,3,4,10b-tetrahydro-9-ethyl-7-methoxy-pyrazino[2,1-a]isoindol-6(2H)-one hydrochloric acid and (S)-1,3,4,10b-tetrahydro-9-ethyl-7-methoxy-pyrazino[2,1-a]isoindol-6(2H)-one hydrochloric acid Prepared according to procedures described in Example 1 Steps B-D with substitution of N,N-diethyl-4-ethyl-2-methoxybenzamide for N,N-diethyl-2-trifluoromethoxybenzamide at Step B followed by the separation of enantiomers according to the procedures described in Example 2 with the modification of 35% 1:1 MeOH:EtOH for 20% 1:1 MeOH:EtOH. MS (ESI) 247 (M−Cl).

Examples 161 and 162

Preparation of (R)-1,3,4,10b-tetrahydro-9-ethyl-7-hydroxy-pyrazino[2,1-a]isoindol-6(2H)-one hydrochloric acid and (S)-1,3,4,10b-tetrahydro-9-ethyl-7-hydroxy-pyrazino[2,1-a]isoindol-6(2H)-one hydrochloric acid

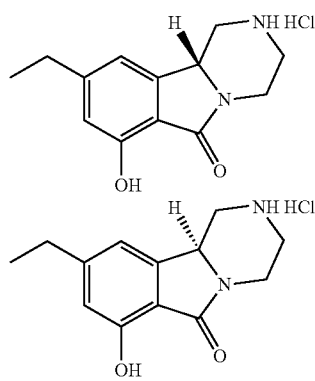

Prepared according to procedures described in Example 128 Step A with substitution of N-(t-butoxycarbonyl)-(±)-1,3,4,10b-tetrahydro-9-ethyl-7-methoxy-pyrazino[2,1-a]isoindol-6(2H)-one for N-(t-butoxycarbonyl)-(±)-1,3,4,10b-tetrahydro-9-methoxy-7-trifluoromethoxy-pyrazino[2,1-a]isoindol-6(2H)-one. Followed by the separation of enantiomers according to the procedures described in Example 128 Step D. MS (ESI) 233 (M−Cl).

Examples 163 and 164

Preparation of (R)-1,3,4,10b-tetrahydro-7-ethoxy-9-ethyl-pyrazino[2,1-a]isoindol-6(2H)-one hydrochloric acid and (S)-1,3,4,10b-tetrahydro-7-ethoxy-9-ethyl-pyrazino[2,1-a]isoindol-6(2H)-one hydrochloric acid

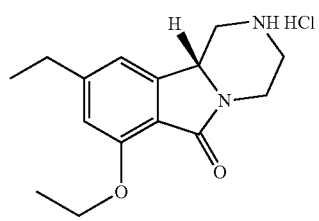

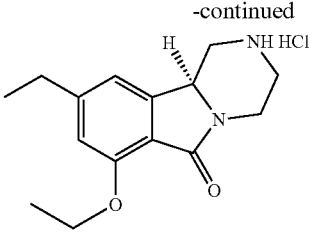

Prepared according to procedures described in Example 115 with substitution of N-(t-butoxycarbonyl)-(R)-1,3,4,10b-tetrahydro-9-ethyl-7-hydroxy-pyrazino[2,1-a]isoindol-6(2H)-one for N-(t-butoxycarbonyl)-(R)-1,3,4,10b-tetrahydro-9-hydroxy-7-trifluoromethyl-pyrazino[2,1-a]isoindol-6(2H)-one and ethyl iodide for methyl iodide in Step A. Followed by the separation of enantiomers according to the procedures described in Example 128 Step D. MS (ESI) 261 (M−Cl).

Examples 165 and 166

Preparation of (R)-1,3,4,10b-tetrahydro-9-ethyl-7-isopropoxy-pyrazino[2,1-a]isoindol-6(2H)-one hydrochloric acid and (S)-1,3,4,10b-tetrahydro-9-ethyl-7-isopropoxy-pyrazino[2,1-a]isoindol-6(2H)-one hydrochloric acid

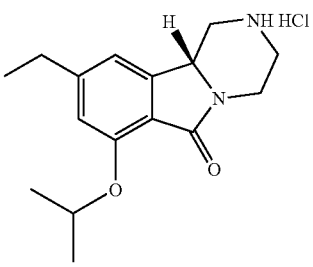

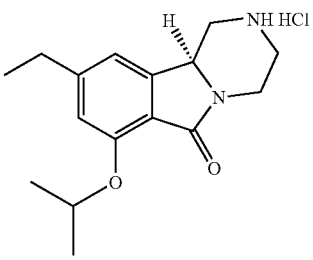

Prepared according to procedures described in Example 115 with substitution of N-(t-butoxycarbonyl)-(R)-1,3,4,10b-tetrahydro-9-ethyl-7-hydroxy-pyrazino[2,1-a]isoindol-6(2H)-one for N-(t-butoxycarbonyl)-(R)-1,3,4,10b-tetrahydro-9-hydroxy-7-trifluoromethyl-pyrazino[2,1-a]isoindol-6(2H)-one and isopropyl iodide for methyl iodide in Step A. Followed by the separation of enantiomers according to the procedures described in Example 128 Step D. MS (ESI) 261 (M−Cl).

Examples 167 and 168

Preparation of (R)-1,3,4,10b-tetrahydro-7-cyclopropyl-9-ethyl-pyrazino[2,1-a]isoindol-6(2H)-one hydrochloric acid and (S)-1,3,4,10b-tetrahydro-7-cyclopropyl-9-ethyl-pyrazino[2,1-a]isoindol-6(2H)-one hydrochloric acid

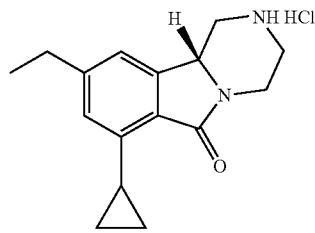

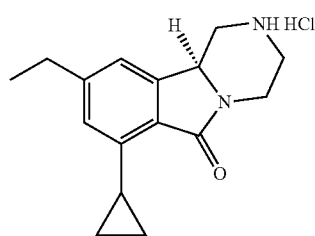

Prepared according to procedures described in Example 128 Steps B-D with substitution of N-(t-butoxycarbonyl)-(±)-1,3,4,10b-tetrahydro-9-ethyl-7-hydroxy-pyrazino[2,1-a]isoindol-6(2H)-one for N-(t-butoxycarbonyl)-(±)-1,3,4,10b-tetrahydro-9-hydroxy-7-trifluoromethoxy-pyrazino[2,1-a]isoindol-6(2H)-one in Step B. MS (ESI) 257 (M–Cl).

Examples 169 and 170

Preparation of (R)-1,3,4,10b-tetrahydro-9-ethyl-7-methyl-pyrazino[2,1-a]isoindol-6(2H)-one hydrochloric acid and (S)-1,3,4,10b-tetrahydro-9-ethyl-7-methyl-pyrazino[2,1-a]isoindol-6(2H)-one hydrochloric acid

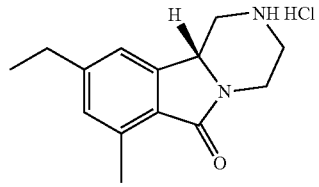

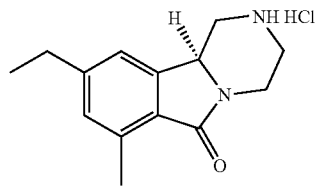

Prepared according to procedures described in Example 167 with substitution of 2,4,6-trimethylcyclotriboroxane pyridine complex for 2-cyclopropyl-4,4,5,5-tetramethyl-1,3,2-dioxaborolane in Step B. MS (ESI) 237 (M–Cl).

Examples 171 and 172

Preparation of (R)-1,3,4,10b-tetrahydro-9-ethyl-7-isopropyl-pyrazino[2,1-a]isoindol-6(2H)-one hydrochloric acid and (S)-1,3,4,10b-tetrahydro-9-ethyl-7-isopropyl-pyrazino[2,1-a]isoindol-6(2H)-one hydrochloric acid

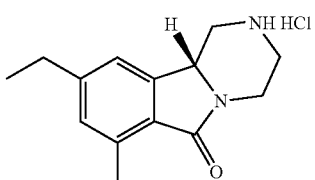

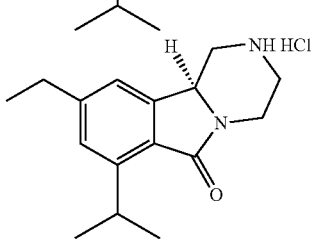

Prepared according to procedures described in Example 130 with substitution of N-(t-butoxycarbonyl)-(±)-1,3,4,10b-tetrahydro-9-ethyl-7-trifluoromethylsulfonyloxy-pyrazino[2,1-a]isoindol-6(2H)-one for N-(t-butoxycarbonyl)-(±)-1,3,4,10b-tetrahydro-7-trifluoromethoxy-9-trifluoromethylsulfonyloxy-pyrazino[2,1-a]isoindol-6(2H)-one in Step A. MS (ESI) 259 (M–Cl).

Examples 173 and 174

Preparation of (R)-1,3,4,10b-tetrahydro-7,9-diethyl-pyrazino[2,1-a]isoindol-6(2H)-one hydrochloric acid and (S)-1,3,4,10b-tetrahydro-7,9-diethyl-pyrazino[2,1-a]isoindol-6(2H)-one hydrochloric acid

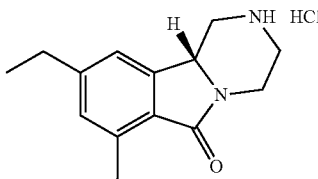

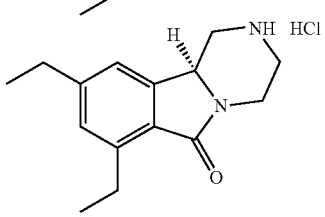

Prepared according to procedures described in Example 130 with substitution of N-(t-butoxycarbonyl)-(±)-1,3,4,10b-tetrahydro-9-ethyl-7-trifluoromethylsulfonyloxy-pyrazino

[2,1-a]isoindol-6(2H)-one for N-(t-butoxycarbonyl)-(±)-1,3,4,10b-tetrahydro-7-trifluoromethoxy-9-trifluoromethylsulfonyloxy-pyrazino[2,1-a]isoindol-6(2H)-one and 2,4,6-trivinylcyclotriboroxane pyridine complex for isopropenyl boronic acid in Step A.

MS (ESI) 245 (M−Cl).

Examples 175 and 176

Preparation of (R)-1,3,4,10b-tetrahydro-9-ethyl-7-propyl-pyrazino[2,1-a]isoindol-6(2H)-one hydrochloric acid and (S)-1,3,4,10b-tetrahydro-9-ethyl-7-propyl-pyrazino[2,1-a]isoindol-6(2H)-one hydrochloric acid

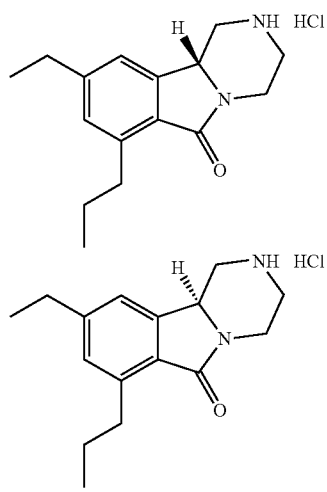

Prepared according to procedures described in Example 130 with substitution of N-(t-butoxycarbonyl)-(±)-1,3,4,10b-tetrahydro-9-ethyl-7-trifluoromethylsulfonyloxy-pyrazino[2,1-a]isoindol-6(2H)-one for N-(t-butoxycarbonyl)-(±)-1,3,4,10b-tetrahydro-7-trifluoromethoxy-9-trifluoromethylsulfonyloxy-pyrazino[2,1-a]isoindol-6(2H)-one and 1-cispropenylboronic acid for isopropenyl boronic acid in Step A. MS (ESI) 259 (M−Cl).

Examples 177 and 178

Preparation of (R)-1,3,4,10b-tetrahydro-9-ethyl-7-(2-methylpropyl)-pyrazino[2,1-a]isoindol-6(2H)-one hydrochloric acid and (S)-1,3,4,10b-tetrahydro-9-ethyl-7-(2-methylpropyl)-pyrazino[2,1-a]isoindol-6(2H)-one hydrochloric acid

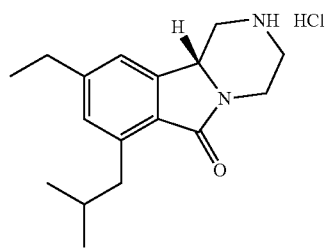

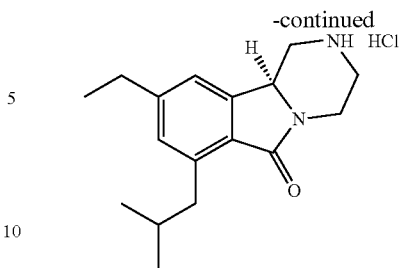

Prepared according to procedures described in Example 130 with substitution of N-(t-butoxycarbonyl)-(±)-1,3,4,10b-tetrahydro-9-ethyl-7-trifluoromethylsulfonyloxy-pyrazino[2,1-a]isoindol-6(2H)-one for N-(t-butoxycarbonyl)-(±)-1,3,4,10b-tetrahydro-7-trifluoromethoxy-9-trifluoromethylsulfonyloxy-pyrazino[2,1-a]isoindol-6(2H)-one and 2,2-dimethylethenylboronic acid for isopropenyl boronic acid in Step A. MS (ESI) 273 (M−Cl).

Examples 179 and 180

Preparation of (R)-1,3,4,10b-tetrahydro-7-cyclopentyl-9-ethyl-pyrazino[2,1-a]isoindol-6(2H)-one hydrochloric acid and (S)-1,3,4,10b-tetrahydro-7-cyclopentyl-9-ethyl-(2-methylpropyl)-pyrazino[2,1-a]isoindol-6(2H)-one hydrochloric acid

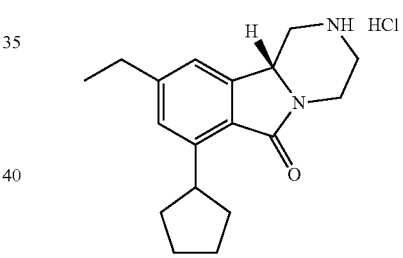

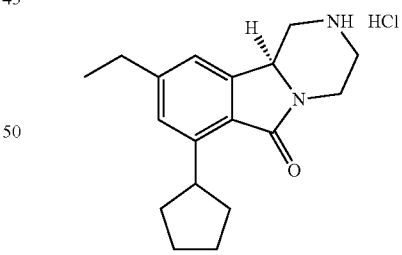

Prepared according to procedures described in Example 130 with substitution of N-(t-butoxycarbonyl)-(±)-1,3,4,10b-tetrahydro-9-ethyl-7-trifluoromethylsulfonyloxy-pyrazino[2,1-a]isoindol-6(2H)-one for N-(t-butoxycarbonyl)-(±)-1,3,4,10b-tetrahydro-7-trifluoromethoxy-9-trifluoromethylsulfonyloxy-pyrazino[2,1-a]isoindol-6(2H)-one and 1-cyclopentenylboronic acid for isopropenyl boronic acid in Step A. MS (ESI) 285 (M−Cl).

Examples 181 and 182

Preparation of (R)-1,3,4,10b-tetrahydro-7-cyclohexyl-9-ethyl-pyrazino[2,1-a]isoindol-6(2H)-one hydrochloric acid and (S)-1,3,4,10b-tetrahydro-7-cyclohexyl-9-ethyl-(2-methylpropyl)-pyrazino[2,1-a]isoindol-6(2H)-one hydrochloric acid

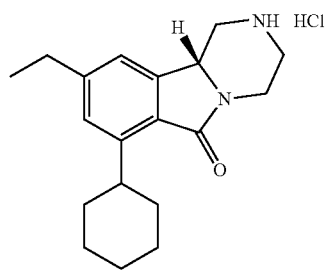

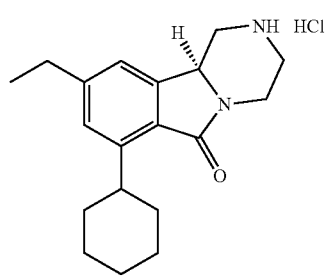

Prepared according to procedures described in Example 130 with substitution of N-(t-butoxycarbonyl)-(±)-1,3,4,10b-tetrahydro-9-ethyl-7-trifluoromethylsulfonyloxy-pyrazino[2,1-a]isoindol-6(2H)-one for N-(t-butoxycarbonyl)-(±)-1,3,4,10b-tetrahydro-7-trifluoromethoxy-9-trifluoromethylsulfonyloxy-pyrazino[2,1-a]isoindol-6(2H)-one and 1-cyclohexenylboronic acid for isopropenyl boronic acid in Step A. MS (ESI) 298 (M−Cl).

Examples 183 and 184

Preparation of (R)-1,3,4,10b-tetrahydro-9-ethyl-7-hydroxymethyl-pyrazino[2,1-a]isoindol-6(2H)-one hydrochloric acid and (S)-1,3,4,10b-tetrahydro-9-ethyl-7-hydroxymethyl-pyrazino[2,1-a]isoindol-6(2H)-one hydrochloric acid

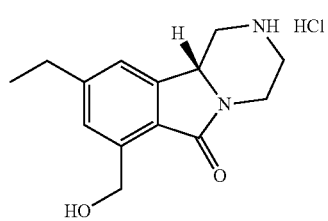

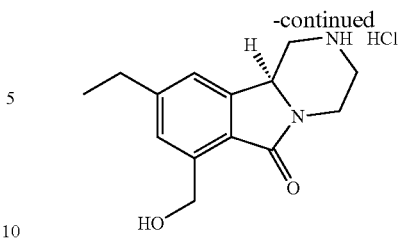

Prepared according to procedures described in Example 111 Step A with substitution of N-(t-butoxycarbonyl)-(±)-1,3,4,10b-tetrahydro-7-ethenyl-9-ethyl-pyrazino[2,1-a]isoindol-6(2H)-one for N-(t-butoxycarbonyl)-(R)-1,3,4,10b-tetrahydro-9-(cis-1-propenyl)-7-trifluoromethyl-pyrazino[2,1-a]isoindol-6(2H)-one. Followed by the separation of enantiomers according to the procedures described in Example 128 Step D. MS (ESI) 247 (M−Cl).

Examples 185 and 186

Preparation of (R)-1,3,4,10b-tetrahydro-9-chloro-7-trifluoromethyl-pyrazino[2,1-a]isoindol-6(2H)-one hydrochloric acid salt and (S)-1,3,4,10b-tetrahydro-9-chloro-7-trifluoromethyl-pyrazino[2,1-a]isoindol-6(2H)-one hydrochloric acid salt

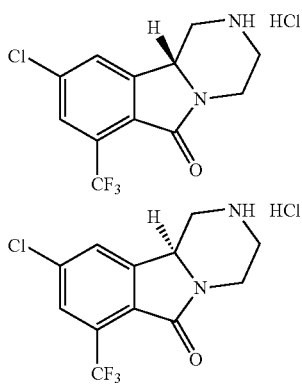

Step A. Preparation of N-(t-butoxycarbonyl)-(±)-1,3,4,10b-tetrahydro-9-chloro-7-trifluoromethyl-pyrazino[2,1-a]isoindol-6(2H)-one To a stirring degassed solution of N-(t-butoxycarbonyl)-(±)-1,3,4,10b-tetrahydro-9-bromo-7-trifluoromethyl-pyrazino[2,1-a]isoindol-6(2H)-one (464 mg, 1.1 mmol) in dry DMF (5 mL) was added copper(I) chloride (211 mg, 2.1 mmol). The reaction was heated to reflux for 4 h and then cooled to room temp. The reaction was treated with di-t-butyl dicarbonate (350 mg, 1.6 mmol). The reaction was stirred for 1 h and then quenched with 9:1 sat. NH4Cl:NH4OH. After 15 min., the reaction was extracted with EtOAc (3×10 mL). The organic layers were combined, dried over $Na_2SO_4$, and conc. in vacuo to a brown oil. The oil was purified by flash chromatography (silica gel, 0-50% EtOAc in hexanes) to yield 140 mg of the desired product as a colorless oil. MS (ESI) 391 (M+H).

Step B. Preparation of (R)-1,3,4,10b-tetrahydro-9-chloro-7-trifluoromethyl-pyrazino[2,1-a]isoindol-6(2H)-one hydrochloric acid salt and (S)-1,3,4,10b-tetrahydro-9-chloro-7-trifluoromethyl-pyrazino[2,1-a]isoindol-6(2H)-one hydrochloric acid salt Prepared according to procedures described in Example 128 Step D with substitution of N-(t-butoxycarbonyl)-(±)-1,3,4,10b-tetrahydro-9-chloro-7-trifluoromethyl-pyrazino[2,1-a]isoindol-6(2H)-one for N-(t-butoxycarbonyl)-(±)-1,3,4,10b-tetrahydro-9-cyclopropyl-7-trifluoromethoxy-pyrazino[2,1-a]isoindol-6(2H)-one. MS (ESI) 291 (M−Cl).

Example 187

Preparation of (R)-1,3,4,10b-tetrahydro-8-bromo-7-trifluoromethoxy-pyrazino[2,1-a]isoindol-6(2H)-one hydrochloric acid salt

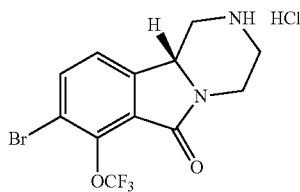

Prepared according to procedures described in Example 11 with substitution of N-(t-butoxycarbonyl)-(±)-1,3,4,10b-tetrahydro-7-trifluoromethoxy-pyrazino[2,1-a]isoindol-6(2H)-one for N-(t-butoxycarbonyl)-(±)-1,3,4,10b-tetrahydro-7-trifluoromethyl-pyrazino[2,1-a]isoindol-6(2H)-one. MS (ESI) 351 (M−Cl).

Examples 188 and 189

Preparation of (R)-1,3,4,10b-tetrahydro-7,9-ditrifluoromethyl-pyrazino[2,1-a]isoindol-6(2H)-one hydrochloric acid salt and (S)-1,3,4,10b-tetrahydro-7,9-ditrifluoromethyl-pyrazino[2,1-a]isoindol-6(2H)-one hydrochloric acid salt

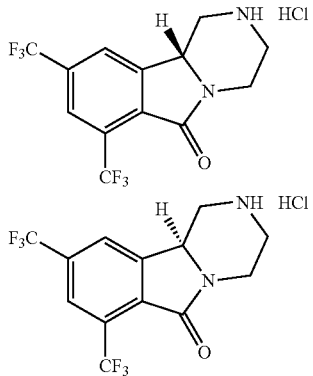

Prepared according to procedures described in Example 43 with substitution of 2,4-ditrifluoromethylbenzoic acid for 2-chlorobenzoic acid followed by separation of enantiomers according to the procedures described in Example 2 with substitution of AD column with 85% heptane with 0.1% diethylamine and 15% 1:1 MeOH:EtOH with 0.1% diethylamine for OD column with 80% heptane with 0.1% diethylamine and 20% 1:1 MeOH:EtOH with 0.1% diethylamine. MS (ESI) 325 (M−Cl).

Examples 190 and 191

Preparation of (R)-1,3,4,10b-tetrahydro-10-chloro-7-methoxy-pyrazino[2,1-a]isoindol-6(2H)-one hydrochloric acid salt and (S)-1,3,4,10b-tetrahydro-10-chloro-7-methoxy-pyrazino[2,1-a]isoindol-6(2H)-one hydrochloric acid salt

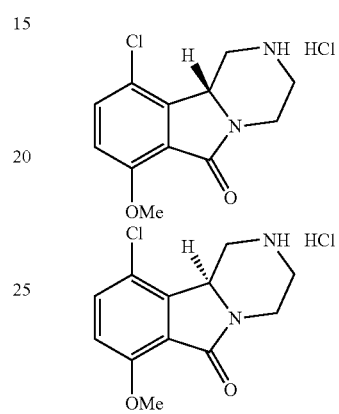

Prepared according to procedures described in Example 43 with substitution of 5-chloro-2-methoxybenzoic acid for 2-chlorobenzoic acid followed by separation of enantiomers according to the procedures described in Example 2. MS (ESI) 253 (M−Cl).

Examples 192 and 193

Preparation of (R)-1,3,4,10b-tetrahydro-7,8-dichloro-pyrazino[2,1-a]isoindol-6(2H)-one hydrochloric acid salt and (S)-1,3,4,10b-tetrahydro-7,8-dichloro-pyrazino[2,1-a]isoindol-6(2H)-one hydrochloric acid salt

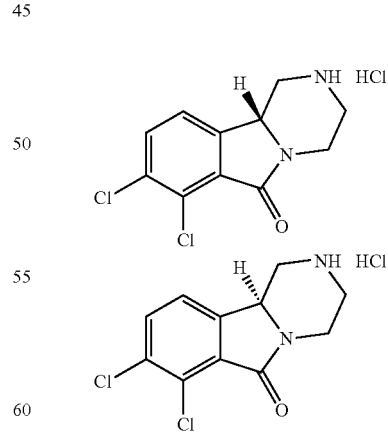

Prepared according to procedures described in Example 43 with substitution of 2,3-dichlorobenzoic acid for 2-chlorobenzoic acid followed by separation of enantiomers according to the procedures described in Example 2. MS (ESI) 257 (M−Cl).

Examples 194 and 195

Preparation of (R)-1,3,4,10b-tetrahydro-8-chloro-7-methoxy-pyrazino[2,1-a]isoindol-6(2H)-one hydrochloric acid salt and (S)-1,3,4,10b-tetrahydro-8-chloro-7-methoxy-pyrazino[2,1-a]isoindol-6(2H)-one hydrochloric acid salt

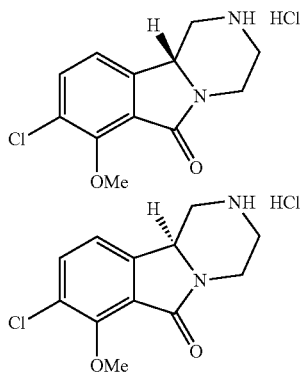

Step A. Preparation of N,N-diethyl-3-chloro-2-hydroxybenzamide

To a stirring solution of 3-chloro-2-hydroxybenzoic acid (7.2 g, 42 mmol) and diethyl amine (15.2 g, 209 mmol) in dry $CH_2Cl_2$ (200 mL) was added benzotriazol-1-yloxy tripyrrolidinophosphonium hexafluorophosphate (22.8 g, 44 mmol) in dry $CH_2Cl_2$ (200 mL). The reaction was stirred overnight and then quenched with 6M HCl. The layers were separated and the aqueous layer was extracted with EtOAc (3×100 mL). The organic layers were combined, dried over $Na_2SO_4$, and conc. in vacuo to a brown oil. The oil was purified by flash chromatography (silica gel, 0-50% EtOAc in hexanes) to yield 7.6 g of the desired product as a reddish oil.

MS (ESI) 228 (M+H).

Step B. Preparation of N,N-diethyl-3-chloro-2-methoxybenzamide

Prepared according to procedures described in Example 115 Step A with substitution of N,N-diethyl-3-chloro-2-hydroxybenzamide for N-(t-butoxycarbonyl)-(R)-1,3,4,10b-tetrahydro-9-hydroxy-7-trifluoromethyl-pyrazino[2,1-a]isoindol-6(2H)-one. MS (ESI) 242 (M+H).

Step C. Preparation of (R)-1,3,4,10b-tetrahydro-8-chloro-7-methoxy-pyrazino[2,1-a]isoindol-6(2H)-one hydrochloric acid salt and (S)-1,3,4,10b-tetrahydro-8-chloro-7-methoxy-pyrazino[2,1-a]isoindol-6(2H)-one hydrochloric acid salt Prepared according to procedures described in Example 43 with substitution of N,N-diethyl-3-chloro-2-methoxybenzamide for N,N-diethyl-2-chlorobenzamide followed by separation of enantiomers according to the procedures described in Example 2. MS (ESI) 253 (M−Cl).

Examples 196 and 197

Preparation of (R)-1,3,4,10b-tetrahydro-8-ethyl-7-methoxy-pyrazino[2,1-a]isoindol-6(2H)-one hydrochloric acid salt and (S)-1,3,4,10b-tetrahydro-8-ethyl-7-methoxy-pyrazino[2,1-a]isoindol-6(2H)-one hydrochloric acid salt

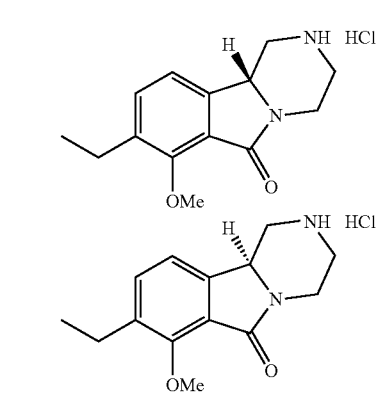

Step A. Preparation of N-(t-butoxycarbonyl)-(±)-1,3,4,10b-tetrahydro-8-ethyl-7-methoxy-pyrazino[2,1-a]isoindol-6(2H)-one Prepared according to procedures described in Example 158 Step B-C with substitution of N-(t-butoxycarbonyl)-(±)-1,3,4,10b-tetrahydro-8-chloro-7-methoxy-pyrazino[2,1-a]isoindol-6(2H)-one for N,N-diethyl-4-chloro-2-methoxybenzamide in Step B. MS (ESI) 347 (M+H).

Step B. Preparation of (R)-1,3,4,10b-tetrahydro-8-ethyl-7-methoxy-pyrazino[2,1-a]isoindol-6(2H)-one hydrochloric acid salt and (S)-1,3,4,10b-tetrahydro-8-ethyl-7-methoxy-pyrazino[2,1-a]isoindol-6(2H)-one hydrochloric acid salt Prepared according to procedures described in Example 128 Step D with substitution of N-(t-butoxycarbonyl)-(±)-1,3,4,10b-tetrahydro-8-ethyl-7-methoxy-pyrazino[2,1-a]isoindol-6(2H)-one for N-(t-butoxycarbonyl)-(±)-1,3,4,10b-tetrahydro-9-cyclopropyl-7-trifluoromethoxy-pyrazino[2,1-a]isoindol-6(2H)-one. MS (ESI) 247 (M−Cl).

Example 198

Preparation of (R)-1,3,4,10b-tetrahydro-7-methoxy-pyrazino[2,1-a]isoindol-6(2H)-one hydrochloric acid salt

Prepared according to procedures described in Example 100 with substitution of N-(t-butoxycarbonyl)-(R)-1,3,4, 10b-tetrahydro-8-chloro-7-methoxy-pyrazino[2,1-a]isoindol-6(2H)-one for N-(t-butoxycarbonyl)-(R)-1,3,4,10b-tetrahydro-9-(2-methyl-1-propenyl)-7-trifluoromethyl-pyrazino[2,1-a] isoindol-6(2H)-one in Step A. MS (ESI) 219 (M–Cl).

Example 199

Preparation of (S)-1,3,4,10b-tetrahydro-7-methoxy-pyrazino[2,1-a]isoindol-6(2H)-one hydrochloric acid salt

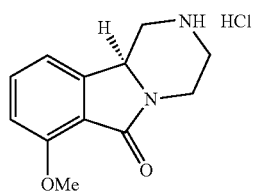

Prepared according to procedures described in Example 100 with substitution of N-(t-butoxycarbonyl)-(S)-1,3,4,10b-tetrahydro-8-chloro-7-methoxy-pyrazino[2,1-a]isoindol-6(2H)-one for N-(t-butoxycarbonyl)-(R)-1,3,4,10b-tetrahydro-9-(2-methyl-1-propenyl)-7-trifluoromethyl-pyrazino[2,1-a]isoindol-6(2H)-one in Step A. MS (ESI) 219 (M–Cl).

Example 200

Preparation of (R)-1,3,4,10b-tetrahydro-7-ethyl-pyrazino[2,1-a]isoindol-6(2H)-one hydrochloric acid salt

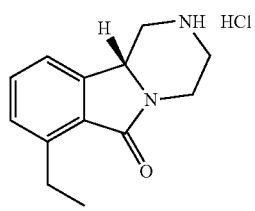

Step A. Preparation of N-(t-butoxycarbonyl)-(R)-1,3,4,10b-tetrahydro-7-ethenyl-pyrazino[2,1-a]isoindol-6(2H)-one Prepared according to procedures described in Example 158 Step B with substitution of N-(t-butoxycarbonyl)-(R)-1,3,4,10b-tetrahydro-7-chloro-pyrazino[2,1-a]isoindol-6(2H)-one for N,N-diethyl-4-chloro-2-methoxybenzamide in. MS (ESI) 315 (M+H).

Step B. Preparation of (R)-1,3,4,10b-tetrahydro-7-ethyl-pyrazino[2,1-a]isoindol-6(2H)-one hydrochloric acid salt Prepared according to procedures described in Example 100 with substitution of N-(t-butoxycarbonyl)-(S)-1,3,4,10b-tetrahydro-7-ethenyl-pyrazino[2,1-a]isoindol-6(2H)-one for N-(t-butoxycarbonyl)-(R)-1,3,4,10b-tetrahydro-9-(2-methyl-1-propenyl)-7-trifluoromethyl-pyrazino[2,1-a]isoindol-6(2H)-one in Step A. MS (ESI) 217 (M–Cl).

Examples 201 and 202

Preparation of (R)-1,3,4,10b-tetrahydro-7-cyclopropyl-pyrazino[2,1-a]isoindol-6(2H)-one hydrochloric acid salt and (S)-1,3,4,10b-tetrahydro-7-cyclopropyl-pyrazino[2,1-a]isoindol-6(2H)-one hydrochloric acid salt

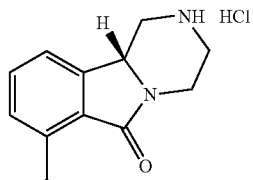

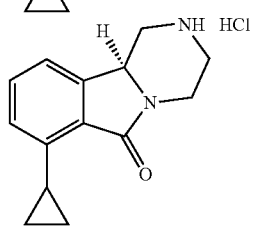

Prepared according to procedures described in Example 128 with substitution of N-(t-butoxycarbonyl)-(±)-1,3,4,10b-tetrahydro-7-methoxy-pyrazino[2,1-a]isoindol-6(2H)-one for N-(t-butoxycarbonyl)-(±)-1,3,4,10b-tetrahydro-9-methoxy-7-trifluoromethoxy-pyrazino[2,1-a]isoindol-6(2H)-one in Step A. MS (ESI) 229 (M–Cl).

Examples 203 and 204

Preparation of (R)-1,3,4,10b-tetrahydro-7-cyclopentyl-pyrazino[2,1-a]isoindol-6(2H)-one hydrochloric acid salt and (S)-1,3,4,10b-tetrahydro-7-cyclopentyl-pyrazino[2,1-a]isoindol-6(2H)-one hydrochloric acid salt

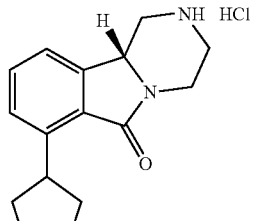

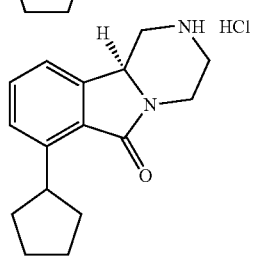

Prepared according to procedures described in Example 128 with substitution of N-(t-butoxycarbonyl)-(±)-1,3,4,10b-tetrahydro-7-methoxy-pyrazino[2,1-a]isoindol-6(2H)-one for N-(t-butoxycarbonyl)-(±)-1,3,4,10b-tetrahydro-9-methoxy-7-trifluoromethoxy-pyrazino[2,1-a]isoindol-6(2H)-one in Step A. MS (ESI) 257 (M−Cl).

Examples 205 and 206

Preparation of (R)-1,3,4,10b-tetrahydro-10b-methyl7-trifluoromethyl-pyrazino[2,1-a]isoindol-6(2H)-one hydrochloric acid salt and (S)-1,3,4,10b-tetrahydro-10b-methyl7-trifluoromethyl-pyrazino[2,1-a]isoindol-6(2H)-one hydrochloric acid salt

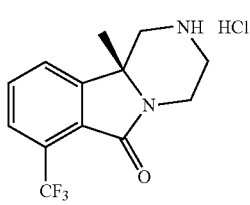

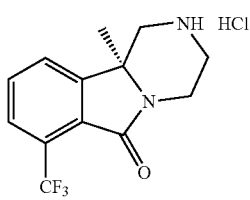

Step A. Preparation of N-(t-butoxycarbonyl)-(±)-1,3,4,10b-tetrahydro-10b-methyl-7-trifluoromethyl-pyrazino[2,1-a]isoindol-6(2H)-one To a stirring solution of N-(t-butoxycarbonyl)-(S)-1,3,4,10b-tetrahydro-7-trifluoromethyl-pyrazino[2,1-a]isoindol-6(2H)-one (150 mg, 0.4 mmol) and methyl iodide (125 mg, 0.9 mmol) in dry DMF (6 mL) was added sodium hydride (15 mg, 0.6 mmol). The reaction was stirred for 3 h and then quenched with brine. The reaction was extracted with EtOAc (3×10 mL). The organic layers were combined, dried over Na$_2$SO$_4$, and conc. in vacuo to a brown oil. The oil was purified by flash chromatography (silica gel, 0-50% EtOAc in hexanes) to yield 59 mg of the desired product as a white solid. MS (ESI) 371 (M+H).

Step B. Preparation of (R)-1,3,4,10b-tetrahydro-10b-methyl7-trifluoromethyl-pyrazino[2,1-a]isoindol-6(2H)-one hydrochloric acid salt and (S)-1,3,4,10b-tetrahydro-10b-methyl7-trifluoromethyl-pyrazino[2,1-a]isoindol-6(2H)-one hydrochloric acid salt Prepared according to procedures described in Example 128 Step D with substitution of N-(t-butoxycarbonyl)-(±)-1,3,4,10b-tetrahydro-10b-methyl-7-trifluoromethyl-pyrazino[2,1-a]isoindol-6(2H)-one for N-(t-butoxycarbonyl)-(±)-1,3,4,10b-tetrahydro-9-cyclopropyl-7-trifluoromethoxy-pyrazino[2,1-a]isoindol-6(2H)-one. MS (ESI) 271 (M−Cl).

Example 207

Preparation of (3R,11aR)-1,2,3,4,11,11a-hexahydro-3-methyl-pyrazino[1,2-b]isoquinolin-6-one

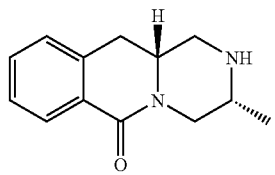

Step A. Preparation of [N-(tert-butyloxycarbonyl)-R-phenylalanyl]-N-(benzyl)-R-alanine, methyl ester To a stirring solution of (R)—N-(tert-butyloxycarbonyl)-phenylalanine (0.50 g, 1.9 mmol) in dry CH$_2$Cl$_2$ (10 mL) was added N-(3-dimethylaminopropyl)-N'-ethylcarbodiimide hydrochloride (0.50 g, 3.2 mmol) and 1-hydroxybenzotriazole hydrate (0.28 g, 2.2 mmol). The reaction was stirred at ambient temperature for 30 min and then N-benzyl-(D)-alanine, methyl ester hydrochloride (0.53 g, 2.3 mmol) and triethylamine (0.34 ml, 2.4 mmol) were added. After stirring at ambient temperature overnight and then at 50° C. for one hour, the reaction was transferred to a separatory funnel with CH$_2$Cl$_2$. Extraction with CH$_2$Cl$_2$ and washing of the organic layer with water, saturated NaHCO$_3$, and brine and drying with MgSO$_4$ afforded 1.0 g of crude product after evaporation of the solvent. Purification by flash chromatography (SiO$_2$, hexanes to 30% EtOAc in hexanes) afforded pure product (0.34 g, 41% yield). MS (ESI) 441 (M+H).

Step B. Preparation of (3R,6R)-1,3-dibenzyl-6-methylpiperazine-2,5-dione

A solution of [N-(tert-butyloxycarbonyl)-R-phenylalanyl]-N-(benzyl)-R-alanine, methyl ester (0.22 g, 0.50 mmol) in EtOAc (5 ml) was cooled to 0° C. Gaseous HCl was slowly bubbled through the solution for 10 min and then the ice bath was removed and the reaction allowed to stir at ambient temperature for 1 h. The reaction mixture was evaporated in vacuo and the residue transferred to a separatory funnel with CH$_2$Cl$_2$. Washing the organic layer with saturated NaHCO$_3$, and brine and drying with MgSO$_4$ afforded product (0.15 g, 100% yield) after evaporation of the solvent. MS (ESI) 309 (M+H). This was used in the next step without further purification.

Step C. Preparation of (2R,5R)-1,5-dibenzyl-2-methylpiperazine

Lithium aluminum hydride (1 M in THF, 4.2 ml, 4.2 mmol) was added dropwise over 15 min to a solution of (3R,6R)-1,3-dibenzyl-6-methylpiperazine-2,5-dione (0.30 g, 0.98 mmol) in THF (6.0 ml) stirring at 0° C. After stirring at 65° C. for 19 h, the reaction was allowed to cool to room temperature and was slowly quenched with water (0.40 ml). Sodium hydroxide (1 N, 0.8 ml) and then water (0.60 ml) were added and the gelatinous solid was filtered rinsing with THF. The filtrate was evaporated in vacuo and the residue was transferred to a separatory funnel with EtOAc. Washing the organic layer with brine and drying with MgSO$_4$ afforded product (0.28 g) after evaporation of the solvent. This was used in the next step without further purification.

Step D. Preparation of (2R,5R)-methyl 2,4-dibenzyl-5-methylpiperazine-1-carboxylate Pyridine (0.3 mL, 3.7 mmol) was added to a stirring solution of (2R,5R)-1,5-dibenzyl-2-methylpiperazine (0.28 g, 1.0 mmol) and methyl chloroformate (0.10 g, 0.087 ml, 1.1 mmol) in $CH_2Cl_2$ (11 ml). After stirring at ambient temperature for 1 day, the reaction was evaporated in vacuo and the residue purified by flash chromatography ($SiO_2$, 5% MeOH in $CH_2Cl_2$) to afford pure product (0.17 g, 49% yield over the two steps). MS (ESI) 339 (M+H).

Step E. Preparation of (3R,11aR)-1,2,3,4,11,11a-hexahydro-2-benzyl-3-methyl-pyrazino[1,2-b]isoquinolin-6-one A mixture of (2R,5R)-methyl 2,4-dibenzyl-5-methylpiperazine-1-carboxylate (0.17 g, 0.5 mmol), phosphorous oxychloride (3 ml) and phosphorous pentoxide (0.28 g, 1.0 mmol) was stirred at 100° C. under nitrogen overnight. The reaction was removed from the heat, quenched with ice, and brought to pH 8 with saturated $NaHCO_3$. Extraction with ethyl acetate (2x) and washing the combined organic layers with brine and drying over $MgSO_4$ afforded 0.13 g of crude product after evaporation of the solvent.

Flash chromatography ($SiO_2$, 4% MeOH in $CH_2Cl_2$) afforded pure product (81 mg, 53% yield). MS (ESI) 307 (M+H).

Step F. Preparation of (3R,11aR)-1,2,3,4,11,11a-hexahydro-3-methyl-pyrazino[1,2-b]isoquinolin-6-one (3R,11aR)-1,2,3,4,11,11a-Hexahydro-2-benzyl-3-methyl-pyrazino[1,2-b]isoquinolin-6-one (81 mg, 0.26 mmol) and 10% palladium on carbon (25 mg) in methanol (6.5 ml) was stirred under a balloon of hydrogen for 19 h. Evaporation of the filtrate after filtration through Celite® afforded pure (3R,11aR)-1,2,3,4,11,11a-hexahydro-3-methyl-pyrazino[1,2-b]isoquinolin-6-one (56 mg, 83% yield). MS (ESI) 217 (M+H).

Example 208

Preparation of (11R,11aR)-1,2,3,4,11,11a-hexahydro-11-methyl-pyrazino[1,2-b]isoquinolin-6-one

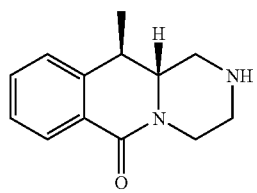

The title compound was prepared according to procedures described in Example 207 from (D)-N-(tert-butyloxycarbonyl)-erythro-β-methylphenylalanine (ARCOS) and N-benzyl glycine, ethyl ester (Aldrich). Final isolation from flash chromatography ($SiO_2$, 10% 1 N ammonia in MeOH/$CH_2Cl_2$) afforded (11R,11aR)-1,2,3,4,11,11a-hexahydro-11-methyl-pyrazino[1,2-b]isoquinolin-6-one [MS (ESI) 217 (M+H)].

Example 209

Preparation of (11aR)-1,2,3,4,11,11a-hexahydro-11a-methyl-pyrazino[1,2-b]isoquinolin-6-one

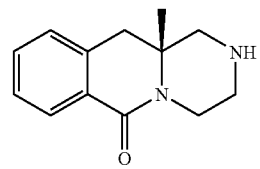

Step A. Preparation of [N-(tert-butyloxycarbonyl)-α-methyl-(R)-phenylalanyl]-glycine, ethyl ester To a stirring solution of (R)—N-(tert-butyloxycarbonyl)-α-methylphenylalanine (0.72 g, 2.6 mmol) in dry $CH_2Cl_2$ (16 mL) was added N-(3-dimethylaminopropyl)-N'-ethylcarbodiimide hydrochloride (0.69 g, 4.4 mmol) and 1-hydroxybenzotriazole hydrate (0.39 g, 2.9 mmol). The reaction was stirred at ambient temperature for 30 min and then glycine, ethyl ester hydrochloride (0.62 g, 5.2 mmol) and triethylamine (0.85 ml, 5.7 mmol) were added. After stirring at ambient temperature for 3 h, the reaction was transferred to a separatory funnel with $CH_2Cl_2$. Extraction with $CH_2Cl_2$ and washing of the organic layer with water, saturated $NaHCO_3$, and brine and drying with $MgSO_4$ afforded 0.94 g of crude product after evaporation of the solvent. Purification by flash chromatography ($SiO_2$, 0.2 to 10% MeOH in $CH_2Cl_2$) afforded pure product (0.87 g, 93% yield). MS (ESI) 365 (M+H).

Step B. Preparation of (α-methyl-(R)-phenylalanyl)glycine, ethyl ester

[N-(tert-butyloxycarbonyl)-α-methyl-(R)-phenylalanyl] glycine, ethyl ester was stirred at ambient temperature in 4N HCl in dioxane (30 ml). After 1.5 h, the solvent was removed in vacuo. The residue was transferred to a separatory funnel with EtOAc. Extraction with EtOAc (2x) and washing of the combined organic layers brine and drying with $MgSO_4$ afforded 0.63 g of crude product after evaporation of the solvent. This was used in the next step without further purification. MS (ESI) 265 (M+H).

Step C. Preparation of (R)-3-benzyl-3-methylpiperazine-2,5-dione

A solution of (α-methyl-(R)-phenylalanyl)glycine, ethyl ester (0.63 g, 2.4 mmol) in sec-butanol (14 ml) and toluene (7 ml) was stirred at reflux. After 21 h, the solvent was removed in vacuo and the residue azeotroped with toluene (3x) to afford the product (0.51 g, 100% yield) as a white solid. MS (ESI) 219 (M+H). This was used in the next step without further purification.

Step D. Preparation of (R)-2-benzyl-2-methylpiperazine

Lithium aluminum hydride (1 M in THF, 7.2 ml, 7.2 mmol) was added dropwise over 15 min to a solution of (R)-3- benzyl-3-methylpiperazine-2,5-dione (0.51 g, 2.4 mmol) in THF (20 ml) stirring at ambient temperature. After stirring at reflux for 6 h, the reaction was allowed to cool to room temperature and was slowly quenched with water (0.27 ml). Sodium hydroxide (1 N, 1.0 ml) and then water (0.10 ml) were added and the gelatinous solid was filtered rinsing with THF. The filtrate was evaporated in vacuo and the residue was transferred to a separatory funnel with EtOAc. Washing the organic layer with brine and drying with MgSO$_4$ afforded product (0.38 g) after evaporation of the solvent. This was used in the next step without further purification. MS (ESI) 191 (M+H).

Step E. Preparation of (R)-dimethyl 2-benzyl-2-methylpiperazine-1,4-dicarboxylate Diethylisopropylamine (0.98 ml, 5.0 mmol) was added to a stirring solution of (R)-2-benzyl-2-methylpiperazine (0.38 g, 2.0 mmol) and methyl chloroformate (0.41 g, 0.35 ml, 2.8 mmol) in CH$_2$Cl$_2$ (20 ml). After stirring at ambient temperature for 2 h, the reaction was evaporated in vacuo and the residue purified by flash chromatography (SiO$_2$, CH$_2$Cl$_2$ to 40% EtOAc in CH$_2$Cl$_2$) to afford pure product (0.28 g, 34% yield over the two steps). MS (ESI) 307 (M+H).

Step F. Preparation of (11aR)-1,2,3,4,11,11a-hexahydro-11a-methyl-pyrazino[1,2-b]isoquinolin-6-one A mixture of (R)-dimethyl 2-benzyl-2-methylpiperazine-1,4-dicarboxylate (0.28 g, 0.91 mmol), phosphorous oxychloride (5.9 ml) and phosphorous pentoxide (0.57 g, 1.8 mmol) was stirred at 100° C. under nitrogen overnight. The reaction was removed from the heat, quenched with ice, and brought to pH 12 with 1N NaOH. Extraction with EtOAc (2×) and washing the combined organic layers with brine and drying over MgSO$_4$ afforded 0.14 g of crude product after evaporation of the solvent. Flash chromatography (SiO$_2$, 0.1 to 10% 2 N ammonia in MeOH/CH$_2$Cl$_2$) afforded pure product (34 mg, 17% yield). MS (ESI) 217 (M+H).

Example 210

Preparation of (3S,11aR)-1,2,3,4,11,11a-hexahydro-3-methyl-pyrazino[1,2-b]isoquinolin-6-one

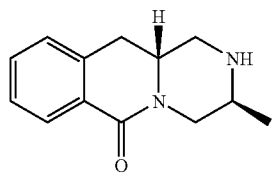

Step A. Preparation of [N-(tert-butyloxycarbonyl)-R-phenylalanyl]-N-(benzyl)-S-alanine, methyl ester To a stirring solution of N-(tert-butyloxycarbonyl)-(R)-phenylalanine (1.8 g, 6.8 mmol) and N-benzyl-(L)-alanine, methyl ester (1.7 g, 7.4 mmol) in dry DMF (10 mL) at 0° C. was added pyBOP (4.1 g, 8.0 mmol) followed by triethylamine (2.4 ml, 16 mmol). After stirring at ambient temperature for 3 days, the reaction was transferred to a separatory funnel with EtOAc. Extraction with EtOAc and washing of the organic layer with water, saturated NaHCO$_3$, and brine and drying with MgSO$_4$ afforded 5.0 g of crude product after evaporation of the solvent. Purification by flash chromatography (SiO$_2$, 15% EtOAc in CH$_2$Cl$_2$) afforded pure product (2.1 g, 66% yield). MS (ESI) 441 (M+H).

Step B. Preparation of (3S,6R)-1,3-dibenzyl-6-methylpiperazine-2,5-dione

A solution of [N-(tert-butyloxycarbonyl)-R-phenylalanyl]-N-(benzyl)-S-alanine, methyl ester. (2.0 g, 4.5 mmol) in EtOAc (47 ml) was cooled to 0° C. Gaseous HCl was slowly bubbled through the solution for 20 min and then the ice bath was removed and the reaction allowed to stir at ambient temperature for 20 h. The reaction mixture was evaporated in vacuo and the residue transferred to a separatory funnel with CH$_2$Cl$_2$. Washing the organic layer with saturated NaHCO$_3$, and brine and drying with MgSO$_4$ afforded product (0.83 g, 60% yield) after evaporation of the solvent. MS (ESI) 309 (M+H). This was used in the next step without further purification.

Step C. Preparation of (2S,5R)-1,5-dibenzyl-2-methylpiperazine

Lithium aluminum hydride (1 M in THF, 4.8 ml, 4.8 mmol) was added dropwise over 30 min to a solution of (3S,6R)-1,3-dibenzyl-6-methylpiperazine-2,5-dione (0.39 g, 1.2 mmol) in THF (7.5 ml) stirring at 0° C. After stirring at 65° C. for 1 day, the reaction was allowed to cool to room temperature and was slowly quenched with water (0.34 ml). Sodium hydroxide (1 N, 0.68 ml) and then water (0.51 ml) were added and the gelatinous solid was filtered rinsing with THF. The filtrate was evaporated in vacuo and the residue transferred to a separatory funnel with EtOAc. Washing the organic layer with brine and drying with MgSO$_4$ afforded product (0.40 g) after evaporation of the solvent. This was used in the next step without further purification.

Step D. Preparation of (2S,5R)-methyl 2,4-dibenzyl-5-methylpiperazine-1-carboxylate Pyridine (0.57 ml, 7.0 mmol) was added to a stirring solution of (2S,5R)-1,5-dibenzyl-2-methylpiperazine (0.40 g, 1.2 mmol) and methyl chloroformate (0.20 ml, 2.5 mmol) in CH$_2$Cl$_2$ (14 ml). After stirring at ambient temperature for 2 h, the reaction was evaporated in vacuo and the residue purified by flash chromatography (SiO$_2$, 3% MeOH in CH$_2$Cl$_2$) to afford pure product (0.28 g, 68% yield over the two steps). MS (ESI) 339 (M+H).

Step E. Preparation of (3S,11aR)-1,2,3,4,11,11a-hexahydro-2-benzyl-3-methyl-pyrazino[1,2-b]isoquinolin-6-one A mixture of (2S,5R)-methyl 2,4-dibenzyl-5-methylpiperazine-1-carboxylate (0.28 g, 0.83 mmol), phosphorous oxychloride (5.0 ml) and phosphorous pentoxide (0.48 g, 1.6 mmol) was stirred at 100° C. under nitrogen overnight. The reaction was removed from the heat, quenched with ice, and brought to pH 7 to 8 with 1 N NaOH. Extraction with EtOAc (3×) and washing the combined organic layers with brine and drying over MgSO$_4$ afforded 0.11 g of crude product after evaporation of the solvent. Flash chromatography (SiO$_2$, CH$_2$Cl$_2$ to 60% EtOAc in CH$_2$Cl$_2$) afforded pure product (47 mg, 19% yield). MS (ESI) 307 (M+H).

Step F. Preparation of (3S,11aR)-1,2,3,4,11,11a-hexahydro-3-methyl-pyrazino[1,2-b]isoquinolin-6-one (3S,11a)-1,2,3,4,11,11a-Hexahydro-2-benzyl-3-methyl-pyrazino[1,2-b]isoquinolin-6-one (77 mg, 0.25 mmol) and 10% palladium on carbon (25 mg) in methanol (6.5 ml) was stirred under a balloon of hydrogen for 3 days. Evaporation of the filtrate after filtration through Celite® afforded 39 mg of crude product. Flash chromatography (SiO$_2$, 10% 1 N ammonia in MeOH/CH$_2$Cl$_2$) gave pure (3,11aR)-1,2,3,4,11,11a-hexahydro-3-methyl-pyrazino[1,2-b]isoquinolin-6-one (29 mg, 54% yield). MS (ESI) 217 (M+H).

Example 211

Preparation of (4R,11aR)-1,2,3,4,11,11a-hexahydro-4-methyl-pyrazino[1,2-b]isoquinolin-6-one and (4S,11aS)-1,2,3,4,11,11a-hexahydro-4-methyl-pyrazino[1,2-b]isoquinolin-6-one

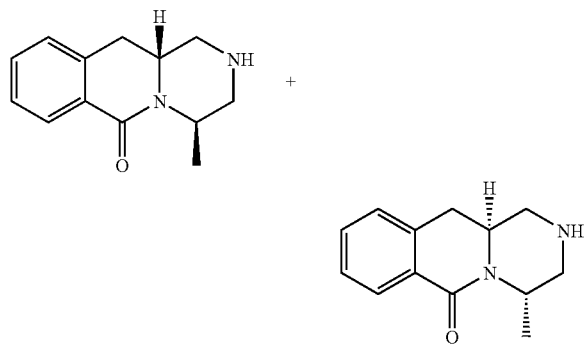

Step A. Preparation of (R)-methyl 1-oxo-1,2,3,4-tetrahydroisoquinoline-3-carboxylate D-Phenylalanine methyl ester (1.56 g of HCl salt, Aldrich in CH$_2$Cl$_2$ washed with saturated NaHCO$_3$ and dried, 7.3 mmol) and diisopropylethylamine (2.1 ml, 8.9 mmol) in 1,2-dichloroethane (13 ml) was added dropwise over 30 min to a stirring solution of triphosgene (1.1 g, 5.2 mmol) in 1,2-dichloroethane (13 ml). After stirring at ambient temperature for 1.5 h, the reaction was cooled to 0° C. and aluminum chloride (2.2 g) was added. After refluxing for 2.5 h, the reaction was once again cooled to 0° C. and quenched by slowly adding water (13 ml). After stirring for 1 h, the reaction mixture was transferred to a separatory funnel with CH$_2$Cl$_2$. Extraction with CH$_2$Cl$_2$ (2×) and drying over MgSO$_4$ afforded 1.8 g of crude product. Flash chromatography (SiO$_2$, 0 to 100% EtOAc in CH$_2$Cl$_2$) afforded pure product (0.65 g, 43% yield). MS (ESI) 206 (M+H).

Step B. Preparation of methyl 2-(1-methoxy-1-oxopropan-2-yl)-1-oxo-1,2,3,4-tetrahydroisoquinoline-3-carboxylate Sodium hydride (60% oil dispersion, 0.51 g, 12.4 mmol) was added to a stirring solution of (R)-methyl 1-oxo-1,2,3,4-tetrahydroisoquinoline-3-carboxylate (1.3 g, 6.2 mmol) in DMF (13 ml). After stirring for 30 min at ambient temperature, methyl 2-bromopropionate (1.1 ml, 9.3 mmol) was added. After stirring at 40° C. for 2 h, the reaction was removed from the heat and quenched with water. The reaction mixture was transferred to a separatory funnel with EtOAc/water. Extraction with EtOAc (2×) and washing the combined organic layers with saturated NaHCO$_3$, water, and brine and drying over MgSO$_4$ afforded 2.0 g of crude product after evaporation of the solvent. Flash chromatography (SiO$_2$, hexanes to 80% EtOAc in hexanes) afforded Isomer A (0.53 g, 29% yield), Isomer B (0.28 g, 15% yield) and a mixture of the two isomers (0.28 g, 15% yield). All have MS (ESI) 292 (M+H).

Step C. Preparation of 3-(hydroxymethyl)-2-(1-hydroxypropan-2-yl)-3,4-dihydroisoquinolin-1(2H)-one Isomer B of methyl 2-(1-methoxy-1-oxopropan-2-yl)-1-oxo-1,2,3,4-tetrahydroisoquinoline-3-carboxylate (0.28 g, 0.96 mmol) in THF (9.8 ml) was added to a stirring solution of LiBH$_4$ (2.0 M in THF, 0.58 ml, 1.2 mmol) in THF (1.5 ml). After refluxing for 1.5 h, the reaction was cooled to room temperature and quenched with 0.036 ml of water. Sodium hydroxide (1N, 0.072 ml) and then water (0.054 ml) were added. The reaction mixture was filtered through Celite, rinsing with THF. Evaporation of the filtrate afforded 0.32 g of crude product. Flash chromatography (SiO$_2$, 0.5 to 10% MeOH in CH$_2$Cl$_2$) afforded pure product (0.20 g, 89% yield). MS (ESI) 236 (M+H).

Step D. Preparation of 3-(chloromethyl)-2-(1-chloropropan-2-yl)-3,4-dihydroisoquinolin-1(2H)-one 3-(Hydroxymethyl)-2-(1-hydroxypropan-2-yl)-3,4-dihydroisoquinolin-1(2H)-one (from Isomer B, 0.20 g, 0.85 mmol) in chloroform (7.6 ml) was added to a stirring solution of thionyl chloride (1.8 ml) in chloroform (10 ml). After refluxing overnight the condenser was removed and the majority of the solvent allowed to evaporate over the next 4 h. The residue was purified by flash chromatography (SiO$_2$, CH$_2$Cl$_2$ to 50% EtOAc in CH$_2$Cl$_2$) affording pure product (0.16 g, 69% yield). MS (ESI) 273/275 (M+H).

Step E. Preparation of 1,2,3,4,11,11a-hexahydro-2-benzyl-4-methyl-pyrazino[1,2-b]isoquinolin-6-one A mixture of 3-(chloromethyl)-2-(1-chloropropan-2-yl)-3,4-dihydroisoquinolin-1(2H)-one (from Isomer B, 0.16 g, 0.58 mmol), K$_2$CO$_3$ (0.16 g, 1.2 mmol), and benzylamine (0.075 ml, 0.67 mmol) in diglyme (1.5 ml) was heated at reflux for 6 h. After cooling to room temperature the reaction was transferred to a separatory funnel with ether and water. Extraction with ether and washing the organic layer with water (4×) and brine, and drying over MgSO$_4$ afforded 0.15 g of crude product after evaporation of the solvent. Flash chromatography (SiO$_2$, hexanes to 60% EtOAc in hexanes) afforded pure product (93 mg, 52% yield). MS (ESI) 307 (M+H).

Step F. Preparation of (4R,11aR)-1,2,3,4,11,11a-hexahydro-4-methyl-pyrazino[1,2-b]isoquinolin-6-one and (4S,11aS)-1,2,3,4,11,11a-Hexahydro-4-methyl-pyrazino[1,2-b]isoquinolin-6-one 1,2,3,4,11,11a-Hexahydro-2-benzyl-4-methyl-pyrazino[1,2-b]isoquinolin-6-one (from Isomer B, 93 mg, 0.30 mmol) and 10% palladium on carbon (40 mg) in EtOAc (9 ml) was stirred under a balloon of hydrogen. After 3 days the reaction was about 60% complete by HPLC. The catalyst was filtered off and then fresh catalyst added. After stirring an additional day under a balloon of hydrogen, the reaction was filtered through Celite® rinsing with EtOAc and methanol to afford 56 mg of crude product. Column purification (Chiralcel OD, 15% 1/1 MeOH/EtOH in hexanes) afforded pure (4R,11aR)-1,2,3,4,11,11a-hexahydro-4-methyl-pyrazino[1,2-b]isoquinolin-6-one (18 mg, 28% yield). MS (ESI) 217 (M+H). Further elution afforded pure (4S,11aS)-1,2,3,4,11,11a-hexahydro-4-methyl-pyrazino[1,2-b]isoquinolin-6-one (16 mg, 25% yield). MS (ESI) 217 (M+H).

Example 212

Preparation of (4R,11aR)-1,2,3,4,11,11a-hexahydro-2,4-dimethyl-pyrazino[1,2-b]isoquinolin-6-one, and (4S,11aS)-1,2,3,4,11,11a-hexahydro-2,4-dimethyl-pyrazino[1,2-b]isoquinolin-6-one

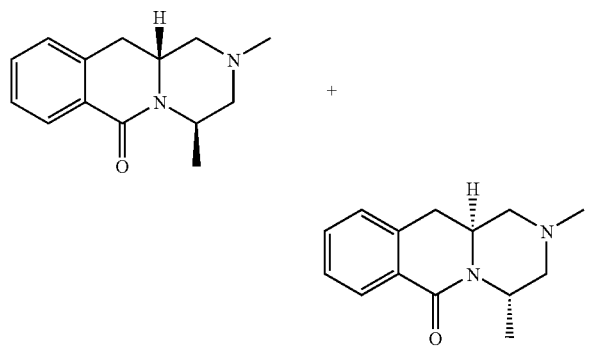

The title compounds were prepared according to procedures described in Example 211 except that the Isomer B and Isomer A were not separated until after Step E. Isomer B was then submitted to the reaction conditions below.

Step F. Preparation of (4R,11aR)-1,2,3,4,11,11a-hexahydro-2,4-dimethyl-pyrazino[1,2-b]isoquinolin-6-one, and (4S,11aS)-1,2,3,4,11,11a-hexahydro-2,4-dimethyl-pyrazino[1,2-b]isoquinolin-6-one 1,2,3,4,11,11a-hexahydro-2-benzyl-4-methyl-pyrazino[1,2-b]isoquinolin-6-one (from Isomer B, 12 mg, 0.04 mmol) and 10% palladium on carbon (5 mg) in MeOH (1 ml) was stirred under a balloon of hydrogen. The catalyst was filtered off and then fresh catalyst added. After stirring an additional 4 h at 40° C. under a balloon of hydrogen, the reaction was filtered through Celite® rinsing with methanol to afford 8 mg of crude product. Column purification (Chiralcel OD, 10% 1/1 MeOH/EtOH in hexanes) afforded pure (4R,11aR)-1,2,3,4,11,11a-hexahydro-2,4-dimethyl-pyrazino[1,2-b]isoquinolin-6-one (1.5 mg, 17% yield) MS (ESI) 231 (M+H). Further elution afforded (4S,11aS)-1,2,3,4,11,11a-hexahydro-2,4-dimethyl-pyrazino[1,2-b]isoquinolin-6-one (1.6 mg, 18% yield) MS (ESI) 231 (M+H). Further elution also provided (4R,11aR)-1,2,3,4,11,11a-hexahydro-4-methyl-pyrazino[1,2-b]isoquinolin-6-one (2.4 mg, 29% yield) and (4S,11aS)-1,2,3,4,11,11a-hexahydro-4-methyl-pyrazino[1,2-b]isoquinolin-6-one (2.2 mg, 27% yield).

Example 213

Preparation of (4S,11aR)-1,2,3,4,11,11a-hexahydro-4-methyl-pyrazino[1,2-b]isoquinolin-6-one and (4R,11aS)-1,2,3,4,11,11a-hexahydro-4-methyl-pyrazino[1,2-b]isoquinolin-6-one

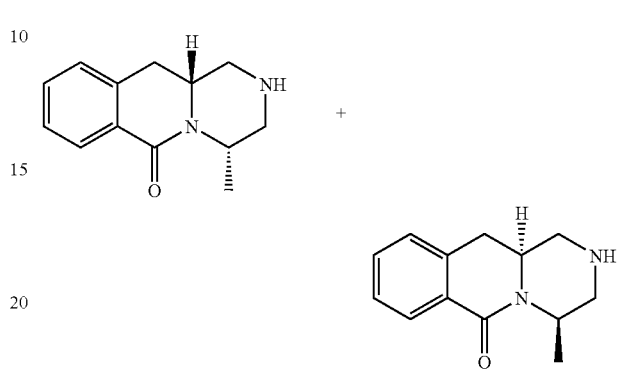

The title compounds were prepared according to procedures described in Example 211 except that the Isomer A was utilized throughout the sequence to afford (4S,11aR)-1,2,3,4,11,11a-hexahydro-4-methyl-pyrazino[1,2-b]isoquinolin-6-one. [MS (ESI) 217 (M+H)] and (4R,11aS)-1,2,3,4,11,11a-hexahydro-4-methyl-pyrazino[1,2-b]isoquinolin-6-one [MS (ESI) 217 (M+H)].

Example 214

Preparation of (11aR)-1,3,4,6,11,11a-hexahydro-4-methyl-2H-pyrazino[1,2-b]isoquinoline

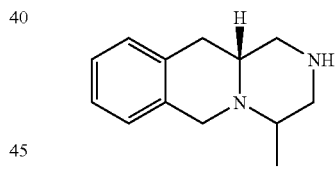

Step A. Preparation of (3R)-tert-butyl 3-(methoxy (methyl)carbamoyl)-3,4-dihydroisoquinoline-2(1H)-carboxylate To a stirring solution of (R)—N-(tert-butyloxycarbonyl)-1,2,3,4-tetrahydroisoquinoline-3-carboxylic acid (Fluka, 1.4 g, 5.0 mmol) in dry CH$_2$Cl$_2$ (31 mL) was added N-(3-dimethylaminopropyl)-N'-ethylcarbodiimide hydrochloride (1.3 g, 8.4 mmol) and 1-hydroxybenzotriazole hydrate (0.76 g, 5.8 mmol). The reaction was stirred at ambient temperature for 20 min and then N,O-dimethylhydroxylamine hydrochloride (0.75 g, 7.5 mmol) and triethylamine (1.2 ml, 7.7 mmol) were added. After stirring at ambient temperature for 1.5 hour, the reaction was transferred to a separatory funnel with CH$_2$Cl$_2$. Extraction with CH$_2$Cl$_2$ and washing of the organic layer with water, saturated NaHCO$_3$, and brine and drying with MgSO$_4$ afforded product (1.7 g, 100% yield). MS (ESI) 221 (M+H–BOC). This was used in the next step without further purification.

Step B. Preparation of (3R)-tert-butyl 3-formyl-3,4-dihydroisoquinoline-2(1H)-carboxylate Lithium aluminum hydride (1 M in THF, 5.3 ml, 5.3 mmol) was added to a solution of (3R)-tert-butyl 3-(methoxy(methyl)carbamoyl)-3,4-dihydroisoquinoline-2(1H)-carboxylate (1.7 g, 5.0 mmol theory) in ether (16 ml) stirring at 0° C. under nitrogen. After stirring at 0° C. for 1 h, the reaction was slowly quenched with water (0.40 ml). Sodium hydroxide (1N, 0.80 ml) followed by water (0.60 ml) were then added and the resultant gelatinous precipitate was filtered through Celite® rinsing with ether and THF. The filtrate was evaporated and the residue transferred to a separatory funnel with EtOAc. Washing with brine and drying with MgSO$_4$ afforded crude product (1.3 g, 100% yield) which was used in the next step without further purification.

Step C. Preparation of (3R)-tert-butyl 3-((2,4-dimethoxybenzylamino)methyl)-3,4-dihydroisoquinoline-2(1H)-carboxylate Sodium triacetoxyborohydride (3.1 g, 15 mm) was added to a mixture of (3R)-tert-butyl 3-formyl-3,4-dihydroisoquinoline-2(1H)-carboxylate (1.3 g, 5.0 mmol theory), 2,4-dimethoxybenzylamine (0.77 ml, 5.5 mmol), and dry 4 A sieves in 1,2-dichloroethane (25 ml) stirring at ambient temperature. After stirring at ambient temperature overnight the reaction solution was transferred to a separatory funnel with EtOAc and saturated NaHCO$_3$. Extraction with EtOAc (2×), washing the combined organic layers with brine and drying over MgSO$_4$ afforded 1.6 g of crude product. Flash chromatography (SiO$_2$, 1 to 10% 2N N$_3$ in MeOH/CH$_2$Cl$_2$) gave pure product (1.3 g, 63% yield over the previous 3 steps). MS (ESI) 413 (M+H).

Step D. Preparation of (3R)-(tert-butyl 3-(N-(2,4-dimethoxybenzyl)-2-chloropropanamido)methyl)-3,4-dihydroisoquinoline-2(1H)-carboxylate 2-Chloropropanoyl chloride (0.19 g, 0.15 ml, 1.5 mmol) was added to a solution of (3R)-tert-butyl 3-((2,4-dimethoxybenzylamino)methyl)-3,4-dihydroisoquinoline-2(1H)-carboxylate (0.41 g, 1.0 mmol) in EtOAc (12 ml) stirring at 0° C. followed by saturated NaHCO$_3$ (0.65 ml). After stirring at 0° C. for 3 h, the reaction was transferred to a separatory funnel with EtOAc and saturated NaHCO$_3$. Extraction with EtOAc (2×), washing the combined organic layers with brine and drying over MgSO$_4$ afforded 0.47 g of crude product. Flash chromatography (SiO$_2$, 0.2 to 10% MeOH in CH$_2$Cl$_2$) gave pure product (0.37 g, 73%). MS (ESI) 503/505 (M+H).

Step E. Preparation of N-(2,4-dimethoxybenzyl)-2-chloro-N-(((3R)-1,2,3,4-tetrahydroisoquinolin-3-yl)methyl)propanamide (3R)-(tert-butyl 3-(N-(2,4-dimethoxybenzyl)-2-chloropropanamido)methyl)-3,4-dihydroisoquinoline-2(1H)-carboxylate (0.36 g, 0.72 mmol) was stirred at ambient temperature in trifluoroacetic acid (3.5 ml) and CH$_2$Cl$_2$ (7 ml). After stirring for 1 h, the solvent was evaporated in vacuo and the residue transferred to a separatory funnel with CH$_2$Cl$_2$. Extraction with CH$_2$Cl$_2$ (2×), washing the combined organic layers with saturated NaHCO$_3$ and drying over MgSO$_4$ afforded 0.18 g of crude product. This material was used in the next step without further purification.

Step F. Preparation of (11aR)-1,2,11,11a-tetrahydro-2-(2,4-dimethoxybenzyl)-4-methyl-4H-pyrazino[1,2-b]isoquinolin-3(6H)-one Cesium carbonate (0.18 g) was added to a solution of N-(2,4-dimethoxybenzyl)-2-chloro-N-(((3R)-1,2,3,4-tetrahydroisoquinolin-3-yl)methyl)propanamide (0.18 g, 0.44 mmol) in DMF (4.7 ml). After stirring at ambient temperature for 3 h, the reaction was transferred to a separatory funnel with EtOAc. Extraction with EtOAc, washing the organic layer with water (3×) and brine and drying over MgSO$_4$ afforded 0.15 g of crude product. Flash chromatography (SiO$_2$, 0.2 to 10% MeOH in CH$_2$Cl$_2$) gave pure product (0.11 g, 68%). MS (ESI) 367 (M+H).

Step G. Preparation of (11aR)-1,3,4,6,11,11a-hexahydro-2-(2,4-dimethoxybenzyl)-4-methyl-2H-pyrazino[1,2-b]isoquinoline Lithium aluminum hydride (1 M in THF, 0.63 ml, 0.63 mmol) was added to a solution of (11aR)-1,2,11,11a-tetrahydro-2-(2,4-dimethoxybenzyl)-4-methyl-4H-pyrazino[1,2-b]isoquinolin-3(6H)-one (0.11 g, 0.31 mmol) in THF (1.8 ml) stirring in a room temperature bath under nitrogen. After stirring at 65° C. for 2 h, the reaction was cooled to room temperature and slowly quenched with water (0.18 ml). Sodium hydroxide (1N, 0.36 ml) followed by water (0.27 ml) were then added and the resultant gelatinous precipitate was filtered through Celite® rinsing THF. The filtrate after evaporation of the solvent was transferred to a separatory funnel with EtOAc. Washing with brine and drying with MgSO$_4$ afforded crude product (0.10 g, 95% yield) after evaporation of the solvent. This material was used in the next step without further purification.

Step H. Preparation of (11aR)-1,3,4,6,11,11a-hexahydro-4-methyl-2H-pyrazino[1,2-b]isoquinoline 1-Chloroethylchloroformate (0.050 ml, 0.47 mmol) was added to a solution of (11aR)-2,3,4,6,11,11a-hexahydro-2-(2,4-dimethoxybenzyl)-4-methyl-1H-pyrazino[1,2-b]isoquinoline (53 mg, 0.15 mmol) in 1,2-dichloroethane (1 ml) stirring at 0° C. The ice bath was removed and the reaction stirred at ambient temperature for 30 min. After refluxing an additional 2 h, the reaction was evaporated in vacuo. Methanol (1.0 ml) was added to the residue and the reaction refluxed under nitrogen for 1 h. Evaporation in vacuo afforded 75 mg of crude product. This crude product was transferred to a separatory funnel with CH$_2$Cl$_2$ and saturated NaHCO$_3$. Extraction with CH$_2$Cl$_2$ (2×) and drying of the combined organic layers over MgSO$_4$ afforded 42 mg which was further purified by flash chromatography (SiO$_2$, 0.2 to 10% 2N N$_3$ in MeOH/CH$_2$Cl$_2$) to give pure product (17 mg, 55%). MS (ESI) 203 (M+H).

Example 215

(−)-1,2,3,4,11,11a-hexahydropyrazino[1,2-b][1,2]benzothiazine 6,6-dioxide

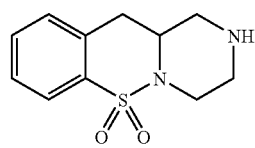

Step A. Preparation of 2-bromo-N-(1,1-dimethylpropyl)benzenesulfonamide

To a solution of 2-methyl-2-butanamine (11.4 mL, 97.8 mmol) in dichloromethane (100 mL) was added, dropwise over a 10 min period, a solution of 2-bromobenzenesulfonyl chloride (10.0 g, 39.1 mmol) in dichloromethane (ca. 50 mL). After stirring for 15 h the reaction was concentrated in vacuo. The residue was crystallized from methyl t-butyl ether to provide 10.5 g (87%) of 2-bromo-N-(1,1-dimethylpropyl)benzenesulfonamide in two crops: LCMS (neg. ion spectrum) m/z 304/306.

Step B. Preparation of N-(1,1-dimethylpropyl) 2-(2-propenyl)benzenesulfonamide To a solution of 2-bromo-N-(1,1-dimethylpropyl)benzenesulfonamide (5.00 g, 16.3 mmol) in dimethylformamide (dry, $N_2$-degassed, 20 mL) were added allyltribuylstannane (6.07 mL, 19.6 mmol) and tetrakis(triphenylphosphine)palladium (0) (189 mg, 0.163 mmol). The mixture was heated at 110° C. for 15 h. The reaction was concentrated in vacuo and the residue was chromatographed (silica, 40% dichloromethane/hexanes to dichloromethane gradient) to provide N-(1,1-dimethylpropyl) 2-(2-propenyl)benzenesulfonamide (4.04 g, 92%) as an off-white solid: LCMS (neg. ion spectrum) m/z 266.

Step C. Preparation of 2-(2-propenyl)benzenesulfonamide

Ice-cold trifluoroacetic acid (50 mL) was added to ice-cold N-(1,1-dimethylpropyl) 2-(2-propenyl)benzenesulfonamide (4.04 g, 15.1 mmol). The reaction was stirred at 0° C. for 3.5 h. The reaction was concentrated in vacuo and the residue was crystallized from methyl tert-butyl ether/hexanes to provide 2-(2-propenyl)benzenesulfonamide as white plates (2.53 g, 85%) in one crop: LCMS (neg. ion spectrum) m/z 196.

Step D. Preparation of 8,8a-dihydro-1H-azirino[1,2-b][1,2]benzothiazine 3,3-dioxide Iodine (6.51 g, 26.7 mmol) was added in one portion to a solution of 2-(2-propenyl)benzenesulfonamide (2.53 g, 12.8 mmol) in $N_2$-degassed dichloromethane (125 mL) containing potassium carbonate (7.09 g, 51.3 mmol). After stirring for 20 min, water (50 mL, containing 2 g of sodium metabisulfite) was carefully added. The layers were separated and the aqueous layer was extracted with dichloromethane (25 mL). The combined organic layers were washed with water (25 mL). To the combined organic layers were added methanol (50 mL) and 0.25 N potassium carbonate in 70% aqueous methanol. After stirring for 10 min, sodium metabisulfite (100 mg) was added to discharge the color. The volatile organic solvents were removed in vacuo. The residue was partitioned between dichloromethane (100 mL) and additional water (30 mL). The aqueous layer was extracted with dichloromethane (25 mL). The combined organic layers were dried (magnesium sulfate) and concentrated in vacuo to provide 8,8a-dihydro-1H-azirino[1,2-b][1,2]benzothiazine 3,3-dioxide as a pale yellow oil which solidified (2.25 g, 90%): LCMS (pos. ion spectrum) m/z 237 (M+H+$CH_3CN$).

Step E. Preparation of 1,1-dimethylethyl [(3,4-dihydro-1,1-dioxido-2H-1,2-benzothiazin-3-yl)methyl]-2-propenylcarbamate A solution of 8,8a-dihydro-1H-azirino[1,2-b][1,2]benzothiazine 3,3-dioxide (514 mg, 2.63 mmol), triethylamine (0.37 mL, 2.6 mmol), and 2-propenamine (0.99 mL, 13 mmol) in tetrahydrofuran (25 mL) was heated at 100° C. in a sealed pressure tube for 14 h. The cooled reaction was concentrated in vacuo to provide a yellow solid. The solid was taken up in tetrahydrofuran (5 mL). Water (3 mL), 1 N NaOH (2.9 mL) and bis(1,1-dimethylethyl)dicarbonate (861 mg, 3.94 mmol) were sequentially added. After stirring for 10 min, the reaction was diluted with water (25 mL) and the mixture was extracted with dichloromethane (2×25 mL). The combined organic layers were dried (magnesium sulfate) and concentrated in vacuo. The residue was chromatographed (silica, 10% ethyl acetate/hexanes to ethyl acetate gradient) to provide 1,1-dimethylethyl[(3,4-dihydro-1,1-dioxido-2H-1,2-benzothiazin-3-yl)methyl]-2-propenylcarbamate (587 mg, 63%) as a colorless oil: LCMS (neg. ion spectrum) m/z 351.

Step F. Preparation of 1,1-dimethylethyl [(3,4-dihydro-1,1-dioxido-2H-1,2-benzothiazin-3-yl)methyl]-(2-hydroxyethyl)carbamate To a stirred solution of 1,1-dimethylethyl [(3,4-dihydro-1,1-dioxido-2H-1,2-benzothiazin-3-yl)methyl]-2-propenylcarbamate (499 mg, 1.42 mmol) in dioxane (25 mL) was added, sequentially, sodium metaperiodate (1.21 g, 5.66 mmol) and osmium tetraoxide (2% w/v in water, 1.8 mL, 0.14 mmol). After stirring for 1.5 h, the thick slurry was diluted with water (75 mL). The mixture was extracted with dichloromethane (3×50 mL). The combined organic layers were washed with saturated sodium chloride (50 mL), 5% sodium thiosulfate (3×50 mL), dried (sodium sulfate), and concentrated in vacuo to an oil. To a 0° C. solution of this residue in ethanol (5 mL) was added sodium borohydride (54 mg, 1.42 mmol). After 10 min, acetone (1 mL) was added. The reaction was concentrated in vacuo. The residue was partitioned between water (15 mL) and dichloromethane (15 mL). The aqueous phase was extracted with dichloromethane (15 mL). The combined organic layers were dried (magnesium sulfate) and concentrated in vacuo. The residue was chromatographed (silica, 50% ethyl acetate/hexanes to ethyl acetate gradient) to provide 1,1-dimethylethyl[(3,4-dihydro-1,1-dioxido-2H-1, 2-benzothiazin-3-yl)methyl]-(2-hydroxyethyl)carbamate as a colorless foam (276 mg, 55%): LCMS (neg. ion spectrum) m/z 355.

Step G. Preparation of 1,1-dimethylethyl 3,4,11,11a-tetrahydropyrazino[1,2-b][1,2]benzothiazine-2(1H)-carboxylate 6,6-dioxide To a 0° C. solution of 1,1-dimethylethyl [(3,4-dihydro-1,1-dioxido-2H-1,2-benzothiazin-3-yl)methyl]-(2-hydroxyethyl)carbamate (276 mg, 0.774 mmol) in dichloromethane (5 mL, dried by passage through Act I neutral alumina) were added triethylamine (0.160 mL, 1.16 mmol) and methanesulfonyl chloride (0.072 mL, 0.929 mmol) sequentially. After 30 min, an additional 0.14-mL portion of methanesulfonyl chloride was added. After an additional 20 min, the reaction was diluted with dichloromethane (25 mL) and washed with half-saturated sodium bicarbonate (10 mL). The organic layer was dried (sodium sulfate) and concentrated in vacuo to provide a colorless foam (349 mg). To a solution of this residue in tetrahydrofuran (25 mL) was added potassium tert-butoxide (99 mg, 0.883 mmol). After 1 h, an additional 10-mg portion of potassium tert-butoxide was added. After 10 min, the reaction was partitioned between dichloromethane (75 mL) and saturated sodium chloride (25 mL). The organic layer was dried (magnesium sulfate) and concentrated in vacuo. The residue was chromatographed (silica, dichloromethane then 10% methanol/dichloromethane) and repurified by chromatography (silica, 10% ethyl acetate to ethyl acetate gradient) to provide 1,1-dimethylethyl 1,2,3,4,11,11a-hexahydropyrazino[1,2-b][1,2]benzothiazine-2-carboxylate 6,6-dioxide as an oil (151 mg, 56%): LCMS (pos. ion spectrum) m/z 694 (2M+H).

Step H. Preparation of (−)-1,2,3,4,11,11a-hexahydropyrazino[1,2-b][1,2]benzothiazine 6,6-dioxide Cold trifluoroacetic acid (2 mL) was added to cold 1,1-dimethylethyl 1,2,3,4,11,11a-hexahydropyrazino[1,2-b][1,2]benzothiazine-2-carboxylate 6,6-dioxide (151 mg, 0.446 mmol). After 1 h, the reaction was concentrated in vacuo. The residue was partitioned between dichloromethane (10 mL) and 0.5 N sodium carbonate (2 mL). The organic layer was dried (sodium sulfate) and concentrated in vacuo. The residue was chromatographed (Diacel Chiracel OJ, 5×50 cm, 35% 1:1 methanol/ethanol:hexanes containing 0.3% triethylamine, 50 mL/min). Fractions containing the more rapidly eluting enantiomer concentrated in vacuo. The residue was taken up in 50% aqueous methanol (1 mL) and was loaded onto a 1-g methanol-activated water-equilibrated SCX-type cation exchange column. The column was washed with water (5 mL) and 25% aqueous methanol (5 mL). The column was eluted with 2 N methanolic ammonia. Concentration of this fraction in vacuo provided (−) 1,2,3,4,11,11a-hexahydropyrazino[1,2-b][1,2]benzothiazine 6,6-dioxide: LCMS (pos. ion spectrum) m/z 239.

Example 216

Preparation of (±)-1,2,3,4,11,11a-hexahydropyrazino[1,2-b][1,2]benzothiazine 6,6-dioxide

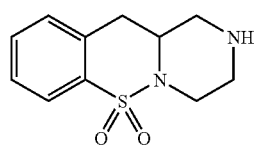

Product-containing fractions from the chiral chromatographic separation in Example 215 Step H were concentrated in vacuo to provide the title compound LCMS (pos. ion spectrum) m/z 239.

Example 217

Preparation of (−)-1,2,3,4,11,11a-hexahydro-2-methyl-pyrazino[1,2-b][1,2]benzothiazine 6,6-dioxide

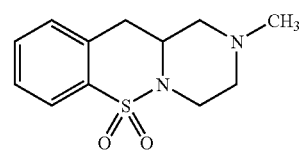

Step A. Preparation of (−)-1,2,3,4,11,11a-hexahydro-2-methyl-pyrazino[1,2-b][1,2]benzothiazine 6,6-dioxide To a solution of the title compound of Example 215 (23.0 mg, 0.0965 mmol) in dimethylformamide (0.75 mL) were added cesium carbonate (94 mg, 0.29 mmol) and methyl iodide (0.0072 mL, 0.12 mmol). After 4.5 h, the reaction was partitioned between dichloromethane (2 mL) and water (2 mL). The aqueous layer was extracted with dichloromethane (2 mL). The combined organic layers were dried (sodium sulfate) and concentrated in vacuo. The residue was taken up in a minimum amount of 50% aqueous methanol and loaded onto a methanol-activated water-equilibrated 1-g SCX-type cation exchange column. The column washed with water (6 mL) and 50% aqueous methanol (6 mL). The column was eluted with 2N methanolic ammonia (8 mL). This fraction was concentrated in vacuo to provide (−)-1,2,3,4,11,11a-hexahydro-2-methyl-pyrazino[1,2-b][1,2]benzothiazine 6,6-dioxide as a white solid (19 mg, 79%): LCMS (pos. ion spectrum) m/z 253.

Example 218

Preparation of (±)-1,2,3,4,11,11a-hexahydro-2-methyl-pyrazino[1,2-b][1,2]benzothiazine 6,6-dioxide

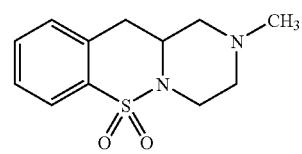

Step A. Preparation of (±)-1,2,3,4,11,11a-hexahydro-2-methyl-pyrazino[1,2-b][1,2]benzothiazine 6,6-dioxide As described for Example 217, the title compound (20 mg, 65%) was prepared from the title compound of Example 216 (29 mg, 0.122 mmol): LCMS (pos. ion spectrum) m/z 253.

Example 219

Preparation of 1,2,3,4,11,11a-hexahydro-8-(trifluoromethyl)pyrazino[1,2-b][1,2]benzothiazine 6,6-dioxide

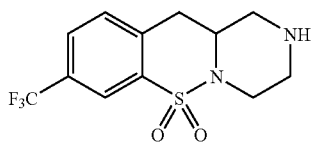

Step A. Preparation of 8,8a-dihydro-5-(trifluoromethyl)-1H-azirino[1,2-b][1,2]benzothiazine 3,3-dioxide As described in steps Example 215 Steps A-C, 2-(2-propenyl)-5-trifluoromethylbenzenesulfonamide was prepared from 5-trifluoromethyl-2-bromobenzenesulfonyl chloride. The intermediate 2-bromo-N-(1,1-dimethyl-2-propyl)-5-trifluoromethylbenzenesulfonamide was recrystallized from toluene; and N-(1,1-dimethyl-2-propyl)-2-(2-propenyl)-5-trifluoromethylbenzenesulfonamide and intermediates 2-(2-propenyl)-5-trifluoromethylbenzenesulfonamide were chromatographed using ethyl acetate-hexanes gradients.

To a solution of 2-(2-propenyl)-5-trifluoromethylbenzenesulfonamide (780 mg, 2.94 mmol) in nitrogen-degassed dichloromethane (30 mL) containing potassium carbonate (1.62 g, 11.8 mmol) was added iodine (1.49 g, 5.88 mmol). After stirring for 2 h, the reaction was quenched with 10% aqueous sodium thiosulfate (ca. 14 mL). The dichloromethane was removed in vacuo and the residue was diluted with methanol (10 mL) and 0.25 N potassium carbonate in 70% aqueous methanol. Additional methanol was added to produce a nearly homogeneous solution. After 10 min, the reaction was concentrated in vacuo to remove most of the methanol. The residue was partitioned between dichloromethane (30 mL) and water (10 mL). The aqueous layer was extracted with dichloromethane (5 mL) and the combined organic layers were dried (magnesium sulfate) and concentrated in vacuo to provide 8,8a-dihydro-5-(trifluoromethyl)-1H-azirino[1,2-b][1,2]benzothiazine 3,3-dioxide as a white solid (685 mg (92%): LCMS (net. ion spectrum) m/z 262.

Step B. Preparation of 3,4-dihydro-N-(2-hydroxyethyl)-7-(trifluoromethyl)-2H-1,2-benzothiazine-3-methanamine 1,1-dioxide A solution of 8,8a-dihydro-5-(trifluoromethyl)-1H-azirino[1,2-b][1,2]benzothiazine 3,3-dioxide (685 mg, 0.260 mmol), ethanolamine (0.785 mL, 13.0 mmol) and triethylamine (0.33 mL, 2.6 mmol) in tetrahydrofuran (25 mL) was heated in a sealed tube at 100° C. for 3 h. The cooled reaction was concentrated in vacuo. The residue was chromatographed (silica, 2%-20% methanol/dichloromethane gradient) to provide 3,4-dihydro-N-(2-hydroxyethyl)-7-(trifluoromethyl)-2H-1,2-benzothiazine-3-methanamine 1,1-dioxide as a white solid (124 mg) and additional impure material: LCMS (neg. ion spectrum) m/z 323.

Step C. Preparation of phenylmethyl [(3,4-dihydro-1,1-dioxido-7-(trifluoromethyl)-2H-1,2-benzothiazin-3-yl)methyl](2-hydroxyethyl)carbamate To a solution of 3,4-dihydro-N-(2-hydroxyethyl)-7-(trifluoromethyl)-2H-1,2-benzothiazine-3-methanamine 1,1-dioxide (124 mg, 0.382 mmol) in tetrahydrofuran (4 mL) was added, sequentially, 0.5 N aqueous sodium carbonate (2 mL, 1 mmol) and benzyl chloroformate (0.066 mL, 0.46 mmol). The reaction was stirred for 25 min. The layers were separated and the aqueous layer was extracted with dichloromethane (5 mL). The combined organic layers were washed with saturated sodium chloride (5 mL) and were concentrated in vacuo. To the residue taken up in methanol (5 mL) was added 2 N potassium hydroxide (0.5 mL). After 15 min, the reaction was brought to pH 4 with 1 N HCl. The reaction was concentrated in vacuo to remove the methanol. The residue was partitioned between dichloromethane (10 mL) and water (5 mL). The organic layer was dried (magnesium sulfate) and concentrated in vacuo to provide a yellow oil. Chromatography of this residue (silica, 30% ethyl acetate/hexanes to ethyl acetate gradient) provided 90 mg (51%) of a phenylmethyl [(3,4-dihydro-1,1-dioxido-7-(trifluoromethyl)-2H-1,2-benzothiazin-3-yl)methyl](2-hydroxyethyl)carbamate as a white solid: LCMS (neg. ion spectrum) m/z 457.

Step D. Preparation of phenylmethyl 3,4,11,11a-Tetrahydro-8-(trifluoromethyl)pyrazino[1,2-b][1,2]benzothiazine-2(1H)-carboxylate 6,6-dioxide To a 0° C. solution of phenylmethyl [(3,4-dihydro-1,1-dioxido-7-(trifluoromethyl)-2H-1,2-benzothiazin-3-yl)methyl](2-hydroxyethyl)carbamate (400 mg, 0.873 mmol) in dichloromethane (20 mL, dried by passage through Act I neutral alumina) was added triethylamine (0.243 mL, 1.74 mmol) and methanesulfonic anhydride (228 mg, 1.31 mmol). After 3 h, an additional 70-mg portion of methanesulfonic anhydride was added. After an additional 1 h, a 228-mg portion of methanesulfonic anhydride and a 0.243-mL portion of triethylamine were added. After 10 min, the reaction was diluted with dichloromethane (20 mL), washed with saturated sodium bicarbonate (10 mL), dried (sodium sulfate) and concentrated in vacuo. To a 0° C. solution of this residue in tetrahydrofuran (10 mL) was added, dropwise, lithium bis(trimethylsilyl)amide (1 N in tetrahydrofuran, 1.10 mL, 1.10 mmol). After 20 min, an additional 0.15-mL portion of lithium bis(trimethylsilyl)amide was added dropwise to produce an orange solution. The reaction was diluted with saturated sodium chloride (20 mL). The aqueous layer was extracted with dichloromethane (2×20 mL). The combined organic layers were dried (sodium sulfate) and concentrated in vacuo. The residue was purified by chromatography (silica, 10% ethyl acetate/hexanes to ethyl acetate gradient) to provide phenylmethyl 3,4,11,11a-tetrahydro-8-(trifluoromethyl)pyrazino[1,2-b][1,2]benzothiazine-2(1H)-carboxylate 6,6-dioxide (321 mg, 83%) as a white foam. LCMS (neg. ion spectrum) m/z 439.

Step E. Preparation of 1,2,3,4,11,11a-hexahydro-8-(trifluoromethyl)-pyrazino[1,2-b][1,2]benzothiazine 6,6-dioxide To a solution of phenylmethyl 3,4,11,11a-tetrahydro-8-(trifluoromethyl)pyrazino[1,2-b][1,2]benzothiazine-2(1H)-carboxylate 6,6-dioxide (59.0 mg, 0.134 mmol) in methanol (2 mL) under a nitrogen atmosphere was added 10% Pd—C (6 mg). The nitrogen atmosphere was exchanged for hydrogen (provided by a balloon) using 3 pump/purge cycles. The reaction was stirred for 1 h. The hydrogen atmosphere was exchanged for nitrogen and the reaction was filtered through Celite® AFA. The pad was rinsed with methanol (1 mL). The combined filtrates were concentrated in vacuo to provide the title compound: LCMS (pos. ion spectrum) m/z 307.

Example 220

Preparation of (R)-2-benzyl-8-trifluoromethyl-1,2,3,4,11,11a-hexahydro-pyrazino[1,2-b]isoquinolin-6-one trifluoroacetic acid salt

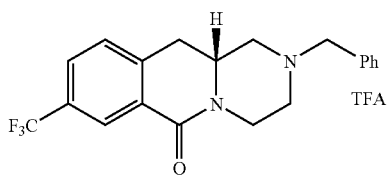

Step A. Preparation of (R)-[benzyl-[2-tert-butoxycarbonylamino-3-(4-trifluoromethyl-phenyl)-propionyl]-amino]-acetic acid ethyl ester To a stirred solution of N-(t-butoxycarbonyl)-D-4-trifluoromethylphenylalanine (1.0 g, 3.0 mmol, Synthetech) and EDC (0.69 g, 3.6 mmol) in dry $CH_2Cl_2$ (15 mL), N-benzylglycine ethyl ester (0.7 g, 3.6 mmol) followed by DMAP (0.07 g, 0.57 mmol) was added. The reaction was stirred for 20 h and then diluted with EtOAc (70 mL), washed with 1N HCl (15 mL), saturated $NaHCO_3$ (15 mL) and brine (15 mL). The organic layer was dried over $MgSO_4$, and conc in vacuo to yield 1.5 grams (98%) of the product as a colorless oil. MS (ESI) 509 (M+H).

Step B. Preparation of (R)-1-benzyl-3-(4-trifluoromethyl-benzyl)-piperazine-2,5-dione To a stirred solution of [benzyl-[2-tert-butoxycarbonylamino-3-(4-trifluoromethyl-phenyl)-propionyl]-amino]-acetic acid ethyl ester (1.5 g, 2.95 mmol) in dry $CH_2Cl_2$ (50 mL), 4N HCl in dioxane (25 mL, Aldrich) was added and stirred at room temperature for 2 h and then conc in vacuo. The rxn product was partitioned between $CH_2Cl_2$ (100 mL) and saturated $NaHCO_3$ (20 mL). The organic layer was separated, dried over $MgSO_4$ and conc in vacuo to give a clear oil. The oil was diluted in dichloroethane (50 mL) and stirred in 60° C. bath for 2 h to yield 1.02 g (95%) of the product as a off white solid. MS (ESI) 363 (M+H).

Step C. Preparation of (R)-1-benzyl-3-(4-trifluoromethyl-benzyl)-piperazine

To a stirred solution of 1-benzyl-3-(4-trifluoromethyl-benzyl)-piperazine-2,5-dione (0.53 g, 1.46 mmol) in dry THF (15 mL), 1M LAH in THF (6.14 mL, Aldrich) was slowly added at 0° C. and then heated to reflux for 18 h under argon. The reaction was cooled to room temperature and carefully quenched with $H_2O$ (1 mL), 1N NaOH (1 mL) and $H_2O$ (1 mL). The reaction mixture was filtered through bed of celite and rinsed with THF (100 mL). The filtrate was conc in vacuo and then dissolved in EtOAc (100 mL), washed with brine (2×10 mL), dried over $MgSO_4$, and conc in vacuo to yield 0.45 g (92%) of the product as a colorless oil. MS (ESI) 335 (M+H).

Step D. Preparation of (R)-4-benzyl-2-(4-trifluoromethyl-benzyl)-piperazine-1-carboxylic acid methyl ester To a stirred solution of 1-benzyl-3-(4-trifluoromethyl-benzylpiperazine (0.44 g, 1.32 mmol) in dry $CH_2Cl_2$ (10 mL), methylchloroformate (137 mg, 1.45 mmol) followed by pyridine (0.5 mL) was added. The reaction was stirred for 5 h and conc in vacuo and purified by prep TLC (SiO2, 95:5, $CH_2Cl_2$:MeOH) to yield 0.29 g (56%) of the product as a white solid. MS (ESI) 393 (M+H).

Step E. Preparation of (R)-2-benzyl-8-trifluoromethyl-1,2,3,4,11,11a-hexahydro-pyrazino[1,2-b]isoquinolin-6-one trifluoroacetic acid salt Mixture of 4-benzyl-2-(4-trifluoromethyl-benzyl)-piperazine-1-carboxylic acid methyl ester (160 mg, 0.4 mmol) and $P_2O_5$ (232 mg, 0.8 mmol) in $POCl_3$ (2 mL) was stirred at 100° C. for 18 h. The reaction mixture was cooled to room temperature and more $P_2O_5$ (100 mg, 0.35 mmol) was added and heated to 100° C. for 24 h and then cooled to RT to give very dark reaction mixture. The reaction was carefully quenched with ice (20 g) and adjusted pH to 9 with saturated $Na_2CO_3$ solution. The mixture was extracted with EtOAc (2×70 mL) and combined organic layers were washed with brine (15 mL), dried over $Na_2SO_4$, and conc in vacuo to give crude product. Purification on prep HPLC (Phenomenex Luna 5u C18 21.2×100, $H_2O$/MeOH/0.1% TFA) and lyophilization yielded 80 mg (42%) of the product as a off white oil. MS (ESI) 361 (M+H).

Example 221

Preparation of (R)-8-trifluoromethyl-1,2,3,4,11,11a-hexahydro-pyrazino[1,2-b]isoquinolin-6-one trifluoroacetic acid salt

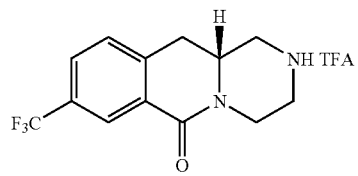

A mixture of (R)-2-benzyl-8-trifluoromethyl-1,2,3,4,11,11a-hexahydro-pyrazino[1,2-b]isoquinolin-6-one (36 mg, 0.076 mmol) and 10% palladium on carbon (10 mg, Aldrich) in MeOH (2 mL) was hydrogenated at 1 atm. The reaction was stirred for 1.5 h. and filtered off the catalyst to give crude product. Purification on prep HPLC (Phenomenex Luna 5u C18 21.2×100, $H_2O$/MeOH/0.1% TFA) and lyophilization yielded 14.3 mg (49%) of the product as a white lyophilate. MS (ESI) 271 (M+H).

Example 222

Preparation of (R)-2-benzyl-10-trifluoromethyl-1,2,3,4,11,11a-hexahydro-pyrazino[1,2-b]isoquinolin-6-one trifluoroacetic acid salt

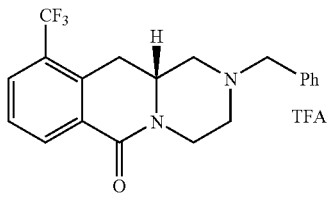

Prepared according to procedures described in Example 220 with the substitution of N-(t-butoxycarbonyl)-D-2-trifluoromethylphenylalanine for N-(t-butoxycarbonyl)-D-4-trifluoromethylphenylalanine in step A. MS (ESI) 361 (M+H).

Example 223

Preparation of (R)-10-trifluoromethyl-1,2,3,4,11,11a-hexahydro-pyrazino[1,2-b]isoquinolin-6-one trifluoroacetic acid salt

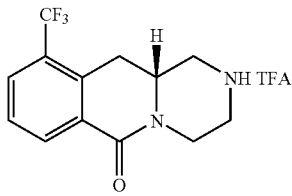

Prepared according to procedures described in Example 221 with the substitution of (R)-2-benzyl-10-trifluoromethyl-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 271 (M+H).

Examples 224 and 225

Preparation of (R)-2-benzyl-9-trifluoromethyl-1,2,3,4,11,11a-hexahydro-pyrazino[1,2-b]isoquinolin-6-one trifluoroacetic acid salt and (R)-2-benzyl-7-trifluoromethyl-1,2,3,4,11,11a-hexahydro-pyrazino[1,2-b]isoquinolin-6-one trifluoroacetic acid salt

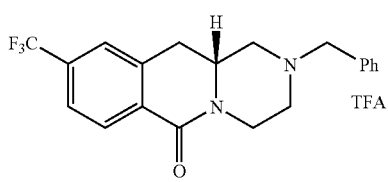

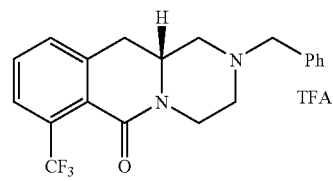

Prepared according to the procedures described in Example 220, with the substitution of N-(t-butoxycarbonyl)-D-3-trifluoromethylphenylalanine for N-(t-butoxycarbonyl)-D-4-trifluoromethylphenylalanine in Step A and separation of regioisomers by prep HPLC (Phenomenex Luna 5u C18 21.2×100, H₂O/MeOH/0.1% TFA) in Step E. MS (ESI) 361 (M+H) and MS (ESI) 361 (M+H).

Examples 226 and 227

Preparation of (R)-9-trifluoromethyl-1,2,3,4,11,11a-hexahydro-pyrazino[1,2-b]isoquinolin-6-one trifluoroacetic acid salt and (R)-7-trifluoromethyl-1,2,3,4,11,11a-hexahydro-pyrazino[1,2-b]isoquinolin-6-one trifluoroacetic acid salt

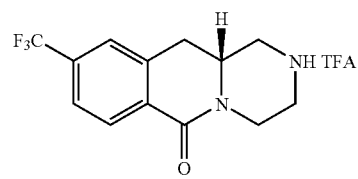

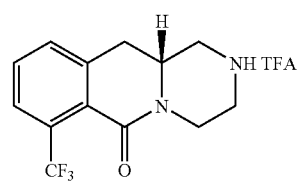

Step A: Preparation of (R)-9-trifluoromethyl-1,2,3,4,11,11a-hexahydro-pyrazino[1,2-b]isoquinolin-6-one trifluoroacetic acid salt Prepared according to procedures described in Example 221 with the substitution of (R)-2-Benzyl-9-trifluoromethyl-1,2,3,4,11,11a-hexahydro-pyrazino[1,2-b]isoquinolin-6-one for (R)-2-Benzyl-8-trifluoromethyl-1,2,3,4,11,11a-hexahydro-pyrazino[1,2-b]isoquinolin-6-one. MS (ESI) 271 (M+H).

Step B: Preparation of (R)-7-trifluoromethyl-1,2,3,4,11,11a-hexahydro-pyrazino[1,2-b]isoquinolin-6-one trifluoroacetic acid salt Prepared according to procedures described in Example 221 with the substitution of (R)-2-Benzyl-7-trifluoromethyl-1,2,3,4,11,11a-hexahydro-pyrazino[1,2-b]isoquinolin-6-one for (R)-2-Benzyl-8-trifluoromethyl-1,2,3,4,11,11a-hexahydro-pyrazino[1,2-b]isoquinolin-6-one. MS (ESI) 271 (M+H).

Example 228

Preparation of (R)-2-benzyl-8-bromo-1,2,3,4,11,11a-hexahydro-pyrazino[1,2-b]isoquinolin-6-one trifluoroacetic acid salt

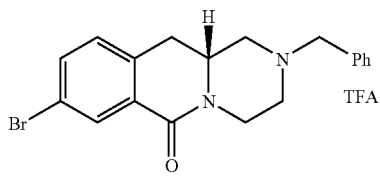

Step A. Preparation of (R)-1-benzyl-3-(4-bromo-benzyl)-piperazine-2,5-dione Prepared according to the procedures described in Example 220, Step A-B, with the substitution of N-(t-butoxycarbonyl)-D-4-bromophenylalanine for N-(t-butoxycarbonyl)-D-4-trifluoromethylphenylalanine in Step A MS (ESI) 373 (M+H).

Step B. Preparation of (R)-1-benzyl-3-(4-bromo-benzyl)-piperazine

To (R)-1-benzyl-3-(4-bromo-benzyl)-piperazine-2,5-dione (0.5 g, 1.34 mmol) in THF (10 mL) was added 2M $B_3.SMe_2$ (2.68 mL, 5.36 mmol). The mixture was stirred in RT under argon for 4 days; more 2M $B_3.SMe_2$ (2.68 mL, 5.36 mmol) was added and stirred for 3 days. Reaction mixture was quenched with EtOH (3 mL) and removed the solvent in rotavap, added EtOH (5 mL) and stirred at 70° C. for 2 hr and concentrated to give colorless oil as a crude product. MS (ESI) 345 (M+H).

Step C. Preparation of (R)-2-benzyl-8-bromo-1,2,3,4,11,11a-hexahydro-pyrazino[1,2-b]isoquinolin-6-one Prepared according to the procedures described in Example 220, Step D-E, with the substitution of (R)-1-benzyl-3-(4-bromo-benzyl)-piperazine for 1-benzyl-3-(4-trifluoromethyl-benzylpiperazine in Step D. MS (ESI) 371 (M+H).

Example 229

Preparation of (R)-8-bromo-1,2,3,4,11,11a-hexahydro-pyrazino[1,2-b]isoquinolin-6-one trifluoroacetic acid salt

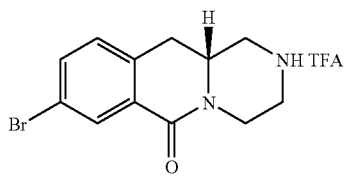

To a stirred solution of (R)-2-benzyl-8-bromo-1,2,3,4,11,11a-hexahydro-pyrazino[1,2-b]isoquinolin-6-one (25 mg, 0.067 mmol) in dry dichloroethane (1.5 mL), 1-chloroethyl-chloroformate (14.4 mg, 0.1 mmol) was added. The reaction was stirred for 2 h under reflux and cooled to RT over night. Reaction mixture was concentrated in rotavap. Added MeOH (2 mL) and heated at reflux for 1 hr and conc in vacuo. Took half portion and purified by prep HPLC (Phenomenex Luna 5u C18 21.2×100, H2O/MeOH/0.1% TFA) to yield 2.0 mg (15%) of the product as a white lyophilate. MS (ESI) 281 (M+H).

Example 230

Preparation of (R)-8-cyano-1,2,3,4,11,11a-hexahydro-pyrazino[1,2-b]isoquinolin-6-one trifluoroacetic acid salt

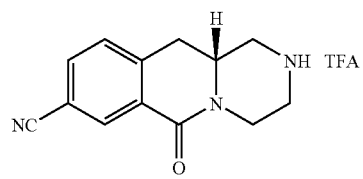

Step A. Preparation of (R)-2-benzyl-8-cyano-1,2,3,4,11,11a-hexahydro-pyrazino[1,2-b]isoquinolin-6-one Mixture of (R)-2-benzyl-8-bromo-1,2,3,4,11,11a-hexahydro-pyrazino[1,2-b]isoquinolin-6-one (25 mg, 0.067 mmol), CuCN (12.9 mg, 0.14 mmol) and CuI (3.7 mg, 0.29 mmol) in 1,3-dimethyl-2-imidazolidinone (1.5 mL) was stirred at 190° C. for 83 min in microwave. The reaction was cooled to RT and added EtOAc (20 mL) and $H_2O$ (5 mL). Filtered off the precipitate and rinsed with EtOAc (50 mL). The organic layer was separated and washed with brine (5 mL), dried over $MgSO_4$, and conc in vacuo to give crude product. Purified by prep TLC (SiO2, 95:5, $CH_2Cl_2$:MeOH) to yield crude product as a yellow oil. MS (ESI) 318 (M+H).

Step B. Preparation of (R)-8-cyano-1,2,3,4,11,11a-hexahydro-pyrazino[1,2-b]isoquinolin-6-one trifluoroacetic acid salt Prepared according to the procedures described in Example 229, with the substitution of (R)-2-benzyl-8-cyano-1,2,3,4,11,11a-hexahydro-pyrazino[1,2-b]isoquinolin-6-one for (R)-2-benzyl-8-bromo-1,2,3,4,11,11a-hexahydro-pyrazino[1,2-b]isoquinolin-6-one. MS (ESI) 228 (M+H).

Example 231

Preparation of (R)-2-benzyl-8-methoxy-1,2,3,4,11,11a-hexahydro-pyrazino[1,2-b]isoquinolin-6-one trifluoroacetic acid salt

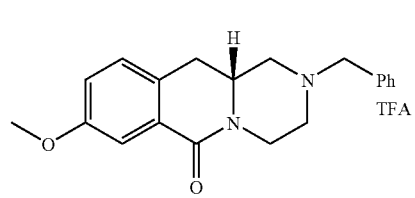

Prepared according to procedures described in Example 220 with the substitution of N-(t-butoxycarbonyl)-D-4-methoxyphenylalanine for N-(t-butoxycarbonyl)-D-4-trifluoromethylphenylalanine in step A. MS (ESI) 323 (M+H).

Example 232

Preparation of (R)-8-methoxy-1,2,3,4,11,11a-hexahydro-pyrazino[1,2-b]isoquinolin-6-one trifluoroacetic acid salt

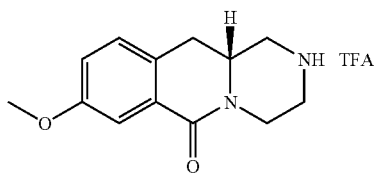

Prepared according to procedures described in Example 221 with the substitution of (R)-2-benzyl-8-methoxy-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 233 (M+H).

Example 233

Preparation of (R)-8-chloro-1,2,3,4,11,11a-hexahydro-pyrazino[1,2-b]isoquinolin-6-one trifluoroacetic acid salt

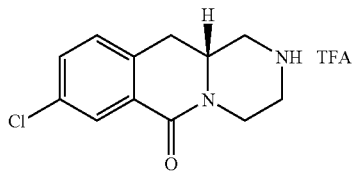

Prepared according to procedures described in Example 220 with the substitution of N-(t-butoxycarbonyl)-D-4-chlorophenylalanine for N-(t-butoxycarbonyl)-D-4-trifluoromethylphenylalanine in step A. And substitution of (R)-2-Benzyl-8-chloro-1,2,3,4,11,11a-hexahydro-pyrazino[1,2-b]isoquinolin-6-one for (R)-2-Benzyl-8-bromo-1,2,3,4,11,11a-hexahydro-pyrazino[1,2-b]isoquinolin-6-one in Example 230. MS (ESI) 237 (M+H).

Example 234

Preparation of (R)-8-fluoro-1,2,3,4,11,11a-hexahydro-pyrazino[1,2-b]isoquinolin-6-one trifluoroacetic acid salt

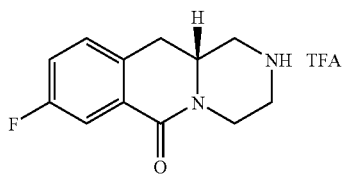

Prepared according to procedures described in Example 220 with the substitution of N-(t-butoxycarbonyl)-D-4-chlorophenylalanine for N-(t-butoxycarbonyl)-D-4-trifluoromethylphenylalanine in step A. And substitution of (R)-2-benzyl-8-fluoro-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one in Example 222. MS (ESI) 221 (M+H).

Examples 235 and 236

Preparation of (R)-9-fluoromethyl-1,2,3,4,11,11a-hexahydro-pyrazino[1,2-b]isoquinolin-6-one trifluoroacetic acid salt and (R)-7-fluoromethyl-1,2,3,4,11,11a-hexahydro-pyrazino[1,2-b]isoquinolin-6-one trifluoroacetic acid

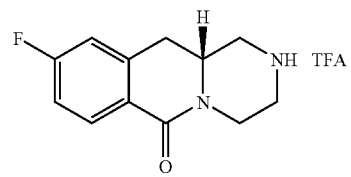

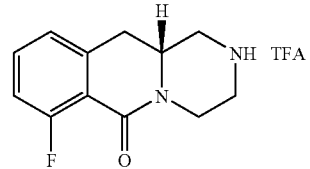

Step A. Preparation of (R)-2-benzyl-9-fluoromethyl-1,2,3,4,11,11a-hexahydro-pyrazino[1,2-b]isoquinolin-6-one trifluoroacetic acid salt and (R)-2-benzyl-7-fluoromethyl-1,2,3,4,11,11a-hexahydro-pyrazino[1,2-b]isoquinolin-6-one trifluoroacetic acid salt Prepared according to the procedures described in Example 220, with the substitution of N-(t-butoxycarbonyl)-D-3-fluoromethylphenylalanine for N-(t-butoxycarbonyl)-D-4-trifluoromethylphenylalanine in Step A and purified by silica gel chromatography, MeOH/CH2Cl2 (0-5% gradient) to give mixture of regioisomers. MS (ESI) 311 (M+H) and MS (ESI) 311 (M+H).

Step B. Preparation of (R)-9-fluoromethyl-1,2,3,4,11,11a-hexahydro-pyrazino[1,2-b]isoquinolin-6-one trifluoroacetic acid salt Prepared according to procedures described in Example 221 with the substitution of (R)-2-benzyl-9-fluoromethyl-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 221 (M+H).

Step C. Preparation of (R)-7-fluoromethyl-1,2,3,4, 11,11a-hexahydro-pyrazino[1,2-b]isoquinolin-6-one trifluoroacetic acid salt Prepared according to procedures described in Example 221 with the substitution of (R)-2-benzyl-7-fluoromethyl-1, 2,3,4,11,11a-hexahydro-pyrazino[1,2-b]isoquinolin-6-on for (R)-2-benzyl-8-trifluoromethyl-1,2,3,4,11,11a-hexahydro-pyrazino[1,2-b]isoquinolin-6-one. MS (ESI) 221 (M+H).

Examples 237 and 238

Preparation of (R)-2-benzyl-9-methoxy-1,2,3,4,11, 11a-hexahydro-pyrazino[1,2-b]isoquinolin-6-one trifluoroacetic acid salt and (R)-2-benzyl-7-methoxy-1,2,3,4,11,11a-hexahydro-pyrazino[1,2-b]isoquinolin-6-one trifluoroacetic acid salt

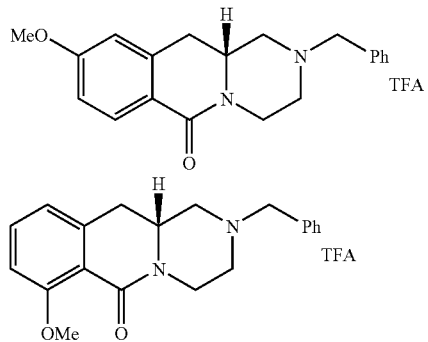

Prepared according to the procedures described in Example 220, with the substitution of N-(t-butoxycarbonyl)-D-3-methoxyphenylalanine for N-(t-butoxycarbonyl)-D-4-trifluoromethylphenylalanine in Step A and purified by prep TLC (SiO2, 95:5, CH$_2$Cl$_2$:MeOH) to give mixture of regioisomers. MS (ESI) 323 (M+H) and MS (ESI) 323 (M+H).

Examples 239 and 240

Preparation of (R)-9-methoxy-1,2,3,4,11,11a-hexahydro-pyrazino[1,2-b]isoquinolin-6-one trifluoroacetic acid salt and (R)-7-methoxy-1,2,3,4,11,11a-hexahydro-pyrazino[1,2-b]isoquinolin-6-one trifluoroacetic acid salt

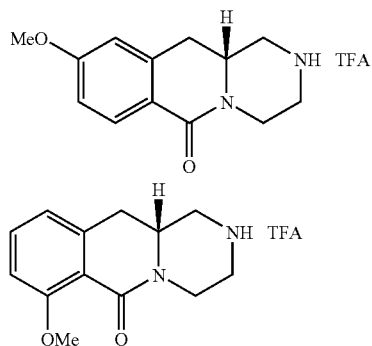

Step A. Preparation of (R)-9-methoxy-1,2,3,4,11, 11a-hexahydro-pyrazino[1,2-b]isoquinolin-6-one trifluoroacetic acid salt Prepared according to procedures described in Example 221 with the substitution of (R)-benzyl-9-methoxy-1,2,3,4, 11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 233 (M+H).

Step B. Preparation of (R)-7-methoxy-1,2,3,4,11, 11a-hexahydro-pyrazino[1,2-b]isoquinolin-6-one trifluoroacetic acid salt Prepared according to procedures described in Example 221 with the substitution of (R)-2-benzyl-7-methoxy-1,2,3, 4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 233 (M+H).

Example 241

Preparation of (R)-8-methyl-1,2,3,4,11,11a-hexahydro-pyrazino[1,2-b]isoquinolin-6-one trifluoroacetic acid salt

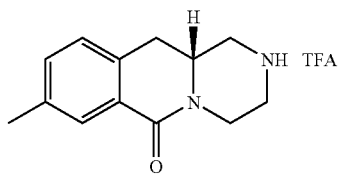

Step A. Preparation of (R)-2-benzyl-8-methyl-1,2,3, 4,11,11a-hexahydro-pyrazino[1,2-b]isoquinolin-6-one Degassed mixture of (R)-2-benzyl-8-methyl-1,2,3,4,11, 11a-hexahydro-pyrazino[1,2-b]isoquinolin-6-one (50 mg, 0.13 mmol), trimethylboroxine (25 mg, 0.20 mmol), tetrakis(triphenylphosphine)palladium (15 mg, 0.013 mmol) and K$_2$CO$_3$ (56 mg, 0.4 mmol) in DMF (1 mL) was heated at 110° C. for 18 h to give dark brownish reaction mixture. The mixture was then cooled, diluted with ethyl acetate (10 mL) and filtered through bed of celite and rinsed with more ethyl acetate (20 mL). Filtrate was concentrated and purified by prep TLC (SiO2, 95:5, CH$_2$Cl$_2$:MeOH) to give (21 mg, 51%) as a faint yellow oil. MS (ESI) 307 (M+H).

Step D. Preparation of (R)-8-methyl-1,2,3,4,11,11a-hexahydro-pyrazino[1,2-b]isoquinolin-6-one trifluoroacetic acid salt Prepared according to procedures described in Example 221 with the substitution of (R)-2-benzyl-8-methyl-1,2,3,4, 11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 217 (M+H).

Example 242

Preparation of (R)-8-ethyl-1,2,3,4,11,11a-hexahydro-pyrazino[1,2-b]isoquinolin-6-one trifluoroacetic acid salt

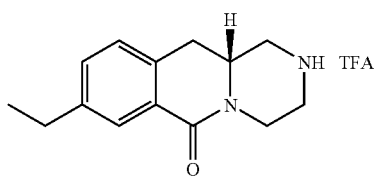

Step A. Preparation of (R)-2-benzyl-8-vinyl-1,2,3,4,11,11a-hexahydro-pyrazino[1,2-b]isoquinolin-6-one Degassed mixture of (R)-2-benzyl-8-methyl-1,2,3,4,11,11a-hexahydro-pyrazino[1,2-b]isoquinolin-6-one (50 mg, 0.13 mmol), tributyl(vinyl)tin (64 mg, 0.20 mmol), dichlorobis(triphenylphosphine)palladium (9.1 mg, 0.013 mmol) and LiCl (27.5 mg, 0.65 mmol) in toluene (1 mL) was heated at 110° C. for 18 h to give dark brownish reaction mixture. The mixture was then cooled, diluted with ethyl acetate (10 mL) and filtered through bed of celite and rinsed with more ethyl acetate (20 mL). Filtrate was concentrated and purified by prep TLC (SiO2, 95:5, CH$_2$Cl$_2$:MeOH) to give (25 mg, 60%) as a faint yellow oil. MS (ESI) 319 (M+H).

Step B. Preparation of (R)-8-ethyl-1,2,3,4,11,11a-hexahydro-pyrazino[1,2-b]isoquinolin-6-one trifluoroacetic acid salt Prepared according to procedures described in Example 221 with the substitution of (R)-2-benzyl-8-vinyl-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 231 (M+H).

Example 243

Preparation of (R)-7-bromo-10-methoxy-1,2,3,4,11,11a-hexahydro-pyrazino[1,2-b]isoquinolin-6-one trifluoroacetic acid salt

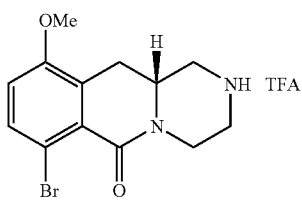

Step A. Preparation of (R)-1-benzyl-3-(5-bromo-2-methoxy-benzyl)-piperazine-2,5-dione Prepared according to the procedures described in Example 220, Step A-B, with the substitution of N-(t-butoxycarbonyl)-D-5-bromo-2-methoxyphenylalanine for N-(t-butoxycarbonyl)-D-4-trifluoromethylphenylalanine in Step A MS (ESI) 405 (M+H).

Step B. Preparation of (R)-1-benzyl-3-(5-bromo-2-methoxy-benzyl)-piperazine Prepared according to the procedures described in Example 220, Step C, with the substitution of (R)-1-benzyl-3-(5-bromo-2-methoxy-benzyl)-piperazine-2,5-dione for 1-benzyl-3-(4-trifluoromethyl-benzyl)-piperazine-2,5-dione and heating for only 4 h gave the product MS (ESI) 377 (M+H).

Step C. Preparation of (R)-2-benzyl-7-bromo-10-methoxy-1,2,3,4,11,11a-hexahydro-pyrazino[1,2-b]isoquinolin-6-one Prepared according to the procedures described in Example 220, Step D-E, with the substitution of (R)-1-benzyl-3-(5-bromo-2-methoxy-benzyl)-piperazine for 1-benzyl-3-(4-trifluoromethyl-benzylpiperazine in Step D. MS (ESI) 403 (M+H).

Step D. Preparation of (R)-7-bromo-10-methoxy-1,2,3,4,11,11a-hexahydro-pyrazino[1,2-b]isoquinolin-6-one trifluoroacetic acid salt Prepared according to procedures described in Example 229 with the substitution of (R)-2-benzyl-7-bromo-10-methoxy-1,2,3,4,11,11a-hexahydro-pyrazino[1,2-b]isoquinolin-6-one for (R)-2-benzyl-8-bromo-1,2,3,4,11,11a-hexahydro-pyrazino[1,2-b]isoquinolin-6-one. MS (ESI) 311, 313 (M+H).

Example 244

Preparation of (R)-10-methoxy-1,2,3,4,11,11a-hexahydro-pyrazino[1,2-b]isoquinolin-6-one trifluoroacetic acid salt

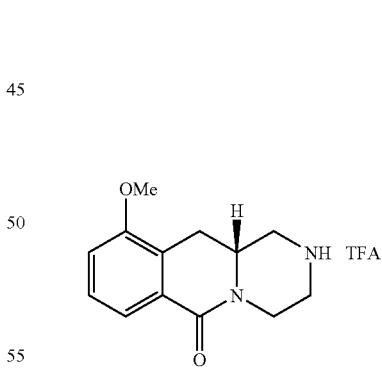

Prepared according to procedures described in Example 221 with the substitution of (R)-2-benzyl-7-bromo-10-methoxy-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 233 (M+H).

Example 245

Preparation of (R)-7-cyano-10-methoxy-1,2,3,4,11,11a-hexahydro-pyrazino[1,2-b]isoquinolin-6-one trifluoroacetic acid salt

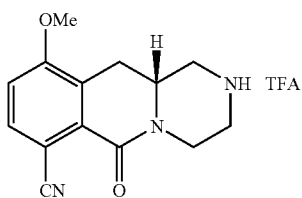

Step A. Preparation of (R)-2-benzyl-7-cyano-10-methoxy-1,2,3,4,11,11a-hexahydro-pyrazino[1,2-b]isoquinolin-6-one Prepared according to the procedures described in Example 230, Step A, with the substitution of (R)-2-benzyl-8-bromo-1,2,3,4,11,11a-hexahydro-pyrazino[1,2-b]isoquinolin-6-one for (R)-2-benzyl-7-bromo-10-methoxy-1,2,3,4,11,11a-hexahydro-pyrazino[1,2-b]isoquinolin-6-one MS (ESI) 348 (M+H).

Step B. Preparation of (R)-7-cyano-10-methoxy-1,2,3,4,11,11a-hexahydro-pyrazino[1,2-b]isoquinolin-6-one trifluoroacetic acid salt Prepared according to procedures described in Example 229 with the substitution of (R)-2-benzyl-8-bromo-1,2,3,4,11,11a-hexahydro-pyrazino[1,2-b]isoquinolin-6-one for (R)-2-benzyl-7-cyano-10-methoxy-1,2,3,4,11,11a-hexahydro-pyrazino[1,2-b]isoquinolin-6-one. MS (ESI) 258 (M+H).

Example 246

Preparation of (R)-7-methyl-10-methoxy-1,2,3,4,11,11a-hexahydro-pyrazino[1,2-b]isoquinolin-6-one trifluoroacetic acid salt

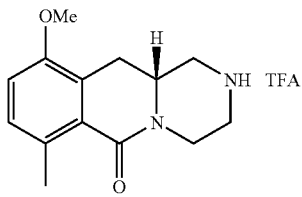

Step A. Preparation of (R)-1-benzyl-3-(5-methyl-2-methoxy-benzyl)-piperazine-2,5-dione To a degassed mixture of (R)-1-benzyl-3-(5-bromo-2-methoxy-benzyl)-piperazine-2,5-dione (1.91 g, 4.74 mmol) and Pd(dppf)Cl$_2$ (0.12 g, 0.14 mmol) in dioxane (18 mL), 2M dimethyl zinc in toluene (4.74 mL, 9.48 mmol) was slowly added at 0° C. and heated at reflux for 1 h to give dark brownish reaction mixture. The mixture was then cooled RT and quenched with methanol (10 mL) and filtered off the precipitate and rinsed with more methanol (20 mL). Filtrate was concentrated and purified (SiO2, 95:5, CH$_2$Cl$_2$:MeOH) to give (1.33 g, 83%) as a amber oil. MS (ESI) 339 (M+H).

Step B. Preparation of (R)-7-methyl-10-methoxy-1,2,3,4,11,11a-hexahydro-pyrazino[1,2-b]isoquinolin-6-one trifluoroacetic acid salt Prepared according to the procedures described in Example 220, Step C-E, with the substitution of (R)-1-benzyl-3-(5-methyl-2-methoxy-benzyl)-piperazine-2,5-dione for 1-benzyl-3-(4-trifluoromethyl-benzyl)-piperazine-2,5-dione in Step C. And substitution of (R)-2-benzyl-7-methyl-10-methoxy-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one in Example 221 to give faint yellow lyophilate MS (ESI) 247 (M+H).

Example 247

Preparation of (R)-7-methyl-9-ethyl-1,2,3,4,11,11a-hexahydro-pyrazino[1,2-b]isoquinolin-6-one trifluoroacetic acid salt

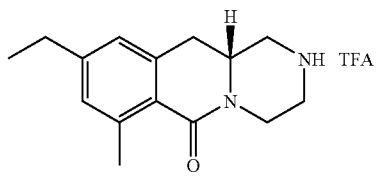

Step A. Preparation of (R)-2-benzyl-7-methyl-10-hydroxy-1,2,3,4,11,11a-hexahydro-pyrazino[1,2-b]isoquinolin-6-one To a stirred solution of (R)-2-benzyl-7-methyl-10-methoxy-1,2,3,4,11,11a-hexahydro-pyrazino[1,2-b]isoquinolin-6-one (210 mg, 0.625 mmol) in dry dichloromethane (7 mL), 1M BBr$_3$ in dichloromethane (3.1 mL, 3.1 mmol) was added at −78° C. The reaction was stirred for 2.5 h at RT under Argon. Slowly quenched with MeOH (5 mL) and conc in vacuo to give light brownish residue. MS (ESI) 323 (M+H).

Step B. Preparation of (R)-2-benzyl-7-methyl-9-bromo-10-hydroxy-1,2,3,4,11,11a-hexahydro-pyrazino[1,2-b]isoquinolin-6-one To a stirred solution of (R)-2-benzyl-7-methyl-10-hydroxy-1,2,3,4,11,11a-hexahydro-pyrazino[1,2-b]isoquinolin-6-one (190 mg, 0.59 mmol) in dry CH$_2$Cl$_2$:methanol (4:2 mL), tetrabutylammonium tribromide (331 mg, 0.68 mmol) was added. The reaction was stirred for 1 h under Argon added more tetrabutylammonium tribromide (45 mg, 0.09 mmol). After 20 min removed solvent in rotavap and then diluted with dichloromethane (100 mL), washed with 5% Na$_2$S$_2$O$_3$ (10 mL), saturated NaHCO$_3$ (10 mL) and brine (15 mL). The organic layer was dried over MgSO$_4$, and conc in vacuo and purified by prep TLC (SiO2, 95:5, CH$_2$Cl$_2$:MeOH) to yield 86 mg (36%) of the product as a faint brown oil. MS (ESI) 401, 403 (M+H).

Step C. Preparation of (R)-2-benzyl-7-methyl-9-ethyl-10-hydroxy-1,2,3,4,11,11a-hexahydro-pyrazino[1,2-b]isoquinolin-6-one To a degassed mixture of (R)-2-benzyl-7-methyl-9-bromo-10-hydroxy-1,2,3,4,11,11a-hexahydro-pyrazino[1,2-b]isoquinolin-6-one (45 mg, 0.11 mmol) and Pd(dppf)Cl$_2$ (0.12 g, 0.14 mmol) in dioxane (1.25 mL), 1.1M diethyl zinc in toluene (0.21 mL, 0.22 mmol) was slowly added at 0° C. and heated at reflux for 1 h to give dark brownish reaction mixture. The mixture was then cooled RT and quenched with methanol (10 mL) and filtered off the precipitate and rinsed with more methanol (20 mL). Filtrate was concentrated and purified on prep TLC (SiO2, 95:5, CH$_2$Cl$_2$:MeOH) to give (50 mg, 93%) as a faint yellow oil. MS (ESI) 351 (M+H).

Step D. Preparation of (R)-2-benzyl-7-methyl-9-ethyl-10-OTf-1,2,3,4,11,11a-hexahydro-pyrazino[1,2-b]isoquinolin-6-one To a stirred solution of (R)-2-benzyl-7-methyl-9-ethyl-10-hydroxy-1,2,3,4,11,11a-hexahydro-pyrazino[1,2-b]isoquinolin-6-one (50 mg, 0.14 mmol) in dry CH$_2$Cl$_2$ (3 mL), trifluoromethanesulfonic anhydride (48 mg, 0.17 mmol) followed by pyridine (82 mg, 1.05 mmol) was added at 0° C. The reaction was stirred for 2 h in RT under Argon to give burgundy reaction. Quenched with H$_2$O (10 mL) and extracted with dichloromethane (2×50 mL). Combined organic layers were washed with 1N HCl (10 mL), H$_2$O (10 mL) and dried over Na$_2$SO$_4$, and conc in vacuo to yield 63 mg (94%) of the product as a burgundy oil. MS (ESI) 483 (M+H).

Step E. Preparation of (R)-7-methyl-9-ethyl-1,2,3,4,11,11a-hexahydro-pyrazino[1,2-b]isoquinolin-6-one trifluoroacetic acid salt Mixture of (R)-2-benzyl-7-methyl-9-ethyl-10-OTf-1,2,3,4,11,11a-hexahydro-pyrazino[1,2-b]isoquinolin-6-one (30 mg, 0.12 mmol), 10% palladium on carbon (~30 mg, Aldrich) and Et$_3$N (25 mg, 0.25 mmol) in MeOH (4 mL) was hydrogenated at 70 psi. The reaction was stirred for 4 h. and filtered off the catalyst to give crude product. Purification on prep HPLC (Phenomenex Luna 5u C18 21.2×100, H2O/MeOH/0.1% TFA) and lyophilization yielded 7.4 mg (17%) of the product as a faint yellow lyophilate. MS (ESI) 245 (M+H).

Example 248

Preparation of (R)-7,9-di-methyl-10-hydroxy-1,2,3,4,11,11a-hexahydro-pyrazino[1,2-b]isoquinolin-6-one trifluoroacetic acid salt

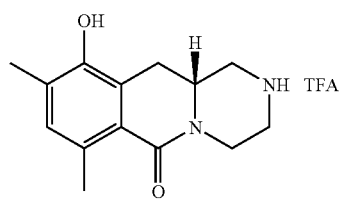

Step A. Preparation of (R)-2-benzyl-7,9-di-methyl-10-hydroxy-1,2,3,4,11,11a-hexahydro-pyrazino[1,2-b]isoquinolin-6-one Prepared according to procedures described in Example 247, Step C, with the substitution of 1.0M diethyl zinc in toluene for 1.1M diethyl zinc in toluene. MS (ESI) 337 (M+H).

Step B. Preparation of (R)-7,9-di-methyl-10-hydroxy-1,2,3,4,11,11a-hexahydro-pyrazino[1,2-b]isoquinolin-6-one trifluoroacetic acid salt Prepared according to procedures described in Example 221 with the substitution of (R)-2-benzyl-7,9-di-methyl-10-hydroxy-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 247 (M+H).

Examples 249 and 250

Preparation of (R)-8,9-di-chloro-1,2,3,4,11,11a-hexahydro-pyrazino[1,2-b]isoquinolin-6-one trifluoroacetic acid salt and (R)-7,8-di-chloro-1,2,3,4,11,11a-hexahydro-pyrazino[1,2-b]isoquinolin-6-one trifluoroacetic acid salt

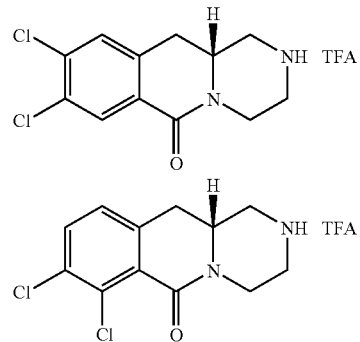

Step A. Preparation of (R)-2-benzyl-8,9-di-chloro-1,2,3,4,11,11a-hexahydro-pyrazino[1,2-b]isoquinolin-6-one and (R)-2-benzyl-7,8-di-chloro-1,2,3,4,11,11a-hexahydro-pyrazino[1,2-b]isoquinolin-6-one Prepared according to procedures described in Example 220 with the substitution of N-(t-butoxycarbonyl)-D-3,4,di-chlorophenylalanine for N-(t-butoxycarbonyl)-D-4-trifluoromethylphenylalanine in step A. MS (ESI) 271, 273 (M+H).

Step B. Preparation of (R)-8,9-di-chloro-1,2,3,4,11,11a-hexahydro-pyrazino[1,2-b]isoquinolin-6-one trifluoroacetic acid salt and (R)-7,8-di-chloro-1,2,3,4,11,11a-hexahydro-pyrazino[1,2-b]isoquinolin-6-one trifluoroacetic acid salt Prepared according to procedures described in Example 229 with the substitution of (R)-2-benzyl-8,9-di-chloro-1,2,3,4,11,11a-hexahydro-pyrazino[1,2-b]isoquinolin-6-one for (R)-2-benzyl-8-bromo-1,2,3,4,11,11a-hexahydro-pyrazino[1,2-b]isoquinolin-6-one. MS (ESI) 271, 273 and 271, 273 (M+H).

Example 251

Preparation of (R)-7-methyl-10-hydroxy-1,2,3,4,11,11a-hexahydro-pyrazino[1,2-b]isoquinolin-6-one trifluoroacetic acid salt

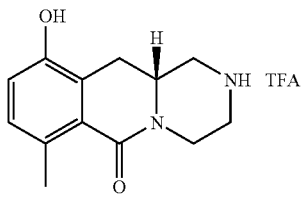

Prepared according to procedures described in Example 221 with the substitution of (R)-benzyl-7-methyl-10-hydroxy-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 233 (M+H).

Example 252

Preparation of (R)-9-hydroxy-1,2,3,4,11,11a-hexahydro-pyrazino[1,2-b]isoquinolin-6-one trifluoroacetic acid salt

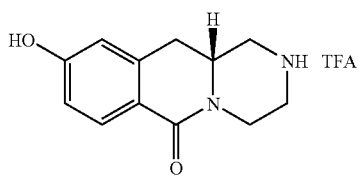

Step A. Preparation of (R)-2-benzyl-9-hydroxy-1,2,3,4,11,11a-hexahydro-pyrazino[1,2-b]isoquinolin-6-one Prepared according to procedures described in Example 247, Step A, with the substitution of (R)-2-benzyl-9-methoxy-1,2,3,4,11,11a-hexahydro-pyrazino[1,2-b]isoquinolin-6-one for (R)-2-benzyl-7-methyl-10-methoxy-1,2,3,4,11,11a-hexahydro-pyrazino[1,2-b]isoquinolin-6-one. MS (ESI) 309 (M+H).

Step B. Preparation of (R)-9-hydroxy-1,2,3,4,11,11a-hexahydro-pyrazino[1,2-b]isoquinolin-6-one trifluoroacetic acid salt Prepared according to procedures described in Example 221 with the substitution of (R)-2-benzyl-9-hydroxy-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 219 (M+H).

Examples 253 and 254

Preparation of (R)-9-hydroxy-10-methyl-1,2,3,4,11,11a-hexahydro-pyrazino[1,2-b]isoquinolin-6-one trifluoroacetic acid salt and (R)-9-hydroxy-8,10-dimethyl-1,2,3,4,11,11a-hexahydro-pyrazino[1,2-b]isoquinolin-6-one trifluoroacetic acid salt

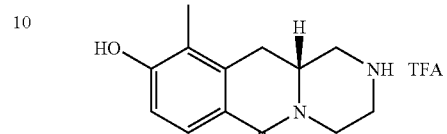

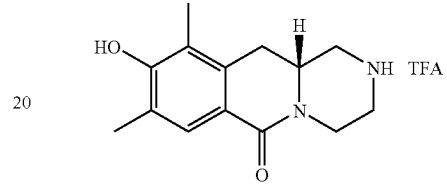

Step A. Preparation of (R)-2-benzyl-9-hydroxy-10-bromo-1,2,3,4,11,11a-hexahydro-pyrazino[1,2-b]isoquinolin-6-one and (R)-2-benzyl-9-hydroxy-8,10-di-bromo-1,2,3,4,11,11a-hexahydro-pyrazino[1,2-b]isoquinolin-6-one Prepared according to procedures described in Example 247, Step B, with the substitution of (R)-2-benzyl-9-hydroxy-1,2,3,4,11,11a-hexahydro-pyrazino[1,2-b]isoquinolin-6-one for (R)-2-benzyl-7-methyl-10-hydroxy-1,2,3,4,11,11a-hexahydro-pyrazino[1,2-b]isoquinolin-6-one and separation of the mono brominated product, MS (ESI) 387, 389 (M+H), and the di-brominated product. MS (ESI) 467 (M+H)

Step B. Preparation of (R)-2-benzyl-9-hydroxy-10-methyl-1,2,3,4,11,11a-hexahydro-pyrazino[1,2-b]isoquinolin-6-one Prepared according to procedures described in Example 246, Step A, with the substitution of (R)-2-benzyl-9-hydroxy-10-bromo-1,2,3,4,11,11a-hexahydro-pyrazino[1,2-b]isoquinolin-6-one for (R)-1-benzyl-3-(5-bromo-2-methoxybenzyl)-piperazine-2,5-dione. MS (ESI) 323 (M+H).

Step C. Preparation of (R)-2-benzyl-9-hydroxy-8,10-dimethyl-1,2,3,4,11,11a-hexahydro-pyrazino[1,2-b]isoquinolin-6-one Prepared according to procedures described in Example 246, Step A, with the substitution of (R)-2-benzyl-9-hydroxy-8,10-di-bromo-1,2,3,4,11,11a-hexahydro-pyrazino[1,2-b]isoquinolin-6-one for (R)-1-benzyl-3-(5-bromo-2-methoxybenzyl)-piperazine-2,5-dione. MS (ESI) 337 (M+H).

Step D. Preparation of (R)-9-hydroxy-10-methyl-1,2,3,4,11,11a-hexahydro-pyrazino[1,2-b]isoquinolin-6-one trifluoroacetic acid salt Prepared according to procedures described in Example 221 with the substitution of (R)-2-benzyl-9-hydroxy-10-methyl-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 233 (M+H).

Step E. Preparation of (R)-9-hydroxy-8,10-dimethyl-1,2,3,4,11,11a-hexahydro-pyrazino[1,2-b]isoquinolin-6-one trifluoroacetic acid salt Prepared according to procedures described in Example 221 with the substitution of (R)-2-benzyl-9-hydroxy-8,10-dimethyl-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 247 (M+H).

Examples 255 and 256

Preparation of (R)-2-benzyl-9-chloro-1,2,3,4,11,11a-hexahydro-pyrazino[1,2-b]isoquinolin-6-one and (R)-2-benzyl-7-chloro-1,2,3,4,11,11a-hexahydro-pyrazino[1,2-b]isoquinolin-6-one

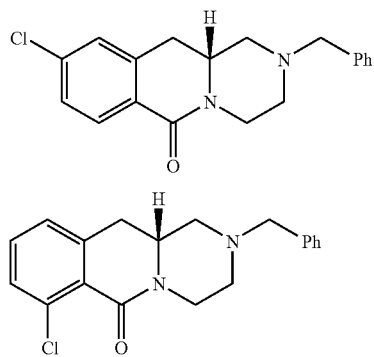

Prepared according to the procedures described in Example 220, with the substitution of N-(t-butoxycarbonyl)-D-3-chlorophenylalanine for N-(t-butoxycarbonyl)-D-4-trifluoromethylphenylalanine in Step A and purified by silica gel chromatography, MeOH/CH$_2$Cl$_2$ (0-5% gradient) to give a mixture of regioisomers (9-Cl:7-Cl=3:1). A half of the mixture was separated by chiral prep HPLC (OJ column, 15% iPrOH in Heptane). MS (ESI) 327 (M+H) and MS (ESI) 327 (M+H).

Examples 257 and 258

Preparation of (R)-9-chloro-1,2,3,4,11,11a-hexahydropyrazino[1,2-b]isoquinolin-6-one trifluoroacetic acid salt and (R)-7-chloro-1,2,3,4,11,11a-hexahydro-pyrazino[1,2-b]isoquinolin-6-one trifluoroacetic acid salt

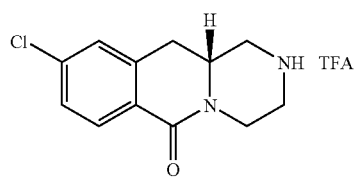

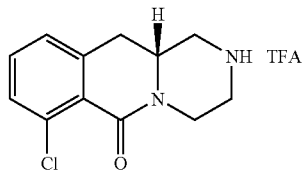

Prepared according to procedures described in Example 229 with the substitution of a mixture of (R)-2-benzyl-9-chloro-1,2,3,4,11,11a-hexahydro-pyrazino[1,2-b]isoquinolin-6-one and (R)-2-benzyl-7-chloro-1,2,3,4,11,11a-hexahydro-pyrazino[1,2-b]isoquinolin-6-one for (R)-2-benzyl-8-bromo-1,2,3,4,11,11a-hexahydro-pyrazino[1,2-b]isoquinolin-6-one. MS (ESI) 237 (M+H) and 237 (M+H).

Example 259

Preparation of (R)-7-chloro-2,3,4,6,11,11a-hexahydro-1H-pyrazino[1,2-b]isoquinoline di-trifluoroacetic acid salt

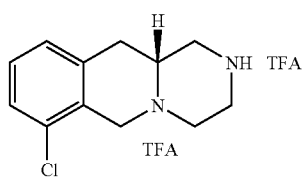

Step A. Preparation of (R)-7-chloro-1,2,3,4,11,11a-hexahydro-pyrazino[1,2-b]isoquinolin-6-one hydrochloric acid salt Prepared according to the procedures described in Example 229, with the substitution of (R)-2-benzyl-7-chloro-1,2,3,4,11,11a-hexahydro-pyrazino[1,2-b]isoquinolin-6-one for (R)-2-benzyl-8-bromo-1,2,3,4,11,11a-hexahydro-pyrazino[1,2-b]isoquinolin-6-one. The desired crude product was used for next step without further purification MS (ESI) 237 (M+H).

Step B. Preparation of (R)-7-chloro-2,3,4,6,11,11a-hexahydro-1H-pyrazino[1,2-b]isoquinoline di-trifluoroacetic acid salt Prepared according to the procedures described in Example 220 step C, with the substitution of (R)-7-chloro-1,2,3,4,11,11a-hexahydro-pyrazino[1,2-b]isoquinolin-6-one hydrochloric acid salt for 1-benzyl-3-(4-trifluoromethyl-benzyl)-piperazine-2,5-dione. Purification on prep HPLC (Phenomenex Luna 5u C18 21.2×100, H2O/MeOH/0.1% TFA) and lyophilization yielded the product as a tan solid. MS (ESI) 223, 225 (M+H).

Example 260

Preparation of (R)-9-propyl-1,2,3,4,11,11a-hexahydropyrazino[1,2-b]isoquinolin-6-one trifluoroacetic acid salt

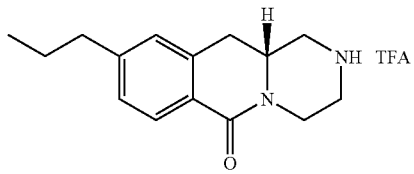

Step A. Preparation of (R)-2-benzyl-9-propyl-1,2,3,4,11,11a-hexahydro-pyrazino[1,2-b]isoquinolin-6-one A mixture of (R)-9-chloro-1,2,3,4,11,11a-hexahydro-pyrazino[1,2-b]isoquinolin-6-one (50 mg, 0.15 mmol), bis(tri-t-butyl phosphine) palladium (2.3 mg, 0.0045 mmol), propyl boronic acid (16 mg, 0.18 mmol), and potassium fluoride (19 mg, 0.33 mmol) in anhydrous 1,4-dioxane (2 mL) was degassed, heated to 100° C. and stirred for 6 h under nitrogen atmosphere. Then the mixture was cooled down to room temperature, diluted with 10 ml of EtOAc and filtered through celite pad. The filtrate was concentrated to give the desired product which was used for next step without further purification. MS (ESI) 335 (M+H).

Step B. Preparation of (R)-9-propyl-1,2,3,4,11,11a-hexahydro-pyrazino[1,2-b]isoquinolin-6-one trifluoroacetic acid salt Prepared according to procedures described in Example 221 with the substitution of (R)-2-benzyl-9-propyl-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 245 (M+H).

Examples 261 and 262

Preparation of (R)-2-benzyl-9-bromo-1,2,3,4,11,11a-hexahydro-pyrazino[1,2-b]isoquinolin-6-one and (R)-2-benzyl-7-bromo-1,2,3,4,11,11a-hexahydro-pyrazino[1,2-b]isoquinolin-6-one

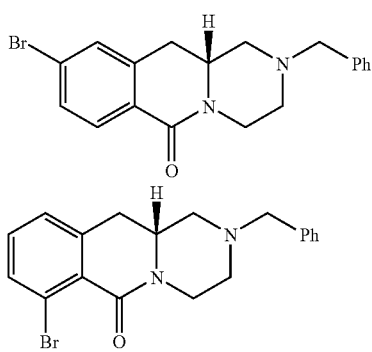

Prepared according to the procedures described in Example 220, with the substitution of N-(t-butoxycarbonyl)-D-3-bromophenylalanine for N-(t-butoxycarbonyl)-D-4-trifluoromethylphenylalanine in Step A and purified by silica gel chromatography, MeOH/CH2Cl2 (0-4% gradient) to give a mixture of regioisomers. MS (ESI) 371, 373 (M+H) and MS (ESI) 371, 373 (M+H).

Examples 263 and 264

Preparation of (R)-9-bromo-1,2,3,4,11,11a-hexahydro-pyrazino[1,2-b]isoquinolin-6-one trifluoroacetic acid salt and (R)-7-bromo-1,2,3,4,11,11a-hexahydro-pyrazino[1,2-b]isoquinolin-6-one trifluoroacetic acid salt

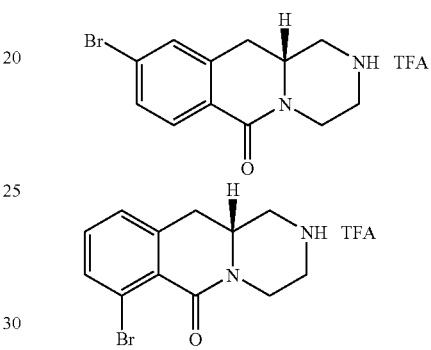

Prepared according to procedures described in Example 229 with the substitution of a mixture of (R)-2-benzyl-9-bromo-1,2,3,4,11,11a-hexahydro-pyrazino[1,2-b]isoquinolin-6-one and (R)-2-benzyl-7-bromo-1,2,3,4,11,11a-hexahydro-pyrazino[1,2-b]isoquinolin-6-one for (R)-2-benzyl-8-bromo-1,2,3,4,11,11a-hexahydro-pyrazino[1,2-b]isoquinolin-6-one. MS (ESI) 281, 283 (M+H) and 281, 283 (M+H).

Examples 265 and 266

Preparation of (R)-9-methyl-1,2,3,4,11,11a-hexahydro-pyrazino[1,2-b]isoquinolin-6-one trifluoroacetic acid salt and (R)-7-methyl-1,2,3,4,11,11a-hexahydro-pyrazino[1,2-b]isoquinolin-6-one trifluoroacetic acid salt

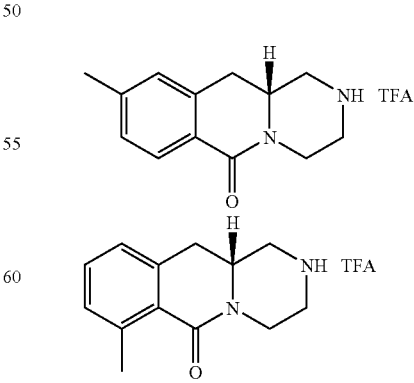

Prepared according to procedures described in Example 241 with the substitution of a mixture of (R)-2-benzyl-9- methyl-1,2,3,4,11,11a-hexahydro-pyrazino[1,2-b]isoquinolin-6-one and (R)-2-benzyl-7-methyl-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 217 (M+H) and MS (ESI) 217 (M+H).

Examples 267 and 268

Preparation of (R)-9-ethyl-1,2,3,4,11,11a-hexahydro-pyrazino[1,2-b]isoquinolin-6-one trifluoroacetic acid salt and (R)-7-ethyl-1,2,3,4,11,11a-hexahydro-pyrazino[1,2-b]isoquinolin-6-one trifluoro acetic acid salt

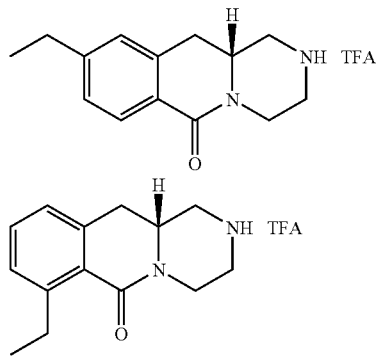

Prepared according to procedures described in Example 242 with the substitution of a mixture of (R)-2-benzyl-9-methyl-1,2,3,4,11,11a-hexahydro-pyrazino[1,2-b]isoquinolin-6-one and (R)-2-benzyl-7-methyl-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. MS (ESI) 221 (M+H) and MS (ESI) 221 (M+H).

Example 269

Preparation of (R)-9-isopropyl-1,2,3,4,11,11a-hexahydro-pyrazino[1,2-b]isoquinolin-6-one trifluoroacetic acid salt

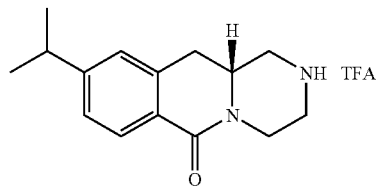

Step A. Preparation of (R)-2-benzyl-9-isopropenyl-1,2,3,4,11,11a-hexahydro-pyrazino[1,2-b]isoquinolin-6-one A degassed mixture of (R)-2-benzyl-9-bromo-1,2,3,4,11,11a-hexahydro-pyrazino[1,2-b]isoquinolin-6-one with (R)-2-benzyl-7-bromo-1,2,3,4,11,11a-hexahydro-pyrazino[1,2-b]isoquinolin-6-one (9-Br:7-Br=11:2, 100 mg, 0.27 mmol), isopropenyl boronic acid (46 mg, 0.54 mmol), tetrakis(triphenylphosphine)palladium (16 mg, 0.013 mmol) and K$_2$CO$_3$ (82 mg, 0.59 mmol) in DME (2 mL) and water (0.6 mL) was heated at 80° C. for 9 h to give dark brownish reaction mixture. The mixture was then cooled, quenched with 10 mL of water, extracted with ethyl acetate (3×10 mL), dried over MgSO$_4$, and concentrated in vacuo to give the desired product as brown oil (No 7-isomeric product was observed).

MS (ESI) 333 (M+H). The crude product was utilized for next step without further purification.

Step B. (R)-9-isopropyl-1,2,3,4,11,11a-hexahydro-pyrazino[1,2-b]isoquinolin-6-one trifluoroacetic acid salt Prepared according to procedures described in Example 221 with the substitution of (R)-2-benzyl-9-isopropenyl-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. The desired product was obtained as a white lyophilate (27 mg, 42% for 2 steps). MS (ESI) 245 (M+H).

Examples 270 and 271

Preparation of (R)-9-cyclopropyl-1,2,3,4,11,11a-hexahydro-pyrazino[1,2-b]isoquinolin-6-one trifluoroacetic acid salt and (R)-7-cyclopropyl-1,2,3,4,11,11a-hexahydro-pyrazino[1,2-b]isoquinolin-6-one trifluoroacetic acid salt

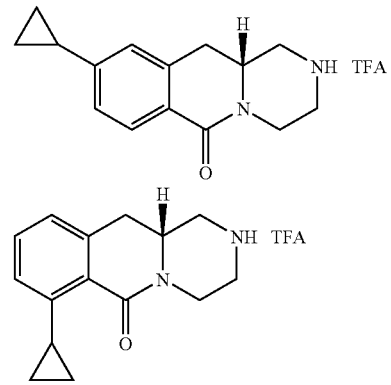

Step A. Preparation of (R)-2-benzyl-9-isopropenyl-1,2,3,4,11,11a-hexahydro-pyrazino[1,2-b]isoquinolin-6-one A degassed mixture of (R)-2-benzyl-9-bromo-1,2,3,4,11,11a-hexahydro-pyrazino[1,2-b]isoquinolin-6-one with (R)-2-benzyl-7-bromo-1,2,3,4,11,11a-hexahydro-pyrazino[1,2-b]isoquinolin-6-one (9-Br:7-Br=1:2, 100 mg, 0.27 mmol), isopropenyl boronic acid (46 mg, 0.54 mmol), tetrakis(triphenylphosphine)palladium (16 mg, 0.013 mmol) and K$_2$CO$_3$ (82 mg, 0.59 mmol) in DME (2 mL) and water (0.6 mL) was heated at 80° C. for 9 h to give dark brownish reaction mixture. The mixture was then cooled, quenched with 10 mL of water, extracted with ethyl acetate (3×10 mL), dried over MgSO$_4$, and concentrated in vacuo to give the desired product as brown oil (No 7-isomeric product was observed).

MS (ESI) 333 (M+H). The crude product was utilized for next step without further purification.

Step B. (R)-8-ethyl-1,2,3,4,11,11a-hexahydro-pyrazino[1,2-b]isoquinolin-6-one trifluoroacetic acid salt Prepared according to procedures described in Example 221 with the substitution of (R)-2-benzyl-9-isopropenyl-1,2,3,4,11,11a-hexahydro-pyrazino[1,2-b]isoquinolin-6-one for (R)-2-benzyl-8-trifluoromethyl-1,2,3,4,11,11a-hexahydro-pyrazino[1,2-b]isoquinolin-6-one. The desired product was obtained as a white lyophilate (27 mg, 42% for 2 steps). MS (ESI) 245 (M+H).

Examples 272 and 273

Preparation of (R)-9-cyano-1,2,3,4,11,11a-hexahydro-pyrazino[1,2-b]isoquinolin-6-one trifluoroacetic acid salt and of (R)-7-cyano-1,2,3,4,11,11a-hexahydro-pyrazino[1,2-b]isoquinolin-6-one trifluoroacetic acid salt

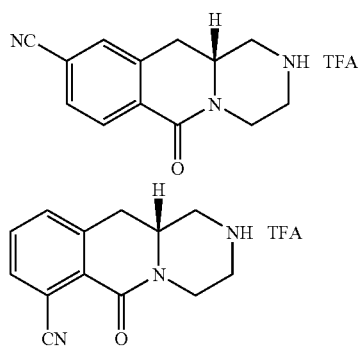

Prepared according to the procedures described in Example 230, with the substitution of a mixture of (R)-2-benzyl-9-bromo-1,2,3,4,11,11a-hexahydro-pyrazino[1,2-b]isoquinolin-6-one and (R)-2-benzyl-7-bromo-1,2,3,4,11,11a-hexahydro-pyrazino[1,2-b]isoquinolin-6-one for (R)-2-benzyl-8-bromo-1,2,3,4,11,11a-hexahydro-pyrazino[1,2-b]isoquinolin-6-one. MS (ESI) 228 (M+H).

Example 274

Preparation of (R)-2-benzyl-10-bromo-1,2,3,4,11,11a-hexahydro-pyrazino[1,2-b]isoquinolin-6-one

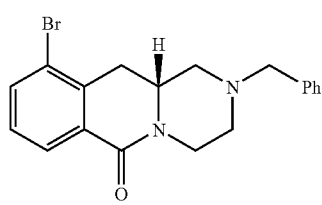

Prepared according to the procedures described in Example 220, with the substitution of N-(t-butoxycarbonyl)-D-2-bromophenylalanine for N-(t-butoxycarbonyl)-D-4-trifluoromethylphenylalanine in Step A and purified by silica gel chromatography, MeOH/CH2Cl2 (0-4% gradient) to give the desired product as a yellowish oil. MS (ESI) 371, 373 (M+H).

Example 275

Preparation of (R)-10-bromo-1,2,3,4,11,11a-hexahydro-pyrazino[1,2-b]isoquinolin-6-one trifluoroacetic acid salt

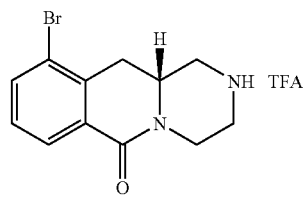

Prepared according to procedures described in Example 229 with the substitution of (R)-2-benzyl-10-bromo-1,2,3,4,11,11a-hexahydro-pyrazino[1,2-b]isoquinolin-6-one for (R)-2-benzyl-8-bromo-1,2,3,4,11,11a-hexahydro-pyrazino[1,2-b]isoquinolin-6-one. MS (ESI) 281, 283 (M+H).

Example 276

Preparation of (R)-10-methyl-1,2,3,4,11,11a-hexahydro-pyrazino[1,2-b]isoquinolin-6-one trifluoroacetic acid salt

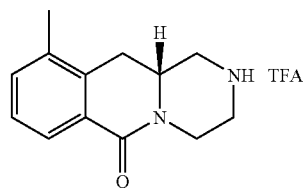

Prepared according to procedures described in Example 266 with the substitution of (R)-2-benzyl-10-bromo-1,2,3,4,11,1a-hexahydro-pyrazino[1,2-b]isoquinolin-6-one for a mixture of (R)-2-benzyl-9-bromo-1,2,3,4,11,11a-hexahydro-pyrazino[1,2-b]isoquinolin-6-one and (R)-2-benzyl-7-bromo-1,2,3,4,11,11a-hexahydro-pyrazino[1,2-b]isoquinolin-6-one, and the substitution of methyl boronic acid for isopropenyl boronic acid in step A. MS (ESI) 217 (M+H).

Example 277

Preparation of (R)-10-ethyl-1,2,3,4,11,11a-hexahydro-pyrazino[1,2-b]isoquinolin-6-one trifluoroacetic acid salt

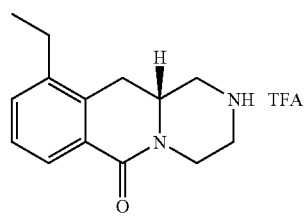

Prepared according to procedures described in Example 242 with the substitution of (R)-2-benzyl-10-bromo-1,2,3,4, 11,11a-hexahydro-pyrazino[1,2-b]isoquinolin-6-one for a mixture of (R)-2-benzyl-9-bromo-1,2,3,4,11,11a-hexahydro-pyrazino[1,2-b]isoquinolin-6-one and (R)-2-benzyl-7-bromo-1,2,3,4,11,11a-hexahydro-pyrazino[1,2-b]isoquinolin-6-one, and the substitution of trivinylcyclotriboroxane for isopropenyl boronic acid in step A. MS (ESI) 231 (M+H).

Example 278

Preparation of (R)-10-propyl-1,2,3,4,11,11a-hexahydro-pyrazino[1,2-b]isoquinolin-6-one trifluoroacetic acid salt

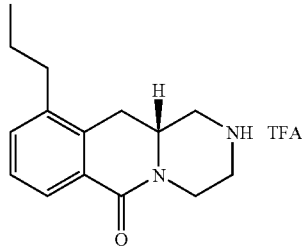

Prepared according to procedures described in Example 242 with the substitution of (R)-2-benzyl-10-bromo-1,2,3,4, 11,11a-hexahydro-pyrazino[1,2-b]isoquinolin-6-one for a mixture of (R)-2-benzyl-9-bromo-1,2,3,4,11,11a-hexahydro-pyrazino[1,2-b]isoquinolin-6-one and (R)-2-benzyl-7-bromo-1,2,3,4,11,11a-hexahydro-pyrazino[1,2-b]isoquinolin-6-one, and the substitution of cis-propenyl boronic acid for isopropenyl boronic acid in step A. MS (ESI) 245 (M+H).

Example 279

Preparation of (R)-10-bromo-8-trifluoromethyl-1,2,3,4,11,11a-hexahydropyrazino[1,2-b]isoquinolin-6-one

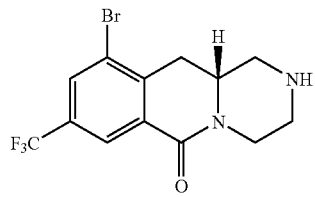

Step A. Preparation of (R)-8 trifluoromethyl-1,2,3,4,11,11a-hexahydro-pyrazino[1,2-b]isoquinolin-6-one Prepared according to the procedures described in Example 221. Purification by flash column chromatography (SiO$_2$, 95:5:1 methylene chloride/methanol/triethylamine) yielded the desired product as a white solid. MS (ESI) 271 (M+H).

Step B. Preparation of (R)-10-bromo-8-trifluoromethyl-1,2,3,4,11,11a-hexahydropyrazino[1,2-b]isoquinolin-6-one A solution of (R)-8 trifluoromethyl-1,2,3,4,11,11a-hexahydro-pyrazino[1,2-b]isoquinolin-6-one (245 mg, 0.9 mmol) in H$_2$SO$_4$ (2 mL) was treated with NBS (210 mg, 1.17 mmol) at room temperature. After 48 h, the reaction mixture was quenched with saturated aqueous NaHCO$_3$ and diluted with EtOAc (15 mL). The solution was extracted with EtOAc (50 mL) and the organic layer was dried over Na$_2$SO$_4$, filtered, and concentrated in vacuo to afford a yellow oil. Purification of the oil by flash column chromatography (SiO$_2$, 96:4:1 methylene chloride/methanol/triethylamine) provided (R)-10-bromo-8-trifluoromethyl-1,2,3,4,11,11a-hexahydro-pyrazino[1,2-b]isoquinolin-6-one (80 mg, 25%) as an off-white solid. MS (ESI) 349 (M+H).

Example 280

Preparation of (R)-10-ethyl-8-trifluoromethyl-1,2,3,4,11,11a-hexahydropyrazino[1,2-b]isoquinolin-6-one hydrochloric acid salt

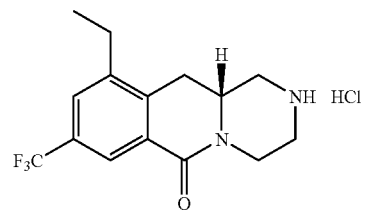

Step A. Preparation of (R)-2-N-(t-butoxycarbonyl)-10-bromo-8-trifluoromethyl-1,2,3,4,11,11a-hexahydropyrazino[1,2-b]isoquinolin-6-one Prepared according to procedures described in Example 2 with the substitution of (R)-10-bromo-8-trifluoromethyl-1,2,3,4,11,11a-hexahydropyrazino[1,2-b]isoquinolin-6-one for (±)-1,3,4,10b-tetrahydro-7-trifluoromethoxy-pyrazino[2,1-a]isoindol-6(2H)-one, at step A. MS (ESI) 359 (M+H).

Step B. Preparation of (R)-10-ethyl-8-trifluoromethyl-1,2,3,4,11,11a-hexahydropyrazino[1,2-b]isoquinolin-6-one hydrochloric acid salt To a mixture of (R)-2-N-(t-butoxycarbonyl)-10-bromo-8-trifluoromethyl-1,2,3,4,11,11a-hexahydropyrazino[1,2-b]isoquinolin-6-one (61 mg, 0.135 mmol) and 2,4,6-trivinylcyclotriboroxane pyridine complex (33 mg, 0.135 mmol) in DME (2 mL) was added K$_2$CO$_3$ (20 mg, 0.135 mmol) and water (1 mL). The mixture was degassed under reduced pressure and purged with argon; tetrakis(triphenylphosphine)palladium (0) (20 mg, 0.135 mmol) was added. The reaction mixture was heated to 90° C. for 18 h. The reaction was cooled to room temperature, and diluted with EtOAc (50 mL). The EtOAc layer was dried over Na$_2$SO$_4$, filtered, and concentrated in vacuo to afford crude alkene 6a as a yellow oil.
MS (ESI) 340 (M+H). Crude (R)-2-N-(t-butoxycarbonyl)-10-ethyl-8-trifluoromethyl-1,2,3,4,11,11a-hexahydropyrazino[1,2-b]isoquinolin-6-one was dissolved in EtOH (2 mL) and hydrogenated [10% Pd/C (50 mg), H$_2$ (30 psi)]. The reaction mixture was filtered through diatomaceous earth, and then purified by flash column chromatography (silica gel, 4:1 hexanes/EtOAc). The resulting material was deprotected using 4 N HCl in 1,4-dioxane (200 μL, 0.8 mmol), followed by trituration with diethyl ether, to provide the desired product (18 mg, 40% over 3 steps) as a white solid. MS (ESI) 299 (M+H).

Example 281

Preparation of (R)-10-methyl-8-trifluoromethyl-1,2,3,4,11,11a-hexahydropyrazino[1,2-b]isoquinolin-6-one hydrochloric acid salt

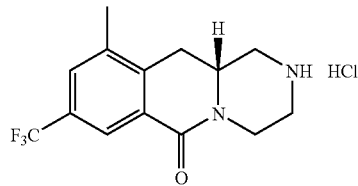

Prepared according to procedures described in Example 280 with the substitution of trimethylboroxane for 2,4,6-trivinylcyclotriboroxane pyridine complex and excluding the hydrogenation at step B. MS (ESI) 285 (M+H).

Example 282

Preparation of (R)-10-propyl-8-trifluoromethyl-1,2,3,4,11,11a-hexahydropyrazino[1,2-b]isoquinolin-6-one hydrochloric aci salt

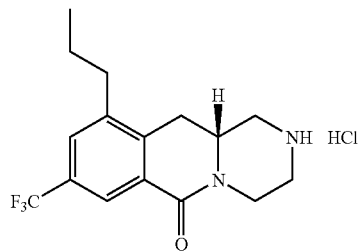

Prepared according to procedures described in Example 280 with the substitution of cis-propenyl boronic acid for 2,4,6-trivinylcyclotriboroxane pyridine complex at step B. MS (ESI) 313 (M+H).

Examples 283 and 284

Preparation of (1S,10bR)-1,3,4,10b-tetrahydro-1-methyl-7-trifluoromethyl-pyrazino[2,1-a]isoindol-6(2H)-one hydrochloric acid salt and (1R,10bS)-1,3,4,10b-tetrahydro-1-methyl-7-trifluoromethyl-pyrazino[2,1-a]isoindol-6(2H)-one hydrochloric acid salt

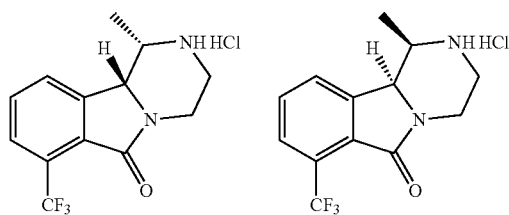

Step A. Preparation of N,N-diethyl-2-carboxaldehyde-6-trifluoromethylbenzamide

Prepared according to the procedures described in Example 1, Steps A-B, substituting 2-trifluoromethylbenzoic acid for 2-trifluoromethoxybenzoic acid at Step A. MS (ESI) 274 (M+H).

Step B. Preparation of 3-hydroxy-7-(trifluoromethyl)isobenzofuran-1(3H)-one

To N,N-diethyl-2-carboxaldehyde-6-trifluoromethylbenzamide (23.3 g, 85 mmol) from Step A was added 6N aqueous hydrogen chloride (500 mL). The resulting mixture was warmed to 100° C. and maintained at this temperature for 12 hr. The reaction was then cooled to 23° C. and extracted with ethyl acetate (×6). The combined organic layers were dried over sodium sulfate, filtered and the filtrate was concentrated. The resulting residue was triturated with hexanes and dried in a vacuum oven to afford 3-hydroxy-7-(trifluoromethyl)isobenzofuran-1(3H)-one (16.2 g, 88%) as a beige solid. MS (ESI) 219 (M+H).

Step C. Preparation of 2-[2-[(tert-butoxycarbonyl)amino]ethyl]-1,3-dihydro-4-trifluoromethyl-isoindol-3(1H)-one To 3-hydroxy-7-(trifluoromethyl)isobenzofuran-1(3H)-one (5.6 g, 25.7 mmol) from Step B in 10% acetic acid in 1,2-dichloroethane (250 mL) was added N-(tert-butoxycarbonyl)ethylenediamine (3.7 mL, 23.4 mmol) and sodium triacetoxyborohydride (7.4 g, 35.1 mmol). The resulting mixture was warmed to 50° C. and maintained at this temperature for 14 hr. The reaction was cooled to 23° C., diluted with saturated aqueous sodium chloride and extracted with ethyl acetate (×3). The combined organic layers were dried over sodium sulfate, filtered and the filtrate was concentrated. The resulting residue was purified by flash column chromatography (SiO$_2$, 0-80% ethyl acetate in hexanes) to afford 2-[2-[(tert-butoxycarbonyl)amino]ethyl]-1,3-dihydro-4-trifluoromethyl-isoindol-3(1H)-one (7.9 g, 89%) as an off-white oily solid. MS (ESI) 345 (M+H).

Step D. Preparation of (±)-2-[2-[(tert-butoxycarbonyl)amino]ethyl]-1-(1-hydroxyethyl)-1,3-dihydro-4-trifluoromethyl-isoindol-3(1H)-one To 2-[2-[(tert-butoxycarbonyl)amino]ethyl]-1,3-dihydro-4-trifluoromethyl-isoindol-3(1H)-one (2.31 g, 6.71 mmol) from Step C in tetrahydrofuran at −78° C. was added sec-butyllithium (12.3 mL, 14.8 mmol; ACROS, titrated with diphenylacetic acid, 1.2 M) in cyclohexane/hexane (92/8) in one portion. After stirring the reaction at −78° C. for 15 min, acetaldehyde (1.88 mL, 33.6 mmol) was added in one portion. The brown-green solution was warmed to 0° C. over 5 min and was then quenched with aqueous hydrogen chloride (1N) and saturated aqueous sodium chloride. The mixture was extracted with ethyl acetate (×3), and the combined organic layers were dried over sodium sulfate, filtered and the filtrate was concentrated. The resulting residue was purified by flash column chromatography (SiO$_2$, 0-50% ethyl acetate in hexanes) to afford (±)-2-[2-[(tert-butoxycarbonyl)amino]ethyl]-1-(1-hydroxyethyl)-1,3-dihydro-4-trifluoromethyl-isoindol-3(1H)-one (2.2 g, 84%) as a white foam-like solid. MS (ESI) 389 (M+H).

Step E. Preparation of (±)-2-[2-[(tert-butoxycarbonyl)amino]ethyl]-1-(1-oxoethyl)-1,3-dihydro-4-trifluoromethyl-isoindol-3(1H)-one To (±)-2-[2-[(tert-butoxycarbonyl)amino]ethyl]-1-(1-hydroxyethyl)-1,3-dihydro-4-trifluoromethyl-isoindol-3(1H)-one (2.2 g, 5.7 mmol) from Step C in dichloromethane at 23° C. was added Dess-Martin periodinane (3.4 g, 7.9 mmol) in one portion. After 20 min, the reaction was quenched with methanol (10 mL) and concentrated. The resulting white mixture was purified by flash column flash column chromatography (SiO₂, 0-50% ethyl acetate in hexanes) to afford (±)-2-[2-[(tert-butoxycarbonyl)amino]ethyl]-1-(1-oxoethyl)-1,3-dihydro-4-trifluoromethyl-isoindol-3(1H)-one (1.9 g, 86%) as a white solid. MS (ESI) 387 (M+H).

Step F. Preparation of N-(t-butoxycarbonyl)-3,4-dihydro-1-methyl-7-trifluoromethyl-pyrazino[2,1-a]isoindol-6(2H)-one Concentrated aqueous hydrogen chloride (5 mL) was added to a mixture of diethyl ether (20 mL) and (±)-2-[2-[(tert-butoxycarbonyl)amino]ethyl]-1-(1-oxoethyl)-1,3-dihydro-4-trifluoromethyl-isoindol-3(1H)-one (1.9 g, 4.9 mmol). The resulting mixture stirred for 5 min and became a yellow solution. The solution was concentrated to dryness, and toluene was added (5 mL). The mixture was again concentrated to dryness, and this procedure was repeated. Finally, the residue was treated with dichloromethane (5 mL) and concentrated to a yellow orange solid. Di-tert-butyl dicarbonate (4.8 g, 22 mmol) was added to the residue, and the mixture was warmed to 55° C. To this mixture was added 4-(dimethylamino)-pyridine (1.2 g, 9.8 mmol). After 5 min, the orange brown solution was directly purified by flash column chromatography (SiO₂, 0-30% ethyl acetate in hexanes) to afford N-(t-butoxycarbonyl)-3,4-dihydro-1-methyl-7-trifluoromethyl-pyrazino[2,1-a]isoindol-6(2H)-one (1.5 g, 83%) as a yellow solid. MS (ESI) 369 (M+H).

Step G. Preparation of N-(t-butoxycarbonyl)-(±)-1,3,4,10b-tetrahydro-1-methyl-7-trifluoromethyl-pyrazino[2,1-a]isoindol-6(2H)-one To a solution of N-(t-butoxycarbonyl)-3,4-dihydro-1-methyl-7-trifluoromethyl-pyrazino[2,1-a]isoindol-6(2H)-one (0.20 g, 0.54 mmol) in methanol (10 mL) was added palladium on carbon (20 mg, 10 wt'; Aldrich). The resulting mixture was degassed (vacuum then argon, ×3) and subjected to a hydrogen atmosphere (60 psi) for 12 hr. The mixture was then filtered, and the filtrate was concentrated. The resulting residue was purified by flash column chromatography (SiO₂, 0-50% ethyl acetate in hexanes) to afford N-(t-butoxycarbonyl)-(±)-1,3,4,10b-tetrahydro-1-methyl-7-trifluoromethyl-pyrazino[2,1-a]isoindol-6(2H)-one (0.19 g, 94%) as a white solid. MS (ESI) 371 (M+H).

Step H. Preparation of (1S,10bR)-1,3,4,10b-tetrahydro-1-methyl-7-trifluoromethyl-pyrazino[2,1-a]isoindol-6(2H)-one hydrochloric acid salt and (1R,10bS)-1,3,4,10b-tetrahydro-1-methyl-7-trifluoromethyl-pyrazino[2,1-a]isoindol-6(2H)-one hydrochloric acid salt The mixture of enantiomers contained in N-(t-butoxycarbonyl)-(±)-1,3,4,10b-tetrahydro-1-methyl-7-trifluoromethyl-pyrazino[2,1-a]isoindol-6(2H)-one (81 mg, 0.22 mmol) was separated by chiral HPLC using an AD column with 90% heptane containing 0.1% diethylamine and 10% 1:1 MeOH:EtOH containing 0.1% diethylamine. The resulting solids were individually repurified by ISCO flash column chromatography (SiO₂, 0-50% ethyl acetate in hexanes) to yield 35 mg of the (1S,10bR) enantiomer and 36 mg of the (1R,10bS) enantiomer as white solids. The solids were individually dissolved in dry ether (1 mL) and the treated with hydrochloric acid (1 mL). The reactions were stirred for 5 min and then conc. in vacuo to a white solid. The solids were dissolved in water and lyophilized to yield 28 mg (quant) of the (1S,10bR) enantiomer and 28 mg (93%) of the (1R,10bS) enantiomer as white solids. MS (ESI) 271 (M–Cl).

Examples 285 and 286

Preparation of (1S,10bR)-1,3,4,10b-tetrahydro-1-ethyl-7-trifluoromethyl-pyrazino[2,1-a]isoindol-6(2H)-one hydrochloric acid salt and (1R,10bS)-1,3,4,10b-tetrahydro-1-ethyl-7-trifluoromethyl-pyrazino[2,1-a]isoindol-6(2H)-one hydrochloric acid salt

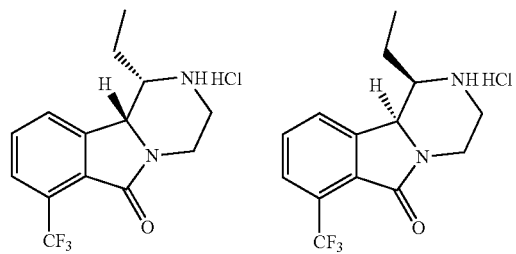

Prepared according to the procedures described in Example 283, steps A-H, with substitution of propionaldehyde for acetaldehyde at step D and N-(t-butoxycarbonyl)-(±)-1,3,4,10b-tetrahydro-1-ethyl-7-trifluoromethyl-pyrazino[2,1-a]isoindol-6(2H)-one for N-(t-butoxycarbonyl)-(±)-1,3,4,10b-tetrahydro-1-methyl-7-trifluoromethyl-pyrazino[2,1-a]isoindol-6(2H)-one at Step H. MS (ESI) 285 (M–Cl).

Examples 287 and 288

Preparation of (1S,10bR)-1,3,4,10b-tetrahydro-1-propyl-7-trifluoromethyl-pyrazino[2,1-a]isoindol-6(2H)-one hydrochloric acid salt and (1R,10bS)-1,3,4,10b-tetrahydro-1-propyl-7-trifluoromethyl-pyrazino[2,1-a]isoindol-6(2H)-one hydrochloric acid salt

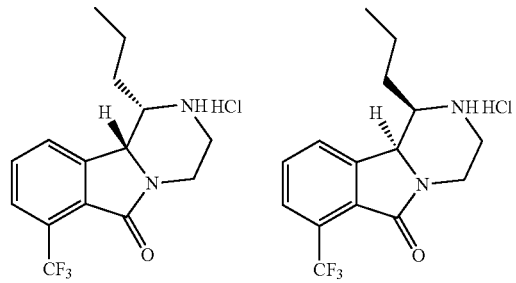

Prepared according to the procedures described in Example 283, steps A-H, with substitution of butyraldehyde for acetaldehyde at step D, N-(t-butoxycarbonyl)-(±)-1,3,4, 10b-tetrahydro-1-propyl-7-trifluoromethyl-pyrazino[2,1-a]isoindol-6(2H)-one for N-(t-butoxycarbonyl)-(±)-1,3,4,10b-tetrahydro-1-methyl-7-trifluoromethyl-pyrazino[2,1-a]isoindol-6(2H)-one at Step H, and 80% heptane containing 0.1% diethylamine for 90% heptane containing 0.1% diethylamine at step H. MS (ESI) 299 (M−Cl).

Examples 289 and 290

Preparation of (1S,10bR)-1,3,4,10b-tetrahydro-1-cyclopropyl-7-trifluoromethyl-pyrazino[2,1-a]isoindol-6(2H)-one hydrochloric acid salt and (1R,10bS)-1,3,4,10b-tetrahydro-1-cyclopropyl-7-trifluoromethyl-pyrazino[2,1-a]isoindol-6(2H)-one hydrochloric acid salt

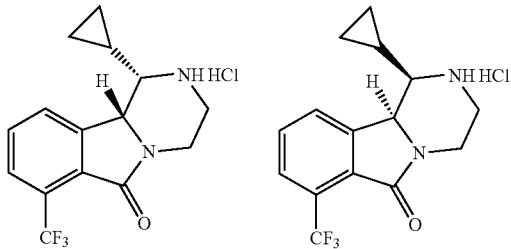

Prepared according to the procedures described in Example 283, steps A-H, with substitution of cyclopropanecarbaldehyde for acetaldehyde at step D and N-(t-butoxycarbonyl)-(±)-1,3,4,10b-tetrahydro-1-cyclopropyl-7-trifluoromethyl-pyrazino[2,1-a]isoindol-6(2H)-one for N-(t-butoxycarbonyl)-(±)-1,3,4,10b-tetrahydro-1-methyl-7-trifluoromethyl-pyrazino[2,1-a]isoindol-6(2H)-one at Step H. MS (ESI) 297 (M−Cl).

Examples 291 and 292

Preparation of (1S,10bR)-1,3,4,10b-tetrahydro-1-isopropyl-7-trifluoromethyl-pyrazino[2,1-a]isoindol-6(2H)-one hydrochloric acid salt and (1R,10bS)-1,3,4,10b-tetrahydro-1-isopropyl-7-trifluoromethyl-pyrazino[2,1-a]isoindol-6(2H)-one hydrochloric acid salt

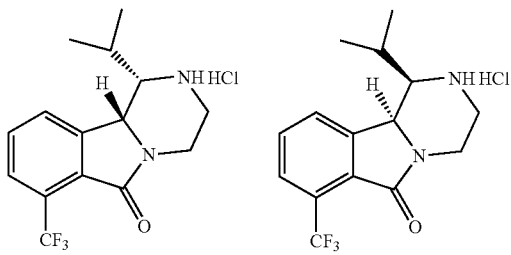

Step A. Preparation of (±)-2-[2-[bis(tert-butoxycarbonyl)amino]ethyl]-1-(1-oxo-2-methylpropyl)-1,3-dihydro-4-trifluoromethyl-isoindol-3(1H)-one Prepared according to the procedures of Example 283, Steps A-F, substituting 2-methylpropionaldehyde for acetaldehyde at Step D. MS (ESI) 515 (M+H).

Step B. Preparation of (±)-1,3,4,10b-tetrahydro-1-isopropyl-7-trifluoromethyl-pyrazino[2,1-a]isoindol-6(2H)-one To (±)-2-[2-[bis(tert-butoxycarbonyl)amino]ethyl]-1-(1-oxo-2-methylpropyl)-1,3-dihydro-4-trifluoromethyl-isoindol-3(1H)-one (277 mg, 0.54 mmol) was added concentrated aqueous hydrogen chloride The resulting mixture was stirred for 35 min and became a yellow solution. The solution was concentrated to dryness, and toluene was added (5 mL). The mixture was again concentrated to dryness, and this procedure was repeated. Finally, the residue was treated with dichloromethane (5 mL) and concentrated to a yellow orange solid. The residue was dissolved in methanol (20 mL) and palladium on carbon (20 mg, 10 wt % 1; Aldrich) was added in one portion under a stream of argon. The resulting mixture was degassed (vacuum then argon, x3) and subjected a hydrogen atmosphere (60 psi) for 11 days. The mixture was then filtered and the filtrate was concentrated. The residue was treated with saturated aqueous ammonium hydroxide, concentrated, and the resulting white solid was purified by flash column chromatography (SiO$_2$, 0-50% ethyl acetate in hexanes) to afford (±)-1,3,4,10b-tetrahydro-1-isopropyl-7-trifluoromethyl-pyrazino[2,1-a]isoindol-6(2H)-one (151 mg, 94%) as a white residue.

MS (ESI) 299 (M+H).

Step C. Preparation of N-(t-butoxycarbonyl)-(±)-1,3,4,10b-tetrahydro-1-isopropyl-7-trifluoromethyl-pyrazino[2,1-a]isoindol-6(2H)-one To (±)-1,3,4,10b-tetrahydro-1-isopropyl-7-trifluoromethyl-pyrazino[2,1-a]isoindol-6(2H)-one (0.151 g, 0.51 mmol) was added di-tert-butyl dicarbonate (0.59 g, 2.7 mmol), and the mixture was warmed to 55° C. To this mixture was added 4-(dimethylamino)-pyridine (0.12 g, 1.0 mmol). After 5 min, the orange brown solution was directly purified by flash column chromatography (SiO$_2$, 0-50% ethyl acetate in hexanes) to afford N-(t-butoxycarbonyl)-(±)-1,3,4,10b-tetrahydro-1-isopropyl-7-trifluoromethyl-pyrazino[2,1-a]isoindol-6(2H)-one (0.089 g, 44%) as a yellow solid.

MS (ESI) 399 (M+H).

Step C. Preparation of (1S,10bR)-1,3,4,10b-tetrahydro-1-isopropyl-7-trifluoromethyl-pyrazino[2,1-a]isoindol-6(2H)-one hydrochloric acid salt and (1R,10bS)-1,3,4,10b-tetrahydro-1-isopropyl-7-trifluoromethyl-pyrazino[2,1-a]isoindol-6(2H)-one hydrochloric acid salt Prepared according to the procedure described in Example 283, Step H, substituting N-(t-butoxycarbonyl)-(±)-1,3,4,10b-tetrahydro-1-isopropyl-7-trifluoromethyl-pyrazino[2,1-a] isoindol-6(2H)-one for N-(t-butoxycarbonyl)-(±)-1,3,4,10b-tetrahydro-1-methyl-7-trifluoromethyl-pyrazino[2,1-a]isoindol-6(2H)-one.

MS (ESI) 299 (M−Cl).

Example 293 and 294

Preparation of (1S,10bR)-1,3,4,10b-tetrahydro-9-bromo-1-methyl-7-trifluoromethyl-pyrazino[2,1-a]isoindol-6(2H)-one hydrochloric acid salt and (1R,10bS)-1,3,4,10b-tetrahydro-9-bromo-1-methyl-7-trifluoromethyl-pyrazino[2,1-a]isoindol-6(2H)-one hydrochloric acid salt

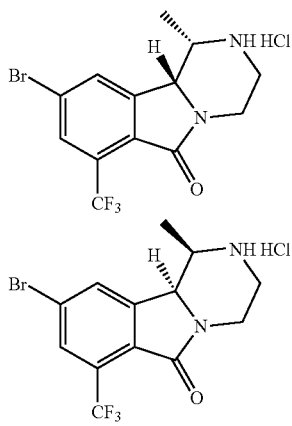

Step A. Preparation of N-(t-butoxycarbonyl)-(±)-1,3,4,10b-tetrahydro-9-bromo-1-methyl-7-trifluoromethyl-pyrazino[2,1-a]isoindol-6(2H)-one To N-(t-butoxycarbonyl)-(±)-1,3,4,10b-tetrahydro-1-methyl-7-trifluoromethyl-pyrazino[2,1-a]isoindol-6(2H)-one (364 mg, 0.98 mmol) was added concentrated aqueous hydrogen chloride (5 mL). The resulting mixture was stirred for five minutes and then concentrated. The resulting residue was treated with concentrated aqueous sulfuric acid (2.0 mL) and N-bromosuccinimide (193 mg, 1.1 mmol). The resulting brown solution was degassed (vacuum then argon), covered with aluminum foil and stirred in the dark for 24 h. The reaction was then diluted with ice water and basified with saturated aqueous sodium bicarbonate. The resulting mixture was diluted with ethyl acetate (15 mL) and treated with di-tert-butyl dicarbonate (excess). After 1 hr, the reaction washed with ethyl acetate (3×50 mL), and the combined organic layers were dried over sodium sulfate, filtered, and concentrated. The resulting residue was purified by flash column chromatography (SiO$_2$, 0-30% ethyl acetate in hexanes) to afford N-(t-butoxycarbonyl)-(±)-1,3,4,10b-tetrahydro-9-bromo-1-methyl-7-trifluoromethyl-pyrazino[2,1-a]isoindol-6(2H)-one (261 mg, 59%) as a white foam-like solid. MS (ESI) 449, 451 (M+H).

Step B. Preparation of N-(t-butoxycarbonyl)-(1S,10bR)-1,3,4,10b-tetrahydro-9-bromo-1-methyl-7-trifluoromethyl-pyrazino[2,1-a]isoindol-6(2H)-one and N-(t-butoxycarbonyl)-(1R,10bS)-1,3,4,10b-tetrahydro-9-bromo-1-methyl-7-trifluoromethyl-pyrazino[2,1-a]isoindol-6(2H)-one The mixture of enantiomers contained in N-(t-butoxycarbonyl)-(±)-1,3,4,10b-tetrahydro-9-bromo-1-methyl-7-trifluoromethyl-pyrazino[2,1-a]isoindol-6(2H)-one (498 mg, 1.1 mmol) was separated by chiral HPLC using an AD column with 90% heptane with 0.1% diethylamine and 10% 1:1 MeOH:EtOH with 0.1% diethylamine. The resulting solids were individually repurified by ISCO flash column chromatography (SiO$_2$, 0-50% ethyl acetate in hexanes) to yield 155 mg of the (1S,10bR) enantiomer and 156 mg of the (1R,10bS) enantiomer as white solids. MS (ESI) 449, 451 (M+H).

Step C. Preparation of (1S,10bR)-1,3,4,10b-tetrahydro-9-bromo-1-methyl-7-trifluoromethyl-pyrazino[2,1-a]isoindol-6(2H)-one hydrochloric acid salt and (1R,10bS)-1,3,4,10b-tetrahydro-9-bromo-1-methyl-7-trifluoromethyl-pyrazino[2,1-a]isoindol-6(2H)-one hydrochloric acid salt To N-(t-butoxycarbonyl)-(1S,10bR)-1,3,4,10b-tetrahydro-9-bromo-1-methyl-7-trifluoromethyl-pyrazino[2,1-a]isoindol-6(2H)-one (16.7 mg, 0.037 mmol) and N-(t-butoxycarbonyl)-(1R,10bS)-1,3,4,10b-tetrahydro-9-bromo-1-methyl-7-trifluoromethyl-pyrazino[2,1-a]isoindol-6(2H)-one (17.8 mg, 0.040 mmol) was added (in separate flasks) dry ether (1 mL) and hydrochloric acid (1 mL). The reactions were stirred for 5 min and then conc. in vacuo to a white solid. The solids were dissolved in water and lyophilized to yield 12 mg (84%) of the (1S,10bR) enantiomer and 13 mg (88%) of the (1R,10bS) enantiomer as white solids. MS (ESI) 271 (M−Cl).

Example 295

Preparation of (1S,10bR)-1,3,4,10b-tetrahydro-9-ethyl-1-methyl-7-trifluoromethyl-pyrazino[2,1-a]isoindol-6(2H)-one hydrochloric acid salt

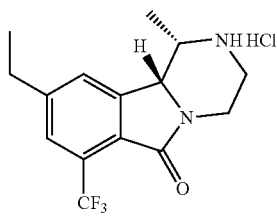

Step A. Preparation of N-(t-butoxycarbonyl)-(1S,10bR)-1,3,4,10b-tetrahydro-9-ethyl-1-methyl-7-trifluoromethyl-pyrazino[2,1-a]isoindol-6(2H)-one Prepared according to the procedures of Example 122, Steps B-C, substituting N-(t-butoxycarbonyl)-(1S,10bR)-1,3,4,10b-tetrahydro-9-bromo-1-methyl-7-trifluoromethyl-pyrazino[2,1-a]isoindol-6(2H)-one for N,N-diethyl-4-bromo-2-(trifluoromethoxy)benzamide at Step B. MS (ESI) 399 (M+H).

Step B. Preparation of (1S,10bR)-1,3,4,10b-tetrahydro-9-bromo-1-methyl-7-trifluoromethyl-pyrazino[2,1-a]isoindol-6(2H)-one hydrochloric acid salt Prepared according to the procedures of Example 2, Step B, substituting N-(t-butoxycarbonyl)-(1S,10bR)-1,3,4,10b-tetrahydro-9-ethyl-1-methyl-7-trifluoromethyl-pyrazino[2,1-a]isoindol-6(2H)-one for N-(t-butoxycarbonyl)-(R)-1,3,4, 10b-tetrahydro-7-trifluoromethoxy-pyrazino[2,1-a]isoindol-6(2H)-one. MS (ESI) 299 (M−Cl).

Example 296

Preparation of (1S,10bR)-1,3,4,10b-tetrahydro-9-isopropyl-1-methyl-7-trifluoromethyl-pyrazino[2,1-a]isoindol-6(2H)-one hydrochloric acid salt

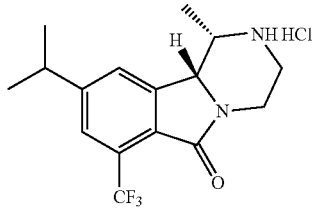

Prepared according to the procedures of Example 295, Steps A-B, substituting isopropenylboronic acid for 2,4,6-trivinylcyclotriboroxane pyridine complex at Step A. MS (ESI) 313 (M+H).

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

What is claimed is:

1. A compound according to the following formula:

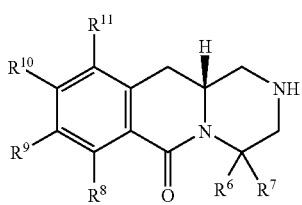

or stereoisomers or pharmaceutically acceptable salt forms thereof, wherein:
   $R^6$ and $R^7$ are each independently selected from the group consisting of H and $C_1$-$C_4$ alkyl;
   $R^8$ is selected from the group consisting of H, alkyl, halogen, perfluoroalkyl and oxyalkyl;
   $R^9$ is selected from the group consisting of H, alkyl, halogen and oxyalkyl;
   $R^{10}$ is selected from the group consisting of H, alkyl and halogen; and
   $R^{11}$ is selected from the group consisting of H and alkyl, provided the compound is not

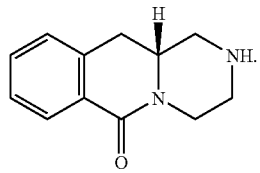

2. The compound according to claim 1, wherein:
   $R^6$ is H.
3. The compound according to claim 2, wherein:
   $R^{10}$ is selected from the group consisting of H, $C_1$-$C_4$ alkyl and halogen.
4. The compound according to claim 3, wherein:
   $R^8$ is selected from the group consisting of H, $C_1$-$C_4$ alkyl, $CF_3$ and $C_1$-$C_4$ oxyalkyl.
5. The compound according to claim 4, wherein:
   $R^7$ is H.
6. The compound according to claim 1, wherein the compound is selected from the group consisting of
   (4R,11aR)-4-methyl-1,2,3,4,11,11a-hexahydropyrazino[1,2-b]isoquinolin-6-one;
   (R)-7-(trifluoromethyl)-1,2,3,4,11,11a-hexahydropyrazino[1,2-b]isoquinolin-6-one;
   (R)-7-chloro-1,2,3,4,11,11a-hexahydropyrazino[1,2-b]isoquinolin-6-one;
   (R)-7-chloro-1,2,3,4,11,11a-hexahydropyrazino[1,2-b]isoquinolin-6-one;
   (R)-7-methyl-1,2,3,4,11,11a-hexahydropyrazino[1,2-b]isoquinolin-6-one;
   (R)-7-ethyl-1,2,3,4,11,11a-hexahydropyrazino[1,2b]isoquinolin-6-one;
   (R)-8-(trifluoromethyl)-1,2,3,4,11,11a-hexahydropyrazino[1,2-b]isoquinolin-6-one;
   (R)-8-bromo-1,2,3,4,11,11a-hexahydropyrazino[1,2-b]isoquinolin-6-one;
   (R)-8-chloro-1,2,3,4,11,11a-hexahydropyrazino[1,2-b]isoquinolin-6-one;
   (R)-8-methoxy-1,2,3,4,11,11a-hexahydropyrazino[1,2-b]isoquinolin-6-one;
   (R)-8-ethyl-1,2,3,4,11,11a-hexahydropyrazino[1,2-b]isoquinolin-6-one;
   (R)-9-(trifluoromethyl)-1,2,3,4,11,11a-hexahydropyrazino[1,2-b]isoquinolin-6-one;
   (R)-9-ethyl-1,2,3,4,11,11a-hexahydropyrazino[1,2-b]isoquinolin-6-one;
   (R)-10-methoxy-1,2,3,4,11,11a-hexahydropyrazino[1,2-b]isoquinolin-6-one;
   (R)-10-ethoxy-1,2,3,4,11,11a-hexahydropyrazino[1,2-b]isoquinolin-6-one;
   (R)-7-bromo-10-methoxy-1,2,3,4,11,11a-hexahydropyrazino[1,2-b]isoquinolin-6-one;
   (R)-10-methoxy-7-methyl-1,2,3,4,11,11a-hexahydropyrazino[1,2-b]isoquinolin-6-one;
   (R)-10-ethy8-(trifluoromethyl)-1,2,3,4,11,11a-hexahydropyrazino[1,2-b]isoquinolin-6-one;
   (R)-7,8-dichloro-1,2,3,4,11,11a-hexahydropyrazino[1,2-b]isoquinolin-6-one;
   (R)-8,9-dichloro-1,2,3,4,11,11a-hexahydropyrazino[1,2-b]isoquinolin-6-one;
   (R)-8,9-dimethyl-1,2,3,4,11,11a-hexahydropyrazino[1,2-b]isoquinolin-6-one;
   (R)-8-chloro-9-methyl-1,2,3,4,11,11a-hexahydropyrazino[1,2-b]isoquinolin-6-one;

(R)-7,9-dimethyl-1,2,3,4,11,11a-hexahydropyrazino[1,2-b]isoquinolin-6-one; and
(R)-8,9,10-trimethyl-1,2,3,4,11,11a-hexahydropyrazino[1,2-b]isoquinolin-6-one.

7. A pharmaceutical composition, comprising:
at least one compound according to claim 1; and
at least one pharmaceutically acceptable carrier or diluent.

8. A compound according to the following formula:

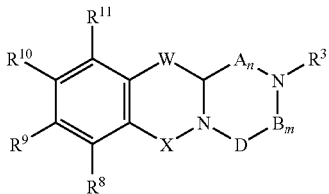

or stereoisomers or pharmaceutically acceptable salt forms thereof, wherein:

A is $CR^1R^2$;
B is $CR^4R^5$;
D is $CR^6R^7$ or CO;
W is selected from the group consisting of $CR^{12}R^{13}$ and CO;
X is $CR^{14}R^{15}$;
m is 1;
n is 1;
$R^1$, $R^2$, $R^4$, $R^5$, $R^6$ and $R^7$ are each independently selected from the group consisting of H, $C_1$-$C_4$ alkyl, $C_2$-$C_4$ alkenyl, cycloalkyl, alkylaryl, alkylheteroaryl, aryl and heteroaryl,
wherein each $C_1$-$C_4$ alkyl, alkylaryl, alkylheteroaryl, aryl and heteroaryl,
may optionally be substituted with one or more hydroxy, alkyl, alkenyl, alkynyl, oxyalkyl, oxyalkenyl, oxyalkynyl, oxycycloalkyl, oxyperfluoroalkyl, —$OCF_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalkynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl;

$R^3$ is selected from the group consisting of H, $C_1$-$C_4$ alkyl, cycloalkyl, alkylaryl, alkylheteroaryl, aryl and heteroaryl;

$R^8$ is selected from the group consisting of hydroxy, alkenyl, alkynyl oxyalkyl, oxyperfluoroalkyl, —$OCF_3$ and cycloalkyl;

$R^9$, $R^{10}$ and $R^{11}$ are each independently selected from the group consisting of H, hydroxy, alkyl, alkenyl, alkynyl, oxyalkyl, oxyalkenyl, oxyalkynyl, oxycycloalkyl, oxyperfluoroalkyl, —$OCF_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl, wherein each alkyl, alkenyl, alkynyl, oxyalkyl, oxyalkenyl, oxyalkynyl, oxycycloalkyl, thioalkyl, thioalkenyl, thioalkynyl, thioaryl, thioheteroaryl, thiocycloalkyl, aryl, heteroaryl, heterocyclyl, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl of $R^8$, $R^9$, $R^{10}$ and $R^{11}$, may optionally be substituted with one or more hydroxy, alkyl, alkenyl, alkynyl, oxyalkyl, oxyalkenyl, oxyalkynyl, oxycycloalkyl, oxyperfluoroalkyl, —$OCF_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl;

$R^{12}$ and $R^{13}$ are each independently selected from the group consisting of H, $C_1$-$C_4$ alkyl, hydroxy, oxyalkyl, cycloalkyl, aryl and heteroaryl; and $R^{14}$ and $R^{15}$ are each independently selected from the group consisting of H, $C_1$-$C_4$ alkyl, cycloalkyl, aryl and alkylaryl;

wherein $R^1$ and $R^4$ taken together can form a 5 or 6 membered ring.

9. A compound according to the following formula:

or stereoisomers or pharmaceutically acceptable salt forms thereof, wherein:

A is $CR^1R^2$;

B is $CR^4R^5$;

D is $CR^6R^7$ or CO;

W is selected from the group consisting of $CR^{12}R^{13}$ and CO;

X is $CR^{14}R^{15}$;

m is 1;

n is 1;

$R^1$, $R^2$, $R^4$, $R^5$, $R^6$ and $R^7$ are each independently selected from the group consisting of H, $C_1$-$C_4$ alkyl, $C_2$-$C_4$ alkenyl, cycloalkyl, alkylaryl, alkylheteroaryl, aryl and heteroaryl, wherein each $C_1$-$C_4$ alkyl, alkylaryl, alkylheteroaryl, aryl and heteroaryl, may optionally be substituted with one or more hydroxy, alkyl, alkenyl, alkynyl, oxyalkyl, oxyalkenyl, oxyalkynyl, oxycycloalkyl, oxyperfluoroalkyl, —$OCF_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl;

$R^3$ is selected from the group consisting of H, $C_1$-$C_4$ alkyl, cycloalkyl, alkylaryl, alkylheteroaryl, aryl and heteroaryl;

$R^8$ is selected from the group consisting of H, alkyl, oxyalkenyl, oxyalkynyl, oxycycloalkyl, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and sulfoheterocyclyl;

$R^9$ is selected from the group consisting of hydroxy, alkenyl, alkynyl and cycloalkyl that is substituted with at least one alkyl;

$R^{10}$ and $R^{11}$ are independently selected from the group consisting of H, hydroxy, alkyl, alkenyl, alkynyl, oxyalkyl, oxyalkenyl, oxyalkynyl, oxycycloalkyl, oxyperfluoroalkyl, —$OCF_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl, wherein each alkyl, alkenyl, alkynyl, oxyalkyl, oxyalkenyl, oxyalkynyl, oxycycloalkyl, thioalkyl, thioalkenyl, thioalkynyl, thioaryl, thioheteroaryl, thiocycloalkyl, aryl, heteroaryl, heterocyclyl, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl of $R^8$, $R^9$, $R^{10}$ and $R^{11}$, may optionally be substituted with one or more hydroxy, alkyl, alkenyl, alkynyl, oxyalkyl, oxyalkenyl, oxyalkynyl, oxycycloalkyl, oxyperfluoroalkyl, —OCF$_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, CF$_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheterocyclyl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, sulfoalkyl, sulfoalkenyl, sulfoalkynyl, sulfocycloalkyl, sulfoaryl, sulfoheteroaryl, sulfoheterocyclyl and cycloalkyl;

$R^{12}$ and $R^{13}$ are each independently selected from the group consisting of H, C$_1$-C$_4$ alkyl, hydroxy, oxyalkyl, cycloalkyl, aryl and heteroaryl; and $R^{14}$ and $R^{15}$ are each independently selected from the group consisting of H, C$_1$-C$_4$ alkyl, cycloalkyl, aryl and alkylaryl;

wherein $R^1$ and $R^4$ taken together can form a 5 or 6 membered ring, with the following provisos the compound is not

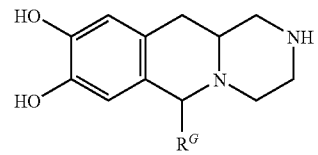

wherein
$R^G$ is substituted or unsubstituted phenyl or substituted or unsubstituted heteroaryl.

10. A compound according to the following formula:

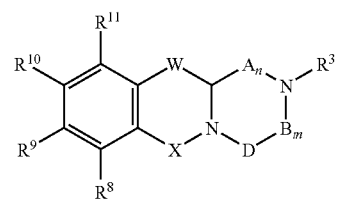

or stereoisomers or pharmaceutically acceptable salt forms thereof, wherein:
A is $CR^1R^2$;
B is $CR^4R^5$;
D is $CR^6R^7$ or CO;
W is selected from the group consisting of $CR^{12}R^{13}$ and CO;
X is $CR^{14}R^{15}$;
m is 1;
n is 1;
$R^1$, $R^2$, $R^4$, $R^5$, $R^6$ and $R^7$ are each independently selected from the group consisting of H, C$_1$-C$_4$ alkyl, C$_2$-C$_4$ alkenyl, cycloalkyl, alkylaryl, alkylheteroaryl, aryl and heteroaryl, wherein each C$_1$-C$_4$ alkyl, alkylaryl, alkylheteroaryl, aryl and heteroaryl, may optionally be substituted with one or more hydroxy, alkyl, alkenyl, alkynyl, oxyalkyl, oxyalkenyl, oxyalkynyl, oxycycloalkyl, oxyperfluoroalkyl, —OCF$_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, CF$_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl;

$R^3$ is selected from the group consisting of H, $C_1$-$C_4$ alkyl, cycloalkyl, alkylaryl, alkylheteroaryl, aryl and heteroaryl;

$R^8$ is selected from the group consisting of H, alkyl, oxyalkyl, oxyalkynyl, oxycycloalkyl, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl and sulfoheterocyclyl;

$R^9$ is selected from the group consisting of H, alkyl, oxyalkyl, oxyalkenyl, oxyalkynyl, oxycycloalkyl, oxyperfluoroalkyl, —$OCF_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl and sulfoheterocyclyl;

$R^{10}$ is selected from the group consisting of hydroxyl, alkenyl, alkynyl and cycloalkyl that is substituted with at least one alkyl;

$R^{11}$ is selected from the group consisting of H, hydroxy, alkyl, alkenyl, alkynyl, oxyalkyl, oxyalkenyl, oxyalkynyl, oxycycloalkyl, oxyperfluoroalkyl, —$OCF_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl, wherein each alkyl, alkenyl, alkynyl, oxyalkyl, oxyalkenyl, oxyalkynyl, oxycycloalkyl, thioalkyl, thioalkenyl, thioalkynyl, thioaryl, thioheteroaryl, thiocycloalkyl, aryl, heteroaryl, heterocyclyl, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheterocyclyl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl of $R^8$, $R^9$, $R^{10}$ and $R_{11}$, may optionally be substituted with one or more hydroxy, alkyl, alkenyl, alkynyl, oxyalkyl, oxyalkenyl, oxyalkynyl, oxycycloalkyl, oxyperfluoroalkyl, —$OCF_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheterocyclyl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl;

$R^{12}$ and $R^{13}$ are each independently selected from the group consisting of H, $C_1$-$C_4$ alkyl, hydroxy, oxyalkyl, cycloalkyl, aryl and heteroaryl; and $R^{14}$ and $R^{15}$ are each independently selected from the group consisting of H, $C_1$-$C_4$ alkyl, cycloalkyl, aryl and alkylaryl;

wherein $R^1$ and $R^4$ taken together can form a 5 or 6 membered ring.

11. A compound according to the following formula:

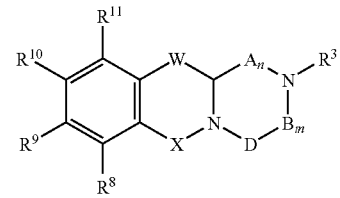

or stereoisomers or pharmaceutically acceptable salt forms thereof, wherein:

A is $CR^1R^2$;

B is $CR^4R^5$;

D is $CR^6R^7$ or CO;

W is selected from the group consisting of $CR^{12}R^{13}$ and CO;

X is $CR^{14}R^{15}$;

m is 1;

n is 1;

$R^1$, $R^2$, $R^4$, $R^5$, $R^6$ and $R^7$ are each independently selected from the group consisting of H, $C_1$-$C_4$ alkyl, $C_2$-$C_4$ alkenyl, cycloalkyl, alkylaryl, alkylheteroaryl, aryl and heteroaryl, wherein each $C_1$-$C_4$ alkyl, alkylaryl, alkylheteroaryl, aryl and heteroaryl, may optionally be substituted with one or more hydroxy, alkyl, alkenyl, alkynyl, oxyalkyl, oxyalkenyl, oxyalkynyl, oxycycloalkyl, oxyperfluoroalkyl, —$OCF_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl;

$R^3$ is selected from the group consisting of H, $C_1$-$C_4$ alkyl, cycloalkyl, alkylaryl, alkylheteroaryl, aryl and heteroaryl;

$R^8$ is selected from the group consisting of H, alkyl, oxyalkenyl, oxyalkynyl, oxycycloalkyl, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl and sulfoheterocyclyl;

$R^9$ and $R^{19}$ are independently selected from the group consisting of H, alkyl, oxyalkyl, oxyalkenyl, oxyalkynyl, oxycycloalkyl, oxyperfluoroalkyl, —$OCF_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl and sulfoheterocyclyl;

$R^{11}$ is selected from the group consisting of hydroxy, oxyalkyl, substituted alkyl, thioalkyl, thioalkenyl, thioalkynyl, thioaryl, thioheteroaryl, thiocycloalkyl, sulfoalkyl, sulfoalkenyl, sulfoalkynyl, sulfocycloalkyl, sulfoaryl, sulfoheteroaryl and sulfoheterocyclyl, wherein each alkenyl, alkynyl, oxyalkyl, oxyalkenyl, oxyalkynyl, oxycycloalkyl, thioalkyl, thioalkenyl, thioalkynyl, thioaryl, thioheteroaryl, thiocycloalkyl, heteroaryl, heterocyclyl, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkenyl, sulfoaminoalykynyl, sulfoaminoheteroaryl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl of $R^8$, $R^9$, $R^{10}$ and $R_{11}$, may optionally be substituted with one or more hydroxy, alkyl, alkenyl, alkynyl, oxyalkyl, oxyalkenyl, oxyalkynyl, oxycycloalkyl, oxyperfluoroalkyl, —$OCF_3$, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoakynyl, carboaminoaryl, carboaminocycloalkyl, carboalkyl, carboalkenyl, carboalkynyl, carboaryl, carbocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboaminoheterocyclyl, aminocarboaminoheteroaryl, perfluoroalkyl, $CF_3$, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, aminoheterocyclyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, carboxyheterocyclyl, oxycarboalkyl, oxycarboalkenyl, oxycarboalkynyl, oxycarboaryl, oxycarboheteroaryl, oxycarbocycloalkyl, oxycarboheterocyclyl, sulfoaminoalkyl, sulfoaminoalkenyl, sulfoaminoalykynyl, sulfoaminoaryl, sulfoaminoheteroaryl, sulfoaminocycloalkyl, sulfoaminoheterocyclyl, aminosulfoalkyl, aminosulfoalkenyl, aminosulfoalkynyl, aminosulfocycloalkyl, aminosulfoaryl, aminosulfoheteroaryl, aminosulfoheterocyclyl, sulfoalkyl, sulfoalkenyl, sulfoalkynyl, sulfocycloalkyl, sulfoaryl, sulfoheteroaryl, sulfoheterocyclyl and cycloalkyl;

$R^{12}$ and $R^{13}$ are each independently selected from the group consisting of H, $C_1$-$C_4$ alkyl, hydroxy, oxyalkyl, cycloalkyl, aryl and heteroaryl; and $R^{14}$ and $R^{15}$ are each independently selected from the group consisting of H, $C_1$-$C_4$ alkyl, cycloalkyl, aryl and alkylaryl;

wherein $R^1$ and $R^4$ taken together can form a 5 or 6 membered ring.

* * * * *

UNITED STATES PATENT AND TRADEMARK OFFICE
CERTIFICATE OF CORRECTION

PATENT NO. : 7,812,024 B2  Page 1 of 1
APPLICATION NO. : 11/748078
DATED : October 12, 2010
INVENTOR(S) : Guohua Zhao et al.

It is certified that error appears in the above-identified patent and that said Letters Patent is hereby corrected as shown below:

In the Claims:

Claim 6:

Column 182, line 29, change "chloro" to -- bromo --.

Column 182, line 33, change "[1,2b]" to -- [1,2-b] --.

Column 182, line 58, change "ethy8" to -- ethyl-8 --.

Claim 13:

Column 196, line 13, change "$R^{19}$" to -- $R^{10}$ --.

Signed and Sealed this
Twenty-ninth Day of November, 2011

David J. Kappos
*Director of the United States Patent and Trademark Office*